(12) United States Patent
Mayfield et al.

(10) Patent No.: US 8,669,059 B2
(45) Date of Patent: Mar. 11, 2014

(54) HIGH THROUGHPUT SCREENING OF GENETICALLY MODIFIED PHOTOSYNTHETIC ORGANISMS

(75) Inventors: Stephen Mayfield, Cardiff-by-the-Sea, CA (US); Bryan O'Neill, San Diego, CA (US); Michael Mendez, San Diego, CA (US); Kari Mikkelson, San Diego, CA (US); Yan Poon, San Diego, CA (US)

(73) Assignees: The Scripps Research Institute, La Jolla, CA (US); Sapphire Energy, Inc., San Diego, CA (US)

( * ) Notice: Subject to any disclaimer, the term of this patent is extended or adjusted under 35 U.S.C. 154(b) by 0 days.

(21) Appl. No.: 13/585,758

(22) Filed: Aug. 14, 2012

(65) Prior Publication Data

US 2012/0309014 A1    Dec. 6, 2012

Related U.S. Application Data

(63) Continuation of application No. 12/156,432, filed on May 30, 2008, now Pat. No. 8,268,553.

(60) Provisional application No. 60/941,452, filed on Jun. 1, 2007, provisional application No. 60/070,384, filed on Mar. 20, 2008, provisional application No. 61/070,437, filed on Mar. 20, 2008.

(51) Int. Cl.
*C12Q 1/68* (2006.01)
*C12P 19/34* (2006.01)
*C07H 21/02* (2006.01)
*C07H 21/04* (2006.01)

(52) U.S. Cl.
USPC .......... 435/6.1; 435/91.2; 536/23.1; 536/24.3

(58) Field of Classification Search
None
See application file for complete search history.

(56) References Cited

U.S. PATENT DOCUMENTS

| | | | |
|---|---|---|---|
| 4,297,109 | A | 10/1981 | Sugito et al. |
| 4,341,038 | A | 7/1982 | Bloch et al. |
| 4,795,479 | A | 1/1989 | Karol |
| 5,200,215 | A | 4/1993 | Slade et al. |

(Continued)

FOREIGN PATENT DOCUMENTS

| | | |
|---|---|---|
| EP | 0 468 596 A1 | 1/1992 |
| EP | 0 904 095 B1 | 3/1999 |

(Continued)

OTHER PUBLICATIONS

Mannerlof, M. et al., Plant Mol. Biol. Rep., vol. 15, pp. 38-45 (1997).*

(Continued)

*Primary Examiner* — Teresa E Strzelecka
(74) *Attorney, Agent, or Firm* — James E. Butler; Thomas Fitting; Arnold & Porter LLP

(57) ABSTRACT

The present invention provides a method and compositions for high throughput screening of genetically modified photosynthetic organisms for plasmic state. The present invention provides methods of producing one or more proteins, including biomass degrading enzymes in a plant. Also provided are the methods of producing biomass degradation pathways in alga cells, particularly in the chloroplast. Single enzymes or multiple enzymes may be produced by the methods disclosed. The methods disclosed herein allow for the production of biofuel, including ethanol.

26 Claims, 15 Drawing Sheets

Gene:

Control:

WT:

(56) References Cited

U.S. PATENT DOCUMENTS

| | | | |
|---|---|---|---|
| 5,451,513 | A | 9/1995 | Maliga et al. |
| 5,545,817 | A | 8/1996 | McBride et al. |
| 5,545,818 | A | 8/1996 | McBride et al. |
| 5,607,486 | A | 3/1997 | Wilkins, Jr. |
| 5,661,017 | A | 8/1997 | Dunahay et al. |
| 5,693,507 | A | 12/1997 | Daniell et al. |
| 5,871,988 | A | 2/1999 | Croteau et al. |
| 5,958,761 | A | 9/1999 | Yogev et al. |
| 6,072,045 | A | 6/2000 | Chappell et al. |
| 6,083,740 | A | 7/2000 | Kodo et al. |
| 6,156,517 | A | 12/2000 | Mayfield |
| 6,271,444 | B1 | 8/2001 | McBride et al. |
| 6,284,509 | B1 | 9/2001 | Ferrer et al. |
| 6,297,054 | B1 | 10/2001 | Maliga et al. |
| RE37,629 | E | 4/2002 | Wilkins, Jr. |
| 6,388,168 | B1 | 5/2002 | Maliga et al. |
| 6,495,354 | B2 | 12/2002 | Chappell et al. |
| 6,642,053 | B1 | 11/2003 | Daniell et al. |
| 6,680,426 | B2 | 1/2004 | Daniell et al. |
| 6,872,516 | B2 | 3/2005 | Evans et al. |
| 6,891,086 | B2 | 5/2005 | Chaudhuri et al. |
| 7,030,294 | B2 | 4/2006 | Lebel et al. |
| 7,129,391 | B1 | 10/2006 | Daniell |
| 7,129,392 | B2 | 10/2006 | Hahn et al. |
| 7,135,620 | B2 | 11/2006 | Daniell et al. |
| 7,172,886 | B2 | 2/2007 | Keasling et al. |
| 7,259,293 | B2 | 8/2007 | Staub |
| 7,361,806 | B2 | 4/2008 | Lebel et al. |
| 2001/0051359 | A1 | 12/2001 | Ohto et al. |
| 2002/0062502 | A1 | 5/2002 | Lebel et al. |
| 2002/0106772 | A1 | 8/2002 | Croteau et al. |
| 2003/0041353 | A1 | 2/2003 | Daniell et al. |
| 2003/0148479 | A1 | 8/2003 | Keasling et al. |
| 2003/0166255 | A1 | 9/2003 | Chappell et al. |
| 2003/0219798 | A1 | 11/2003 | Gokarn et al. |
| 2004/0014174 | A1 | 1/2004 | Mayfield et al. |
| 2004/0055209 | A1 | 3/2004 | Jakkula et al. |
| 2004/0074760 | A1 | 4/2004 | Portnoff et al. |
| 2004/0133937 | A1 | 7/2004 | Boudreau et al. |
| 2004/0161819 | A1 | 8/2004 | Aharoni et al. |
| 2004/0253586 | A1 | 12/2004 | Reddy et al. |
| 2005/0154669 | A1 | 7/2005 | Streetman |
| 2005/0204417 | A1 | 9/2005 | Croteau et al. |
| 2005/0239182 | A1 | 10/2005 | Berzin |
| 2005/0260553 | A1 | 11/2005 | Berzin |
| 2005/0287655 | A1 | 12/2005 | Tabata et al. |
| 2006/0194975 | A1 | 8/2006 | Narayan et al. |
| 2006/0234368 | A1 | 10/2006 | Fukuda et al. |
| 2007/0048848 | A1 | 3/2007 | Sears |
| 2007/0048859 | A1 | 3/2007 | Sears |
| 2007/0077616 | A1 | 4/2007 | Keasling et al. |
| 2007/0092931 | A1 | 4/2007 | Keasling et al. |
| 2007/0099261 | A1 | 5/2007 | Keasling et al. |
| 2008/0038805 | A1 | 2/2008 | Melis |
| 2008/0098645 | A1 | 5/2008 | Renninger et al. |
| 2008/0171378 | A1 | 7/2008 | Keasling et al. |
| 2009/0061493 | A1 | 3/2009 | Trimbur et al. |
| 2009/0328259 | A1 | 12/2009 | Harris et al. |

FOREIGN PATENT DOCUMENTS

| | | |
|---|---|---|
| EP | 1 574 580 A2 | 9/2005 |
| WO | WO 95/16783 A1 | 6/1995 |
| WO | WO 95/24493 A1 | 9/1995 |
| WO | WO 98/31823 A1 | 7/1998 |
| WO | WO 00/07431 A1 | 2/2000 |
| WO | WO 01/64929 A1 | 9/2001 |
| WO | WO 01/72959 A2 | 10/2001 |
| WO | WO 01/72959 A3 | 10/2001 |
| WO | WO 03/091413 A2 | 11/2003 |
| WO | WO 03/091413 A3 | 11/2003 |
| WO | WO 2006/111924 A2 | 10/2006 |
| WO | WO 2006/111924 A3 | 10/2006 |
| WO | WO 2007/005604 A2 | 1/2007 |
| WO | WO 2007/005646 A2 | 1/2007 |
| WO | WO 2007/133558 A2 | 11/2007 |
| WO | WO 2008/003078 A2 | 1/2008 |
| WO | WO 2008/003078 A3 | 1/2008 |

OTHER PUBLICATIONS

GenBank Accession No. J01399 (Dec. 1995).*
GenBank Accession No. AB044470 (Apr. 2001).*
Affek et al., "Natural Abundance Carbon Isotope Composition of Isoprene Reflects Incomplete Coupling Between Isoprene Synthesis and Photosynthetic Carbon Flow," *Plant Physiol.*, 131(4):1727-1736 (2003), provided in U.S. Appl. No. 12/156,432.
Akin et al., "Removal of CO2 from flue gases by algae," Final Technical Report to DOE, USA (2007), available at www.oilgae.com/blog/2007/02/removal-of-co2-from-glue-gases-by-algae.html, provided in U.S. Appl. No. 12/156,432.
Bateman, "Tools for chloroplast transformation in *Chlamydomonas*: expression vectors and a new dominant selectable marker," *Mol Gen Genet.*, 263(3):404-410 (2000), provided in U.S. Appl. No. 12/156,432.
Bock, "Transgenic Plastids in Basic Research and Plant Biotechnology," *J. Mol Biol.*, 312(3):425-438 (2001), provided in U.S. Appl. No. 12/156,432.
Boynton et al., "Chloroplast Transformation in *Chlamydomonas* with High Velocity Microprojectiles," *Science*, 240:1534-1538 (1988), provided in U.S. Appl. No. 12/156,432.
Carrer et al., "Kanamycin resistance as a selectable marker for plastid transformation in tobacco," *Mol Gen Genet.*, 241(1-2):49-56 (1993), provided in U.S. Appl. No. 12/156,432.
Cheng et al., "The *Klebsiella pnuemoniae* nitrogenase Fe protein gene (nifH) functionally substitutes for the chIL gene in *Chlamydomonas reinhardtii*," *Biochem. Biophys. Res. Comm.*, 329(3):966-975 (2005), provided in U.S. Appl. No. 12/156,432.
Christou, "Transformation technology," *Trends in Plant Science*, 1:423-431(1996), provided in U.S. Appl. No. 12/156,432.
Cohen et al., "Translation Regulation of Chloroplast Gene Expression in *Chlamydomonas reinhardtii*," *Meth. Enzymol.*, 297:192-208 (1998), provided in U.S. Appl. No. 12/156,432.
Criss, "Stable Isotope Distribution: Variations from Temperature, Organic and Water-Rock Interactions," *Global Earth Physics: a Handbook of Physical Constants.* AGU Reference Shelf 1:292-307 (1995), provided in U.S. Appl. No. 12/156,432.
Disch et al., "Distribution of the mevalonate and glyceraldehyde phosphate/pyruvate pathways for isoprenoid biosynthesis in unicellular algae and the cyanobacterium *Synechocysitis* PCC 6714," *Biochem. J.*, 333:381-388 (1998), provided in U.S. Appl. No. 12/156,432.
Farquhar et al., "Carbon isotope discrimination and photosynthesis," *Annu. Rev. Plant Physiol. Plant Mol. Biol.*, 40:503-537 (1989), provided in U.S. Appl. No. 12/156,432.
Fisseha et al., "Determination of stable carbon isotopes of organic acids and carbonaceous aerosols in the atmosphere," *Rapid Commun. Mass Spectrom.*, 20(15):2343-2347 (2006), provided in U.S. Appl. No. 12/156,432.
Franklin et al., "Development of a GFP reporter gene for *Chlamydomonas reinhardtii* chloroplast," *The Plant Journal*, 30(6):733-744 (2002), provided in U.S. Appl. No. 12/156,432.
Franklin et al., "Prospects for molecular farming in the green alga *Chlamydomonas reinhardtii*," *Current Opinion in Plant Biology*, 7:159-165 (2004), provided in U.S. Appl. No. 12/156,432.
Fukusaki et al., "Introduction of the Archaebacterial Geranylgeranyl Pyrophosphate Synthase Gene into *Chlamydomonas reinhardtii* Chloroplast," *Journal of Bioscience and Bioengineering*, 95(3):283-287 (2003), provided in U.S. Appl. No. 12/156,432.
GenBank Accession No. AAA34213 (GI:170549) (1994), provided in U.S. Appl. No. 12/156,432.
GenBank Accession No. BAA74959 (GI:4249562) (2002), provided in U.S. Appl. No. 12/156,432.
GenBank Accession No. DQ404589 (109290446) (2006), provided in U.S. Appl. No. 12/156,432.
GenBank Accession No. P00725 (GI:121853) (2004), provided in U.S. Appl. No. 12/156,432.

(56) References Cited

OTHER PUBLICATIONS

GenBank Accession No. X69573 (GI:396563) (2006), provided in U.S. Appl. No. 12/156,432.

Gleason et al., "Stable isotope compositions of gases and vegetation near naturally burning coal," *Nature*, 307:254-257 (1984), provided in U.S. Appl. No. 12/156,432.

Goldschmidt-Clermont, "Transgenic expression of aminoglycoside adenine transferase in the chloroplast: a selectable marker for site-directed transformation of *Chlamydomonas*," *Nucleic Acids Res.*, 19(15):4083-4089 (1991), provided in U.S. Appl. No. 12/156,432.

Hallman, "Algal Transgenics and Biotechnology," *Transgenic Plant Journal*, 1:81-98 (2007), provided in U.S. Appl. No. 12/156,432.

Halpin et al., "Self-processing 2A-polyproteins—a system for co-ordinate expression of multiple proteins in transgenic plants," *The Plant Journal*, 17(4):453-459 (1999), provided in U.S. Appl. No. 12/156,432.

Harris et al., "Chloroplast Ribosomes and Protein Synthesis," *Microbiol. Rev.*, 58(4):700-754 (1994), provided in U.S. Appl. No. 12/156,432.

He et al., "Recombination and expression of classical swine fever virus (CSFV) structural protein E2 gene in *Chlamydomonas reinhardtii* chloroplasts," *Colloids and Surfaces B: Biointerfaces*, 55:26-30 (2007), provided in U.S. Appl. No. 12/156,432.
Heifetz, "Genetic engineering of the chloroplast," *Biochimie*, 82(6-7):655-666 (2000), provided in U.S. Appl. No. 12/156,432.
Ikegami, "Biological C 02 Fixation and Utilization by Micro-algal Photosynthesis." Available at http://biozine.kribb.re.kr/bodo/bodo_view.html?code=vision&num=176&GotoPage=23&sname =&sval. Accessed Sep. 19, 2007, provided in U.S. Appl. No. 12/156,432.
International Search Report mailed on Dec. 11, 2008, in International Application No. PCT/US2008/006876, provided in U.S. Appl. No. 12/156,432.
International Search Report mailed on Dec. 26, 2008, in International Application No. PCT/US2008/006879, provided in U.S. Appl. No. 12/156,432.
Ishikura et al., "Expression of a Foreign Gene in *Chlamydomonas reinhardtii* Chloroplast," *Journal of Bioscience and Bioengineering*, 87(3):307-314 (1999), provided in U.S. Appl. No. 12/156,432.
Kindle et al., "Engineering the chloroplast genome: Techniques and capabilities for chloroplast transformation in *Chlamydomonas reinhardtii," Proc. Natl. Acad. Sci. USA*, 88(5):1721-1725 (1991), provided in U.S. Appl. No. 12/156,432.
Kota et al., "Overexpression of the *Bacilus thuringiensis* (Bt) Cry2Aa2 protein in chloroplasts confers resistance to plants against susceptible and Bt-resistant insects," *Proc. Natl. Acad. Sci. USA*, 96(5):1840-1845 (1999), provided in U.S. Appl. No. 12/156,432.
Kung et al., "Chloroplast promoters from higher plants," *Nucleic Acids Res.*, 13(21):7543-7549 (1985), provided in U.S. Appl. No. 12/156,432.
Lapidot et al., "Stable Chloroplast Transformation of the Unicellular Red Alga *Porphyridium* Species," *Plant Physiology* 129:7-12 (2002), provided in U.S. Appl. No. 12/156,432.
Manuell et al., "Structure of the Chloroplast Ribosome: Novel Domains for Translation Regulation," *PloS Biology*, 5(8):1785-1797 (2007), provided in U.S. Appl. No. 12/156,432.
Mayfield et al., "Expression and assembly of a fully active antibody in algae," *Proc. Natl. Acad. Sci. USA*, 100(2):438-442 (2003), provided in U.S. Appl. No. 12/156,432.
Mayfield et al., "Development of a luciferase reporter gene, luxCt, for *Chlamydomonas reinhardtii* chloroplast," *The Plant Journal*, 37:449-458 (2004), provided in U.S. Appl. No. 12/156,432.
McBride et al., "Controlled expression of plastid transgenes in plants based on a nuclear DNA-encoded and plastid-targeted T7 RNA polymerase," *Proc. Natl. Acad. Sci. USA*, 91(15):7301-7305 (1994), provided in U.S. Appl. No. 12/156,432.
Minko et al.,"*Renilla* luciferase as a vital reporter for chloroplast gene expression in *Chlamydomonas," Molecular and General Genetics*, 262(3):421-425 (1999), provided in U.S. Appl. No. 12/156,432.
O'Leary, "Carbon Isotopes in Photosynthesis," *BioScience*, 38(5):328-336 (1988), provided in U.S. Appl. No. 12/156,432.
Pulz et al., "Valuable products from biotechnology of microalgae," *Appl Microbiol and Biotechnol*, 65(6):635-648 (2004), provided in U.S. Appl. No. 12/156,432.
Raven et al., "Inorganic C-Sources for *Lemanea, Cladophora* and *Ranunculus* in a Fast-Flowing Stream: Measurements of Gas Exchange and of Carbon Isotope Ratio and Their Ecological Implications," *Oecologia*, 53:68-78 (1982), provided in U.S. Appl. No. 12/156,432.
Rochaix et al., "Construction and characterization of autonomously replicating plasmids in the green unicellular alga *Chlamydomonoas reinhardii," Cell*, 36(4):925-931 (1984), provided in U.S. Appl. No. 12/156,432.
Rochaix et al., "Strategy, Progress and Prospects of Transformation in *Chlamydomonas reinhardii," NATO Advanced Science Institutes Series*, 83:579-592 (1985), provided in U.S. Appl. No. 12/156,432.
Sakamoto et al., "In vivo analysis of *Chlamydomonas* chloroplast petD gene expression using stable transformation of beta-glucuronidase translational fusions," *Proc. Natl. Acad Sci. USA*, 90(2):497-501 (1993), provided in U.S. Appl. No. 12/156,432.
Schnitzler et al., "Contribution of Different Carbon Sources to Isoprene Biosynthesis in Poplar Leaves," *Plant Physiol.*, 135(1):152-160 (2004), provided in U.S. Appl. No. 12/156,432.
Sharkey et al., "Isoprene Emission from Plants: Why and How," *Annals of Botany*, 101(1):1-14 (2007), provided in U.S. Appl. No. 12/156,432.
Sheehan et al., "A Look Back at the U.S. Department of Energy's Aquatic Species Program: Biodiesel from Algae," *The National Laboratory of the U.S. Department of Energy*, 328 pages (1998), provided in U.S. Appl. No. 12/156,432.
Sidorov et al., "Stable chloroplast transformation in potato: use of green fluorescent protein as a plastid marker," *The Plant Journal*, 19(2):209-216 (1999), provided in U.S. Appl. No. 12/156,432.
Staub et al., "Accumulation of D1 polypeptide in tobacco plastids is regulated via the untranslated region of the psbA mRNA," *Embo J.*, 12(2):601-606 (1993), provided in U.S. Appl. No. 12/156,432.
Staub et al., "High-yield production of a human therapeutic protein in tobacco chloroplasts," *Nature Biotechnology*, 18(3):333-338 (2000), provided in U.S. Appl. No. 12/156,432.
Svab et al., "Stable transformation of plastids in higher plants," *Proc. of the Natl. Acad. Sci. USA*, 87(21):8526-8530 (1990), provided in U.S. Appl. No. 12/156,432.
Svab et al., "High-frequency plastid transformation in tobacco by selection for a chimeric aadA gene," *Proc. Natl. Acad. Sci. USA*, 90(3):913-917 (1993), provided in U.S. Appl. No. 12/156,432.
Verma et al., "Chloroplast Vector Systems for Biotechnology Applications," *Plant Physiology*, 145:1129-1143 (2007), provided in U.S. Appl. No. 12/156,432.
Viikari et al., "Thermostable Enzymes in Lignocellulose Hydrolysis," *Adv Biochem Engin/Biotechnol*, 108:121-145 (2007), provided in U.S. Appl. No. 12/156,432.
Watson et al., "Expression of *Bacillus anthracis* protective antigen in transgenic chloroplasts of tobacco, a non-food/feed crop," *Vaccine*, 22:4374-4384 (2004), provided in U.S. Appl. No. 12/156,432.
Yang et al., "Expression of human soluble TRAIL in *Chlamydomonas reinhardtii* chloroplast," *Chinese Science Bulletin*, 51(14):1703-1709 (2006), provided in U.S. Appl. No. 12/156,432.
Yu et al., "Production of Eicosapentaenoic Acid by a Recombinant Marine Cyanobacterium, *Synechococcus* sp.," *Lipids*, 35(10):1061-1064 (2000), provided in U.S. Appl. No. 12/156,432.
Yu et al., "Expression of thermostable microbial cellulases in the chloroplasts of nicotine-free tobacco," *Journal of Biotechnology*, 131(3):362-369 (2007), provided in U.S. Appl. No. 12/156,432.

(56) References Cited

OTHER PUBLICATIONS

Zerges et al., "The 5' Leader of a Chloroplast mRNA Mediates the Translational Requirements for Two Nucleus-Encoded Functions in *Chlamydomonoas reinhardtii*" *Mol. Cell Biol.*, 14(8):5268-5277 (1994), provided in U.S. Appl. No. 12/156,432.

Dauvillee et al., "Minimal extent of sequence homology required for homologous recombination at the psbA locus in *Chlamydomonas reinhardtii* chloroplasts using PCR-generated DNA fragments," *Photosynthesis Research*, 79:219-224 (2004).

Gumpel et al., "Studies on homologous recombination in the green alga *Chlamydomonas reinhardtii*," *Current Genetics*, 26:438-442 (1994).

Cone et al., "Coamplified Positive Control Detects Inhibition of Polymerase Chain Reactions," *Journal of Clinical Microbiology*, 30: 3185-3189 (1992).

Kasai et al., "Effect of Coding Regions on Chloroplast Gene Expression in *Chlamydomonas reinhardtii*," *Journal of Bioscience and Bioengineering*, 95: 276-282 (2003).

* cited by examiner

A

B

FIGURE 3
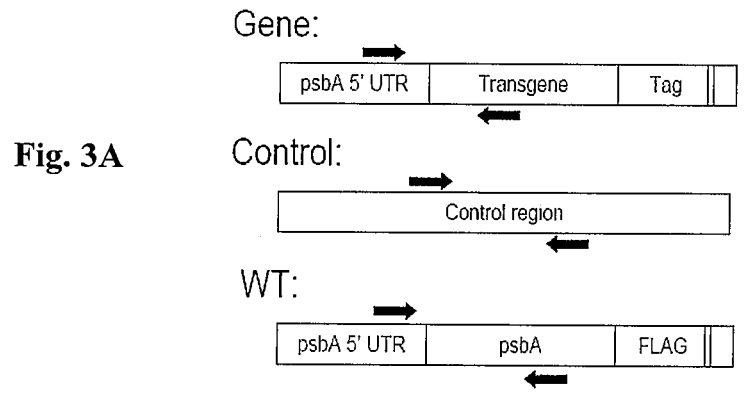
Fig. 3A
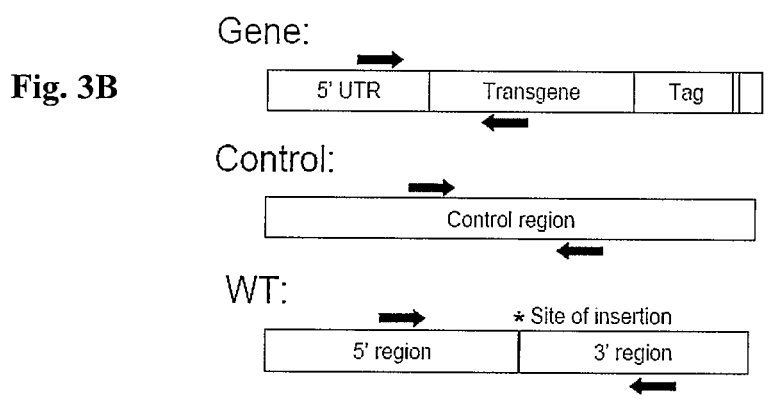
Fig. 3B
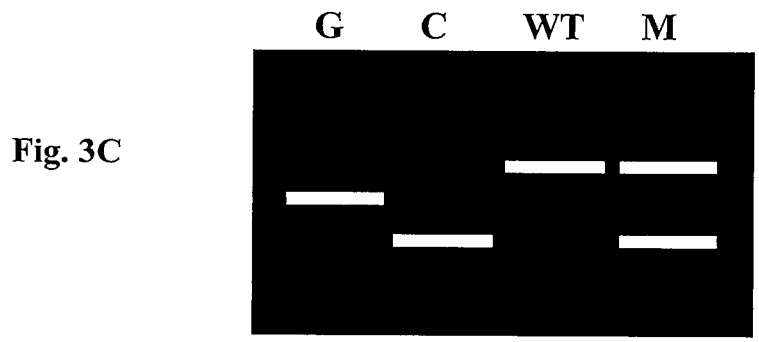
Fig. 3C

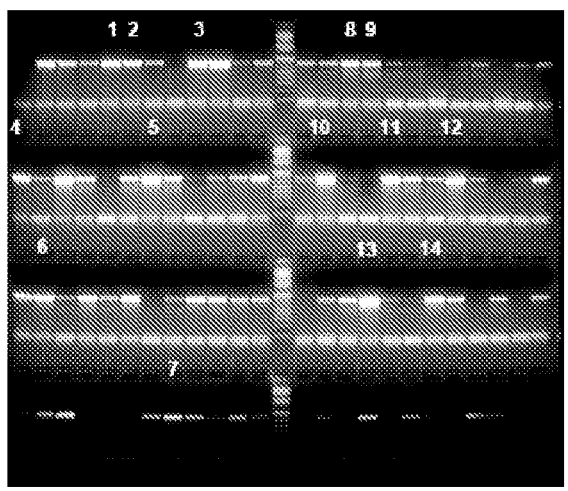 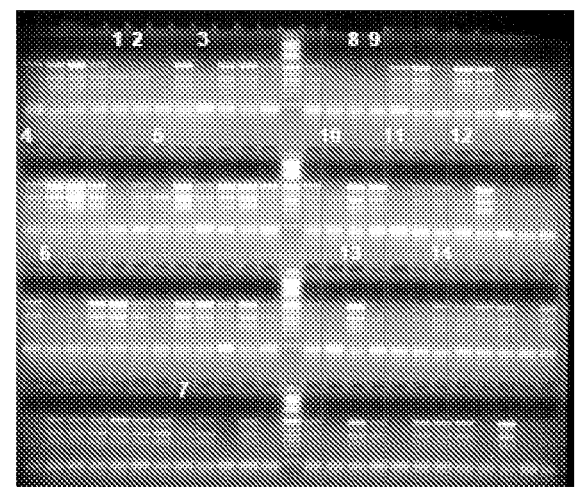
Fig. 4A  Fig. 4B
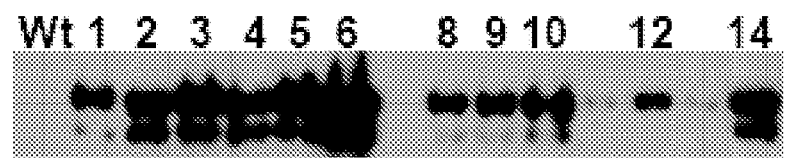
Fig. 4C
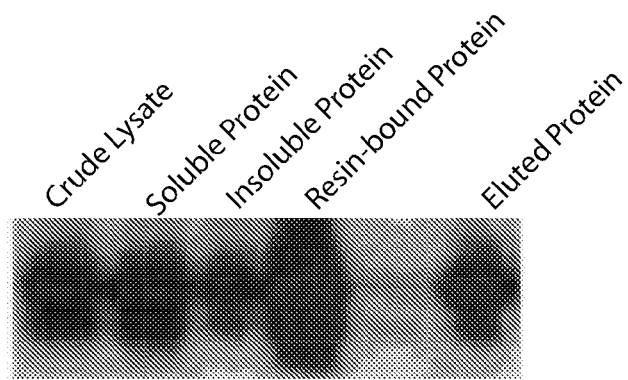
Fig. 4D

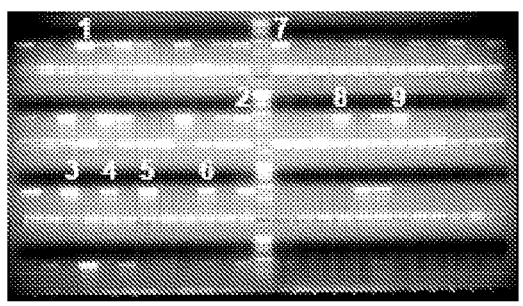
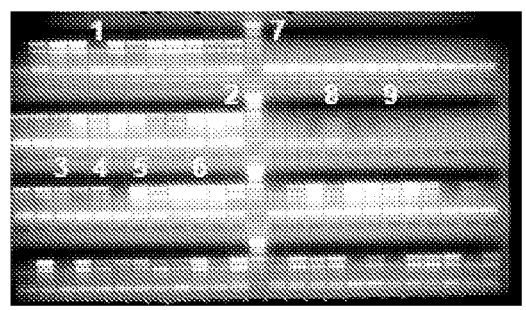
Fig. 7A  Fig. 7B
Fig. 7C
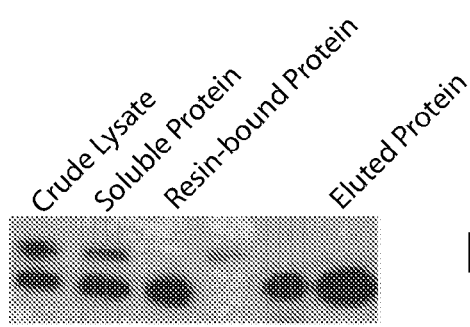
Fig. 7D
Fig. 8

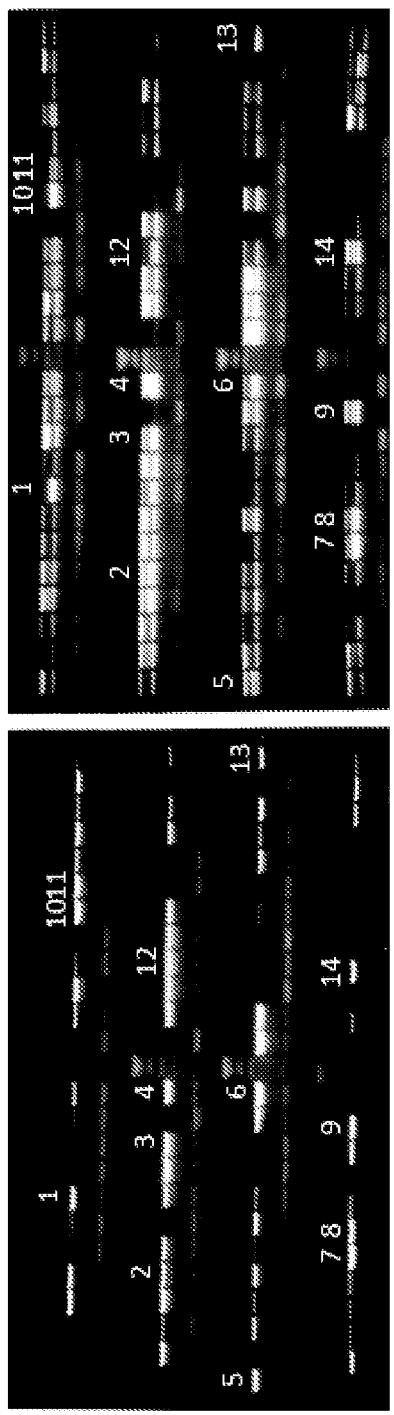
Fig. 14A
Fig. 14B
Fig. 14C

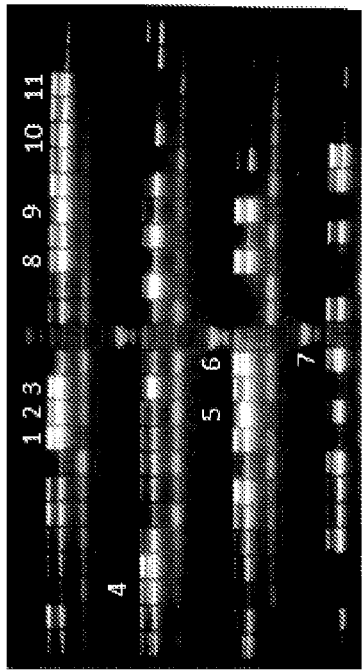
Fig. 16A
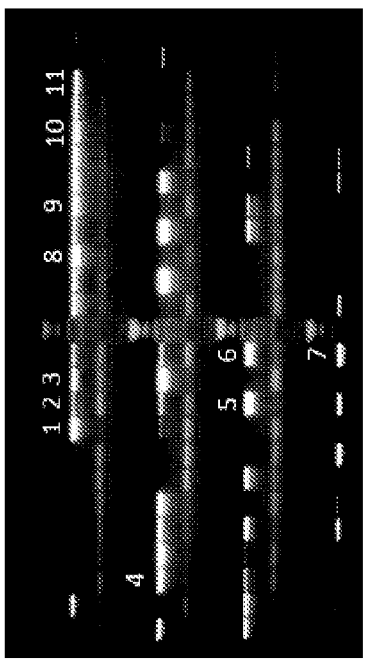
Fig. 16B
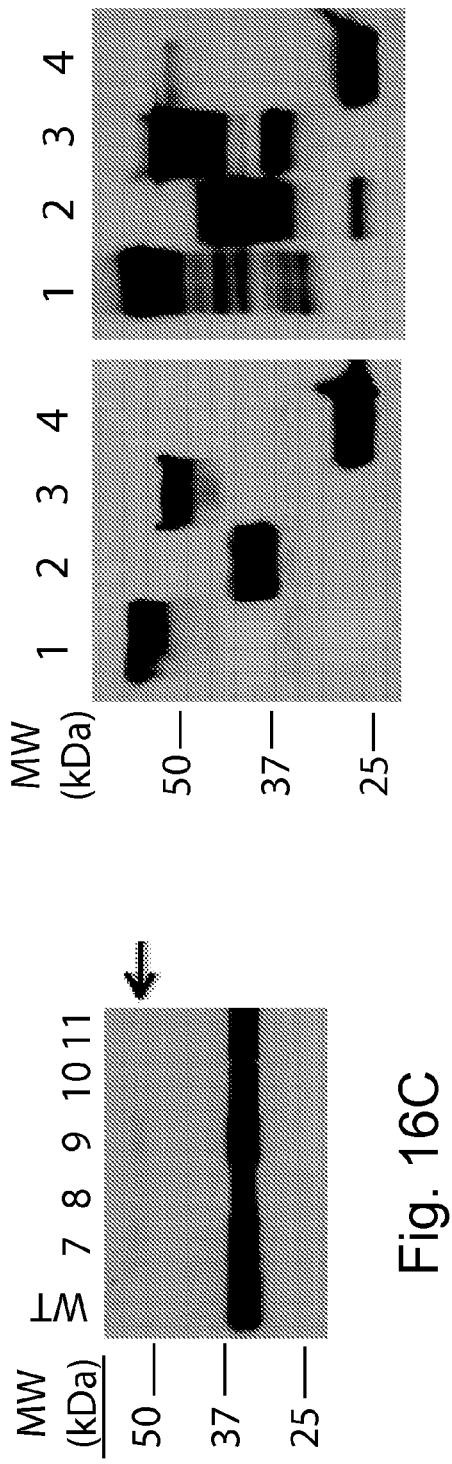
Fig. 17
Fig. 16C

SEQUENCE LISTING

<160> NUMBER OF SEQ ID NOS: 31

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gtgctaggta actaacgttt gattttt                                              27

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaccttccac gttagcttga                                                      20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcattagttg gaccaccttg                                                      20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atcacctgaa gcaggtttga                                                      20

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcactacctg atgaaaaata acc                                                  23

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccgaactgag gttgggttta                                       20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gggggagcga ataggattag                                       20

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggaaggggac gtaggtacat aaa                                   23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttagaacgtg ttttgttccc aat                                   23

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tggtacaaga ggattttgt tgtt                                   24

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaatttaacg taacgatgag ttg                                   23

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccccttacgg gcaagtaaac                                       20

-continued

```
<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctcgcctatc ggctaacaag                                                      20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cacaagaagc aaccccttga                                                      20

<210> SEQ ID NO 15
<211> LENGTH: 543
<212> TYPE: PRT
<213> ORGANISM: Trichoderma viride

<400> SEQUENCE: 15

Met Val Pro Tyr Arg Lys Leu Ala Val Ile Ser Ala Phe Leu Ala Thr
 1               5                   10                  15

Ala Arg Ala Gln Ser Ala Cys Thr Leu Gln Ser Glu Thr His Pro Pro
            20                  25                  30

Leu Thr Trp Gln Lys Cys Ser Ser Gly Gly Thr Cys Thr Gln Gln Thr
        35                  40                  45

Gly Ser Val Val Ile Asp Ala Asn Trp Arg Trp Thr His Ala Thr Asn
    50                  55                  60

Ser Ser Thr Asn Cys Tyr Asp Gly Asn Thr Trp Ser Ser Thr Leu Cys
65                  70                  75                  80

Pro Asp Asn Glu Thr Cys Ala Lys Asn Cys Cys Leu Asp Gly Ala Ala
                85                  90                  95

Tyr Ala Ser Thr Tyr Gly Val Thr Thr Ser Gly Asn Ser Leu Ser Ile
            100                 105                 110

Gly Phe Val Thr Gln Ser Ala Gln Lys Asn Val Gly Ala Arg Leu Tyr
        115                 120                 125

Leu Met Ala Ser Asp Thr Thr Tyr Gln Glu Phe Thr Leu Leu Gly Asn
    130                 135                 140

Glu Phe Ser Phe Asp Val Asp Val Ser Gln Leu Pro Cys Gly Leu Asn
145                 150                 155                 160

Gly Ala Leu Tyr Phe Val Ser Met Asp Ala Asp Gly Gly Val Ser Lys
                165                 170                 175

Tyr Pro Thr Asn Thr Ala Gly Ala Lys Tyr Gly Thr Gly Tyr Cys Asp
            180                 185                 190

Ser Gln Cys Pro Arg Asp Leu Lys Phe Ile Asn Gly Gln Ala Asn Val
        195                 200                 205

Glu Gly Trp Glu Pro Ser Ser Asn Asn Ala Asn Thr Gly Ile Gly Gly
    210                 215                 220

His Gly Ser Cys Cys Ser Glu Met Asp Ile Trp Glu Ala Asn Ser Ile
225                 230                 235                 240

Ser Glu Ala Leu Thr Pro His Pro Cys Thr Thr Val Gly Gln Glu Ile
```

```
                    245                 250                 255
Cys Glu Gly Asp Gly Cys Gly Gly Thr Tyr Ser Asp Asn Arg Tyr Gly
                260                 265                 270

Gly Thr Cys Asp Pro Asp Gly Cys Asp Trp Asp Pro Tyr Arg Leu Gly
            275                 280                 285

Asn Thr Ser Phe Tyr Gly Pro Gly Ser Ser Phe Thr Leu Asp Thr Thr
        290                 295                 300

Lys Lys Leu Thr Val Val Thr Gln Phe Glu Thr Ser Gly Ala Ile Asn
305                 310                 315                 320

Arg Tyr Tyr Val Gln Asn Gly Val Thr Phe Gln Gln Pro Asn Ala Glu
                325                 330                 335

Leu Gly Ser Tyr Ser Gly Asn Gly Leu Asn Asp Asp Tyr Cys Thr Ala
            340                 345                 350

Glu Glu Ala Glu Phe Gly Gly Ser Ser Phe Ser Asp Lys Gly Gly Leu
        355                 360                 365

Thr Gln Phe Lys Lys Ala Thr Ser Gly Gly Met Val Leu Val Met Ser
    370                 375                 380

Leu Trp Asp Asp Tyr Tyr Ala Asn Met Leu Trp Leu Asp Ser Thr Tyr
385                 390                 395                 400

Pro Thr Asn Glu Thr Ser Ser Thr Pro Gly Ala Val Arg Gly Ser Cys
                405                 410                 415

Ser Thr Ser Ser Gly Val Pro Ala Gln Val Glu Ser Gln Ser Pro Asn
            420                 425                 430

Ala Lys Val Thr Phe Ser Asn Ile Lys Phe Gly Pro Ile Gly Ser Thr
        435                 440                 445

Gly Asp Pro Ser Gly Gly Asn Pro Pro Gly Gly Asn Pro Pro Gly Thr
    450                 455                 460

Thr Thr Thr Arg Arg Pro Ala Thr Thr Thr Gly Ser Ser Pro Gly Pro
465                 470                 475                 480

Thr Gln Ser His Tyr Gly Gln Cys Gly Gly Ile Gly Tyr Ser Gly Pro
                485                 490                 495

Thr Val Cys Ala Ser Gly Thr Thr Cys Gln Val Leu Asn Pro Tyr Tyr
            500                 505                 510

Ser Gln Cys Leu Gly Thr Gly Glu Asn Leu Tyr Phe Gln Gly Ser Gly
        515                 520                 525

Gly Gly Gly Ser Asp Tyr Lys Asp Asp Asp Lys Gly Thr Gly
    530                 535                 540

<210> SEQ ID NO 16
<211> LENGTH: 447
<212> TYPE: PRT
<213> ORGANISM: Trichoderma reesei

<400> SEQUENCE: 16

Met Val Pro Asn Lys Ser Val Ala Pro Leu Leu Leu Ala Ala Ser Ile
1               5                   10                  15

Leu Tyr Gly Gly Ala Val Ala Gln Gln Thr Val Trp Gly Gln Cys Gly
            20                  25                  30

Gly Ile Gly Trp Ser Gly Pro Thr Asn Cys Ala Pro Gly Ser Ala Cys
        35                  40                  45

Ser Thr Leu Asn Pro Tyr Tyr Ala Gln Cys Ile Pro Gly Ala Thr Thr
    50                  55                  60

Ile Thr Thr Ser Thr Arg Pro Pro Ser Gly Pro Thr Thr Thr Arg
65                  70                  75                  80

Ala Thr Ser Thr Ser Ser Ser Thr Pro Pro Thr Ser Ser Gly Val Arg
```

-continued

```
                    85                  90                  95
Phe Ala Gly Val Asn Ile Ala Gly Phe Asp Phe Gly Cys Thr Thr Asp
                100                 105                 110
Gly Thr Cys Val Thr Ser Lys Val Tyr Pro Pro Leu Lys Asn Phe Thr
                115                 120                 125
Gly Ser Asn Asn Tyr Pro Asp Gly Ile Gly Gln Met Gln His Phe Val
                130                 135                 140
Asn Glu Asp Gly Met Thr Ile Phe Arg Leu Pro Val Gly Trp Gln Tyr
145                 150                 155                 160
Leu Val Asn Asn Asn Leu Gly Gly Asn Leu Asp Ser Thr Ser Ile Ser
                165                 170                 175
Lys Tyr Asp Gln Leu Val Gln Gly Cys Leu Ser Leu Gly Ala Tyr Cys
                180                 185                 190
Ile Val Asp Ile His Asn Tyr Ala Arg Trp Asn Gly Gly Ile Ile Gly
                195                 200                 205
Gln Gly Gly Pro Thr Asn Ala Gln Phe Thr Ser Leu Trp Ser Gln Leu
                210                 215                 220
Ala Ser Lys Tyr Ala Ser Gln Ser Arg Val Trp Phe Gly Ile Met Asn
225                 230                 235                 240
Glu Pro His Asp Val Asn Ile Asn Thr Trp Ala Ala Thr Val Gln Glu
                245                 250                 255
Val Val Thr Ala Ile Arg Asn Ala Gly Ala Thr Ser Gln Phe Ile Ser
                260                 265                 270
Leu Pro Gly Asn Asp Trp Gln Ser Ala Gly Ala Phe Ile Ser Asp Gly
                275                 280                 285
Ser Ala Ala Ala Leu Ser Gln Val Thr Asn Pro Asp Gly Ser Thr Thr
                290                 295                 300
Asn Leu Ile Phe Asp Val His Lys Tyr Leu Asp Ser Asp Asn Ser Gly
305                 310                 315                 320
Thr His Ala Glu Cys Thr Thr Asn Asn Ile Asp Gly Ala Phe Ser Pro
                325                 330                 335
Leu Ala Thr Trp Leu Arg Gln Asn Asn Arg Gln Ala Ile Leu Thr Glu
                340                 345                 350
Thr Gly Gly Gly Asn Val Gln Ser Cys Ile Gln Asp Met Cys Gln Gln
                355                 360                 365
Ile Gln Tyr Leu Asn Gln Asn Ser Asp Val Tyr Leu Gly Tyr Val Gly
                370                 375                 380
Trp Gly Ala Gly Ser Phe Asp Ser Thr Tyr Val Leu Thr Glu Thr Pro
385                 390                 395                 400
Thr Ser Ser Gly Asn Ser Trp Thr Asp Thr Ser Leu Val Ser Ser Cys
                405                 410                 415
Leu Ala Arg Lys Gly Thr Gly Glu Asn Leu Tyr Phe Gln Gly Ser Gly
                420                 425                 430
Gly Gly Gly Ser Asp Tyr Lys Asp Asp Asp Lys Gly Thr Gly
                435                 440                 445
```

<210> SEQ ID NO 17
<211> LENGTH: 495
<212> TYPE: PRT
<213> ORGANISM: Trichoderma reesei

<400> SEQUENCE: 17

```
Met Val Pro Leu Pro Lys Asp Phe Gln Trp Gly Phe Ala Thr Ala Ala
1               5                   10                  15
Tyr Gln Ile Glu Gly Ala Val Asp Gln Asp Gly Arg Gly Pro Ser Ile
```

-continued

```
                20                  25                  30

Trp Asp Thr Phe Cys Ala Gln Pro Gly Lys Ile Ala Asp Gly Ser Ser
            35                  40                  45

Gly Val Thr Ala Cys Asp Ser Tyr Asn Arg Thr Ala Glu Asp Ile Ala
        50                  55                  60

Leu Leu Lys Ser Leu Gly Ala Lys Ser Tyr Arg Phe Ser Ile Ser Trp
65                  70                  75                  80

Ser Arg Ile Ile Pro Glu Gly Gly Arg Gly Asp Ala Val Asn Gln Ala
                85                  90                  95

Gly Ile Asp His Tyr Val Lys Phe Val Asp Asp Leu Leu Asp Ala Gly
            100                 105                 110

Ile Thr Pro Phe Ile Thr Leu Phe His Trp Asp Leu Pro Glu Gly Leu
        115                 120                 125

His Gln Arg Tyr Gly Gly Leu Leu Asn Arg Thr Glu Phe Pro Leu Asp
    130                 135                 140

Phe Glu Asn Tyr Ala Arg Val Met Phe Arg Ala Leu Pro Lys Val Arg
145                 150                 155                 160

Asn Trp Ile Thr Phe Asn Glu Pro Leu Cys Ser Ala Ile Pro Gly Tyr
                165                 170                 175

Gly Ser Gly Thr Phe Ala Pro Gly Arg Gln Ser Thr Ser Glu Pro Trp
            180                 185                 190

Thr Val Gly His Asn Ile Leu Val Ala His Gly Arg Ala Val Lys Ala
        195                 200                 205

Tyr Arg Asp Asp Phe Lys Pro Ala Ser Gly Asp Gly Gln Ile Gly Ile
    210                 215                 220

Val Leu Asn Gly Asp Phe Thr Tyr Pro Trp Asp Ala Ala Asp Pro Ala
225                 230                 235                 240

Asp Lys Glu Ala Ala Glu Arg Arg Leu Glu Phe Phe Thr Ala Trp Phe
                245                 250                 255

Ala Asp Pro Ile Tyr Leu Gly Asp Tyr Pro Ala Ser Met Arg Lys Gln
            260                 265                 270

Leu Gly Asp Arg Leu Pro Thr Phe Thr Pro Glu Glu Arg Ala Leu Val
        275                 280                 285

His Gly Ser Asn Asp Phe Tyr Gly Met Asn His Tyr Thr Ser Asn Tyr
    290                 295                 300

Ile Arg His Arg Ser Ser Pro Ala Ser Ala Asp Asp Thr Val Gly Asn
305                 310                 315                 320

Val Asp Val Leu Phe Thr Asn Lys Gln Gly Asn Cys Ile Gly Pro Glu
                325                 330                 335

Thr Gln Ser Pro Trp Leu Arg Pro Cys Ala Ala Gly Phe Arg Asp Phe
            340                 345                 350

Leu Val Trp Ile Ser Lys Arg Tyr Gly Tyr Pro Pro Ile Tyr Val Thr
        355                 360                 365

Glu Asn Gly Thr Ser Ile Lys Gly Glu Ser Asp Leu Pro Lys Glu Lys
    370                 375                 380

Ile Leu Glu Asp Asp Phe Arg Val Lys Tyr Tyr Asn Glu Tyr Ile Arg
385                 390                 395                 400

Ala Met Val Thr Ala Val Glu Leu Asp Gly Val Asn Val Lys Gly Tyr
                405                 410                 415

Phe Ala Trp Ser Leu Met Asp Asn Phe Glu Trp Ala Asp Gly Tyr Val
            420                 425                 430

Thr Arg Phe Gly Val Thr Tyr Val Asp Tyr Glu Asn Gly Gln Lys Arg
        435                 440                 445
```

```
Phe Pro Lys Lys Ser Ala Lys Ser Leu Lys Pro Leu Phe Asp Glu Leu
    450                 455                 460

Ile Ala Ala Ala Gly Thr Gly Glu Asn Leu Tyr Phe Gln Gly Ser Gly
465                 470                 475                 480

Gly Gly Gly Ser Asp Tyr Lys Asp Asp Asp Lys Gly Thr Gly
                485                 490                 495

<210> SEQ ID NO 18
<211> LENGTH: 251
<212> TYPE: PRT
<213> ORGANISM: Trichoderma reesei

<400> SEQUENCE: 18

Met Val Pro Val Ser Phe Thr Ser Leu Leu Ala Ala Ser Pro Pro Ser
  1               5                  10                  15

Arg Ala Ser Cys Arg Pro Ala Ala Glu Val Glu Ser Val Ala Val Glu
                 20                  25                  30

Lys Arg Gln Thr Ile Gln Pro Gly Thr Gly Tyr Asn Asn Gly Tyr Phe
             35                  40                  45

Tyr Ser Tyr Trp Asn Asp Gly His Gly Gly Val Thr Tyr Thr Asn Gly
 50                  55                  60

Pro Gly Gly Gln Phe Ser Val Asn Trp Ser Asn Ser Gly Asn Phe Val
 65                  70                  75                  80

Gly Gly Lys Gly Trp Gln Pro Gly Thr Lys Asn Lys Val Ile Asn Phe
                 85                  90                  95

Ser Gly Ser Tyr Asn Pro Asn Gly Asn Ser Tyr Leu Ser Val Tyr Gly
            100                 105                 110

Trp Ser Arg Asn Pro Leu Ile Glu Tyr Tyr Ile Val Glu Asn Phe Gly
        115                 120                 125

Thr Tyr Asn Pro Ser Thr Gly Ala Thr Lys Leu Gly Glu Val Thr Ser
130                 135                 140

Asp Gly Ser Val Tyr Asp Ile Tyr Arg Thr Gln Arg Val Asn Gln Pro
145                 150                 155                 160

Ser Ile Ile Gly Thr Ala Thr Phe Tyr Gln Tyr Trp Ser Val Arg Arg
                165                 170                 175

Asn His Arg Ser Ser Gly Ser Val Asn Thr Ala Asn His Phe Asn Ala
            180                 185                 190

Trp Ala Gln Gln Gly Leu Thr Leu Gly Thr Met Asp Tyr Gln Ile Val
        195                 200                 205

Ala Val Glu Gly Tyr Phe Ser Ser Gly Ser Ala Ser Ile Thr Val Ser
210                 215                 220

Gly Thr Gly Glu Asn Leu Tyr Phe Gln Gly Ser Gly Gly Gly Gly Ser
225                 230                 235                 240

Asp Tyr Lys Asp Asp Asp Lys Gly Thr Gly
                245                 250

<210> SEQ ID NO 19
<211> LENGTH: 10314
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 19
gcacttttcg gggaaatgtg cgcggaaccc ctatttgttt attttctaa atacattcaa      60 atatgtatcc gctcatgaga caataaccct gataaatgct tcaataatat tgaaaaagga   120
```

| | |
|---|---|
| agagtatgag tattcaacat ttccgtgtcg cccttattcc cttttttgcg gcattttgcc | 180 |
| ttcctgtttt tgctcaccca gaaacgctgg tgaaagtaaa agatgctgaa gatcagttgg | 240 |
| gtgcacgagt gggttacatc gaactggatc tcaacagcgg taagatcctt gagagttttc | 300 |
| gccccgaaga acgttttcca atgatgagca cttttaaagt tctgctatgt ggcgcggtat | 360 |
| tatcccgtat tgacgccggg caagagcaac tcggtcgccg catacactat tctcagaatg | 420 |
| acttggttga gtactcacca gtcacagaaa agcatcttac ggatggcatg acagtaagag | 480 |
| aattatgcag tgctgccata accatgagtg ataacactgc ggccaactta cttctgacaa | 540 |
| cgatcggagg accgaaggag ctaaccgctt ttttgcacaa catgggggat catgtaactc | 600 |
| gccttgatcg ttgggaaccg gagctgaatg aagccatacc aaacgacgag cgtgacacca | 660 |
| cgatgcctgt agcaatggca acaacgttgc gcaaactatt aactggcgaa ctacttactc | 720 |
| tagcttcccg gcaacaatta atagactgga tggaggcgga taaagttgca ggaccacttc | 780 |
| tgcgctcggc ccttccggct ggctggttta ttgctgataa atctggagcc ggtgagcgtg | 840 |
| ggtctcgcgg tatcattgca gcactggggc cagatggtaa gccctcccgt atcgtagtta | 900 |
| tctacacgac ggggagtcag gcaactatgg atgaacgaaa tagacagatc gctgagatag | 960 |
| gtgcctcact gattaagcat tggtaactgt cagaccaagt ttactcatat atactttaga | 1020 |
| ttgatttaaa acttcatttt taatttaaaa ggatctaggt gaagatcctt tttgataatc | 1080 |
| tcatgaccaa aatcccttaa cgtgagtttt cgttccactg agcgtcagac cccgtagaaa | 1140 |
| agatcaaagg atcttcttga gatcctttt ttctgcgcgt aatctgctgc ttgcaaacaa | 1200 |
| aaaaaccacc gctaccagcg gtggtttgtt tgccggatca gagctacca actcttttc | 1260 |
| cgaaggtaac tggcttcagc agagcgcaga taccaaatac tgtccttcta gtgtagccgt | 1320 |
| agttaggcca ccacttcaag aactctgtag caccgcctac atacctcgct ctgctaatcc | 1380 |
| tgttaccagt ggctgctgcc agtggcgata agtcgtgtct taccgggttg gactcaagac | 1440 |
| gatagttacc ggataaggcg cagcggtcgg gctgaacggg gggttcgtgc acacagccca | 1500 |
| gcttggagcg aacgacctac accgaactga gatacctaca gcgtgagcta tgagaaagcg | 1560 |
| ccacgcttcc cgaagggaga aaggcggaca ggtatccggt aagcggcagg gtcggaacag | 1620 |
| gagagcgcac gagggagctt ccagggggaa acgcctggta tctttatagt cctgtcgggt | 1680 |
| ttcgccacct ctgacttgag cgtcgatttt tgtgatgctc gtcagggggg cggagcctat | 1740 |
| ggaaaaacgc cagcaacgcg gcctttttac ggttcctggc cttttgctgg ccttttgctc | 1800 |
| acatgttctt tcctgcgtta tcccctgatt ctgtggataa ccgtattacc gcctttgagt | 1860 |
| gagctgatac cgctcgccgc agccgaacga ccgagcgcag cgagtcagtg agcgaggaag | 1920 |
| cggaagagcg cccaatacgc aaaccgcctc tccccgcgcg ttggccgatt cattaatgca | 1980 |
| gctggcacga caggtttccc gactggaaag cgggcagtga gcgcaacgca attaatgtga | 2040 |
| gttagctcac tcattaggca ccccaggctt tacactttat gcttccggct cgtatgttgt | 2100 |
| gtggaattgt gagcggataa caatttcaca caggaaacag ctatgaccat gattacgcca | 2160 |
| agctcgaaat taaccctcac taaagggaac aaaagctgga gctccaccgc ggtggcggcc | 2220 |
| gctctagcac tagtggatcg cccgggctgc aggaattcca tatttagata acgatttca | 2280 |
| agcagcagaa ttagctttat tagaacaaac ttgtaaagaa atgaatgtac caatgccgcg | 2340 |
| cattgtagaa aaaccagata attattatca aattcgacgt atacgtgaat taaaacctga | 2400 |
| tttaacgatt actggaatgg cacatgcaaa tccattagaa gctcgaggta ttacaacaaa | 2460 |
| atggtcagtt gaatttactt ttgctcaaat tcatggattt actaatacac gtgaaatttt | 2520 |

| | | | | |
|---|---|---|---|---|
| agaattagta | acacagcctc | ttagacgcaa | tctaatgtca | aatcaatctg taaatgctat | 2580 |
| ttcttaatat | aaatcccaaa | agatttttt | tataatactg | agacttcaac acttacttgt | 2640 |
| ttttatttt | tgtagttaca | attcactcac | gttaaagaca | ttggaaaatg aggcaggacg | 2700 |
| ttagtcgata | tttatacact | cttaagttta | cttgcccaat | attatatta ggacgtcccc | 2760 |
| ttcgggtaaa | taaattttag | tggcagtggt | accaccactg | cctatttaa tactccgaag | 2820 |
| catataaata | tacttcggag | tatataaata | tccactaata | tttatattag gcagttggca | 2880 |
| ggcaacaata | aataaatttg | tcccgtaagg | ggacgtcccg | aaggggaagg ggaagaaggc | 2940 |
| agttgcctcg | cctatcggct | aacaagttcc | tttggagtat | ataaccgcct acaggtaact | 3000 |
| taaagaacat | tgttacccg | taggggttta | tacttctaat | tgcttcttct gaacaataaa | 3060 |
| atggtttgtg | tggtctgggc | taggaaactt | gtaacaatgt | gtagtgtcgc ttccgcttcc | 3120 |
| cttcgggacg | tccccttcgg | gtaagtaaac | ttaggagtat | taaatcggga cgtccccttc | 3180 |
| gggtaaataa | atttcagtgg | acgtcccctt | acgggacgcc | agtagacgtc agtggcagtt | 3240 |
| gcctcgccta | tcggctaaca | agttccttcg | gagtatataa | atatagaatg tttacatact | 3300 |
| cctaagttta | cttgcctcct | tcggagtata | aaatatccc | gaaggggaag gaggacgcca | 3360 |
| gtggcagtgg | taccgccact | gcctgcttcc | tccttcggag | tatgtaaacc ccttcgggca | 3420 |
| actaaagtt | atcgcagtat | ataaatatag | gcagttggca | ggcaactgcc actgacgtcc | 3480 |
| tattttaata | ctccgaagga | ggcagttggc | aggcaactgc | cactgacgtc ccgtaagggt | 3540 |
| aaggggacgt | ccactggcgt | cccgtaaggg | gaaggggacg | taggtacata aatgtgctag | 3600 |
| gtaactaacg | tttgattttt | tgtggtataa | tatatgtacc | atgcttttaa tagaagcttg | 3660 |
| aatttataaa | ttaaaatatt | tttacaatat | tttacggaga | aattaaaact ttaaaaaaat | 3720 |
| taacatatgg | taccatatcg | taaacttgct | gttattagtg | ctttcttagc tactgctcgt | 3780 |
| gcacagtcag | catgtacctt | acaatctgaa | actcatcctc | cattaacatg gcaaaaatgt | 3840 |
| tcttcaggag | gtacttgtac | acaacaaact | ggctctgtag | taattgatgc taactggcgt | 3900 |
| tggacacatg | ccactaatag | ttcaactaat | tgttatgacg | gtaatacttg gtcatcaaca | 3960 |
| ctttgtcccg | ataacgaaac | ttgtgctaaa | aattgttgtt | tagatggtgc agcttacgct | 4020 |
| tcaacttacg | gcgttactac | atcaggtaac | tcattatcaa | ttggtttcgt gactcaatca | 4080 |
| gcacaaaaa | atgtaggcgc | acgtttatac | ttaatggcaa | gtgacacaac ctatcaagaa | 4140 |
| tttacattat | taggtaatga | gttcagtttc | gacgtagatg | tgagtcaatt accatgtggt | 4200 |
| ttaaatggtg | ctctttattt | cgtttcaatg | gacgctgatg | gcggtgtaag caaatatcct | 4260 |
| actaatacag | caggtgctaa | atacggaaca | ggctattgtg | attctcagtg tcctcgtgat | 4320 |
| ttaaagttta | ttaacggtca | agctaacgtg | gaaggttggg | aaccaagtag taataatgca | 4380 |
| aatactggaa | ttggtggtca | cggatcttgt | tgttctgaaa | tggatatttg ggaagctaat | 4440 |
| tcaattagta | aagcattaac | tccacatcct | tgtactaccg | ttggccaaga aatttgtgaa | 4500 |
| ggcgacggtt | gcggtggaac | atacagtgat | aaccgttatg | tggtacatg tgatcctgat | 4560 |
| ggctgcgatt | gggacccata | tcgtttagga | aatacatctt | tttatggacc aggaagttca | 4620 |
| ttcacattag | atacaactaa | aaagttaaca | gttgttacac | agttcgaaac tagcggtgct | 4680 |
| attaatcgtt | attacgtgca | aaatggtgta | acttttcaac | aaccaaatgc agaattaggt | 4740 |
| tcttattctg | gtaacggcct | taatgacgat | tattgtacag | cagaagaagc agaatttggt | 4800 |
| ggtagcagct | tctcagataa | aggtggttta | actcaattca | agaaagcaac atcaggtggt | 4860 |
| atggtttag | ttatgtcatt | atgggatgac | tattatgcta | atatgttatg gttagatagt | 4920 |

| | | | | | |
|---|---|---|---|---|---|
| acatatccta | caaacgaaac | ttcaagcact | cctggtgctg | ttcgtggttc | atgttcaact | 4980 |
| tcaagtggtg | tacctgctca | agttgaaagc | caaagtccta | atgcaaaagt | aacttttagt | 5040 |
| aatatcaaat | ttggtccaat | tggctctaca | ggcgatcctt | caggtggtaa | tccaccaggt | 5100 |
| ggaaatccac | ctggcaccac | tacaacacgt | cgtcctgcta | ctaccacagg | ttcttctcct | 5160 |
| ggaccaacac | aatctcatta | cggtcaatgt | ggtggtattg | gttattcagg | tccaactgtg | 5220 |
| tgtgcatcag | gaactacatg | tcaagtttta | aatccatatt | atagccaatg | tttaggtacc | 5280 |
| ggtgaaaact | tatactttca | aggctcaggt | ggcggtggaa | gtgattacaa | agatgatgat | 5340 |
| gataaaggaa | ccggttaatc | tagacttagc | ttcaactaac | tctagctcaa | caactaattt | 5400 |
| ttttttttaaa | ctaaaataaa | tctggttaac | catacctggt | ttatttttagt | ttagtttata | 5460 |
| cacacttttc | atatatatat | acttaatagc | taccataggc | agttggcagg | acgtcccctt | 5520 |
| acgggacaaa | tgtatttatt | gttgcctgcc | aactgcctaa | tataaatatt | agtggacgtc | 5580 |
| cccttcccct | tacgggcaag | taaacttagg | gattttaatg | ctccgttagg | aggcaaataa | 5640 |
| attttagtgg | cagttgcctc | gcctatcggc | taacaagttc | cttcggagta | tataaatatc | 5700 |
| ctgccaactg | ccgatattta | tatactaggc | agtggcggta | ccactcgacg | gatcctacgt | 5760 |
| aatcgatgaa | ttcgatccca | tttttataac | tggtctcaaa | atacctataa | acccattgtt | 5820 |
| cttctctttt | agctctaaga | acaatcaatt | tataaatata | tttattatta | tgctataata | 5880 |
| taaatactat | ataaatacat | ttaccttttt | ataaatacat | ttacctttttt | tttaatttgc | 5940 |
| atgattttaa | tgcttatgct | atctttttta | tttagtccat | aaaacctttta | aaggaccttt | 6000 |
| tcttatggga | tatttatatt | ttcctaacaa | agcaatcggc | gtcataaact | ttagttgctt | 6060 |
| acgacgcctg | tggacgtccc | ccccttcccc | ttacgggcaa | gtaaacttag | ggattttaat | 6120 |
| gcaataaata | aatttgtcct | cttcgggcaa | atgaatttta | gtatttaaat | atgacaaggg | 6180 |
| tgaaccatta | cttttgttaa | caagtgatct | taccactcac | tatttttgtt | gaattttaaa | 6240 |
| cttatttaaa | attctcgaga | aagattttaa | aaataaactt | tttaatctt | ttatttattt | 6300 |
| tttcttttttt | cgtatggaat | tgcccaatat | tattcaacaa | tttatcggaa | acagcgtttt | 6360 |
| agagccaaat | aaaattggtc | agtcgccatc | ggatgtttat | tcttttaatc | gaaataatga | 6420 |
| aactttttttt | cttaagcgat | ctagcacttt | atatacagag | accacataca | gtgtctctcg | 6480 |
| tgaagcgaaa | atgttgagtt | ggctctctga | gaaattaaag | gtgcctgaac | tcatcatgac | 6540 |
| ttttcaggat | gagcagtttg | aatttatgat | cactaaagcg | atcaatgcaa | accaatttc | 6600 |
| agcgcttttt | ttaacagacc | aagaattgct | tgctatctat | aaggaggcac | tcaatctgtt | 6660 |
| aaattcaatt | gctattattg | attgtccatt | tatttcaaac | attgatcatc | ggttaaaaga | 6720 |
| gtcaaaattt | tttattgata | accaactcct | tgacgtata | gatcaagatg | attttgacac | 6780 |
| tgaattatgg | ggagaccata | aaacttacct | aagtctatgg | aatgagttaa | ccgagactcg | 6840 |
| tgttgaagaa | agattggttt | tttctcatgg | cgatatcacg | gatagtaata | ttttttataga | 6900 |
| taaattcaat | gaaatttatt | ttttagacct | tggtcgtgct | gggttagcag | atgaatttgt | 6960 |
| agatatatcc | tttgttgaac | gttgcctaag | agaggatgca | tcggaggaaa | ctgcgaaaat | 7020 |
| atttttaaag | catttaaaaa | atgatagacc | tgacaaaagg | aattattttt | taaaacttga | 7080 |
| tgaattgaat | tgattccaag | cattatctaa | aatactctgc | aggcacgcta | gcttgtactc | 7140 |
| aagctcgtaa | cgaaggtcgt | gaccttgctc | gtgaaggtgg | cgacgtaatt | cgttcagctt | 7200 |
| gtaaatggtc | tccagaactt | gctgctgcat | gtgaagtttg | gaaagaaatt | aaattcgaat | 7260 |
| ttgatactat | tgacaaactt | taattttttat | ttttcatgat | gtttatgtga | aatagcataaa | 7320 |

```
catcgttttt attttttatg gtgtttaggt taaataccta aacatcattt tacattttta    7380
aaattaagtt ctaaagttat cttttgttta aatttgcctg tgctttataa attacgatgt    7440
gccagaaaaa taaaatctta gcttttatt atagaattta tctttatgta ttatatttta    7500
taagttataa taaaagaaat agtaacatac taaagcggat gtagcgcgtt tatcttaacg    7560
gaaggaattc ggcgcctacg taggatccgt atccatgcta gcaatatctg atggtacttg    7620
catttcataa gtttggcctg gaataaccac cgtttcggaa gtacctgtcg ctttaagttt    7680
tatagctaaa tctaaagttt ctttaagtct tttagctgta ttaaatactc cacgactttc    7740
ccttacggga caataaataa atttgtcccc ttccccttac gtgacgtcag tggcagttgc    7800
ctgccaactg cctccttcgg agtattaaaa tcctatattt atatactcct aagtttactt    7860
gcccaatatt tatattaggc agttggcagg caactgccac tgacgtcccg aaggggaagg    7920
ggaaggacgt cccccttcgg taaataaatt ttagtggcag tggtaccacc actgcctgct    7980
tcctccttcc ccttcgggca agtaaactta gaataaaatt tatttgctgc gctagcaggt    8040
ttacatactc ctaagtttac ttgcccgaag gggaaggagg acgtccccctt acgggaatat    8100 aaatattagt ggcagtggta caataaataa attgtatgta aaccccttcg ggcaactaaa    8160
gtttatcgca gtatataaat atagaatgtt tacatactcc gaaggaggac gccagtggca    8220
gtggtaccgc cactgcctgt ccgcagtatt aacatcctat tttaatactc cgaaggaggc    8280
agttggcagg caactgccac taatatttat attcccgtaa ggggacgtcc taatttaata    8340
ctccgaagga ggcagttggc aggcaactgc cactaaaatt tatttgcctc ctaacggagc    8400
attaaaatcc cgaaggggac gtcccgaagg ggaaggggaa ggaggcaact gcctgcttcc    8460
tccttcccct tcgggcaagt aaacttagaa taaaatttat ttgctgcgct agcaggttta    8520
catactccta agtttacttg cccgaagggg aaggaggacg tccccttacg ggaatataaa    8580
tattagtggc agtggtacaa taaataaatt gtatgtaaac cccttcgggc aactaaagtt    8640
tatcgcagta tataaatatc ggcagttggc aggcaactgc cactaaaatt catttgcccg    8700
aaggggacgt ccactaatat ttatattccc gtaaggggac gtcccgaagg ggaaggggac    8760
gtcctaaacg gagcattaaa atccctaagt ttacttgcct aggcagttgg caggatattt    8820
atatacgata ttaatacttt tgctactggc acactaaaat ttatttgccc gtaaggggac    8880
gtccttcggt ggttatataa ataatcccgt aggggagggg gatgtcccg tagggggagg    8940 ggagtggagg ctccaacgga ggttggagct tctttggttt cctaggcatt atttaaatat    9000 ttttttaaccc tagcactaga actgagattc cagacggcga cccgtaaagt tcttcagtcc    9060
cctcagcttt ttcacaacca agttcgggat ggattggtgt gggtccaact gagcaaagag    9120
caccaaggtt aactgcatct ctgtgagatg ctagttaaac taagcttagc ttagctcata    9180
aacgatagtt acccgcaagg ggttatgtaa ttatattata aggtcaaaat caaacggcct    9240
ttagtatatc tcggctaaag ccattgctga ctgtacacct gatacctata taacggcttg    9300
tctagccgcg gccttagaga gcactcatct tgagtttagc ttcctactta gatgctttca    9360
gcagttatct atccatgcgt agctacccag cgtttcccat tggaatgaga actggtacac    9420
aattggcatg tcctttcagg tcctctcgta ctatgaaagg ctactctcaa tgctctaacg    9480
cctacaccgg atatggacca aactgtctca cgcatgaaat tttaaagccg aataaaactt    9540
gcggtcttta aaactaaccc ctttactttc gtaaaggcat ggactatgtc ttcatcctgc    9600
tactgttaat ggcaggagtc ggcgtattat actttcccac tctcgagggg gggcccggta    9660
cccaattcgc cctatagtga gtcgtattac aattcactgg ccgtcgtttt acaacgtcgt    9720
```

-continued

| | |
|---|---|
| gactgggaaa accctggcgt tacccaactt aatcgccttg cagcacatcc cccttcgcc | 9780 |
| agctggcgta atagcgaaga ggcccgcacc gatcgccctt cccaacagtt gcgcagcctg | 9840 |
| aatggcgaat gggacgcgcc ctgtagcggc gcattaagcg cggcgggtgt ggtggttacg | 9900 |
| cgcagcgtga ccgctacact tgccagcgcc ctagcgcccg ctcctttcgc tttcttccct | 9960 |
| tcctttctcg ccacgttcgc cggctttccc cgtcaagctc taaatcgggg ctcccttta | 10020 |
| gggttccgat ttagtgcttt acggcacctc gaccccaaaa aacttgatta gggtgatggt | 10080 |
| tcacgtagtg ggccatcgcc ctgatagacg ttttttcgcc ctttgacgtt ggagtccacg | 10140 |
| ttctttaata gtggactctt gttccaaact ggaacaacac tcaaccctat ctcggtctat | 10200 |
| tcttttgatt tataagggat tttgccgatt tcggcctatt ggttaaaaaa tgagctgatt | 10260 |
| taacaaaaat ttaacgcgaa ttttaacaaa atattaacgc ttacaattta ggtg | 10314 |

<210> SEQ ID NO 20
<211> LENGTH: 10026
<212> TYPE: DNA
<213> ORGANISM: Artificial Sequence
<220> FEATURE:
<223> OTHER INFORMATION: Description of Artificial Sequence: Synthetic construct

<400> SEQUENCE: 20

| | |
|---|---|
| gcactttcg gggaaatgtg cgcggaaccc ctatttgttt atttttctaa atacattcaa | 60 |
| atatgtatcc gctcatgaga caataaccct gataaatgct tcaataatat tgaaaaagga | 120 |
| agagtatgag tattcaacat ttccgtgtcg cccttattcc cttttttgcg gcattttgcc | 180 |
| ttcctgtttt tgctcaccca gaaacgctgg tgaaagtaaa agatgctgaa gatcagttgg | 240 |
| gtgcacgagt gggttacatc gaactggatc tcaacagcgg taagatcctt gagagttttc | 300 |
| gccccgaaga acgttttcca atgatgagca cttttaaagt tctgctatgt ggcgcggtat | 360 |
| tatcccgtat tgacgccggg caagagcaac tcggtcgccg catacactat tctcagaatg | 420 |
| acttggttga gtactcacca gtcacagaaa agcatcttac ggatggcatg acagtaagag | 480 |
| aattatgcag tgctgccata accatgagtg ataacactgc ggccaactta cttctgacaa | 540 |
| cgatcggagg accgaaggag ctaaccgctt ttttgcacaa catgggggat catgtaactc | 600 |
| gccttgatcg ttgggaaccg gagctgaatg aagccatacc aaacgacgag cgtgacacca | 660 |
| cgatgcctgt agcaatggca acaacgttgc gcaaactatt aactggcgaa ctacttactc | 720 |
| tagcttcccg gcaacaatta atagactgga tggaggcgga taaagttgca ggaccacttc | 780 |
| tgcgctcggc ccttccggct ggctggttta ttgctgataa atctggagcc ggtgagcgtg | 840 |
| ggtctcgcgg tatcattgca gcactggggc cagatggtaa gccctcccgt atcgtagtta | 900 |
| tctacacgac ggggagtcag gcaactatgg atgaacgaaa tagacagatc gctgagatag | 960 |
| gtgcctcact gattaagcat tggtaactgt cagaccaagt ttactcatat atactttaga | 1020 |
| ttgatttaaa acttcatttt taatttaaaa ggatctaggt gaagatcctt tttgataatc | 1080 |
| tcatgaccaa aatcccttaa cgtgagtttt cgttccactg agcgtcagac cccgtagaaa | 1140 |
| agatcaaagg atcttcttga gatccttttt ttctgcgcgt aatctgctgc ttgcaaacaa | 1200 |
| aaaaaccacc gctaccagcg gtggtttgtt tgccggatca agagctacca actctttttc | 1260 |
| cgaaggtaac tggcttcagc agagcgcaga taccaaatac tgtccttcta gtgtagccgt | 1320 |
| agttaggcca ccacttcaag aactctgtag caccgcctac atacctcgct ctgctaatcc | 1380 |
| tgttaccagt ggctgctgcc agtggcgata agtcgtgtct taccgggttg gactcaagac | 1440 |
| gatagttacc ggataaggcg cagcggtcgg gctgaacggg gggttcgtgc acacagccca | 1500 |

```
gcttggagcg aacgacctac accgaactga gatacctaca gcgtgagcta tgagaaagcg    1560
ccacgcttcc cgaagggaga aaggcggaca ggtatccggt aagcggcagg gtcggaacag    1620
gagagcgcac gagggagctt ccaggqggaa acgcctggta tctttatagt cctgtcgggt    1680
ttcgccacct ctgacttgag cgtcgatttt tgtgatgctc gtcagggggg cggagcctat    1740
ggaaaaacgc cagcaacgcg gccttttac ggttcctggc cttttgctgg ccttttgctc    1800
acatgttctt tcctgcgtta tcccctgatt ctgtggataa ccgtattacc gcctttgagt    1860
gagctgatac cgctcgccgc agccgaacga ccgagcgcag cgagtcagtg agcgaggaag    1920
cggaagagcg cccaatacgc aaaccgcctc tccccgcgcg ttggccgatt cattaatgca    1980
gctggcacga caggtttccc gactggaaag cgggcagtga gcgcaacgca attaatgtga    2040
gttagctcac tcattaggca ccccaggctt tacactttat gcttccggct cgtatgttgt    2100
gtggaattgt gagcggataa caatttcaca caggaaacag ctatgaccat gattacgcca    2160
agctcgaaat taaccctcac taagggaac aaaagctgga ctccaccgc ggtggcggcc    2220
gctctagcac tagtggatcg cccgggctgc aggaattcca tatttagata acgatttca    2280
agcagcagaa ttagctttat tagaacaaac ttgtaaagaa atgaatgtac caatgccgcg    2340
cattgtagaa aaaccagata attattatca aattcgacgt atacgtgaat taaaacctga    2400
tttaacgatt actggaatgg cacatgcaaa tccattagaa gctcgaggta ttacaacaaa    2460
atggtcagtt gaatttactt ttgctcaaat tcatggattt actaatacac gtgaaatttt    2520
agaattagta acacagcctc ttagacgcaa tctaatgtca aatcaatctg taaatgctat    2580
ttcttaatat aaatcccaaa agatttttt tataatactg agacttcaac acttacttgt    2640
ttttattttt tgtagttaca attcactcac gttaaagaca ttggaaaatg aggcaggacg    2700
ttagtcgata tttatacact cttaagttta cttgcccaat atttatatta ggacgtcccc    2760
ttcgggtaaa taaattttag tggcagtggt accaccactg cctattttaa tactccgaag    2820
catataaata tacttcggag tatataaata tccactaata tttatattag gcagttggca    2880
ggcaacaata aataaatttg tcccgtaagg ggacgtcccg aagggaagg ggaagaaggc    2940
agttgcctcg cctatcggct aacaagttcc tttggagtat ataaccgcct acaggtaact    3000
taaagaacat ttgttacccg taggggttta tacttctaat tgcttcttct gaacaataaa    3060
atggtttgtg tggtctgggc taggaaactt gtaacaatgt gtagtgtcgc ttccgcttcc    3120
cttcgggacg tccccttcgg gtaagtaaac ttaggagtat taaatcggga cgtcccttc    3180
gggtaaataa atttcagtgg acgtcccctt acgggacgcc agtagacgtc agtggcagtt    3240
gcctcgccta tcggctaaca agttccttcg gagtatataa atatagaatg tttacatact    3300
cctaagttta cttgcctcct tcggagtata taaatatccc gaaggggaag gaggacgcca    3360
gtggcagtgg taccgccact gcctgcttcc tccttcggag tatgtaaacc ccttcgggca    3420
actaaagttt atcgcagtat ataaatatag gcagttggca ggcaactgcc actgacgtcc    3480
tattttaata ctccgaagga ggcagttggc aggcaactgc cactgacgtc ccgtaagggt    3540
aagggqacgt ccactggcgt cccgtaaggg aaggggacg taggtacata aatgtgctag    3600
gtaactaacg tttgattttt tgtggtataa tatatgtacc atgcttttaa tagaagcttg    3660
aatttataaa ttaaaatatt tttacaatat tttacgqaga aattaaaact ttaaaaaaat    3720
taacatatgg taccaaacaa aagcgtagca ccattattac ttgctgcatc tatcttatat    3780
ggtggtgctt ttgctcaaca gactgtttgg ggtcagtgtg gtggtattgg ttggtctggt    3840
cctaccaatt gtgctcctgg ctcagcatgt agtaccttaa atccttacta tgctcaatgt    3900
```

-continued

| | |
|---|---|
| attccaggtg caacaactat aacaacatca actcgccctc cttcaggtcc aactacaaca | 3960 |
| actcgtgcta ctagcacttc tagcagcaca cctcctacat cttctggagt acgtttcgct | 4020 |
| ggtgttaata ttgcaggttt cgattttggt tgtactaccg atggtacatg tgttaccagt | 4080 |
| aaagtttatc cccctttaaa aaattttact ggctcaaaca attatccaga tggcattggt | 4140 |
| caaatgcaac actttgtaaa tgaagatggt atgactattt tccgtttacc agtgggctgg | 4200 |
| caatacttag ttaacaacaa tttaggtggt aacttagata gtacatcaat tagtaaatat | 4260 |
| gatcaattag tacaaggttg cttatcttta ggtgcctatt gtattgttga tattcataat | 4320 |
| tatgcccgtt ggaacggtgg tattattggt caaggtggtc caactaatgc tcaatttaca | 4380 |
| tcattatgga gccaattagc ttcaaaatat gctagtcaat cacgtgtttg gttcggtatt | 4440 |
| atgaatgaac ctcacgatgt gaacataaat acttgggctg caactgtgca agaagtagta | 4500 |
| actgctattc gtaatgctgg tgcaacatca caattcatta gtttaccagg caacgattgg | 4560 |
| caatctgccg gcgcttttat ttctgacggt agcgcagctg ctcttagtca agtgactaac | 4620 |
| ccagacggta gtaccactaa cttaatattc gatgtacata aatatcttga ttctgataat | 4680 |
| agcggaacac acgccgaatg taccacaaat aatattgatg gtgcttttag tccttttagca | 4740 |
| acttggttac gtcaaaataa tcgccaagcc attttaactg aaacaggtgg tggaaacgtg | 4800 |
| cagagttgta tccaagacat gtgtcaacaa attcagtact aaatcaaaa ctctgacgtg | 4860 |
| tacttaggtt atgtaggttg gggtgctggt tcttttgatt caacttatgt attaaccgaa | 4920 |
| acccctactt cttctggaaa ctcatggaca gacacttcat tagtaagtag ttgtttagct | 4980 |
| cgcaagggta ccgtgaaaa cttatacttt caaggctcag gtggcggtgg aagtgattac | 5040 |
| aaagatgatg atgataaagg aaccggttaa tctagactta gcttcaacta actctagctc | 5100 |
| aaacaactaa ttttttttta aactaaaata aatctggtta accatacctg gtttatttta | 5160 |
| gtttagttta tacacacttt tcatatatat atacttaata gctaccatag gcagttggca | 5220 |
| ggacgtcccc ttacgggaca atgtatttta ttgttgcctg ccaactgcct aatataaata | 5280 |
| ttagtggacg tcccttccc cttacgggca agtaaactta gggattttaa tgctccgtta | 5340 |
| ggaggcaaat aaatttagt ggcagttgcc tcgcctatcg gctaacaagt tccttcggag | 5400 |
| tatataaata tcctgccaac tgccgatatt tatatactag gcagtggcgg taccactcga | 5460 |
| cggatcctac gtaatcgatg aattcgatcc catttttata actggtctca aaataccat | 5520 |
| aaacccattg ttcttctctt ttagctctaa gaacaatcaa tttataaata tatttattat | 5580 |
| tatgctataa tataaatact atataaatac atttaccttt ttataaatac atttaccttt | 5640 |
| tttttaattt gcatgatttt aatgcttatg ctatcttttt tatttagtcc ataaaacctt | 5700 |
| taaaggacct tttcttatgg gatatttata tttcctaac aaagcaatcg gcgtcataaa | 5760 |
| ctttagttgc ttacgacgcc tgtggacgtc ccccccttcc ccttacgggc aagtaaactt | 5820 |
| agggatttta atgcaataaa taaatttgtc ctcttcgggc aaatgaattt tagtatttaa | 5880 |
| atatgacaag ggtgaaccat tacttttgtt aacaagtgat cttaccactc actattttg | 5940 |
| ttgaatttta aacttattta aaattctcga gaaagatttt aaaaataaac ttttttaatc | 6000 |
| ttttatttat tttttctttt ttcgtatgga attgcccaat attattcaac aatttatcgg | 6060 |
| aaacagcgtt ttagagccaa ataaaattgg tcagtcgcca tcggatgttt attcttttaa | 6120 |
| tcgaaataat gaaacttttt ttcttaagcg atctagcact ttatatacag agaccacata | 6180 |
| cagtgtctct cgtgaagcga aaatgttgag ttggctctct gagaaattaa aggtgcctga | 6240 |
| actcatcatg acttttcagg atgagcagtt tgaatttatg atcactaaag cgatcaatgc | 6300 |

```
aaaaccaatt tcagcgcttt ttttaacaga ccaagaattg cttgctatct ataaggaggc    6360
actcaatctg ttaaattcaa ttgctattat tgattgtcca tttatttcaa acattgatca    6420
tcggttaaaa gagtcaaaat tttttattga taaccaactc cttgacgata tagatcaaga    6480
tgattttgac actgaattat ggggagacca taaaacttac ctaagtctat ggaatgagtt    6540
aaccgagact cgtgttgaag aaagattggt tttttctcat ggcgatatca cggatagtaa    6600 tattttata gataaattca atgaaattta ttttttagac cttggtcgtg ctgggttagc    6660
agatgaattt gtagatatat cctttgttga acgttgccta agagaggatg catcggagga    6720
aactgcgaaa atattttaa agcatttaaa aaatgataga cctgacaaaa ggaattattt    6780
tttaaaactt gatgaattga attgattcca agcattatct aaaatactct gcaggcacgc    6840
tagcttgtac tcaagctcgt aacgaaggtc gtgaccttgc tcgtgaaggt ggcgacgtaa    6900
ttcgttcagc ttgtaaatgg tctccagaac ttgctgctgc atgtgaagtt tggaaagaaa    6960
ttaaattcga atttgatact attgacaaac tttaattttt attttcatg atgtttatgt    7020 gaatagcata aacatcgttt ttattttta tggtgtttag gttaaatacc taaacatcat    7080
tttacatttt taaaattaag ttctaaagtt atcttttgtt taaatttgcc tgtgctttat    7140
aaattacgat gtgccagaaa aataaaatct tagcttttta ttatagaatt tatctttatg    7200
tattatattt tataagttat aataaaagaa atagtaacat actaaagcgg atgtagcgcg    7260
tttatcttaa cggaaggaat tcggcgccta cgtaggatcc gtatccatgc tagcaatatc    7320
tgatggtact tgcatttcat aagtttggcc tggaataacc accgtttcgg aagtacctgt    7380
cgctttaagt tttatagcta aatctaaagt ttctttaagt cttttagctg tattaaatac    7440
tccacgactt tcccttacgg gacaataaat aaatttgtcc ccttcccctt acgtgacgtc    7500
agtggcagtt gcctgccaac tgcctccttc ggagtattaa aatcctatat ttatatactc    7560
ctaagtttac ttgcccaata tttatattag gcagttggca ggcaactgcc actgacgtcc    7620
cgaaggggaa ggggaaggac gtccccttcg ggtaaataaa ttttagtggc agtggtacca    7680
ccactgcctg cttcctcctt cccccttcggg caagtaaact tagaataaaa tttatttgct    7740
gcgctagcag gtttacatac tcctaagttt acttgcccga aggggaagga ggacgtcccc    7800
ttacgggaat ataaatatta gtggcagtgg tacaataaat aaattgtatg taaaccccctt    7860 cgggcaacta aagtttatcg cagtatataa atatagaatg tttacatact ccgaaggagg    7920
acgccagtgg cagtggtacc gccactgcct gtccgcagta ttaacatcct atttttaatac    7980 tccgaaggag gcagttggca ggcaactgcc actaatattt atattccgt aagggacgt    8040 cctaatttaa tactccgaag gaggcagttg gcaggcaact gccactaaaa tttatttgcc    8100
tcctaacgga gcattaaaat cccgaagggg acgtcccgaa ggggaagggg aaggaggcaa    8160
ctgcctgctt cctccttccc cttcgggcaa gtaaacttag aataaaattt atttgctgcg    8220
ctagcaggtt tacatactcc taagtttact tgcccgaagg ggaaggagga cgtcccctta    8280
cgggaatata aatattagtg gcagtggtac aataaataaa ttgtatgtaa acccctttcgg    8340 gcaactaaag tttatcgcag tatataaata tcggcagttg gcaggcaact gccactaaaa    8400
ttcatttgcc cgaaggggac gtccactaat atttatattc cgtaagggg acgtcccgaa    8460 ggggaagggg acgtcctaaa cggagcatta aaatccctaa gtttacttgc ctaggcagtt    8520
ggcaggatat ttatatacga tattaatact tttgctactg gcacactaaa atttatttgc    8580
ccgtaagggg acgtccttcg gtggttatat aaataatccc gtaggggag ggggatgtcc    8640 cgtaggggga ggggagtgga ggctccaacg gaggttggag cttcttggt ttcctaggca    8700
```

```
ttatttaaat attttttaac cctagcacta gaactgagat tccagacggc gacccgtaaa     8760
gttcttcagt cccctcagct ttttcacaac caagttcggg atggattggt gtgggtccaa     8820
ctgagcaaag agcaccaagg ttaactgcat ctctgtgaga tgctagttaa actaagctta     8880
gcttagctca taaacgatag ttacccgcaa ggggttatgt aattatatta taaggtcaaa     8940
atcaaacggc ctttagtata tctcggctaa agccattgct gactgtacac ctgatacccta    9000 tataacggct tgtctagccg cggccttaga gagcactcat cttgagttta gcttcctact     9060
tagatgcttt cagcagttat ctatccatgc gtagctaccc agcgtttccc attggaatga     9120
gaactggtac acaattggca tgtcctttca ggtcctctcg tactatgaaa ggctactctc     9180
aatgctctaa cgcctacacc ggatatggac caaactgtct cacgcatgaa attttaaagc     9240
cgaataaaac ttgcggtctt taaaactaac ccctttactt tcgtaaaggc atggactatg     9300
tcttcatcct gctactgtta atggcaggag tcggcgtatt atactttccc actctcgagg     9360
gggggcccgg tacccaattc gccctatagt gagtcgtatt acaattcact ggccgtcgtt     9420
ttacaacgtc gtgactggga aaaccctggc gttacccaac ttaatcgcct tgcagcacat     9480
ccccctttcg ccagctggcg taatagcgaa gaggcccgca ccgatcgccc ttcccaacag     9540
ttgcgcagcc tgaatggcga atgggacgcg ccctgtagcg cgcattaag cgcggcgggt      9600 gtggtggtta cgcgcagcgt gaccgctaca cttgccagcg ccctagcgcc cgctcctttc     9660
gctttcttcc cttcctttct cgccacgttc gccggctttc cccgtcaagc tctaaatcgg     9720
gggctccctt tagggttccg atttagtgct ttacggcacc tcgaccccaa aaaacttgat    9780
tagggtgatg gttcacgtag tgggccatcg ccctgataga cggttttcg cccttttgacg     9840 ttggagtcca cgttctttaa tagtggactc ttgttccaaa ctggaacaac actcaaccct     9900
atctcggtct attctttga tttataaggg attttgccga tttcggccta ttggttaaaa    9960
aatgagctga tttaacaaaa atttaacgcg aattttaaca aaatattaac gcttacaatt    10020
taggtg                                                                10026
```

<210> SEQ ID NO 21
<211> LENGTH: 10170
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 21

```
gcactttcg gggaaatgtg cgcggaaccc ctatttgttt attttctaa atacattcaa         60 atatgtatcc gctcatgaga caataaccct gataaatgct tcaataatat tgaaaaagga      120
agagtatgag tattcaacat ttccgtgtcg cccttattcc cttttttgcg gcattttgcc     180
ttcctgtttt tgctcaccca gaaacgctgg tgaaagtaaa agatgctgaa gatcagttgg     240
gtgcacgagt gggttacatc gaactggatc tcaacagcgg taagatcctt gagagttttc     300
gccccgaaga acgttttcca atgatgagca cttttaaagt tctgctatgt ggcgcggtat     360
tatcccgtat tgacgccggg caagagcaac tcggtcgccg catacactat tctcagaatg     420
acttggttga gtactcacca gtcacagaaa agcatcttac ggatggcatg acagtaagag     480
aattatgcag tgctgccata accatgagtg ataacactgc ggccaactta cttctgacaa     540
cgatcggagg accgaaggag ctaaccgctt ttttgcacaa catgggggat catgtaactc     600
gccttgatcg ttgggaaccg gagctgaatg aagccatacc aaacgacgag cgtgacacca     660
```

```
cgatgcctgt agcaatggca acaacgttgc gcaaactatt aactggcgaa ctacttactc    720
tagcttcccg gcaacaatta atagactgga tggaggcgga taaagttgca ggaccacttc    780
tgcgctcggc ccttccggct ggctggttta ttgctgataa atctggagcc ggtgagcgtg    840
ggtctcgcgt tatcattgca gcactggggc cagatggtaa gccctcccgt atcgtagtta    900
tctacacgac ggggagtcag gcaactatgg atgaacgaaa tagacagatc gctgagatag    960
gtgcctcact gattaagcat tggtaactgt cagaccaagt ttactcatat atactttaga   1020
ttgatttaaa acttcatttt taatttaaaa ggatctaggt gaagatcctt tttgataatc   1080
tcatgaccaa aatcccttaa cgtgagtttt cgttccactg agcgtcagac cccgtagaaa   1140
agatcaaagg atcttcttga gatccttttt ttctgcgcgt aatctgctgc ttgcaaacaa   1200
aaaaaccacc gctaccagcg gtggtttgtt tgccggatca agagctacca actctttttc   1260
cgaaggtaac tggcttcagc agagcgcaga taccaaatac tgtccttcta gtgtagccgt   1320
agttaggcca ccacttcaag aactctgtag caccgcctac atacctcgct ctgctaatcc   1380
tgttaccagt ggctgctgcc agtggcgata gtcgtgtct taccgggttg gactcaagac   1440
gatagttacc ggataaggcg cagcggtcgg gctgaacggg gggttcgtgc acacagccca   1500
gcttggagcg aacgacctac accgaactga gatacctaca gcgtgagcta tgagaaagcg   1560
ccacgcttcc cgaagggaga aaggcggaca ggtatccggt aagcggcagg gtcggaacag   1620
gagagcgcac gagggagctt ccaggggaa acgcctggta tctttatagt cctgtcgggt   1680
ttcgccacct ctgacttgag cgtcgatttt tgtgatgctc gtcagggggg cggagcctat   1740
ggaaaaacgc cagcaacgcg gcctttttac ggttcctggc cttttgctgg ccttttgctc   1800
acatgttctt tcctgcgtta tcccctgatt ctgtggataa ccgtattacc gcctttgagt   1860
gagctgatac cgctcgccgc agccgaacga ccgagcgcag cgagtcagtg agcgaggaag   1920
cggaagagcg cccaatacgc aaaccgcctc tccccgcgcg ttggccgatt cattaatgca   1980
gctggcacga caggtttccc gactggaaag cgggcagtga gcgcaacgca attaatgtga   2040
gttagctcac tcattaggca ccccaggctt tacactttat gcttccggct cgtatgttgt   2100
gtggaattgt gagcggataa caatttcaca caggaaacag ctatgaccat gattacgcca   2160
agctcgaaat taaccctcac taaagggaac aaaagctgga gctccaccgc ggtggcggcc   2220
gctctagcac tagtggatcg cccgggctgc aggaattcca tatttagata aacgatttca   2280
agcagcagaa ttagctttat tagaacaaac ttgtaaagaa atgaatgtac caatgccgcg   2340
cattgtagaa aaaccagata attattatca aattcgacgt atacgtgaat taaaacctga   2400
tttaacgatt actggaatgg cacatgcaaa tccattagaa gctcgaggta ttacaacaaa   2460
atggtcagtt gaatttactt ttgctcaaat tcatggattt actaatacac gtgaaatttt   2520
agaattagta acacagcctc ttagacgcaa tctaatgtca aatcaatctg taaatgctat   2580
ttcttaatat aaatcccaaa agattttttt tataatactg agacttcaac acttacttgt   2640
ttttattttt tgtagttaca attcactcac gttaaagaca ttggaaaatg aggcaggacg   2700
ttagtcgata tttatacact cttaagttta cttgcccaat atttatatta ggacgtcccc   2760
ttcgggtaaa taaattttag tggcagtggt accaccactg cctatttaa tactccgaag   2820
catataaata tacttcggag tatataaata tccactaata tttatattag gcagttggca   2880
ggcaacaata aataaatttg tcccgtaagg ggacgtcccg aaggggaagg ggaagaaggc   2940
agttgcctcg cctatcggct aacaagttcc tttggagtat ataaccgcct acaggtaact   3000
taaagaacat ttgttacccg taggggttta tacttctaat tgcttcttct gaacaataaa   3060
```

```
atggtttgtg tggtctgggc taggaaactt gtaacaatgt gtagtgtcgc ttccgcttcc    3120
cttcgggacg tccccttcgg gtaagtaaac ttaggagtat taaatcggga cgtccccttc    3180
gggtaaataa atttcagtgg acgtcccctt acgggacgcc agtagacgtc agtggcagtt    3240
gcctcgccta tcggctaaca agttccttcg gagtatataa atatagaatg tttacatact    3300
cctaagttta cttgcctcct tcggagtata taaatatccc gaaggggaag gaggacgcca    3360
gtggcagtgg taccgccact gcctgcttcc tccttcggag tatgtaaacc ccttcgggca    3420
actaaagttt atcgcagtat ataaatatag gcagttggca ggcaactgcc actgacgtcc    3480
tattttaata ctccgaagga ggcagttggc aggcaactgc cactgacgtc ccgtaagggt    3540
aaggggacgt ccactggcgt cccgtaaggg gaaggggacg taggtacata aatgtgctag    3600
gtaactaacg tttgattttt tgtggtataa tatatgtacc atgctttaa tagaagcttg     3660 aatttataaa ttaaaatatt tttacaatat tttacggaga aattaaaact ttaaaaaaat    3720
taacatatgg taccattacc aaaggatttc caatggggtt tcgctaccgc agcttatcaa    3780
attgaaggtg cagttgatca agatggacgt ggaccttcta tttgggacac attctgtgca    3840
caaccaggta aaattgctga tggttcatca ggtgtaacag catgtgactc atataatcgt    3900
acagctgaag acattgcact tttaaaatct ttaggtgcta aatcatatcg tttctctatc    3960
tcatggtcaa gaattattcc tgaaggtggc cgtggtgacg cagtaaatca agctggtatt    4020
gatcactatg ttaaatttgt agatgactta ttagacgcag gtattacacc ttttatcact    4080
ttatttcact gggatttacc tgaaggttta caccaacgtt atggtggtct tttaaaccgt    4140
acagaatttc ctttagattt cgaaaactat gcaagagtta tgtttcgtgc acttcccaaa    4200
gtaagaaact ggattacttt taatgaacct ttatgttctg ctattcctgg ttatggttca    4260
ggcacctttg ccccaggcag acaaagtaca agtgagccct ggacagtggg ccataacatt    4320
ttagtagctc acgtagagc tgtaaaagca tatagagatg atttcaaacc tgcttcaggt    4380
gatggtcaaa taggtattgt gttaaatggt gacttcacat atccctggga tgccgctgat    4440
cctgcagata agaagccgc tgaacgtcgc ttagaatttt tcactgcttg gtttgctgac    4500
cccatctatc ttggtgatta tcctgcttca atgcgtaaac aattaggtga tcgtttacct    4560
acttttacac cagaagaacg tgctttagtt catggtagta atgacttta tggtatgaac    4620 cactatactt caaactatat tcgtcaccgt agctcacccg caagtgctga tgacacagta    4680
ggtaatgtag atgttttatt tactaataaa caaggtaatt gtatcggtcc tgaaacacag    4740 agccctggc ttcgtccttg tgcagctggt ttccgtgact tccttgtatg gataagcaaa      4800
cgttatggtt atccaccaat ttatgttaca gaaaacggaa catcaataaa aggtgaaagt    4860
gacttaccaa aggaaaagat tcttgaagat gattttcgtg ttaagtatta taacgaatac    4920
attagagcta tggttacagc cgttgaatta gatggtgtaa atgtaaaagg ttatttcgca    4980
tggtctttaa tggataactt tgaatgggct gatggttacg ttacacgttt tggtgtaacc    5040
tacgttgatt acgaaaacgg ccaaaaacgt ttccctaaaa agagtgctaa aagtttaaaa    5100
cctttatttg atgaattaat agctgctgca ggtaccggtg aaaacttata ctttcaaggc    5160
tcaggtggcg gtggaagtga ttacaaagat gatgatgata aggaaccgg ttaatctaga    5220 cttagcttca actaactcta gctcaaacaa ctaatttttt tttaaactaa aataaatctg    5280
gttaaccata cctggtttat tttagtttag tttatacaca cttttcatat atatatactt    5340
aatagctacc ataggcagtt ggcaggacgt cccccttacgg gacaaatgta tttattgttg    5400
cctgccaact gcctaatata aatattagtg gacgtcccct tccccttacg ggcaagtaaa    5460
```

```
cttagggatt ttaatgctcc gttaggaggc aaataaattt tagtggcagt tgcctcgcct    5520
atcggctaac aagttccttc ggagtatata aatatcctgc caactgccga tatttatata    5580
ctaggcagtg gcggtaccac tcgacggatc ctacgtaatc gatgaattcg atcccatttt    5640
tataactggt ctcaaaatac ctataaaccc attgttcttc tcttttagct ctaagaacaa    5700
tcaatttata aatatattta ttattatgct ataatataaa tactatataa atacatttac    5760 cttttttataa atacatttac cttttttttta atttgcatga ttttaatgct tatgctatct    5820
tttttattta gtccataaaa cctttaaagg acctttcctt atgggatatt tatattttcc    5880
taacaaagca atcggcgtca taaactttag ttgcttacga cgcctgtgga cgtccccccc    5940 ttcccttac gggcaagtaa acttagggat tttaatgcaa taaataaatt tgtcctcttc    6000
gggcaaatga attttagtat ttaaatatga caagggtgaa ccattacttt tgttaacaag    6060
tgatcttacc actcactatt tttgttgaat tttaaactta tttaaaattc tcgagaaaga    6120
ttttaaaaat aaacttttttt aatcttttat ttattttttc tttttttcgta tggaattgcc    6180 caatatatt caacaatta tcggaaacag cgttttagag ccaaataaaa ttggtcagtc    6240
gccatcggat gttattctt ttaatcgaaa taatgaaact tttttttctta agcgatctag    6300 cactttatat acagagacca catacagtgt ctctcgtgaa gcgaaaatgt tgagttggct    6360
ctctgagaaa ttaaaggtgc ctgaactcat catgactttt caggatgagc agtttgaatt    6420
tatgatcact aaagcgatca atgcaaaacc aatttcagcg ctttttttaa cagaccaaga    6480
attgcttgct atctataagg aggcactcaa tctgttaaat tcaattgcta ttattgattg    6540
tccatttatt tcaaacattg atcatcggtt aaaagagtca aaattttta ttgataacca    6600 actccttgac gatatagatc aagatgattt tgacactgaa ttatggggag accataaaac    6660
ttacctaagt ctatggaatg agttaaccga gactcgtgtt aagaaagat tggttttttc    6720 tcatggcgat atcacggata gtaatatttt tatagataaa ttcaatgaaa tttattttt    6780 agaccttggt cgtgctgggt tagcagatga atttgtagat atatcctttg ttgaacgttg    6840
cctaagagag gatgcatcgg aggaaactgc gaaaatattt ttaaagcatt taaaaaatga    6900
tagacctgac aaaaggaatt ttttttttaaa acttgatgaa ttgaattgat tccaagcatt    6960
atctaaaata ctctgcaggc acgctagctt gtactcaagc tcgtaacgaa ggtcgtgacc    7020
ttgctcgtga aggtggcgac gtaattcgtt cagcttgtaa atggtctcca gaacttgctg    7080
ctgcatgtga agtttggaaa gaaattaaat tcgaatttga tactattgac aaactttaat    7140 ttttatttt catgatgttt atgtgaatag cataaacatc gttttatttt tttatggtgt    7200
ttaggttaaa tacctaaaca tcattttaca ttttttaaaat taagttctaa agttatcttt    7260
tgtttaaatt tgcctgtgct ttataaatta cgatgtgcca gaaaaataaa atcttagctt    7320
tttattatag aatttatctt tatgtattat atttttataag ttataataaa agaaatagta    7380
acatactaaa gcggatgtag cgcgtttatc ttaacggaag gaattcggcg cctacgtagg    7440
atccgtatcc atgctagcaa tatctgatgg tacttgcatt tcataagttt ggcctggaat    7500
aaccaccgtt tcgaagtac ctgtcgcttt aagttttata gctaaatcta agtttctttt    7560
aagtctttta gctgtattaa atactccacg actttcccctt acgggacaat aaataaattt    7620
gtccccttcc ccttacgtga cgtcagtggc agttgcctgc caactgcctc cttcggagta    7680
ttaaaatcct atatttatat actcctaagt ttacttgccc aatatttata ttaggcagtt    7740
ggcaggcaac tgccactgac gtcccgaagg ggaaggggaa ggacgtcccc ttcgggtaaa    7800 taaatttttag tggcagtggt accaccactg cctgcttcct ccttcccctt cgggcaagta    7860
```

```
aacttagaat aaaatttatt tgctgcgcta gcaggtttac atactcctaa gtttacttgc    7920
ccgaagggga aggaggacgt ccccttacgg aatataaat attagtggca gtggtacaat    7980
aaataaattg tatgtaaacc ccttcgggca actaaagttt atcgcagtat ataaatatag    8040
aatgtttaca tactccgaag gaggacgcca gtggcagtgg taccgccact gcctgtccgc    8100
agtattaaca tcctatttta atactccgaa ggaggcagtt ggcaggcaac tgccactaat    8160
atttatattc ccgtaagggg acgtcctaat ttaatactcc gaaggaggca gttggcaggc    8220
aactgccact aaaatttatt tgcctcctaa cggagcatta aaatcccgaa ggggacgtcc    8280
cgaaggggaa ggggaaggag gcaactgcct gcttcctcct tccccttcgg gcaagtaaac    8340
ttagaataaa atttatttgc tgcgctagca ggtttacata ctcctaagtt tacttgcccg    8400
aaggggaagg aggacgtccc cttacgggaa tataaatatt agtggcagtg gtacaataaa    8460
taaattgtat gtaaacccct cgggcaact aaagtttatc gcagtatata aatatcggca    8520
gttggcaggc aactgccact aaaattcatt tgcccgaagg ggacgtccac taatatttat    8580
attcccgtaa ggggacgtcc cgaaggggaa ggggacgtcc taaacggagc attaaaatcc    8640
ctaagtttac ttgcctaggc agttggcagg atatttatat acgatattaa tacttttgct    8700
actggcacac taaaatttat ttgcccgtaa ggggacgtcc ttcggtggtt atataaataa    8760
tcccgtaggg ggaggggat gtcccgtagg ggaggggag tggaggctcc aacggaggtt     8820
ggagcttctt tggtttccta ggcattattt aaatatttt taaccctagc actagaactg    8880
agattccaga cggcgacccg taaagttctt cagtcccctc agcttttca caaccaagtt    8940 cgggatggat tggtgtgggt ccaactgagc aaagagcacc aaggttaact gcatctctgt    9000
gagatgctag ttaaactaag cttagcttag ctcataaacg atagttaccc gcaaggggtt    9060
atgtaattat attataaggt caaatcaaa cggcctttag tatatctcgg ctaaagccat     9120
tgctgactgt acacctgata cctatataac ggcttgtcta gccgcggcct tagagagcac    9180
tcatcttgag tttagcttcc tacttagatg ctttcagcag ttatctatcc atgcgtagct    9240
acccagcgtt tcccattgga atgagaactg tacacaatt ggcatgtcct ttcaggtcct     9300
ctcgtactat gaaaggctac tctcaatgct ctaacgccta caccggatat ggaccaaact    9360
gtctcacgca tgaaatttta aagccgaata aaacttgcgg tctttaaaac taacccttt     9420 actttcgtaa aggcatggac tatgtcttca tcctgctact gttaatgcaa ggagtcggcg    9480
tattatactt tcccactctc gagggggggc ccggtaccca attcgcccta tagtgagtcg    9540
tattacaatt cactggccgt cgttttacaa cgtcgtgact gggaaaaccc tggcgttacc    9600
caacttaatc gccttgcagc acatccccct ttcgccagct ggcgtaatag cgaagaggcc    9660
cgcaccgatc gcccttccca cagttgcgc agcctgaatg gcgaatggga cgcgccctgt    9720
agcggcgcat taagcgcggc gggtgtggtg gttacgcgca gcgtgaccgc tacacttgcc    9780
agcgccctag cgcccgctcc tttcgctttc ttcccttcct ttctcgccac gttcgccggc    9840
tttccccgtc aagctctaaa tcgggggctc cctttagggt tccgatttag tgctttacgg    9900
cacctcgacc ccaaaaaact tgattagggt gatggttcac gtagtgggcc atcgccctga    9960
tagacggttt ttcgcccttt gacgttggag tccacgttct ttaatagtgg actcttgttc   10020
caaactggaa caacactcaa ccctatctcg gtctattctt ttgatttata agggattttg   10080
ccgatttcgg cctattggtt aaaaaatgag ctgatttaac aaaaatttaa cgcgaatttt   10140
aacaaaatat taacgcttac aatttaggtg                                    10170
```

<210> SEQ ID NO 22

<211> LENGTH: 9438
<212> TYPE: DNA
<213> ORGANISM: Artificial Sequence
<220> FEATURE:
<223> OTHER INFORMATION: Description of Artificial Sequence: Synthetic construct

<400> SEQUENCE: 22

| | | | | | |
|---|---|---|---|---|---|
| gcacttttcg | gggaaatgtg | cgcggaaccc | ctatttgttt | attttctaa | atacattcaa | 60 |
| atatgtatcc | gctcatgaga | caataaccct | gataaatgct | tcaataatat | tgaaaaagga | 120 |
| agagtatgag | tattcaacat | ttccgtgtcg | cccttattcc | cttttttgcg | gcattttgcc | 180 |
| ttcctgtttt | tgctcaccca | gaaacgctgg | tgaaagtaaa | agatgctgaa | gatcagttgg | 240 |
| gtgcacgagt | gggttacatc | gaactggatc | tcaacagcgg | taagatcctt | gagagttttc | 300 |
| gccccgaaga | acgttttcca | atgatgagca | cttttaaagt | tctgctatgt | ggcgcggtat | 360 |
| tatcccgtat | tgacgccggg | caagagcaac | tcggtcgccg | catacactat | tctcagaatg | 420 |
| acttggttga | gtactcacca | gtcacagaaa | agcatcttac | ggatggcatg | acagtaagag | 480 |
| aattatgcag | tgctgccata | accatgagtg | ataacactgc | ggccaactta | cttctgacaa | 540 |
| cgatcggagg | accgaaggag | ctaaccgctt | ttttgcacaa | catgggggat | catgtaactc | 600 |
| gccttgatcg | ttgggaaccg | gagctgaatg | aagccatacc | aaacgacgag | cgtgacacca | 660 |
| cgatgcctgt | agcaatggca | acaacgttgc | gcaaactatt | aactggcgaa | ctacttactc | 720 |
| tagcttcccg | gcaacaatta | atagactgga | tggaggcgga | taaagttgca | ggaccacttc | 780 |
| tgcgctcggc | ccttccggct | ggctggttta | ttgctgataa | atctggagcc | ggtgagcgtg | 840 |
| ggtctcgcgg | tatcattgca | gcactggggc | cagatggtaa | gccctcccgt | atcgtagtta | 900 |
| tctacacgac | ggggagtcag | gcaactatgg | atgaacgaaa | tagacagatc | gctgagatag | 960 |
| gtgcctcact | gattaagcat | tggtaactgt | cagaccaagt | ttactcatat | atactttaga | 1020 |
| ttgatttaaa | acttcatttt | taatttaaaa | ggatctaggt | gaagatcctt | tttgataatc | 1080 |
| tcatgaccaa | aatcccttaa | cgtgagtttt | cgttccactg | agcgtcagac | cccgtagaaa | 1140 |
| agatcaaagg | atcttcttga | gatcctttt | ttctgcgcgt | aatctgctgc | ttgcaaacaa | 1200 |
| aaaaaccacc | gctaccagcg | gtggtttgtt | tgccggatca | agagctacca | actctttttc | 1260 |
| cgaaggtaac | tggcttcagc | agagcgcaga | taccaaatac | tgtccttcta | gtgtagccgt | 1320 |
| agttaggcca | ccacttcaag | aactctgtag | caccgcctac | atacctcgct | ctgctaatcc | 1380 |
| tgttaccagt | ggctgctgcc | agtggcgata | agtcgtgtct | taccgggttg | gactcaagac | 1440 |
| gatagttacc | ggataaggcg | cagcggtcgg | gctgaacggg | gggttcgtgc | acacagccca | 1500 |
| gcttggagcg | aacgacctac | accgaactga | gatacctaca | gcgtgagcta | tgagaaagcg | 1560 |
| ccacgcttcc | cgaagggaga | aaggcggaca | ggtatccggt | aagcggcagg | gtcggaacag | 1620 |
| gagagcgcac | gagggagctt | ccagggggaa | acgcctggta | tctttatagt | cctgtcgggt | 1680 |
| ttcgccacct | ctgacttgag | cgtcgatttt | tgtgatgctc | gtcagggggg | cggagcctat | 1740 |
| ggaaaaacgc | cagcaacgcg | gcctttttac | ggttcctggc | cttttgctgg | ccttttgctc | 1800 |
| acatgttctt | tcctgcgtta | tcccctgatt | ctgtggataa | ccgtattacc | gcctttgagt | 1860 |
| gagctgatac | cgctcgccgc | agccgaacga | ccgagcgcag | cgagtcagtg | agcgaggaag | 1920 |
| cggaagagcg | cccaatacgc | aaaccgcctc | tccccgcgcg | ttggccgatt | cattaatgca | 1980 |
| gctggcacga | caggtttccc | gactggaaag | cgggcagtga | gcgcaacgca | attaatgtga | 2040 |
| gttagctcac | tcattaggca | ccccaggctt | tacactttat | gcttccggct | cgtatgttgt | 2100 |
| gtggaattgt | gagcggataa | caatttcaca | caggaaacag | ctatgaccat | gattacgcca | 2160 |

```
agctcgaaat taaccctcac taaagggaac aaaagctgga gctccaccgc ggtggcggcc   2220
gctctagcac tagtggatcg cccgggctgc aggaattcca tatttagata aacgatttca   2280
agcagcagaa ttagctttat tagaacaaac ttgtaaagaa atgaatgtac caatgccgcg   2340
cattgtagaa aaaccagata attattatca aattcgacgt atacgtgaat taaaacctga   2400
tttaacgatt actggaatgg cacatgcaaa tccattagaa gctcgaggta ttacaacaaa   2460
atggtcagtt gaatttactt ttgctcaaat tcatggattt actaatacac gtgaaatttt   2520
agaattagta acacagcctc ttagacgcaa tctaatgtca aatcaatctg taaatgctat   2580
ttcttaatat aaatcccaaa agatttttt tataatactg agacttcaac acttacttgt   2640 tttattttt tgtagttaca attcactcac gttaaagaca ttggaaaatg aggcaggacg   2700
ttagtcgata tttatacact cttaagttta cttgcccaat atttatatta ggacgtcccc   2760
ttcgggtaaa taaattttag tggcagtggt accaccactg cctattttaa tactccgaag   2820
catataaata tacttcggag tatataaata tccactaata tttatattag gcagttggca   2880
ggcaacaata aataaatttg tcccgtaagg ggacgtcccg aaggggaagg ggaagaaggc   2940
agttgcctcg cctatcggct aacaagttcc tttggagtat ataaccgcct acaggtaact   3000
taaagaacat ttgttacccg taggggtta tacttctaat tgcttcttct gaacaataaa   3060
atggtttgtg tggtctgggc taggaaactt gtaacaatgt gtagtgtcgc ttccgcttcc   3120
cttcgggacg tccccttcgg gtaagtaaac ttaggagtat taaatcggga cgtccccttc   3180
gggtaaataa atttcagtgg acgtcccctt acgggacgcc agtagacgtc agtggcagtt   3240
gcctcgccta tcggctaaca agttccttcg gagtatataa atatagaatg tttacatact   3300
cctaagttta cttgcctcct tcggagtata taaatatccc gaaggggaag gaggacgcca   3360
gtggcagtgg taccgccact gcctgcttcc tccttcggag tatgtaaacc ccttcgggca   3420
actaaagttt atcgcagtat ataaatatag gcagttggca ggcaactgcc actgacgtcc   3480 tatttaata ctccgaagga ggcagttggc aggcaactgc cactgacgtc ccgtaagggt   3540
aaggggacgt ccactggcgt cccgtaaggg gaaggggacg taggtacata aatgtgctag   3600
gtaactaacg tttgatttt tgtggtataa tatatgtacc atgcttttaa tagaagcttg   3660
aatttataaa ttaaaatatt tttacaatat tttacggaga aattaaaact ttaaaaaaat   3720
taacatatgg taccagtatc tttcacaagt ctttttagcag catctccacc ttcacgtgca   3780
agttgccgtc cagctgctga agtggaatca gttgcagtag aaaaacgtca aacaattcaa   3840
ccaggtacag gttacaataa cggttacttt tattcttact ggaatgatgg acacggtggt   3900
gttacatata ctaatggacc tggtggtcaa tttagtgtaa attggagtaa ctcaggcaat   3960
tttgttggag gaaaaggttg gcaacctggt acaaagaata aggtaatcaa tttctctggt   4020
agttacaacc ctaatggtaa ttcttattta agtgtatacg gttggagccg taacccatta   4080
attgaatatt atattgtaga gaactttggt acatacaacc cttcaacagg tgctactaaa   4140
ttaggtgaag ttacttcaga tggatcagtt tatgatattt atcgtactca acgcgtaaat   4200
caaccatcta taattggaac tgccactttc taccaatact ggagtgtaag acgtaatcat   4260
cgttcaagtg gtagtgttaa tacagcaaac cactttaatg catgggctca acaaggttta   4320
acattaggta caatggacta tcaaattgta gctgttgaag gttattttc atcaggtagt   4380 gcttctatca ctgttagcgg taccggtgaa aacttatact ttcaaggctc aggtggcggt   4440
ggaagtgatt acaaagatga tgatgataaa ggaaccggtt aatctagact tagcttcaac   4500
taactctagc tcaaacaact aatttttttt taaactaaaa taaatctggt taaccatacc   4560
```

```
tggtttattt tagtttagtt tatacacact tttcatatat atatacttaa tagctaccat    4620
aggcagttgg caggacgtcc ccttacggga caaatgtatt tattgttgcc tgccaactgc    4680
ctaatataaa tattagtgga cgtcccette cccttacggg caagtaaact tagggatttt    4740
aatgctccgt taggaggcaa ataaatttta gtggcagttg cctcgcctat cggctaacaa    4800
gttccttcgg agtatataaa tatcctgcca actgccgata tttatatact aggcagtggc    4860
ggtaccactc gacggatcct acgtaatcga tgaattcgat cccatttta taactggtct     4920 caaaatacct ataaacccat tgttcttctc ttttagctct aagaacaatc aatttataaa    4980
tatatttatt attatgctat aatataaata ctatataaat acatttacct ttttataaat    5040
acatttacct tttttttaat ttgcatgatt ttaatgctta tgctatcttt tttatttagt    5100
ccataaaacc tttaaaggac cttttcttat gggatattta tattttccta acaaagcaat    5160
cggcgtcata aactttagtt gcttacgacg cctgtggacg tccccccctt cccttacgg     5220 gcaagtaaac ttagggattt taatgcaata aataaatttg tcctcttcgg gcaaatgaat    5280
tttagtattt aaatatgaca agggtgaacc attacttttg ttaacaagtg atcttaccac    5340
tcactatttt tgttgaattt taaacttatt taaaattctc gagaaagatt ttaaaaataa    5400 actttttaa tcttttattt attttttctt ttttcgtatg gaattgccca atattattca     5460
acaatttatc ggaaacagcg ttttagagcc aaataaaatt ggtcagtcgc catcggatgt    5520
ttattctttt aatcgaaata atgaaacttt ttttcttaag cgatctagca cttatatac     5580 agagaccaca tacagtgtct ctcgtgaagc gaaaatgttg agttggctct ctgagaaatt    5640
aaaggtgcct gaactcatca tgacttttca ggatgagcag tttgaattta tgatcactaa    5700
agcgatcaat gcaaaaccaa tttcagcgct ttttttaaca gaccaagaat tgcttgctat    5760
ctataaggag gcactcaatc tgttaaattc aattgctatt attgattgtc catttatttc    5820
aaacattgat catcggttaa aagagtcaaa attttttatt gataaccaac tccttgacga    5880
tatagatcaa gatgattttg acactgaatt atggggagac cataaaactt acctaagtct    5940
atggaatgag ttaaccgaga ctcgtgttga agaaagattg gttttttctc atggcgatat    6000
cacggatagt aatattttta tagataaatt caatgaaatt tatttttag accttggtcg     6060 tgctgggtta gcagatgaat tgtagatat atcctttgtt gaacgttgcc taagagagga    6120
tgcatcggag gaaactgcga aaatattttt aaagcattta aaaaatgata gacctgacaa    6180
aaggaattat tttttaaaac ttgatgaatt gaattgattc caagcattat ctaaaatact    6240
ctgcaggcac gctagcttgt actcaagctc gtaacgaagg tcgtgacctt gctcgtgaag    6300
gtggcgacgt aattcgttca gcttgtaaat ggtctccaga acttgctgct gcatgtgaag    6360
tttggaaaga aattaaattc gaatttgata ctattgacaa actttaattt ttattttca     6420 tgatgtttat gtgaatagca taaacatcgt tttatttt tatggtgttt aggttaaata     6480
cctaaacatc attttacatt tttaaaatta agttctaaag ttatcttttg tttaaatttg    6540
cctgtgcttt ataaattacg atgtgccaga aaataaaat cttagctttt tattatagaa     6600
tttatcttta tgtattatat tttataagtt ataataaaag aaatagtaac atactaaagc    6660
ggatgtagcg cgtttatctt aacggaagga attcggcgcc tacgtaggat ccgtatccat    6720
gctagcaata tctgatggta cttgcatttc ataagtttgg cctggaataa ccaccgtttc    6780
ggaagtacct gtcgctttaa gttttatagc taaatctaaa gtttctttaa gtcttttagc    6840
tgtattaaat actccacgac tttcccttac gggacaataa ataaatttgt cccctt cccc   6900 ttacgtgacg tcagtggcag ttgcctgcca actgcctcct tcggagtatt aaaatcctat    6960
```

```
atttatatac tcctaagttt acttgcccaa tatttatatt aggcagttgg caggcaactg    7020
ccactgacgt cccgaagggg aaggggaagg acgtcccctt cgggtaaata aattttagtg    7080
gcagtggtac caccactgcc tgcttcctcc ttccccttcg ggcaagtaaa cttagaataa    7140
aatttatttg ctgcgctagc aggtttacat actcctaagt ttacttgccc gaaggggaag    7200
gaggacgtcc ccttacggga atataaatat tagtggcagt ggtacaataa ataaattgta    7260
tgtaaacccc ttcgggcaac taaagtttat cgcagtatat aaatatagaa tgtttacata    7320
ctccgaagga ggacgccagt ggcagtggta ccgccactgc ctgtccgcag tattaacatc    7380
ctattttaat actccgaagg aggcagttgg caggcaactg ccactaatat ttatattccc    7440
gtaaggggac gtcctaattt aatactccga aggaggcagt tggcaggcaa ctgccactaa    7500
aatttatttg cctcctaacg gagcattaaa atcccgaagg ggacgtcccg aaggggaagg    7560
ggaaggaggc aactgcctgc ttcctccttc cccttcgggc aagtaaactt agaataaaat    7620
ttatttgctg cgctagcagg tttacatact cctaagttta cttgcccgaa ggggaaggag    7680
gacgtcccct tacggaaata taaatattag tggcagtggt acaataaata aattgtatgt    7740
aaaccccttc gggcaactaa agtttatcgc agtatataaa tatcggcagt ggcaggcaa    7800 ctgccactaa aattcatttg cccgaagggg acgtccacta atatttatat tcccgtaagg    7860
ggacgtcccg aaggggaagg ggacgtccta aacggagcat taaaatccct aagtttactt    7920
gcctaggcag ttggcaggat atttatatac gatattaata cttttgctac tggcacacta    7980
aaatttattt gcccgtaagg ggacgtcctt cggtggttat ataaataatc cgtaggggg     8040 aggggatgt cccgtagggg gaggggagtg gaggctccaa cggaggttgg agcttctttg    8100
gtttcctagg cattatttaa atatttttta accctagcac tagaactgag attccagacg    8160
gcgacccgta aagttcttca gtcccctcag cttttttcaca accaagttcg ggatggattg    8220
gtgtgggtcc aactgagcaa agagcaccaa ggttaactgc atctctgtga gatgctagtt    8280
aaactaagct tagcttagct cataaacgat agttacccgc aaggggttat gtaattatat    8340
tataaggtca aaatcaaacg gccttttagta tatctcggct aaagccattg ctgactgtac    8400
acctgatacc tatataacgg cttgtctagc cgcggcctta gagagcactc atcttgagtt    8460
tagcttccta cttagatgct ttcagcagtt atctatccat gcgtagctac ccagcgtttc    8520
ccattggaat gagaactggt acacaattgg catgtccttt caggtcctct cgtactatga    8580
aaggctactc tcaatgctct aacgcctaca ccggatatgg accaaactgt ctcacgcatg    8640 aaatttaaa gccgaataaa acttgcggtc tttaaaacta acccccttac tttcgtaaag     8700
gcatggacta tgtcttcatc ctgctactgt taatggcagg agtcggcgta ttatactttc    8760
ccactctcga gggggggccc ggtacccaat tcgccctata gtgagtcgta ttacaattca    8820
ctggccgtcg ttttacaacg tcgtgactgg gaaaaccctg gcgttaccca acttaatcgc    8880
cttgcagcac atccccttt cgccagctgg cgtaatagcg aagaggcccg caccgatcgc    8940
ccttcccaac agttgcgcag cctgaatggc gaatgggacg cgccctgtag cggcgcatta    9000
agcgcggcgg gtgtggtggt tacgcgcagc gtgaccgcta cacttgccag cgccctagcg    9060
cccgctcctt tcgctttctt cccttccttt ctcgccacgt tcgccggctt tccccgtcaa    9120
gctctaaatc gggggctccc tttagggttc cgatttagtg ctttacgca cctcgacccc     9180 aaaaaacttg attagggtga tggttcacgt agtgggccat cgccctgata cggttttt     9240 cgcccttga cgttggagtc cacgttcttt aatagtggac tcttgttcca aactggaaca    9300
acactcaacc ctatctcggt ctattctttt gatttataag ggattttgcc gatttcggcc    9360
```
tattggttaa aaaatgagct gatttaacaa aaatttaacg cgaattttaa caaaatatta   9420
acgcttacaa tttaggtg                                                  9438

<210> SEQ ID NO 23
<211> LENGTH: 10162
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 23
gtgcactctc agtacaatct gctctgatgc cgcatagtta agccagcccc gacacccgcc     60
aacacccgct gacgcgccct gacgggcttg tctgctcccg gcatccgctt acagacaagc    120
tgtgaccgtc tccgggagct gcatgtgtca gaggttttca ccgtcatcac cgaaacgcgc    180
gagacgaaag ggcctcgtga tacgcctatt tttataggtt aatgtcatga taataatggt    240
ttcttagacg tcaggtggca cttttcgggg aaatgtgcgc ggaaccccta tttgtttatt    300
tttctaaata cattcaaata tgtatccgct catgagacaa taaccctgat aaatgcttca    360
ataatattga aaaggaaga gtatgagtat tcaacatttc cgtgtcgccc ttattccctt    420
ttttgcggca ttttgccttc ctgttttttgc tcacccagaa acgctggtga agtaaaaga    480 tgctgaagat cagttgggtg cacgagtggg ttacatcgaa ctggatctca acagcggtaa    540
gatccttgag gttttcgcc ccgaagaacg ttttccaatg atgagcactt ttaaagttct    600
gctatgtggc gcggtattat cccgtattga cgccgggcaa gagcaactcg gtcgccgcat    660
acactattct cagaatgact tggttgagta ctcaccagtc acagaaaagc atcttacgga    720
tggcatgaca gtaagagaat tatgcagtgc tgccataacc atgagtgata acactgcggc    780
caacttactt ctgacaacga tcggaggacc gaaggagcta accgcttttt tgcacaacat    840
gggggatcat gtaactcgcc ttgatcgttg ggaaccggag ctgaatgaag ccataccaaa    900
cgacgagcgt gacaccacga tgcctgtagc aatggcaaca acgttgcgca aactattaac    960
tggcgaacta cttactctag cttcccggca acaattaata gactggatgg aggcggataa   1020
agttgcagga ccacttctgc gctcggccct tccggctggc tggtttattg ctgataaatc   1080
tggagccggt gagcgtgggt ctcgcggtat cattgcagca ctggggccag atggtaagcc   1140
ctcccgtatc gtagttatct acacgacggg gagtcaggca actatggatg aacgaaatag   1200
acagatcgct gagataggtg cctcactgat taagcattgg taactgtcag accaagttta   1260
ctcatatata ctttagattg atttaaaact tcatttttaa tttaaaagga tctaggtgaa   1320
gatccttttt gataatctca tgaccaaaat cccttaacgt gagttttcgt tccactgagc   1380
gtcagacccc gtagaaaaga tcaaaggatc ttcttgagat cctttttttc tgcgcgtaat   1440
ctgctgcttg caaacaaaaa aaccaccgct accagcggtg gtttgtttgc cggatcaaga   1500
gctaccaact ctttttccga aggtaactgg cttcagcaga gcgcagatac caaatactgt   1560
tcttctagtg tagccgtagt taggccacca cttcaagaac tctgtagcac cgcctacata   1620
cctcgctctg ctaatcctgt taccagtggc tgctgccagt ggcgataagt cgtgtcttac   1680
cgggttggac tcaagacgat agttaccgga taaggcgcag cggtcgggct gaacggggg    1740 ttcgtgcaca cagcccagct tggagcgaac gacctacacc gaactgagat acctacagcg   1800
tgagctatga gaaagcgcca cgcttcccga agggagaaag gcggacaggt atccggtaag   1860
cggcagggtc ggaacaggag agcgcacgag ggagcttcca gggggaaacg cctggtatct   1920

```
ttatagtcct gtcgggtttc gccacctctg acttgagcgt cgattttgt gatgctcgtc    1980 agggggggcgg agcctatgga aaaacgccag caacgcggcc tttttacggt tcctggcctt    2040
ttgctggcct tttgctcaca tgttctttcc tgcgttatcc cctgattctg tggataaccg    2100
tattaccgcc tttgagtgag ctgataccgc tcgccgcagc cgaacgaccg agcgcagcga    2160
gtcagtgagc gaggaagcgg aagagcgccc aatacgcaaa ccgcctctcc ccgcgcgttg    2220
gccgattcat taatgcagct ggcacgacag gtttcccgac tggaaagcgg gcagtgagcg    2280
caacgcaatt aatgtgagtt agctcactca ttaggcaccc caggctttac actttatgct    2340
tccggctcgt atgttgtgtg gaattgtgag cggataacaa tttcacacag gaaacagcta    2400
tgaccatgat tacgccaagc tcgcggccgc agtactctgc agattttatg caaaattaaa    2460
gtcttgtgac aacagctttc tccttaagtg caaatatcgc ccattctttc ctctttttcgt    2520 atataaatgc tgtaatagta ggatgtcgta cccgtaaagg tacgacattg aatattaata    2580
tactcctaag tttactttcc caatatttat attaggacgt cccccttcggg taaataaatt    2640 ttagtggcag tggtaccgcc actccctatt ttaatactgc gaaggaggca gttggcaggc    2700
aactcgtcgt tcgcagtata taaatatcca ctaatattta tattcccgta aggggacgtc    2760
ccgaagggga agggaaaga agcagtcgcc tccttgcgaa aaggtttact tgcccgacca    2820
gtgaaaagca tgctgtaaga tataaatcta ccctgaaagg gatgcatttc accataatac    2880
tatacaaatg gtgttacccct tgaggatca taacggtgct actggaatat atggtctctt    2940
catggataga cgatagccat ttatttaccc attaagggga cattagtggc ctgtcactgc    3000
tccttacgag acgccagtgg acgttcgtcc tagaaaattt atgcgctgcc tagaagcccc    3060
aaaagggaag tttactgact cgttagagcg tgcgctaaca ggtttaaaata cttcaatatg    3120 tatattagga cgccggtggc agtggtaccg ccactgccac cgtcggagga cgtcccttac    3180
ggtatattat atactaggat tttaatactc cgaaggaggc agtggcggta ccactgccac    3240
taatatttat attcccgtaa gggacgtcct ccttcggagt atgtaaacat tctaagttta    3300
cttgcccaat atttatatta ggcagttggc aggcaactgc tagctctcct ccttcggagt    3360
atgtaaacat cgcagtatat aaatatccac taatatttat attcccgtaa ggggacgtcc    3420
cgaaggggaa ggggaaggac gtcagtggca gttgcctgcc aactgcctag gcaagtaaac    3480
ttaggagtat ataaatatag gcagtcgcgg taccactgcc actgacgtcc tgccaactgc    3540
ctaggcaagt aaacttaagt ggcactaaaa tgcatttgcc cgaaggggaa ggaggacgcc    3600
agtggcagtg gtaccgccac tgcctccttc ggagtattaa aatcctagta tgtaaatctg    3660
ctagcgcagg aaataaattt tattctattt atatactccg ttaggaggta agtaaacccc    3720
ttccccttcg gacgtcagt gcagttgcct gccaactgcc taatataaat attagaccac    3780
taaagtttgg caactgccaa ctgttgtcct tcggaggaaa aaaaatggtt aactcgcaag    3840
cagttaacat aactaaagtt tgttacttta ccgaagacgt ttaccctttc tcggttaagg    3900
agacggagac agttgcactg tgactgccta gtatagcaat tttgttttg tttatatgct    3960 cgacaaaatg actttcataa aaatataaag tagttagcta gttatttat atcactataa    4020 ctagggttct cagaggcacc gaagtcactt gtaaaaatag tacttttaa cttgtttaat    4080 cttcgtgttc ttcaaaagga tcacgtaatt tttttgaagg tggaccaaaa ctaacataaa    4140
ctgaatagcc agttacactt aacagaagaa accataaaaa aaggtaaag aaaaagctg    4200 gactttccat agctcattta ataataaaat tattctcttt tcaacatatc tcttagatag    4260
ttcaaaagac ttgacgactg tgtcccacat ttttaaacaa aattaatcta ctcaaaattt    4320
```

```
tgccctgaga aagaataact tacttcgttt ttgcagtagc cattcatgtc actttgaaac    4380
tgtccttaca aagttaaaca ttaattaaaa attatttaat ttttatataa caaatattat    4440
attaaataaa aaatgaacaa agaacttcta agatcgtctt tagtgagtaa ttaaagagtt    4500
ttacttacca gacaaggcag ttttttcatt ctttttaaagc aggcagttct gaaggggaaa    4560
agggactgcc tactgcggtc ctaggtaaat acatttttat gcaatttatt tcttgtgcta    4620
gtaggtttct atactcacaa gaagcaaccc cttgacgaga gaacgttatc ctcagagtat    4680
ttataatcct gagagggaat gcactgaaga atattttcct tatttttttac agaaagtaaa    4740 taaaatagcg ctaataacgc ttaattcatt taatcaatta tggcaacagg aacttctaaa    4800
gctaaaccat caaaagtaaa ttcagacttc caagaacctg gtttagttac accattaggt    4860
actttattac gtccacttaa ctcagaagca ggtaaagtat taccaggctg gggtacaact    4920
gttttaatgg ctgtatttat cctttttattt gcagcattct tattaatcat tttagaaatt    4980
tacaacagtt cttaattttt agatgacgtt tctatgagtt gggaaacttt agctaaagtt    5040
tcttaatttt atttaacaca aacataaaat ataaaactgt ttgttaaggc tagctgctaa    5100
gtcttctttt cgctaaggta aactaagcaa ctcaaccata tttatattcg gcagtggcac    5160
cgccaactgc cactggcctt ccgttaagat aaacgcgtgg atctcacgtg actagtcacc    5220
tagtgtcgag tggtaccgcc actgcctagt atataaatat cggcagttgg caggatattt    5280
atatactccg aaggaacttg ttagccgata ggcgaggcaa ctgccactaa aatttatttg    5340
cctcctaacg gagcattaaa atccctaagt ttacttgccc gtaaggggaa ggggacgtcc    5400
actaatattt atattaggca gttggcaggc aacaataaat acatttgtcc cgtaagggga    5460
cgtcctgcca actgcctatg gtagctatta agtatatata tatgaaaagt gtgtataaac    5520
taaactaaaa taaaccaggt atggttaacc agatttattt tagtttaaaa aaaaattagt    5580
tgtttgagct agagttagtt gaagctaagt ctagattaac cggttccttt atcatcatca    5640
tctttgtaat cacttccacc gccacctgag ccttgaaagt ataagttttc accggtacct    5700
gcagcagcta ttaattcatc aaataaaggt tttaaacttt tagcactctt tttagggaaa    5760 cgttttggc cgttttcgta atcaacgtag gttacaccaa aacgtgtaac gtaaccatca    5820
gcccattcaa agttatccat taaagaccat gcgaaataac cttttacatt tacaccatct    5880
aattcaacgg ctgtaaccat agctctaatg tattcgttat aatacttaac acgaaaatca    5940
tcttcaagaa tcttttcctt tggtaagtca ctttcacctt ttattgatgt tccgttttct    6000
gtaacataaa ttggtggata accataacgt ttgcttatcc atacaaggaa gtcacggaaa    6060
ccagctgcac aaggacgaag ccaggggctc tgtgtttcag gaccgataca attaccttgt    6120
ttattagtaa ataaaacatc tacattacct actgtgtcat cagcacttgc gggtgagcta    6180
cggtgacgaa tatagtttga agtatagtgg ttcataccat aaaagtcatt actaccatga    6240
actaaagcac gttcttctgg tgtaaaagta ggtaaacgat cacctaattg tttacgcatt    6300
gaagcaggat aatcaccaag atagatgggg tcagcaaacc aagcagtgaa aaattctaag    6360
cgacgttcag cggcttcttt atctgcagga tcagcggcat cccagggata tgtgaagtca    6420
ccatttaaca caatacctat ttgaccatca cctgaagcag gtttgaaatc atctctatat    6480
gcttttacag ctctaccgtg agctactaaa atgttatggc ccactgtcca gggctcactt    6540
gtactttgtc tgcctggggc aaaggtgcct gaaccataac caggaatagc agaacataaa    6600
ggttcattaa aagtaatcca gtttcttact ttgggaagtg cacgaaacat aactcttgca    6660
tagttttcga aatctaaagg aaattctgta cggtttaaaa gaccaccata acgttggtgt    6720
```

```
aaaccttcag gtaaatccca gtgaaataaa gtgataaaag gtgtaatacc tgcgtctaat    6780
aagtcatcta caaatttaac atagtgatca ataccagctt gatttactgc gtcaccacgg    6840
ccaccttcag gaataattct tgaccatgag atagagaaac gatatgattt agcacctaaa    6900
gattttaaaa gtgcaatgtc ttcagctgta cgattatatg agtcacatgc tgttacacct    6960
gatgaaccat cagcaatttt acctggttgt gcacagaatg tgtcccaaat agaaggtcca    7020
cgtccatctt gatcaactgc accttcaatt tgataagctg cggtagcgaa accccattgg    7080
aaatcctttg gtaatggtac catatgcact ttgcattacc tccgtacaaa ttattttgat    7140
ttctataaag ttttgcttaa ataaaaattt ttaatttttta acgtccaccc atataaataa    7200
taaatatggt gaaacccttta acaacaaaaa tcctcttgta ccatattaat ccaaaagaat    7260
taaggacaaa agcttatctc caacattttt aaaacacaga gtaaaaataa tgttgttttt    7320
aagaatagaa ttttataact tgtattttaa atatgatcta atttatttgt gctaaaaatt    7380
gcagttggaa agtaatttta aaaataattt agatcatatt tattaaataa agttgattta    7440
aaacaactta atcgttttta attgttaatt aaaaacataa ttttaaatct ttttatattt    7500
aaattacctt atatactact agtgatatct acgtaatcga tgaattcgat cccattttta    7560
taactggatc tcaaaatacc tataaaccca ttgttcttct cttttagctc taagaacaat    7620
caatttataa atatatttat tattatgcta aatataaaat actatataaa tacatttacc    7680
ttttataaa tacatttacc tttttttttaa tttgcatgat tttaatgctt atgctatctt    7740
ttttatttag tccataaaac ctttaaagga ccttttctta tgggatattt atattttcct    7800
aacaaagcaa tcggcgtcat aaactttagt tgcttacgac gcctgtggac gtcccccccct    7860
tcccccttacg ggcaagtaaa cttagggatt ttaatgcaat aaataaattt gtcctcttcg    7920
ggcaaatgaa ttttagtatt taaatatgac aagggtgaac cattactttt gttaacaagt    7980
gatcttacca ctcactattt ttgttgaatt ttaaacttat ttaaaattct cgagaaagat    8040
tttaaaaata aactttttta atcttttatt tattttttct tttttcgtat ggaattgccc    8100
aatattattc aacaatttat cggaaacagc gttttagagc caaataaaat tggtcagtcg    8160
ccatcggatg tttattcttt taatcgaaat aatgaaactt ttttttcttaa gcgatctagc    8220
actttatata cagagaccac atacagtgtc tctcgtgaag cgaaaatgtt gagttggctc    8280
tctgagaaat taaggtgcc tgaactcatc atgactttc aggatgagca gtttgaattt    8340
atgatcacta aagcgatcaa tgcaaaacca atttcagcgc ttttttttaac agaccaagaa    8400
ttgcttgcta tctataagga ggcactcaat ctgttaaatt caattgctat tattgattgt    8460
ccatttattt caaacattga tcatcggtta aaagagtcaa aatttttttat tgataaccaa    8520
ctccttgacg atatagatca agatgatttt gacactgaat tatggggaga ccataaaact    8580
tacctaagtc tatggaatga gttaaccgag actcgtgttg aagaaagatt ggttttttct    8640
catggcgata tcacgatag taatattttt atagataaat tcaatgaaat ttattttttta    8700
gaccttggtc gtgctgggtt agcagatgaa tttgtagata tatcctttgt tgaacgttgc    8760
ctaagagagg atgcatcgga ggaaactgcg aaaatatttt taaagcattt aaaaaatgat    8820
agacctgaca aaaggaatta tttttttaaaa cttgatgaat tgaattgatt ccaagcatta    8880
tctaaaatac tctgcaggca cgctagcttg tactcaagct cgtaacgaag gtcgtgacct    8940
tgctcgtgaa ggtggcgacg taattcgttc agcttgtaaa tggtctccag aacttgctgc    9000
tgcatgtgaa gtttggaaag aaattaaatt cgaatttgat actattgaca aacttttaatt    9060
tttattttttc atgatgttta tgtgaatagc ataaacatcg tttttatttt tatggtgttt    9120
```

```
aggttaaaata  cctaaacatc  attttacatt  tttaaaatta  agttctaaag  ttatcttttg       9180
tttaaatttg   cctgtcttta  taaattacga  tgtgccagaa  aaataaaatc  ttagcttttt      9240
attatagaat   ttatctttat  gtattatatt  ttataagtta  taataaaaga  aatagtaaca      9300
tactaaagcg   gatgtagcgc  gtttatctta  acggaaggaa  ttcggcgcct  acgtacccgg      9360
gtcgcgagga   tccacgcgtt  aatagctcac  ttttctttaa  atttaatttt  taatttaaag      9420
gtgtaagcaa   attgcctgac  gagagatcca  cttaaaggat  gacagtggcg  ggctactgcc      9480
tacttccctc   cgggataaaa  tttatttgaa  aaacgttagt  tacttcctaa  cggagcattg      9540
acatccccat   atttatatta  ggacgtcccc  ttcgggtaaa  taaattttag  tggacgtccc      9600
cttcgggcaa   ataaatttta  gtggacaata  aataaatttg  ttgcctgcca  actgcctagg      9660
caagtaaact   tgggagtatt  aaaataggac  gtcagtggca  gttgcctgcc  aactgcctat      9720
atttatatac   tgcgaagcag  gcagtggcgg  taccactgcc  actggcgtcc  taatataaat      9780
attgggcaac   taaagtttat  agcagtatta  acatcctata  tttatatact  ccgaaggaac      9840
ttgttagccg   ataggcgagg  caacaaattt  atttattgtc  ccgtaaaagg  atgcctccag      9900
catcgaaggg   gaaggggacg  tcctaggcca  taaaactaaa  gggaaatcca  tagtaactga      9960
tgttataaat   ttatagactc  caaaaaacag  ctgcgttata  aataacttct  gttaaatatg     10020
gccaagggga   caggggcact  ttcaactaag  tgtacattaa  aaattgacaa  ttcaattttt     10080
tttaattata   atatatattt  agtaaaatat  aacaaaaagc  ccccatcgtc  taggtagaat     10140
tccagctggc   ggccgcccta  tg                                                 10162
```

<210> SEQ ID NO 24
<211> LENGTH: 7005
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 24

```
agatctcgat   cccgcgaaat  taatacgact  cactataggg  gaattgtgag  cggataacaa       60
ttcccctcta   gaaataattt  tgtttaactt  taagaaggag  atatacatat  ggtaccatat      120
cgtaaacttg   ctgttattag  tgctttctta  gctactgctc  gtgcacagtc  agcatgtacc      180
ttacaatctg   aaactcatcc  tccattaaca  tggcaaaaat  gttcttcagg  aggtacttgt      240
acacaacaaa   ctggctctgt  agtaattgat  gctaactggc  gttggacaca  tgccactaat      300
agttcaacta   attgttatga  cggtaatact  tggtcatcaa  cactttgtcc  cgataacgaa      360
acttgtgcta   aaaattgttg  tttagatggt  gcagcttacg  cttcaactta  cggcgttact      420
acatcaggta   actcattatc  aattggtttc  gtgactcaat  cagcacaaaa  aaatgtaggc      480
gcacgtttat   acttaatggc  aagtgacaca  acctatcaag  aatttacatt  attaggtaat      540
gagttcagtt   tcgacgtaga  tgtgagtcaa  ttaccatgtg  gtttaaatgg  tgctctttat      600
ttcgtttcaa   tggacgctga  tggcggtgta  agcaaatatc  ctactaatac  agcaggtgct      660
aaatacggaa   caggctattg  tgattctcag  tgtcctcgtg  atttaaagtt  tattaacggt      720
caagctaacg   tggaaggttg  ggaaccaagt  agtaataatg  caaatactgg  aattggtggt      780
cacggatctt   gttgttctga  aatggatatt  tgggaagcta  ttcaattag   tgaagcatta      840 actccacatc   cttgtactac  cgttggccaa  gaatttgtg   aaggcgacgg  ttgcggtgga      900
acatacagtg   ataaccgtta  tggtggtaca  tgtgatcctg  atggctgcga  ttgggacccca     960 tatcgtttag   gaaatacatc  tttttatgga  ccaggaagtt  cattcacatt  agatacaact     1020
```

```
aaaaagttaa cagttgttac acagttcgaa actagcggtg ctattaatcg ttattacgtg    1080
caaaatggtg taacttttca acaccaaat gcagaattag gttcttattc tggtaacggc     1140
cttaatgacg attattgtac agcagaagaa gcagaatttg gtggtagcag cttctcagat    1200
aaaggtggtt taactcaatt caagaaagca acatcaggtg gtatggtttt agttatgtca    1260
ttatgggatg actattatgc taatatgtta tggttagata gtacatatcc tacaaacgaa    1320
acttcaagca ctcctggtgc tgttcgtggt tcatgttcaa cttcaagtgg tgtacctgct    1380
caagttgaaa gccaaagtcc taatgcaaaa gtaactttta gtaatatcaa atttggtcca    1440
attggctcta caggcgatcc ttcaggtggt aatccaccag gtggaaatcc acctggcacc    1500
actacaacac gtcgtcctgc tactaccaca ggttcttctc ctggaccaac acaatctcat    1560
tacggtcaat gtggtggtat tggttattca ggtccaactg tgtgtgcatc aggaactaca    1620
tgtcaagttt taaatccata ttatagccaa tgtttaggta ccggtgaaaa cttatacttt    1680
caaggctcag gtggcggtgg aagtgattac aaagatgatg atgataaagg aaccggttaa    1740
tctagactcg agcaccacca ccaccaccac tgagatccgg ctgctaacaa agcccgaaag    1800
gaagctgagt tggctgctgc caccgctgag caataactag cataaccct tggggcctct     1860 aaacgggtct gagggggttt tttgctgaaa ggaggaacta tatccggatt ggcgaatggg    1920
acgcgccctg tagcggcgca ttaagcgcgg cgggtgtggt ggttacgcgc agcgtgaccg    1980
ctacacttgc cagcgcccta gcgcccgctc ctttcgcttt cttcccttcc tttctcgcca    2040
cgttcgccgg ctttccccgt caagctctaa atcgggggct ccctttaggg ttccgattta    2100
gtgctttacg gcacctcgac cccaaaaaac ttgattaggg tgatggttca cgtagtgggc    2160
catcgccctg atagacggtt tttcgccctt tgacgttgga gtccacgttc tttaatagtg    2220
gactcttgtt ccaaactgga acaacactca accctatctc ggtctattct tttgatttat    2280
aagggatttt gccgatttcg gcctattggt taaaaaatga ctgatttaa caaaaattta     2340 acgcgaattt taacaaaata ttaacgttta caatttcagg tggcacttt cggggaaatg     2400 tgcgcggaac ccctatttgt ttatttttct aaatacattc aaatatgtat ccgctcatga    2460
gacaataacc ctgataaatg cttcaataat attgaaaaag gaagagtatg agtattcaac    2520
atttccgtgt cgcccttatt ccctttttg cggcattttg ccttcctgtt tttgctcacc      2580
cagaaacgct ggtgaaagta aaagatgctg aagatcagtt gggtgcacga gtgggttaca    2640
tcgaactgga tctcaacagc ggtaagatcc ttgagagttt tcgccccgaa gaacgttttc    2700
caatgatgag cacttttaaa gttctgctat gtggcgcggt attatcccgt attgacgccg    2760
ggcaagagca actcggtcgc cgcatacact attctcagaa tgacttggtt gagtactcac    2820
cagtcacaga aaagcatctt acggatggca tgacagtaag agaattatgc agtgctgcca    2880
taaccatgag tgataacact gcggccaact tacttctgac aacgatcgga ggaccgaagg    2940
agctaaccgc ttttttgcac aacatggggg atcatgtaac tcgccttgat cgttgggaac    3000
cggagctgaa tgaagccata ccaaacgacg agcgtgacac cacgatgcct gcagcaatgg    3060
caacaacgtt gcgcaaacta ttaactggcg aactacttac tctagcttcc cggcaacaat    3120
taatagactg gatggaggcg gataaagttg caggaccact tctgcgctcg gcccttccgg    3180
ctggctggtt tattgctgat aaatctggag ccggtgagcg tgggtctcgc ggtatcattg    3240
cagcactggg gccagatggt aagccctccc gtatcgtagt tatctacacg acggggagtc    3300
aggcaactat ggatgaacga aatagacaga tcgctgagat aggtgcctca ctgattaagc    3360
attggtaact gtcagaccaa gtttactcat atatacttta gattgattta aaacttcatt    3420
```

```
tttaatttaa aaggatctag gtgaagatcc tttttgataa tctcatgacc aaaatccctt    3480
aacgtgagtt ttcgttccac tgagcgtcag accccgtaga aagatcaaa ggatcttctt     3540 gagatccttt ttttctgcgc gtaatctgct gcttgcaaac aaaaaaacca ccgctaccag    3600
cggtggtttg tttgccggat caagagctac caactctttt tccgaaggta actggcttca    3660
gcagagcgca gataccaaat actgtccttc tagtgtagcc gtagttaggc caccacttca    3720
agaactctgt agcaccgcct acatacctcg ctctgctaat cctgttacca gtggctgctg    3780
ccagtggcga taagtcgtgt cttaccgggt tggactcaag acgatagtta ccggataagg    3840
cgcagcggtc gggctgaacg gggggttcgt gcacacagcc cagcttggag cgaacgacct    3900
acaccgaact gagataccta cagcgtgagc tatgagaaag cgccacgctt cccgaaggga    3960
gaaaggcgga caggtatccg gtaagcggca gggtcggaac aggagagcgc acgagggagc    4020
ttccaggggg aaacgcctgg tatctttata gtcctgtcgg gtttcgccac ctctgacttg    4080
agcgtcgatt tttgtgatgc tcgtcagggg ggcggagcct atggaaaaac gccagcaacg    4140
cggccttttt acggttcctg gccttttgct ggccttttgc tcacatgttc tttcctgcgt    4200
tatcccctga ttctgtggat aaccgtatta ccgcctttga gtgagctgat accgctcgcc    4260
gcagccgaac gaccgagcgc agcgagtcag tgagcgagga agcggaagag cgcctgatgc    4320
ggtattttct ccttacgcat ctgtgcggta tttcacaccg catatatggt gcactctcag    4380
tacaatctgc tctgatgccg catagttaag ccagtataca ctccgctatc gctacgtgac    4440
tgggtcatgg ctgcgccccg acacccgcca cacccgctg acgcgccctg acgggcttgt     4500
ctgctcccgg catccgctta cagacaagct gtgaccgtct ccgggagctg catgtgtcag    4560
aggttttcac cgtcatcacc gaaacgcgcg aggcagctgc ggtaaagctc atcagcgtgg    4620
tcgtgaagcg attcacagat gtctgcctgt tcatccgcgt ccagctcgtt gagtttctcc    4680
agaagcgtta atgtctggct tctgataaag cgggccatgt taagggcggt ttttcctgt     4740 ttggtcactg atgcctccgt gtaaggggga tttctgttca tgggggtaat gataccgatg    4800 aaacagagaga ggatgctcac gatacgggtt actgatgatg aacatgcccg gttactggaa   4860
cgttgtgagg gtaaacaact ggcggtatgg atgcggcggg accagagaaa aatcactcag    4920
ggtcaatgcc agcgcttcgt taatacagat gtaggtgttc cacagggtag ccagcagcat    4980
cctgcgatgc agatccggaa cataatggtg cagggcgctg acttccgcgt ttccagactt    5040
tacgaaacac ggaaaccgaa gaccattcat gttgttgctc aggtcgcaga cgttttgcag    5100
cagcagtcgc ttcacgttcg ctcgcgtatc ggtgattcat tctgctaacc agtaaggcaa    5160
ccccgccagc ctagccgggt cctcaacgac aggagcacga tcatgcgcac ccgtggggcc    5220
gccatgccgg cgataatggc ctgcttctcg ccgaaacgtt tggtggcggg accagtgacg    5280
aaggcttgag cgagggcgtg caagattccg aataccgcaa cgacaggcc gatcatcgtc     5340 gcgctccagc gaaagcggtc ctcgccgaaa atgacccaga gcgctgccgg cacctgtcct    5400
acgagttgca tgataaagaa gacagtcata agtgcggcga cgatagtcat gccccgcgcc    5460
caccggaagg agctgactgg gttgaaggct ctcaagggca tcggtcgaga tcccggtgcc    5520
taatgagtga gctaacttac attaattgcg ttgcgctcac tgcccgcttt ccagtcggga    5580
aacctgtcgt gccagctgca ttaatgaatc ggccaacgcg cggggagagg cggtttgcgt    5640
attgggcgcc agggtggttt tcttttcac cagtgagacg gcaacagct gattgccctt      5700 caccgcctgg ccctgagaga gttgcagcaa gcggtccacg ctggtttgcc ccagcaggcg    5760
aaaatcctgt ttgatggtgg ttaacggcgg gatataacat gagctgtctt cggtatcgtc    5820
```

```
gtatcccact accgagatat ccgcaccaac gcgcagcccg gactcggtaa tggcgcgcat    5880
tgcgcccagc gccatctgat cgttggcaac cagcatcgca gtgggaacga tgccctcatt    5940
cagcatttgc atggtttgtt gaaaaccgga catggcactc cagtcgcctt cccgttccgc    6000
tatcggctga atttgattgc gagtgagata tttatgccag ccagccagac gcagacgcgc    6060
cgagacagaa cttaatgggc ccgctaacag cgcgatttgc tggtgaccca atgcgaccag    6120
atgctccacg cccagtcgcg taccgtcttc atgggagaaa ataatactgt tgatgggtgt    6180
ctggtcagag acatcaagaa ataacgccgg aacattagtg caggcagctt ccacagcaat    6240
ggcatcctgg tcatccagcg gatagttaat gatcagccca ctgacgcgtt gcgcgagaag    6300
attgtgcacc gccgctttac aggcttcgac gccgcttcgt tctaccatcg acaccaccac    6360
gctggcaccc agttgatcgg cgcgagattt aatcgccgcg acaatttgcg acggcgcgtg    6420
cagggccaga ctggaggtgg caacgccaat cagcaacgac tgtttgcccg ccagttgttg    6480
tgccacgcgg ttgggaatgt aattcagctc cgccatcgcc gcttccactt tttcccgcgt    6540
tttcgcagaa cgtggctgg cctggttcac cacgcgggaa acggtctgat aagagacacc    6600
ggcatactct gcgacatcgt ataacgttac tggtttcaca ttcaccaccc tgaattgact    6660
ctcttccggg cgctatcatg ccataccgcg aaaggttttg cgccattcga tggtgtccgg    6720
gatctcgacg ctctccctta tgcgactcct gcattaggaa gcagcccagt agtaggttga    6780
ggccgttgag caccgccgcc gcaaggaatg gtgcatgcaa ggagatggcg cccaacagtc    6840
ccccggccac ggggcctgcc accatacccca cgccgaaaca agcgctcatg agcccgaagt    6900
ggcgagcccg atcttcccca tcggtgatgt cggcgatata ggcgccagca accgcacctg    6960
tggcgccggt gatgccggcc acgatgcgtc cggcgtagag gatcg            7005
```

<210> SEQ ID NO 25
<211> LENGTH: 6717
<212> TYPE: DNA
<213> ORGANISM: Artificial Sequence
<220> FEATURE:
<223> OTHER INFORMATION: Description of Artificial Sequence: Synthetic construct

<400> SEQUENCE: 25

```
agatctcgat cccgcgaaat taatacgact cactataggg gaattgtgag cggataacaa     60
ttcccctcta gaaataattt tgtttaactt taagaaggag atatacatat ggtaccaaac    120
aaaagcgtag caccattatt acttgctgca tctatcttat atggtggtgc tgttgctcaa    180
cagactgttt ggggtcagtg tggtggtatt ggttggtctg gtcctaccaa ttgtgctcct    240
ggctcagcat gtagtacctt aaatccttac tatgctcaat gtattccagg tgcaacaact    300
ataacaacat caactcgccc tccttcaggt ccaactacaa caactcgtgc tactagcact    360
tctagcagca cacctcctac atcttctgga gtacgtttcg ctggtgttaa tattgcaggt    420
ttcgattttg gttgtactac cgatggtaca tgtgttacca gtaaagtta tcccccttta    480 aaaaatttta ctggctcaaa caattatcca gatggcattg tcaaatgca acactttgta    540 aatgaagatg gtatgactat tttccgttta ccagtgggct ggcaatactt agttaacaac    600
aatttaggtg gtaacttaga tagtacatca attagtaaat atgatcaatt agtacaaggt    660
tgcttatctt taggtgccta ttgtattgtt gatattcata attatgcccg ttggaacggt    720
ggtattattg gtcaaggtgg tccaactaat gctcaattta catcattatg gagccaatta    780
gcttcaaaat atgctagtca atcacgtgtt tggttcggta ttatgaatga acctcacgat    840
```

```
gtgaacataa atacttgggc tgcaactgtg caagaagtag taactgctat tcgtaatgct      900
ggtgcaacat cacaattcat tagtttacca ggcaacgatt ggcaatctgc cggcgctttt      960
atttctgacg gtagcgcagc tgctcttagt caagtgacta acccagacgg tagtaccact     1020
aacttaatat tcgatgtaca taaatatctt gattctgata atagcggaac acacgccgaa     1080
tgtaccacaa ataatattga tggtgctttt agtcctttag caacttggtt acgtcaaaat     1140
aatcgccaag ccatttttaac tgaaacaggt ggtggaaacg tgcagagttg tatccaagac     1200
atgtgtcaac aaattcagta cttaaatcaa aactctgacg tgtacttagg ttatgtaggt     1260
tggggtgctg gttcttttga ttcaacttat gtattaaccg aaaccccctac ttcttctgga     1320 aactcatgga cagacacttc attagtaagt agttgtttag ctcgcaaggg taccggtgaa     1380
aacttatact ttcaaggctc aggtggcggt ggaagtgatt acaaagatga tgatgataaa     1440
ggaaccggtt aatctagact cgagcaccac caccaccacc actgagatcc ggctgctaac     1500
aaagcccgaa aggaagctga gttggctgct gccaccgctg agcaataact agcataaccc     1560 cttgggggcct ctaaacgggt cttgaggggt ttttgctga aggaggaac tatatccgga     1620 ttggcgaatg ggacgcgccc tgtagcggcg cattaagcgc ggcgggtgtg gtggttacgc     1680
gcagcgtgac cgctacactt gccagcgccc tagcgcccgc tcctttcgct ttcttccctt     1740
cctttctcgc cacgttcgcc ggctttcccc gtcaagctct aaatcggggg ctccctttag     1800
ggttccgatt tagtgcttta cggcacctcg accccaaaaa acttgattag ggtgatggtt     1860
cacgtagtgg gccatcgccc tgatagacgg ttttttcgccc tttgacgttg gagtccacgt     1920
tctttaatag tggactcttg ttccaaactg gaacaacact caaccctatc tcggtctatt     1980
cttttgattt ataagggatt ttgccgattt cggcctattg gttaaaaaat gagctgattt     2040
aacaaaaatt taacgcgaat tttaacaaaa tattaacgtt tacaatttca ggtggcactt     2100
ttcggggaaa tgtgcgcgga accccctatt t gtttatttt ctaaatacat tcaaatatgt     2160
atccgctcat gagacaataa ccctgataaa tgcttcaata atattgaaaa aggaagagta     2220
tgagtattca acatttccgt gtcgccctta ttcccttttt tgcggcattt tgccttcctg     2280
tttttgctca cccagaaacg ctggtgaaag taaaagatgc tgaagatcag ttgggtgcac     2340
gagtgggtta catcgaactg gatctcaaca gcggtaagat ccttgagagt tttcgccccg     2400
aagaacgttt tccaatgatg agcactttta aagttctgct atgtggcgcg gtattatccc     2460
gtattgacgc cgggcaagag caactcggtc gccgcataca ctattctcag aatgacttgg     2520
ttgagtactc accagtcaca gaaaagcatc ttacggatgg catgacagta agagaattat     2580
gcagtgctgc cataaccatg agtgataaca ctgcggccaa cttacttctg acaacgatcg     2640
gaggaccgaa ggagctaacc gcttttttgc acaacatggg gatcatgta actcgccttg     2700 atcgttggga accggagctg aatgaagcca taccaaacga cgagcgtgac accacgatgc     2760
ctgcagcaat ggcaacaacg ttgcgcaaac tattaactgg cgaactactt actctagctt     2820
cccggcaaca attaatagac tggatggagg cggataaagt tgcaggacca cttctgcgct     2880
cggcccttcc ggctggctgg tttattgctg ataaatctgg agccggtgag cgtgggtctc     2940
gcggtatcat tgcagcactg gggccagatg gtaagccctc ccgtatcgta gttatctaca     3000
cgacggggag tcaggcaact atggatgaac gaaatagaca gatcgctgag ataggtgcct     3060
cactgattaa gcattggtaa ctgtcagacc aagtttactc atatatactt tagattgatt     3120
taaaacttca tttttaattt aaaaggatct aggtgaagat cctttttgat aatctcatga     3180
ccaaaatccc ttaacgtgag ttttcgttcc actgagcgtc agaccccgta gaaaagatca     3240
```

```
aaggatcttc ttgagatcct ttttttctgc gcgtaatctg ctgcttgcaa acaaaaaaac   3300
caccgctacc agcggtggtt tgtttgccgg atcaagagct accaactctt tttccgaagg   3360
taactggctt cagcagagcg cagataccaa atactgtcct tctagtgtag ccgtagttag   3420
gccaccactt caagaactct gtagcaccgc ctacatacct cgctctgcta atcctgttac   3480
cagtggctgc tgccagtggc gataagtcgt gtcttaccgg gttggactca agacgatagt   3540
taccggataa ggcgcagcgg tcgggctgaa cggggggttc gtgcacacag cccagcttgg   3600
agcgaacgac ctacaccgaa ctgagatacc tacagcgtga gctatgagaa agcgccacgc   3660
ttcccgaagg gagaaaggcg gacaggtatc cggtaagcgg cagggtcgga acaggagagc   3720
gcacgaggga gcttccaggg ggaaacgcct ggtatcttta tagtcctgtc gggtttcgcc   3780
acctctgact tgagcgtcga ttttgtgat gctcgtcagg ggggcggagc ctatggaaaa   3840
acgccagcaa cgcggccttt ttacggttcc tggccttttg ctggcctttt gctcacatgt   3900
tctttcctgc gttatcccct gattctgtgg ataaccgtat taccgccttt gagtgagctg   3960
ataccgctcg ccgcagccga cgaccgagc gcagcgagtc agtgagcgag gaagcggaag   4020
agcgcctgat gcggtatttt ctccttacgc atctgtgcgg tatttcacac cgcatatatg   4080
gtgcactctc agtacaatct gctctgatgc cgcatagtta agccagtata cactccgcta   4140
tcgctacgtg actgggtcat ggctgcgccc cgacacccgc caacacccgc tgacgcgccc   4200
tgacgggctt gtctgctccc ggcatccgct tacagacaag ctgtgaccgt ctccgggagc   4260
tgcatgtgtc agaggttttc accgtcatca ccgaaacgcg cgaggcagct gcggtaaagc   4320
tcatcagcgt ggtcgtgaag cgattcacag atgtctgcct gttcatccgc gtccagctcg   4380
ttgagtttct ccagaagcgt taatgtctgg cttctgataa agcgggccat gttaagggcg   4440
gttttttcct gtttggtcac tgatgcctcc gtgtaagggg gatttctgtt catgggggta   4500
atgataccga tgaaacgaga gaggatgctc acgatacggg ttactgatga tgaacatgcc   4560
cggttactgg aacgttgtga gggtaaacaa ctggcggtat ggatgcggcg ggaccagaga   4620
aaaatcactc agggtcaatg ccagcgcttc gttaatacag atgtaggtgt tccacagggt   4680
agccagcagc atcctgcgat gcagatccgg aacataatgg tgcagggcgc tgacttccgc   4740
gtttccagac tttacgaaac acggaaaccg aagaccattc atgttgttgc tcaggtcgca   4800
gacgttttgc agcagcagtc gcttcacgtt cgctcgcgta tcggtgattc attctgctaa   4860
ccagtaaggc aaccccgcca gcctagccgg gtcctcaacg acaggagcac gatcatgcgc   4920
acccgtgggg ccgccatgcc ggcgataatg gcctgcttct cgccgaaacg tttggtggcg   4980
ggaccagtga cgaaggcttg agcgagggcg tgcaagattc cgaataccgc aagcgacagg   5040
ccgatcatcg tcgcgctcca gcgaaagcgg tcctcgccga aaatgaccca gagcgctgcc   5100
ggcacctgtc ctacgagttg catgataaag aagacagtca taagtgcggc gacgatagtc   5160
atgccccgcg cccaccggaa ggagctgact gggttgaagg ctctcaaggg catcggtcga   5220
gatcccggtg cctaatgagt gagctaactt acattaattg cgttgcgctc actgcccgct   5280
ttccagtcgg gaaacctgtc gtgccagctg cattaatgaa tcggccaacg cgcgggaga   5340 ggcggtttgc gtattgggcg ccagggtggt ttttcttttc accagtgaga cgggcaacag   5400
ctgattgccc ttcaccgcct ggccctgaga gagttgcagc aagcggtcca cgctggtttg   5460
ccccagcagg cgaaaatcct gtttgatggt ggttaacggc gggatataac atgagctgtc   5520
ttcggtatcg tcgtatccca ctaccgagat atccgcacca acgcgcagcc cggactcggt   5580
aatggcgcgc attgcgccca gcgccatctg atcgttggca accagcatcg cagtgggaac   5640
```

-continued

| | |
|---|---|
| gatgccctca ttcagcattt gcatggtttg ttgaaaaccg gacatggcac tccagtcgcc | 5700 |
| ttcccgttcc gctatcggct gaatttgatt gcgagtgaga tatttatgcc agccagccag | 5760 |
| acgcagacgc gccgagacag aacttaatgg gcccgctaac agcgcgattt gctggtgacc | 5820 |
| caatgcgacc agatgctcca cgcccagtcg cgtaccgtct tcatgggaga aaataatact | 5880 |
| gttgatgggt gtctggtcag agacatcaag aaataacgcc ggaacattag tgcaggcagc | 5940 |
| ttccacagca atggcatcct ggtcatccag cggatagtta atgatcagcc cactgacgcg | 6000 |
| ttgcgcgaga agattgtgca ccgccgcttt acaggcttcg acgccgcttc gttctaccat | 6060 |
| cgacaccacc acgctggcac ccagttgatc ggcgcgagat ttaatcgccg cgacaatttg | 6120 |
| cgacggcgcg tgcagggcca gactggaggt ggcaacgcca atcagcaacg actgtttgcc | 6180 |
| cgccagttgt tgtgccacgc ggttgggaat gtaattcagc tccgccatcg ccgcttccac | 6240 |
| ttttttcccgc gttttcgcag aaacgtggct ggcctggttc accacgcggg aaacggtctg | 6300 |
| ataagagaca ccggcatact ctgcgacatc gtataacgtt actggtttca cattcaccac | 6360 |
| cctgaattga ctctcttccg ggcgctatca tgccataccg cgaaaggttt tgcgccattc | 6420 |
| gatggtgtcc gggatctcga cgctctccct tatgcgactc ctgcattagg aagcagccca | 6480 |
| gtagtaggtt gaggccgttg agcaccgccg ccgcaaggaa tggtgcatgc aaggagatgg | 6540 |
| cgcccaacag tcccccggcc acggggcctg ccaccatacc cacgccgaaa caagcgctca | 6600 |
| tgagcccgaa gtggcgagcc cgatcttccc catcggtgat gtcggcgata taggcgccag | 6660 |
| caaccgcacc tgtggcgccg gtgatgccgg ccacgatgcg tccggcgtag aggatcg | 6717 |

<210> SEQ ID NO 26
<211> LENGTH: 6861
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 26

| | |
|---|---|
| agatctcgat cccgcgaaat taatacgact cactataggg gaattgtgag cggataacaa | 60 |
| ttcccctcta gaaataattt tgtttaactt taagaaggag atatacatat ggtaccatta | 120 |
| ccaaaggatt tccaatgggg tttcgctacc gcagcttatc aaattgaagg tgcagttgat | 180 |
| caagatggac gtggaccttc tatttgggac acattctgtg cacaaccagg taaaattgct | 240 |
| gatggttcat caggtgtaac agcatgtgac tcatataatc gtacagctga agacattgca | 300 |
| cttttaaaat ctttaggtgc taaatcatat cgtttctcta tctcatggtc aagaattatt | 360 |
| cctgaaggtg gccgtggtga cgcagtaaat caagctggta ttgatcacta tgttaaattt | 420 |
| gtagatgact tattagacgc aggtattaca ccttttatca ctttatttca ctgggattta | 480 |
| cctgaaggtt tacaccaacg ttatggtggt cttttaaacc gtacagaatt cctttagat | 540 |
| ttcgaaaact atgcaagagt tatgtttcgt gcacttccca agtaagaaa ctggattact | 600 |
| tttaatgaac ctttatgttc tgctattcct ggttatggtt caggcacctt tgccccaggc | 660 |
| agacaaagta caagtgagcc ctggacagtg gccataaca ttttagtagc tcacggtaga | 720 |
| gctgtaaaag catatagaga tgatttcaaa cctgcttcag gtgatggtca aataggtatt | 780 |
| gtgttaaatg gtgacttcac atatccctgg gatgccgctg atcctgcaga taaagaagcc | 840 |
| gctgaacgtc gcttagaatt tttcactgct tggtttgctg accccatcta tcttggtgat | 900 |
| tatcctgctt caatgcgtaa acaattaggt gatcgtttac ctactttac accagaagaa | 960 |
| cgtgctttag ttcatggtag taatgacttt tatggtatga accactatac ttcaaactat | 1020 |

```
attcgtcacc gtagctcacc cgcaagtgct gatgacacag taggtaatgt agatgtttta    1080
tttactaata aacaaggtaa ttgtatcggt cctgaaacac agagcccctg gcttcgtcct    1140
tgtgcagctg gtttccgtga cttccttgta tggataagca aacgttatgg ttatccacca    1200
atttatgtta cagaaaacgg aacatcaata aaaggtgaaa gtgacttacc aaaggaaaag    1260
attcttgaag atgattttcg tgttaagtat tataacgaat acattagagc tatggttaca    1320
gccgttgaat tagatggtgt aaatgtaaaa ggttatttcg catggtcttt aatggataac    1380
tttgaatggg ctgatggtta cgttacacgt tttggtgtaa cctacgttga ttacgaaaac    1440
ggccaaaaac gtttccctaa aaagagtgct aaaagtttaa aacctttatt tgatgaatta    1500
atagctgctg caggtaccgg tgaaaactta tactttcaag gctcaggtgg cggtggaagt    1560
gattacaaag atgatgatga taaaggaacc ggttaatcta gactcgagca ccaccaccac    1620
caccactgag atccggctgc taacaaagcc cgaaaggaag ctgagttggc tgctgccacc    1680
gctgagcaat aactagcata cccccttggg gcctctaaac gggtcttgag ggttttttg     1740 ctgaaaggag gaactatatc cggattggcg aatgggacgc gccctgtagc ggcgcattaa    1800
gcgcggcggg tgtggtggtt acgcgcagcg tgaccgctac acttgccagc gccctagcgc    1860
ccgctccttt cgctttcttc ccttcctttc tcgccacgtt cgccggcttt ccccgtcaag    1920
ctctaaatcg ggggctccct ttagggttcc gatttagtgc tttacggcac ctcgacccca    1980
aaaaacttga ttagggtgat ggttcacgta gtgggccatc gccctgatag acggttttc     2040 gccctttgac gttggagtcc acgttcttta atagtggact cttgttccaa actggaacaa    2100
cactcaaccc tatctcggtc tattcttttg atttataagg gattttgccg atttcggcct    2160
attggttaaa aaatgagctg atttaacaaa aatttaacgc gaattttaac aaaatattaa    2220
cgtttacaat ttcaggtggc acttttcggg gaaatgtgcg cggaacccct atttgtttat    2280
ttttctaaat acattcaaat atgtatccgc tcatgagaca ataaccctga taaatgcttc    2340
aataatattg aaaaaggaag agtatgagta ttcaacattt ccgtgtcgcc cttattccct    2400
tttttgcggc attttgcctt cctgtttttg ctcacccaga aacgctggtg aaagtaaaag    2460
atgctgaaga tcagttgggt gcacgagtgg gttacatcga actggatctc aacagcggta    2520
agatccttga gttttcgc cccgaagaac gttttccaat gatgagcact tttaaagttc       2580
tgctatgtgg cgcggtatta tcccgtattg acgccgggca agagcaactc ggtcgccgca    2640
tacactattc tcagaatgac ttggttgagt actcaccagt cacagaaaag catcttacgg    2700
atggcatgac agtaagagaa ttatgcagtg ctgccataac catgagtgat aacactgcgg    2760
ccaacttact tctgacaacg atcggaggac cgaaggagct aaccgctttt ttgcacaaca    2820
tgggggatca tgtaactcgc cttgatcgtt gggaaccgga gctgaatgaa gccataccaa    2880
acgacgagcg tgacaccacg atgcctgcag caatggcaac aacgttgcgc aaactattaa    2940
ctggcgaact acttactcta gcttcccggc aacaattaat agactggatg gaggcggata    3000
aagttgcagg accacttctg cgctcggccc ttccggctgg ctggtttatt gctgataaat    3060
ctggagccgg tgagcgtggg tctcgcggta tcattgcagc actggggcca gatggtaagc    3120
cctcccgtat cgtagttatc tacacgacgg ggagtcaggc aactatggat gaacgaaata    3180
gacagatcgc tgagataggt gcctcactga ttaagcattg gtaactgtca gaccaagttt    3240
actcatatat actttagatt gatttaaaac ttcatttta atttaaaagg atctaggtga    3300
agatcctttt tgataatctc atgaccaaaa tcccttaacg tgagttttcg ttccactgag    3360
cgtcagaccc cgtagaaaag atcaaaggat cttcttgaga tcctttttt ctgcgcgtaa     3420
```

```
tctgctgctt gcaaacaaaa aaaccaccgc taccagcggt ggtttgtttg ccggatcaag    3480
agctaccaac tcttttccg aaggtaactg gcttcagcag agcgcagata ccaaatactg    3540
tccttctagt gtagccgtag ttaggccacc acttcaagaa ctctgtagca ccgcctacat    3600
acctcgctct gctaatcctg ttaccagtgg ctgctgccag tggcgataag tcgtgtctta    3660
ccgggttgga ctcaagacga tagttaccgg ataaggcgca gcggtcgggc tgaacggggg    3720
gttcgtgcac acagcccagc ttggagcgaa cgacctacac cgaactgaga tacctacagc    3780
gtgagctatg agaaagcgcc acgcttcccg aagggagaaa ggcggacagg tatccggtaa    3840
gcggcagggt cggaacagga gagcgcacga gggagcttcc agggggaaac gcctggtatc    3900
tttatagtcc tgtcgggttt cgccacctct gacttgagcg tcgattttg tgatgctcgt    3960 caggggggcg gagcctatgg aaaaacgcca gcaacgcggc cttttacgg ttcctggcct    4020 tttgctggcc ttttgctcac atgttctttc ctgcgttatc ccctgattct gtggataacc    4080
gtattaccgc ctttgagtga gctgataccg ctcgccgcag ccgaacgacc gagcgcagcg    4140
agtcagtgag cgaggaagcg gaagagcgcc tgatgcggta ttttctcctt acgcatctgt    4200
gcggtatttc acaccgcata tatggtgcac tctcagtaca atctgctctg atgccgcata    4260
gttaagccag tatacactcc gctatcgcta cgtgactggg tcatggctgc gccccgacac    4320
ccgccaacac ccgctgacgc gccctgacgg gcttgtctgc tcccggcatc cgcttacaga    4380
caagctgtga ccgtctccgg gagctgcatg tgtcagaggt tttcaccgtc atcaccgaaa    4440
cgcgcgaggc agctgcggta agctcatca gcgtggtcgt gaagcgattc acagatgtct    4500
gcctgttcat ccgcgtccag ctcgttgagt ttctccagaa gcgttaatgt ctggcttctg    4560
ataaagcggg ccatgttaag gcggttttt cctgtttgg tcactgatgc ctccgtgtaa    4620
gggggatttc tgttcatggg ggtaatgata ccgatgaaac gagagaggat gctcacgata    4680
cgggttactg atgatgaaca tgcccggtta ctggaacgtt gtgagggtaa acaactggcg    4740
gtatggatgc ggcgggacca gagaaaaatc actcagggtc aatgccagcg cttcgttaat    4800
acagatgtag gtgttccaca gggtagccag cagcatcctg cgatgcagat ccggaacata    4860
atggtgcagg gcgctgactt ccgcgtttcc agactttacg aaacacggaa accgaagacc    4920
attcatgttg ttgctcaggt cgcagacgtt ttgcagcagc agtcgcttca cgttcgctcg    4980
cgtatcggtg attcattctg ctaaccagta aggcaacccc gccagcctag ccgggtcctc    5040
aacgacagga gcacgatcat gcgcacccgt ggggccgcca tgccggcgat aatggcctgc    5100
ttctcgccga aacgtttggt ggcgggacca gtgacgaagg cttgagcgag ggcgtgcaag    5160
attccgaata ccgcaagcga caggccgatc atcgtcgcgc tccagcgaaa gcggtcctcg    5220
ccgaaaatga cccagagcgc tgccggcacc tgtcctacga gttgcatgat aaagaagaca    5280
gtcataagtg cggcgacgat agtcatgccc cgcgcccacc ggaaggagct gactgggttg    5340
aaggctctca agggcatcgg tcgagatccc ggtgcctaat gagtgagcta acttacatta    5400
attgcgttgc gctcactgcc cgctttccag tcgggaaacc tgtcgtgcca gctgcattaa    5460
tgaatcggcc aacgcgcggg gagaggcggt ttgcgtattg ggcgcagggg tggttttct    5520 tttcaccagt gagacgggca acagctgatt gcccttcacc gcctggccct gagagagttg    5580
cagcaagcgg tccacgctgg tttgccccag caggcgaaaa tcctgtttga tggtggttaa    5640
cggcgggata acatgagc tgtcttcggt atcgtcgtat cccactaccg agatatccgc    5700
accaacgcgc agcccggact cggtaatggc gcgcattgcg cccagcgcca tctgatcgtt    5760
ggcaaccagc atcgcagtgg gaacgatgcc ctcattcagc atttgcatgg tttgttgaaa    5820
```

| | |
|---|---|
| accggacatg gcactccagt cgccttcccg ttccgctatc ggctgaattt gattgcgagt | 5880 |
| gagatattta tgccagccag ccagacgcag acgcgccgag acagaactta atgggcccgc | 5940 |
| taacagcgcg atttgctggt gacccaatgc gaccagatgc tccacgccca gtcgcgtacc | 6000 |
| gtcttcatgg gagaaaataa tactgttgat gggtgtctgg tcagagacat caagaaataa | 6060 |
| cgccggaaca ttagtgcagg cagcttccac agcaatggca tcctggtcat ccagcggata | 6120 |
| gttaatgatc agcccactga cgcgttgcgc gagaagattg tgcaccgccg ctttacaggc | 6180 |
| ttcgacgccg cttcgttcta ccatcgacac caccacgctg cacccagtt gatcggcgcg | 6240 |
| agatttaatc gccgcgacaa tttgcgacgg cgcgtgcagg gccagactgg aggtggcaac | 6300 |
| gccaatcagc aacgactgtt tgcccgccag ttgttgtgcc acgcggttgg gaatgtaatt | 6360 |
| cagctccgcc atcgccgctt ccactttttc ccgcgttttc gcagaaacgt ggctggcctg | 6420 |
| gttcaccacg cgggaaacgg tctgataaga gacaccggca tactctgcga catcgtataa | 6480 |
| cgttactggt ttcacattca ccaccctgaa ttgactctct tccgggcgct atcatgccat | 6540 |
| accgcgaaag gttttgcgcc attcgatggt gtccgggatc tcgacgctct cccttatgcg | 6600 |
| actcctgcat taggaagcag cccagtagta ggttgaggcc gttgagcacc gccgccgcaa | 6660 |
| ggaatggtgc atgcaaggag atggcgccca acagtccccc ggccacgggg cctgccacca | 6720 |
| tacccacgcc gaaacaagcg ctcatgagcc gaagtggcg agcccgatct tccccatcgg | 6780 |
| tgatgtcggc gatataggcg ccagcaaccg cacctgtggc gccggtgatg ccggccacga | 6840 |
| tgcgtccggc gtagaggatc g | 6861 |

<210> SEQ ID NO 27
<211> LENGTH: 6129
<212> TYPE: DNA
<213> ORGANISM: Artificial Sequence
<220> FEATURE:
<223> OTHER INFORMATION: Description of Artificial Sequence: Synthetic construct

<400> SEQUENCE: 27

| | |
|---|---|
| agatctcgat cccgcgaaat taatacgact cactataggg gaattgtgag cggataacaa | 60 |
| ttcccctcta gaaataattt tgtttaactt taagaaggag atatacatat ggtaccagta | 120 |
| tctttcacaa gtcttttagc agcatctcca ccttcacgtg caagttgccg tccagctgct | 180 |
| gaagtggaat cagttgcagt agaaaaacgt caaacaattc aaccaggtac aggttacaat | 240 |
| aacggttact tttattctta ctggaatgat ggacacggtg gtgttacata tactaatgga | 300 |
| cctggtggtc aatttagtgt aaattggagt aactcaggca attttgttgg aggaaaaggt | 360 |
| tggcaacctg gtacaaagaa taaggtaatc aatttctctg gtagttacaa ccctaatggt | 420 |
| aattcttatt taagtgtata cggttggagc cgtaacccat taattgaata ttatattgta | 480 |
| gagaactttg gtacatacaa cccttcaaca ggtgctacta attaggtga agttacttca | 540 |
| gatggatcag tttatgatat ttatcgtact caacgcgtaa atcaaccatc tataattgga | 600 |
| actgccactt ctaccaata ctggagtgta agacgtaatc atcgttcaag tggtagtgtt | 660 |
| aatacagcaa accacttaa tgcatgggct caacaaggtt taacattagg tacaatggac | 720 |
| tatcaaattg tagctgttga aggttatttt tcatcaggta gtgcttctat cactgttagc | 780 |
| ggtaccggtg aaaacttata ctttcaaggc tcaggtggcg gtggaagtga ttacaaagat | 840 |
| gatgatgata aggaaccgg ttaatctaga ctcgagcacc accaccacca ccactgagat | 900 |
| ccggctgcta acaaagcccg aaaggaagct gagttggctg ctgccaccgc tgagcaataa | 960 |

-continued

```
ctagcataac cccttggggc ctctaaacgg gtcttgaggg gttttttgct gaaaggagga    1020
actatatccg gattggcgaa tgggacgcgc cctgtagcgg cgcattaagc gcggcgggtg    1080
tggtggttac gcgcagcgtg accgctacac ttgccagcgc cctagcgccc gctcctttcg    1140
ctttcttccc ttcctttctc gccacgttcg ccggctttcc ccgtcaagct ctaaatcggg    1200
ggctcccttt agggttccga tttagtgctt tacggcacct cgaccccaaa aaacttgatt    1260
agggtgatgg ttcacgtagt gggccatcgc cctgatagac ggttttttcgc cctttgacgt    1320 tggagtccac gttctttaat agtggactct tgttccaaac tggaacaaca ctcaaccccta    1380 tctcggtcta ttcttttgat ttataaggga ttttgccgat ttcggcctat tggttaaaaa    1440
atgagctgat ttaacaaaaa tttaacgcga attttaacaa aatattaacg tttacaattt    1500
caggtggcac ttttcgggga aatgtgcgcg gaacccctat ttgtttattt ttctaaatac    1560
attcaaatat gtatccgctc atgagacaat aaccctgata aatgcttcaa taatattgaa    1620
aaaggaagag tatgagtatt caacatttcc gtgtcgccct tattccctttt tttgcggcat    1680 tttgccttcc tgtttttgct cacccagaaa cgctggtgaa agtaaaagat gctgaagatc    1740
agttgggtgc acgagtgggt tacatcgaac tggatctcaa cagcggtaag atccttgaga    1800
gttttcgccc cgaagaacgt tttccaatga tgagcacttt taaagttctg ctatgtggcg    1860
cggtattatc ccgtattgac gccgggcaag agcaactcgg tcgccgcata cactattctc    1920
agaatgactt ggttgagtac tcaccagtca cagaaaagca tcttacggat ggcatgacag    1980
taagagaatt atgcagtgct gccataacca tgagtgataa cactgcggcc aacttacttc    2040
tgacaacgat cggaggaccg aaggagctaa ccgcttttt gcacaacatg ggggatcatg    2100
taactcgcct tgatcgttgg gaaccggagc tgaatgaagc cataccaaac gacgagcgtg    2160
acaccacgat gcctgcagca atggcaacaa cgttgcgcaa actattaact ggcgaactac    2220
ttactctagc ttcccggcaa caattaatag actggatgga ggcggataaa gttgcaggac    2280
cacttctgcg ctcggccctt ccggctggct ggtttattgc tgataaatct ggagccggtg    2340
agcgtgggtc tcgcggtatc attgcagcac tggggccaga tggtaagccc tcccgtatcg    2400
tagttatcta cacgacgggg agtcaggcaa ctatggatga acgaaataga cagatcgctg    2460
agataggtgc ctcactgatt aagcattggt aactgtcaga ccaagtttac tcatatatac    2520
tttagattga tttaaaactt cattttttaat ttaaaaggat ctaggtgaag atcctttttg    2580
ataatctcat gaccaaaatc ccttaacgtg agttttcgtt ccactgagcg tcagaccccg    2640
tagaaaagat caaaggatct tcttgagatc cttttttttct gcgcgtaatc tgctgcttgc    2700
aaacaaaaaa accaccgcta ccagcggtgg tttgtttgcc ggatcaagag ctaccaactc    2760 ttttccgaa ggtaactggc ttcagcagag cgcagatacc aaatactgtc cttctagtgt    2820
agccgtagtt aggccaccac ttcaagaact ctgtagcacc gcctacatac ctcgctctgc    2880
taatcctgtt accagtggct gctgccagtg gcgataagtc gtgtcttacc gggttggact    2940
caagacgata gttaccggat aaggcgcagc ggtcgggctg aacggggggt tcgtgcacac    3000
agcccagctt ggagcgaacg acctacaccg aactgagata cctacagcgt gagctatgag    3060
aaagcgccac gcttcccgaa gggagaaagg cggacaggta tccggtaagc ggcagggtcg    3120
gaacaggaga gcgcacgagg gagcttccag ggggaaacgc ctggtatctt tatagtcctg    3180
tcgggtttcg ccacctctga cttgagcgtc gatttttgtg atgctcgtca ggggggcgga    3240
gcctatggaa aaacgccagc aacgcggcct ttttacggtt cctggccttt tgctggcctt    3300
ttgctcacat gttctttcct gcgttatccc ctgattctgt ggataaccgt attaccgcct    3360
```

```
ttgagtgagc tgataccgct cgccgcagcc gaacgaccga gcgcagcgag tcagtgagcg    3420
aggaagcgga agagcgcctg atgcggtatt ttctccttac gcatctgtgc ggtatttcac    3480
accgcatata tggtgcactc tcagtacaat ctgctctgat gccgcatagt taagccagta    3540
tacactccgc tatcgctacg tgactgggtc atggctgcgc cccgacaccc gccaacaccc    3600
gctgacgcgc cctgacgggc ttgtctgctc ccggcatccg cttacagaca agctgtgacc    3660
gtctccggga gctgcatgtg tcagaggttt tcaccgtcat caccgaaacg cgcgaggcag    3720
ctgcggtaaa gctcatcagc gtggtcgtga agcgattcac agatgtctgc ctgttcatcc    3780
gcgtccagct cgttgagttt ctccagaagc gttaatgtct ggcttctgat aaagcgggcc    3840
atgttaaggg cggtttttc ctgtttggtc actgatgcct ccgtgtaagg gggatttctg    3900
ttcatggggg taatgatacc gatgaaacga gagaggatgc tcacgatacg ggttactgat    3960
gatgaacatg cccggttact ggaacgttgt gagggtaaac aactggcggt atggatgcgg    4020
cgggaccaga gaaaaatcac tcagggtcaa tgccagcgct tcgttaatac agatgtaggt    4080
gttccacagg gtagccagca gcatcctgcg atgcagatcc ggaacataat ggtgcagggc    4140
gctgacttcc gcgtttccag actttacgaa acacggaaac cgaagaccat tcatgttgtt    4200
gctcaggtcg cagacgtttt gcagcagcag tcgcttcacg ttcgctcgcg tatcggtgat    4260
tcattctgct aaccagtaag gcaaccccgc cagcctagcc gggtcctcaa cgacaggagc    4320
acgatcatgc gcacccgtgg ggccgccatg ccggcgataa tggcctgctt ctcgccgaaa    4380
cgtttggtgg cgggaccagt gacgaaggct tgagcgaggg cgtgcaagat tccgaatacc    4440
gcaagcgaca ggccgatcat cgtcgcgctc cagcgaaagc ggtcctcgcc gaaaatgacc    4500
cagagcgctg ccggcacctg tcctacgagt tgcatgataa agaagacagt cataagtgcg    4560
gcgacgatag tcatgccccg cgcccaccgg aaggagctga ctgggttgaa ggctctcaag    4620
ggcatcggtc gagatcccgg tgcctaatga gtgagctaac ttacattaat tgcgttgcgc    4680
tcactgcccg ctttccagtc gggaaacctg tcgtgccagc tgcattaatg aatcggccaa    4740
cgcgcgggga gaggcggttt gcgtattggg cgccagggtg ttttttcttt tcaccagtga    4800
gacgggcaac agctgattgc ccttcaccgc ctggccctga gagagttgca gcaagcggtc    4860
cacgctggtt tgccccagca ggcgaaaatc ctgtttgatg gtggttaacg gcgggatata    4920
acatgagctg tcttcggtat cgtcgtatcc cactaccgag atatccgcac caacgcgcag    4980
cccggactcg gtaatggcgc gcattgcgcc cagcgccatc tgatcgttgg caaccagcat    5040
cgcagtggga acgatgccct cattcagcat ttgcatggtt tgttgaaaac cggacatggc    5100
actccagtcg ccttcccgtt ccgctatcgg ctgaatttga ttgcgagtga gatatttatg    5160
ccagccagcc agacgcagac gcgccgagac agaacttaat gggcccgcta acagcgcgat    5220
ttgctggtga cccaatgcga ccagatgctc cacgcccagt cgcgtaccgt cttcatggga    5280
gaaaataata ctgttgatgg gtgtctggtc agagacatca agaaataacg ccggaacatt    5340
agtgcaggca gcttccacag caatggcatc ctggtcatcc agcggatagt taatgatcag    5400
cccactgacg cgttgcgcga agattgtg caccgccgct ttacaggctt cgacgccgct    5460
tcgttctacc atcgacacca ccacgctggc acccagttga tcggcgcgag atttaatcgc    5520
cgcgacaatt tgcgacggcg cgtgcagggc cagactggag gtggcaacgc caatcagcaa    5580
cgactgtttg cccgccagtt gttgtgccac gcggttggga atgtaattca gctccgccat    5640
cgccgcttcc actttttccc gcgttttcgc agaaacgtgg ctggcctggt tcaccacgcg    5700
ggaaacggtc tgataagaga caccggcata ctctgcgaca tcgtataacg ttactggttt    5760
```

| | |
|---|---|
| cacattcacc accctgaatt gactctcttc cgggcgctat catgccatac cgcgaaaggt | 5820 |
| tttgcgccat tcgatggtgt ccgggatctc gacgctctcc cttatgcgac tcctgcatta | 5880 |
| ggaagcagcc cagtagtagg ttgaggccgt tgagcaccgc cgccgcaagg aatggtgcat | 5940 |
| gcaaggagat ggcgcccaac agtcccccgg ccacggggcc tgccaccata cccacgccga | 6000 |
| aacaagcgct catgagcccg aagtggcgag cccgatcttc cccatcggtg atgtcggcga | 6060 |
| tataggcgcc agcaaccgca cctgtggcgc cggtgatgcc ggccacgatg cgtccggcgt | 6120 |
| agaggatcg | 6129 |

<210> SEQ ID NO 28
<211> LENGTH: 10026
<212> TYPE: DNA
<213> ORGANISM: Artificial Sequence
<220> FEATURE:
<223> OTHER INFORMATION: Description of Artificial Sequence: Synthetic construct

<400> SEQUENCE: 28

| | |
|---|---|
| gtgcactctc agtacaatct gctctgatgc cgcatagtta agccagcccc gacacccgcc | 60 |
| aacaccgct gacgcgccct gacgggcttg tctgctcccg gcatccgctt acagacaagc | 120 |
| tgtgaccgtc tccgggagct gcatgtgtca gaggttttca ccgtcatcac cgaaacgcgc | 180 |
| gagacgaaag ggcctcgtga tacgcctatt tttataggtt aatgtcatga taataatggt | 240 |
| ttcttagacg tcaggtggca cttttcgggg aaatgtgcgc ggaaccccta tttgtttatt | 300 |
| tttctaaata cattcaaata tgtatccgct catgagacaa taaccctgat aaatgcttca | 360 |
| ataatattga aaaggaaga gtatgagtat tcaacatttc cgtgtcgccc ttattccctt | 420 |
| ttttgcggca ttttgccttc ctgttttgc tcacccagaa acgctggtga agtaaaaga | 480 |
| tgctgaagat cagttgggtg cacgagtggg ttacatcgaa ctggatctca acagcggtaa | 540 |
| gatccttgag agttttcgcc ccgaagaacg ttttccaatg atgagcactt ttaaagttct | 600 |
| gctatgtggc gcggtattat cccgtattga cgccgggcaa gagcaactcg gtcgccgcat | 660 |
| acactattct cagaatgact tggttgagta ctcaccagtc acagaaaagc atcttacgga | 720 |
| tggcatgaca gtaagagaat tatgcagtgc tgccataacc atgagtgata acactgcggc | 780 |
| caacttactt ctgacaacga tcggaggacc gaaggagcta accgcttttt tgcacaacat | 840 |
| gggggatcat gtaactcgcc ttgatcgttg ggaaccggag ctgaatgaag ccataccaaa | 900 |
| cgacgagcgt gacaccacga tgcctgtagc aatggcaaca acgttgcgca aactattaac | 960 |
| tggcgaacta cttactctag cttcccggca acaattaata gactggatgg aggcggataa | 1020 |
| agttgcagga ccacttctgc gctcggccct tccggctggc tggtttattg ctgataaatc | 1080 |
| tggagccggt gagcgtgggt ctcgcggtat cattgcagca ctggggccag atggtaagcc | 1140 |
| ctcccgtatc gtagttatct acacgacggg gagtcaggca actatggatg aacgaaatag | 1200 |
| acagatcgct gagataggtg cctcactgat taagcattgg taactgtcag accaagttta | 1260 |
| ctcatatata ctttagattg atttaaaact tcatttttaa tttaaaagga tctaggtgaa | 1320 |
| gatccttttt gataatctca tgaccaaaat cccttaacgt gagttttcgt tccactgagc | 1380 |
| gtcagacccc gtagaaaaga tcaaaggatc ttcttgagat cctttttttc tgcgcgtaat | 1440 |
| ctgctgcttg caaacaaaaa aaccaccgct accagcggtg gtttgtttgc cggatcaaga | 1500 |
| gctaccaact ctttttccga aggtaactgg cttcagcaga gcgcagatac caaatactgt | 1560 |
| tcttctagtg tagccgtagt taggccacca cttcaagaac tctgtagcac cgcctacata | 1620 |
| cctcgctctg ctaatcctgt taccagtggc tgctgccagt ggcgataagt cgtgtcttac | 1680 |

| | |
|---|---|
| cgggttggac tcaagacgat agttaccgga taaggcgcag cggtcgggct gaacgggggg | 1740 |
| ttcgtgcaca cagcccagct tggagcgaac gacctacacc gaactgagat acctacagcg | 1800 |
| tgagctatga gaaagcgcca cgcttcccga agggagaaag gcggacaggt atccggtaag | 1860 |
| cggcagggtc ggaacaggag agcgcacgag ggagcttcca gggggaaacg cctggtatct | 1920 |
| ttatagtcct gtcgggtttc gccacctctg acttgagcgt cgattttgt gatgctcgtc | 1980 |
| aggggggcgg agcctatgga aaaacgccag caacgcggcc ttttacggt tcctggcctt | 2040 |
| ttgctggcct tttgctcaca tgttctttcc tgcgttatcc cctgattctg tggataaccg | 2100 |
| tattaccgcc tttgagtgag ctgataccgc tcgccgcagc cgaacgaccg agcgcagcga | 2160 |
| gtcagtgagc gaggaagcgg aagagcgccc aatacgcaaa ccgcctctcc ccgcgcgttg | 2220 |
| gccgattcat taatgcagct ggcacgacag gtttcccgac tggaaagcgg gcagtgagcg | 2280 |
| caacgcaatt aatgtgagtt agctcactca ttaggcaccc caggctttac actttatgct | 2340 |
| tccggctcgt atgttgtgtg gaattgtgag cggataacaa tttcacacag gaaacagcta | 2400 |
| tgaccatgat tacgccaagc tcgcggccgc agtactctgc agattttatg caaaattaaa | 2460 |
| gtcttgtgac aacagctttc tccttaagtg caaatatcgc ccattctttc ctcttttcgt | 2520 |
| atataaatgc tgtaatagta ggatgtcgta cccgtaaagg tacgacattg aatattaata | 2580 |
| tactcctaag tttactttcc caatatttat attaggacgt ccccttcggg taaataaatt | 2640 |
| ttagtggcag tggtaccgcc actccctatt ttaatactgc gaaggaggca gttggcaggc | 2700 |
| aactcgtcgt tcgcagtata taaatatcca ctaatattta tattcccgta aggggacgtc | 2760 |
| ccgaagggga aggggaaaga agcagtcgcc tccttgcgaa aaggtttact tgcccgacca | 2820 |
| gtgaaaagca tgctgtaaga tataaatcta ccctgaaagg gatgcatttc accataatac | 2880 |
| tatacaaatg gtgttaccct ttgaggatca taacggtgct actggaatat atggtctctt | 2940 |
| catggataga cgatagccat ttatttaccc attagtggga cattagtggc ctgtcactgc | 3000 |
| tccttacgag acgccagtgg acgttcgtcc tagaaaattt atgcgctgcc tagaagcccc | 3060 |
| aaaagggaag tttactgact cgttagagcg tgcgctaaca ggtttaaata cttcaatatg | 3120 |
| tatattagga cgccggtggc agtggtaccg ccactgccac cgtcggagga cgtcccttac | 3180 |
| ggtatattat atactaggat tttaatactc gaaggaggc agtggcggta ccactgccac | 3240 |
| taatatttat attcccgtaa gggacgtcct ccttcggagt atgtaaacat tctaagttta | 3300 |
| cttgcccaat attatatta ggcagttggc aggcaactgc tagctctcct ccttcggagt | 3360 |
| atgtaaacat cgcagtatat aaatatccac taatatttat attcccgtaa ggggacgtcc | 3420 |
| cgaaggggaa ggggaaggac gtcagtggca gttgcctgcc aactgcctag gcaagtaaac | 3480 |
| ttaggagtat ataaatatag gcagtcgcgg taccactgcc actgacgtcc tgccaactgc | 3540 |
| ctaggcaagt aaacttaagt ggcactaaaa tgcatttgcc cgaaggggaa ggaggacgcc | 3600 |
| agtggcagtg gtaccgccac tgcctccttc ggagtattaa aatcctagta tgtaaatctg | 3660 |
| ctagcgcagg aaataaattt tattctattt atatactccg ttaggaggta agtaaacccc | 3720 |
| ttcccccttcg gacgtcagt gcagttgcct gccaactgcc taatataaat attagaccac | 3780 |
| taaagtttgg caactgccaa ctgttgtcct tcggaggaaa aaaatggtt aactcgcaag | 3840 |
| cagttaacat aactaaagtt tgttacttta ccgaagacgt ttacccttc tcggttaagg | 3900 |
| agacggagac agttgcactg tgactgccta gtatagcaat tttgttttg tttatatgct | 3960 |
| cgacaaaatg actttcataa aaatataaag tagttagcta gttatttat atcactataa | 4020 |
| ctagggttct cagaggcacc gaagtcactt gtaaaaatag tacttttaa cttgtttaat | 4080 |

```
cttcgtgttc ttcaaaagga tcacgtaatt tttttgaagg tggaccaaaa ctaacataaa    4140
ctgaatagcc agttacactt aacagaagaa accataaaaa aaaggtaaag aaaaaagctg    4200
gactttccat agctcattta ataataaaat tattctcttt tcaacatatc tcttagatag    4260
ttcaaaagac ttgacgactg tgtcccacat ttttaaacaa aattaatcta ctcaaaattt    4320
tgccctgaga aagaataact tacttcgttt ttgcagtagc cattcatgtc actttgaaac    4380
tgtccttaca aagttaaaca ttaattaaaa attatttaat ttttatataa caaatattat    4440
attaaataaa aaatgaacaa agaacttcta agatcgtctt tagtgagtaa ttaaagagtt    4500
ttacttacca gacaaggcag ttttttcatt cttttaaagc aggcagttct gaaggggaaa    4560
agggactgcc tactgcggtc ctaggtaaat acatttttat gcaatttatt tcttgtgcta    4620
gtaggtttct atactcacaa gaagcaaccc cttgacgaga gaacgttatc ctcagagtat    4680
ttataatcct gagagggaat gcactgaaga atattttcct tatttttttac agaaagtaaa    4740 taaaatagcg ctaataacgc ttaattcatt taatcaatta tggcaacagg aacttctaaa    4800
gctaaaccat caaagtaaa ttcagacttc caagaacctg gtttagttac accattaggt    4860
actttattac gtccacttaa ctcagaagca ggtaaagtat taccaggctg gggtacaact    4920
gttttaatgg ctgtatttat cctttatt tt gcagcattct tattaatcat tttagaaatt    4980
tacaacagtt ctttaattt tagatgacgtt tctatgagtt gggaaacttt agctaaagtt    5040 tcttaattt t atttaacaca aacataaaat ataaaactgt tgttaaggc tagctgctaa    5100 gtcttctttt cgctaaggta aactaagcaa ctcaaccata tttatattcg gcagtggcac    5160
cgccaactgc cactggcctt ccgttaagat aaacgcgtgg atctcacgtg actagtcacc    5220
tagtgtcgag tggtaccgcc actgcctagt atataaatat cggcagttgg caggatattt    5280
atatactccg aaggaacttg ttagccgata ggcgaggcaa ctgccactaa aatttatttg    5340
cctcctaacg gagcattaaa atccctaagt ttacttgccc gtaaggggaa ggggacgtcc    5400
actaatattt atattaggca gttggcaggc aacaataaat acatttgtcc cgtaagggga    5460
cgtcctgcca actgcctatg gtagctatta agtatatata tatgaaaagt gtgtataaac    5520
taaactaaaa taaaccaggt atggttaacc agatttattt tagtttaaaa aaaaattagt    5580
tgtttgagct agagttagtt gaagctaagt ctagattaac cggttccttt atcatcatca    5640
tctttgtaat cacttccacc gccacctgag ccttgaaagt ataagttttc accggtaccc    5700
ttgcgagcta acaactact tactaatgaa gtgtctgtcc atgagtttcc agaagaagta    5760
ggggtttcgg ttaatacata agttgaatca aaagaaccag caccccaacc tacataacct    5820
aagtacacgt cagagttttg atttaagtac tgaatttgtt gacacatgtc ttggatacaa    5880
ctctgcacgt ttccaccacc tgtttcagtt aaaatggctt ggcgattatt ttgacgtaac    5940
caagttgcta aaggactaaa agcaccatca atattatttg tggtacattc ggcgtgtgtt    6000
ccgctattat cagaatcaag atatttatgt acatcgaata ttaagttagt ggtactaccg    6060
tctgggttag tcacttgact aagagcagct gcgctaccgt cagaaataaa agcgccggca    6120
gattgccaat cgttgcctgg taaactaatg aattgtgatg ttgcaccagc attacgaata    6180
gcagttacta cttcttgcac agttgcagcc caagtattta tgttcacatc gtgaggttca    6240
ttcataatac cgaaccaaac acgtgattga ctagcatatt ttgaagctaa ttggctccat    6300
aatgatgtaa attgagcatt agttggacca ccttgaccaa taataccacc gttccaacgg    6360
gcataattat gaatatcaac aatacaatag gcacctaaag ataagcaacc ttgtactaat    6420
tgatcatatt tactaattga tgtactatct aagttaccac ctaaattgtt gttaactaag    6480
```

```
tattgccagc ccactggtaa acggaaaata gtcataccat cttcatttac aaagtgttgc    6540
atttgaccaa tgccatctgg ataattgttt gagccagtaa aatttttta aggggggataa    6600 actttactgg taacacatgt accatcggta gtacaaccaa aatcgaaacc tgcaatatta    6660
acaccagcga aacgtactcc agaagatgta ggaggtgtgc tgctagaagt gctagtagca    6720
cgagttgttg tagttggacc tgaaggaggg cgagttgatg ttgttatagt tgttgcacct    6780
ggaatacatt gagcatagta aggatttaag gtactacatg ctgagccagg agcacaattg    6840
gtaggaccag accaaccaat accaccacac tgacccaaa cagtctgttg agcaacagca    6900
ccaccatata agatagatgc agcaagtaat aatggtgcta cgcttttgtt tggtaccata    6960
tgcactttgc attacctccg tacaaattat tttgatttct ataaagtttt gcttaaataa    7020
aaatttttaa tttttaacgt ccacccatat aaataataaa tatggtgaaa cctttaacaa    7080
caaaaatcct cttgtaccat attaatccaa aagaattaag gacaaaagct tatctccaac    7140 attttaaaa cacagagtaa aaataatgtt gttttttaaga atagaatttt ataacttgta    7200
ttttaaatat gatctaattt atttgtgcta aaaattgcag ttggaaagta attttaaaaa    7260
taatttagat catatttatt aaataaagtt gatttaaaac aacttaatcg tttttaattg    7320
ttaattaaaa acataatttt aaatcttttt atatttaaat taccttatat actactaggt    7380
gactatggat atctacgtaa tcgatgaatt cgatcccatt tttataactg gatctcaaaa    7440
tacctataaa cccattgttc ttctcttta gctctaagaa caatcaattt ataaatatat    7500
ttattattat gctataatat aaatactata taaatacatt taccttttta taaatacatt    7560 taccttttttt ttaatttgca tgatttttaat gcttatgcta tcttttttat ttagtccata    7620 aaaccttttaa aggacctttt cttatgggat atttatattt tcctaacaaa gcaatcggcg    7680
tcataaactt tagttgctta cgacgcctgt ggacgtcccc cccttcccct tacgggcaag    7740
taaacttagg gatttttaatg caataataaa atttgtcctc ttcgggcaaa tgaattttag    7800
tatttaaata tgacaaggggt gaaccattac ttttgttaac aagtgatctt accactcact    7860
atttttgttg aattttaaac ttatttaaaa ttctcgagaa agattttaaa aataaacttt    7920
tttaatcttt tatttatttt ttcttttttc gtatggaatt gcccaatatt attcaacaat    7980
ttatcggaaa cagcgtttta gagccaaata aaattggtca gtcgccatcg gatgtttatt    8040
cttttaatcg aaataatgaa acttttttttc ttaagcgatc tagcacttta tatacagaga    8100
ccacatacag tgtctctcgt gaagcgaaaa tgttgagttg gctctctgag aaattaaagg    8160
tgcctgaact catcatgact tttcaggatg agcagtttga atttatgatc actaaagcga    8220
tcaatgcaaa accaatttca gcgcttttttt taacagacca agaattgctt gctatctata    8280
aggaggcact caatctgtta aattcaattg ctattattga ttgtccattt atttcaaaca    8340
ttgatcatcg gttaaaagag tcaaaatttt ttattgataa ccaactcctt gacgatatag    8400
atcaagatga ttttgacact gaattatggg gagaccataa aacttaccta agtctatgga    8460
atgagttaac cgagactcgt gttgaagaaa gattggtttt ttctcatggc gatatcacgg    8520
atagtaatat ttttatagat aaaattcaatg aaatttattt tttagacctt ggtcgtgctg    8580
ggttagcaga tgaatttgta gatatatcct ttgttgaacg ttgcctaaga gaggatgcat    8640
cggaggaaac tgcgaaaata ttttttaaagc atttaaaaaaa tgatagacct gacaaaagga    8700
attatttttt aaaacttgat gaattgaatt gattccaagc attatctaaa atactctgca    8760
ggcacgctag cttgtactca agctcgtaac gaaggtcgtg accttgctcg tgaaggtggc    8820
gacgtaattc gttcagcttg taaatggtct ccagaacttg ctgctgcatg tgaagtttgg    8880
```

```
aaagaaatta aattcgaatt tgatactatt gacaaacttt aattttttatt tttcatgatg    8940 tttatgtgaa tagcataaac atcgttttta tttttatggt gtttaggtta aatacctaaa    9000
catcatttta cattttttaaa attaagttct aaagttatct tttgtttaaa tttgcctgtc    9060
tttataaatt acgatgtgcc agaaaaataa aatcttagct ttttattata gaatttatct    9120
ttatgtatta tattttataa gttataataa aagaaatagt aacatactaa agcggatgta    9180
gcgcgtttat cttaacggaa ggaattcggc gcctacgtac ccgggtcgcg aggatccacg    9240
cgttaatagc tcacttttct ttaaatttaa tttttaattt aaaggtgtaa gcaaattgcc    9300
tgacgagaga tccacttaaa ggatgacagt ggcgggctac tgcctacttc cctccgggat    9360
aaaatttatt tgaaaaacgt tagttacttc ctaacggagc attgacatcc ccatatttat    9420
attaggacgt ccccttcggg taaataaatt ttagtggacg tccccttcgg gcaaataaat    9480
tttagtggac aataaataaa tttgttgcct gccaactgcc taggcaagta aacttgggag    9540
tattaaaata ggacgtcagt ggcagttgcc tgccaactgc ctatatttat atactgcgaa    9600
gcaggcagtg gcggtaccac tgccactggc gtcctaatat aaatattggg caactaaagt    9660
ttatagcagt attaacatcc tatatttata tactccgaag gaacttgtta gccgataggc    9720
gaggcaacaa atttatttat tgtcccgtaa aaggatgcct ccagcatcga aggggaaggg    9780
gacgtcctag gccataaaac taagggaaa tccatagtaa ctgatgttat aaatttatag    9840
actccaaaaa acagctgcgt tataaataac ttctgttaaa tatggccaag gggacagggg    9900
cactttcaac taagtgtaca ttaaaaattg acaattcaat tttttttaat tataatatat    9960
atttagtaaa atataacaaa aagcccccat cgtctaggta gaattccagc tggcggccgc   10020
cctatg                                                              10026
```

<210> SEQ ID NO 29
<211> LENGTH: 10307
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 29

```
gtgcactctc agtacaatct gctctgatgc cgcatagtta agccagcccc gacacccgcc      60
aacacccgct gacgcgccct gacgggcttg tctgctcccg gcatccgctt acagacaagc     120
tgtgaccgtc tccgggagct gcatgtgtca gaggttttca ccgtcatcac cgaaacgcgc     180
gagacgaaag ggcctcgtga tacgcctatt tttataggtt aatgtcatga taataatggt     240
ttcttagacg tcaggtggca cttttcgggg aaatgtgcgc ggaaccccta tttgtttatt     300
tttctaaata cattcaaata tgtatccgct catgagacaa taaccctgat aaatgcttca     360
ataatattga aaaaggaaga gtatgagtat tcaacatttc cgtgtcgccc ttattccctt     420
ttttgcggca ttttgccttc ctgttttgc tcacccagaa acgctggtga agtaaaaga      480 tgctgaagat cagttgggtg cacgagtggg ttacatcgaa ctggatctca acagcggtaa    540
gatccttgag agttttcgcc ccgaagaacg ttttccaatg atgagcactt ttaaagttct    600
gctatgtggc gcggtattat cccgtattga cgccgggcaa gagcaactcg gtcgccgcat    660
acactattct cagaatgact tggttgagta ctcaccagtc acagaaaagc atcttacgga    720
tggcatgaca gtaagagaat tatgcagtgc tgccataacc atgagtgata acactgcggc    780
caacttactt ctgacaacga tcggaggacc gaaggagcta accgcttttt tgcacaacat    840
```

```
gggggatcat gtaactcgcc ttgatcgttg ggaaccggag ctgaatgaag ccataccaaa    900
cgacgagcgt gacaccacga tgcctgtagc aatggcaaca acgttgcgca aactattaac    960
tggcgaacta cttactctag cttcccggca acaattaata gactggatgg aggcggataa   1020
agttgcagga ccacttctgc gctcggccct tccggctggc tggtttattg ctgataaatc   1080
tggagccggt gagcgtgggt ctcgcggtat cattgcagca ctggggccag atggtaagcc   1140
ctcccgtatc gtagttatct acacgacggg gagtcaggca actatggatg aacgaaatag   1200
acagatcgct gagataggtg cctcactgat taagcattgg taactgtcag accaagttta   1260
ctcatatata ctttagattg atttaaaact tcattttaa tttaaaagga tctaggtgaa   1320
gatccttttt gataatctca tgaccaaaat cccttaacgt gagttttcgt tccactgagc   1380
gtcagacccc gtagaaaaga tcaaaggatc ttcttgagat cctttttttc tgcgcgtaat   1440
ctgctgcttg caaacaaaaa aaccaccgct accagcggtg gtttgtttgc cggatcaaga   1500
gctaccaact ctttttccga aggtaactgg cttcagcaga gcgcagatac caaatactgt   1560
tcttctagtg tagccgtagt taggccacca cttcaagaac tctgtagcac cgcctacata   1620
cctcgctctg ctaatcctgt taccagtggc tgctgccagt ggcgataagt cgtgtcttac   1680
cgggttggac tcaagacgat agttaccgga taaggcgcag cggtcgggct gaacggggggg   1740
ttcgtgcaca gcccagct tggagcgaac gacctacacc gaactgagat acctacagcg   1800
tgagctatga gaaagcgcca cgcttcccga agggagaaag gcggacaggt atccggtaag   1860
cggcagggtc ggaacaggag agcgcacgag ggagcttcca gggggaaacg cctggtatct   1920
ttatagtcct gtcgggtttc gccacctctg acttgagcgt cgatttttgt gatgctcgtc   1980
agggggggcgg agcctatgga aaaacgccag caacgcggcc tttttacggt tcctggcctt   2040
ttgctggcct tttgctcaca tgttctttcc tgcgttatcc cctgattctg tggataaccg   2100
tattaccgcc tttgagtgag ctgataccgc tcgccgcagc cgaacgaccg agcgcagcga   2160
gtcagtgagc gaggaagcgg aagagcgccc aatacgcaaa ccgcctctcc ccgcgcgttg   2220
gccgattcat taatgcagct ggcacgacag gtttcccgac tggaaagcgg gcagtgagcg   2280
caacgcaatt aatgtgagtt agctcactca ttaggcaccc caggctttac actttatgct   2340
tccggctcgt atgttgtgtg gaattgtgag cggataacaa tttcacacag gaaacagcta   2400
tgaccatgat tacgccaagc tcgcggccgc agtactctgc agattttatg caaaattaaa   2460
gtcttgtgac aacagctttc tccttaagtg caaatatcgc ccattctttc ctcttttcgt   2520
atataaatgc tgtaatagta ggatgtcgta cccgtaaagg tacgacattg aatattaata   2580
tactcctaag tttactttcc caatatttat attaggacgt ccccttcggg taaataaatt   2640
ttagtggcag tggtaccgcc actccctatt ttaatactgc gaaggaggca gttggcaggc   2700
aactcgtcgt tcgcagtata taaatatcca ctaatattta tattcccgta aggggacgtc   2760
ccgaagggga aggggaaaga agcagtcgcc tccttgcgaa aaggtttact tgcccgacca   2820
gtgaaaagca tgctgtaaga tataaatcta ccctgaaagg gatgcatttc accataatac   2880
tatacaaatg gtgttaccct ttgaggatca taacggtgct actggaatat atggtctctt   2940
catggataga cgatagccat ttatttaccc attaagggga cattagtggc ctgtcactgc   3000
tccttacgag acgccagtgg acgttcgtcc tagaaaattt atgcgctgcc tagaagcccc   3060
aaaagggaag tttactgact cgttagagcg tgcgctaaca ggtttaaata cttcaatatg   3120
tatattagga cgccggtggc agtggtaccg ccactgccac cgtcggagga cgtcccttac   3180
ggtatattat atactaggat tttaatactc cgaaggaggc agtggcggta ccactgccac   3240
```

```
taatatttat attcccgtaa gggacgtcct ccttcggagt atgtaaacat tctaagttta   3300
cttgcccaat atttatatta ggcagttggc aggcaactgc tagctctcct ccttcggagt   3360
atgtaaacat cgcagtatat aaatatccac taatatttat attcccgtaa ggggacgtcc   3420
cgaaggggaa ggggaaggac gtcagtggca gttgcctgcc aactgcctag gcaagtaaac   3480
ttaggagtat ataaatatag gcagtcgcgg taccactgcc actgacgtcc tgccaactgc   3540
ctaggcaagt aaacttaagt ggcactaaaa tgcatttgcc cgaaggggaa ggaggacgcc   3600
agtggcagtg gtaccgccac tgcctccttc ggagtattaa aatcctagta tgtaaatctg   3660
ctagcgcagg aaataaattt tattctattt atatactccg ttaggaggta agtaaacccc   3720
ttccccttcg ggacgtcagt gcagttgcct gccaactgcc taatataaat attagaccac   3780
taaagtttgg caactgccaa ctgttgtcct tcggaggaaa aaaaatggtt aactcgcaag   3840
cagttaacat aactaaagtt tgttacttta ccgaagacgt ttacccttc tcggttaagg   3900 agacggagac agttgcactg tgactgccta gtatagcaat tttgtttttg tttatatgct   3960
cgacaaaatg actttcataa aaatataaag tagttagcta gttatttat atcactataa    4020 ctagggttct cagaggcacc gaagtcactt gtaaaaatag tactttttaa cttgtttaat   4080
cttcgtgttc ttcaaaagga tcacgtaatt tttttgaagg tggaccaaaa ctaacataaa   4140
ctgaatagcc agttacactt aacagaagaa accataaaaa aaaggtaaag aaaaaagctg   4200
gactttccat agctcattta ataataaaat tattctcttt tcaacatatc tcttagatag   4260
ttcaaaagac ttgacgactg tgtcccacat ttttaaacaa aattaatcta ctcaaaattt   4320
tgccctgaga aagaataact tacttcgttt ttgcagtagc cattcatgtc actttgaaac   4380
tgtccttaca aagttaaaca ttaattaaaa attatttaat ttttatataa caaatattat   4440
attaaataaa aaatgaacaa agaacttcta agatcgtctt tagtgagtaa ttaaagagtt   4500
ttacttacca gacaaggcag tttttcatt cttttaaagc aggcagttct gaaggggaaa    4560
agggactgcc tactgcggtc ctaggtaaat acatttttat gcaatttatt tcttgtgcta   4620
gtaggtttct atactcacaa gaagcaaccc cttgacgaga gaacgttatc ctcagagtat   4680
ttataatcct gagagggaat gcactgaaga atattttcct tatttttac agaaagtaaa    4740 taaaatagcg ctaataacgc ttaattcatt taatcaatta tggcaacagg aacttctaaa   4800
gctaaaccat caaaagtaaa ttcagacttc caagaacctg gtttagttac accattaggt   4860
actttattac gtccacttaa ctcagaagca ggtaaagtat taccaggctg gggtacaact   4920
gttttaatgg ctgtatttat cctttttattt gcagcattct tattaatcat tttagaaatt   4980
tacaacagtt cttttaatttt agatgacgtt tctatgagtt gggaaacttt agctaaagtt   5040
tcttaatttt atttaacaca aacataaaat ataaaactgt tgttaaggc tagctgctaa    5100 gtcttctttt cgctaaggta aactaagcaa ctcaaccata tttatattcg gcagtggcac   5160
cgccaactgc cactgccctt ccgttaagat aaacgcgtgg atctcacgtg actagtgtcg   5220
agtggtaccg ccactgccta gtatataaat atcggcagtt ggcaggatat ttatatactc   5280
cgaaggaact tgttagccga taggcgaggc aactgccact aaaatttatt tgcctcctaa   5340
cggagcatta aaatccctaa gtttacttgc ccgtaagggg aaggggacgt ccactaatat   5400
ttatattagg cagttggcag gcaacaataa atacatttgt cccgtaaggg gacgtcctgc   5460
caactgccta tggtagctat taagtatata tatatgaaaa gtgtgtataa actaaactaa   5520
aataaaccag gtatggttaa ccagatttat tttagtttaa aaaaaaatta gttgtttgag   5580
ctagagttag ttgaagctaa gtctagatta accggttcct ttatcatcat catctttgta   5640
```

```
atcacttcca ccgccacctg agccttgaaa gtataagttt tcaccggtac ctaaacattg   5700
gctataatat ggatttaaaa cttgacatgt agttcctgat gcacacacag ttggacctga   5760
ataaccaata ccaccacatt gaccgtaatg agattgtgtt ggtccaggag aagaacctgt   5820
ggtagtagca ggacgacgtg ttgtagtggt gccaggtgga tttccacctg gtggattacc   5880
acctgaagga tcgcctgtag agccaattgg accaaatttg atattactaa aagttacttt   5940
tgcattagga ctttggcttt caacttgagc aggtacacca cttgaagttg aacatgaacc   6000
acgaacagca ccaggagtgc ttgaagtttc gtttgtagga tatgtactat ctaaccataa   6060
catattagca taatagtcat cccataatga cataactaaa accataccac ctgatgttgc   6120
tttcttgaat tgagttaaac caccttatc tgagaagctg ctaccaccaa attctgcttc    6180
ttctgctgta caataatcgt cattaaggcc gttaccagaa taagaaccta attctgcatt   6240
tggttgttga aaagttacac cattttgcac gtaataacga ttaatagcac cgctagtttc   6300
gaactgtgta caactgtta actttttagt tgtatctaat gtgaatgaac ttcctggtcc    6360
ataaaaagat gtatttccta acgatatgg gtcccaatcg cagccatcag gatcacatgt    6420
accaccataa cggttatcac tgtatgttcc accgcaaccg tcgccttcac aaatttcttg   6480
gccaacggta gtacaaggat gtggagttaa tgcttcacta attgaattag cttcccaaat   6540
atccatttca gaacaacaag atccgtgacc accaattcca gtatttgcat tattactact   6600
tggttcccaa ccttccacgt tagcttgacc gttaataaac tttaaatcac gaggacactg   6660
agaatcacaa tagcctgttc cgtatttagc acctgctgta ttagtaggat atttgcttac   6720
accgccatca gcgtccattg aaacgaaata aagagcacca tttaaaccac atggtaattg   6780
actcacatct acgtcgaaac tgaactcatt acctaataat gtaaattctt gataggttgt   6840
gtcacttgcc attaagtata aacgtgcgcc tacatttttt tgtgctgatt gagtcacgaa   6900
accaattgat aatgagttac ctgatgtagt aacgccgtaa gttgaagcgt aagctgcacc   6960
atctaaacaa caattttag cacaagtttc gttatcggga caaagtgttg atgaccaagt    7020
attaccgtca taacaattag ttgaactatt agtggcatgt gtccaacgcc agttagcatc   7080
aattactaca gagccagttt gttgtgtaca agtacctcct gaagaacatt tttgccatgt   7140
taatggagga tgagtttcag attgtaaggt acatgctgac tgtgcacgag cagtagctaa   7200
gaaagcacta ataacagcaa gtttacgata tggtaccata tgcgtgtatc tccaaaataa   7260
aaaaacaact catcgttacg ttaaatttat tattatttaa ttttaatcat tgtgtattta   7320
atattataac ttatataaaa taaaattaaa aataagcatt tttacacac atattttaa    7380 ataaatcttt aaacgggtta tatatagtta tatatatggg actagaactg ctttgtgcat   7440
agtcatcaca attattatat tataaaccat gaataaaggt tttattatta tgatataaaa   7500
atgcataaaa tttttataaa ttttgcaagt aaaatatata attaggaaaa aatttaaaat   7560
ttaaaatgtt agtcaagttt acaactaata ctttttaattt tgtatttaa gtattggaca   7620 ttttttgtgga attaaatgta ccaaatatcc atttaatttc atactagtga tatctacgta   7680
atcgatgaat tcgatcccat ttttataact ggatctcaaa ataccctataa acccattgtt   7740 cttctctttt agctctaaga acaatcaatt tataaatata tttattatta tgctataata   7800
taaatactat ataatacat ttaccttttt ataaatacat ttaccttttt tttaatttgc    7860
atgattttaa tgcttatgct atcttttta tttagtccat aaaaccttta aaggaccttt    7920
tcttatggga tatttatatt ttcctaacaa agcaatcggc gtcataaact ttagttgctt   7980
acgacgcctg tggacgtccc cccttcccc ttacgggcaa gtaaacttag ggattttaat    8040
```

```
gcaataaata aatttgtcct cttcgggcaa atgaatttta gtatttaaat atgacaaggg     8100
tgaaccatta cttttgttaa caagtgatct taccactcac tatttttgtt gaattttaaa     8160
cttatttaaa attctcgaga aagattttaa aaataaactt ttttaatctt ttatttattt     8220
tttctttttt cgtatggaat tgcccaatat tattcaacaa tttatcggaa acagcgtttt     8280
agagccaaat aaaattggtc agtcgccatc ggatgtttat tcttttaatc gaaataatga     8340 aactttttt cttaagcgat ctagcacttt atatacagag accacataca gtgtctctcg      8400
tgaagcgaaa atgttgagtt ggctctctga gaaattaaag gtgcctgaac tcatcatgac     8460
ttttcaggat gagcagtttg aatttatgat cactaaagcg atcaatgcaa accaatttc      8520 agcgcttttt ttaacagacc aagaattgct tgctatctat aaggaggcac tcaatctgtt     8580
aaattcaatt gctattattg attgtccatt tatttcaaac attgatcatc ggttaaaaga     8640
gtcaaaattt tttattgata accaactcct tgacgatata gatcaagatg attttgacac     8700
tgaattatgg ggagaccata aaacttacct aagtctatgg aatgagttaa ccgagactcg     8760
tgttgaagaa agattggttt tttctcatgg cgatatcacg gatagtaata ttttttataga    8820 taaattcaat gaaatttatt ttttagacct tggtcgtgct gggttagcag atgaatttgt     8880
agatatatcc tttgttgaac gttgcctaag agaggatgca tcggaggaaa ctgcgaaaat     8940 attttttaaag catttaaaaa atgatagacc tgacaaaagg aattatttt taaaacttga     9000 tgaattgaat tgattccaag cattatctaa aatactctgc aggcacgcta gcttgtactc     9060
aagctcgtaa cgaaggtcgt gaccttgctc gtgaaggtgg cgacgtaatt cgttcagctt     9120
gtaaatggtc tccagaactt gctgctgcat gtgaagtttg gaaagaaatt aaattcgaat     9180
ttgatactat tgacaaactt taattttttat ttttcatgat gtttatgtga atagcataaa    9240
catcgttttt atttttatgg tgtttaggtt aaatacctaa acatcatttt acatttttaa     9300
aattaagttc taaagttatc ttttgtttaa atttgcctgt ctttataaat tacgatgtgc     9360
cagaaaaata aaatcttagc ttttttattat agaatttatc tttatgtatt atatttttata   9420 agttataata aaagaaatag taacatacta aagcggatgt agcgcgttta tcttaacgga     9480
aggaattcgg cgcctacgta cccgggtcgc gaggatccac gcgttaatag ctcactttc      9540 tttaaattta attttaatt taaaggtgta agcaaattgc ctgacagag atccacttaa       9600 aggatgacag tggcgggcta ctgcctactt ccctccggga taaatttat ttgaaaaacg      9660 ttagttactt cctaacggag cattgacatc cccatattta tattaggacg tccccttcgg     9720
gtaaataaat tttagtggac gtccccttcg ggcaaataaa ttttagtgga caataaataa     9780
atttgttgcc tgccaactgc ctaggcaagt aaacttggga gtattaaaat aggacgtcag     9840
tggcagttgc ctgccaactg cctatattta tatactgcga agcaggcagt ggcggtacca     9900
ctgccactgg cgtcctaata taaatattgg gcaactaaag tttatagcag tattaacatc     9960 ctatattttat atactccgaa ggaacttgtt agccgatagg cgaggcaaca aatttattta   10020
ttgtcccgta aaaggatgcc tccagcatcg aaggggaagg ggacgtccta ggccataaaa   10080
ctaaagggaa atccatagta actgatgtta taaatttata gactccaaaa aacagctgcg   10140
ttataaataa cttctgttaa atatggccaa ggggacaggg gcactttcaa ctaagtgtac   10200
attaaaaatt gacaattcaa ttttttttaa ttataatata tatttagtaa aatataacaa   10260
aaagccccca tcgtctaggt agaattccag ctggcggccg ccctatg                 10307
```

<210> SEQ ID NO 30
<211> LENGTH: 10019
<212> TYPE: DNA

<213> ORGANISM: Artificial Sequence
<220> FEATURE:
<223> OTHER INFORMATION: Description of Artificial Sequence: Synthetic construct

<400> SEQUENCE: 30

| | |
|---|---|
| gtgcactctc agtacaatct gctctgatgc cgcatagtta agccagcccc gacacccgcc | 60 |
| aacacccgct gacgcgccct gacgggcttg tctgctcccg gcatccgctt acagacaagc | 120 |
| tgtgaccgtc tccgggagct gcatgtgtca gaggttttca ccgtcatcac cgaaacgcgc | 180 |
| gagacgaaag ggcctcgtga tacgcctatt tttataggtt aatgtcatga taataatggt | 240 |
| ttcttagacg tcaggtggca cttttcgggg aaatgtgcgc ggaacccta tttgtttatt | 300 |
| tttctaaata cattcaaata tgtatccgct catgagacaa taaccctgat aaatgcttca | 360 |
| ataatattga aaaggaaga gtatgagtat tcaacatttc cgtgtcgccc ttattccctt | 420 |
| ttttgcggca ttttgccttc ctgttttgc tcacccagaa acgctggtga agtaaaaga | 480 |
| tgctgaagat cagttgggtg cacgagtggg ttacatcgaa ctggatctca acagcggtaa | 540 |
| gatccttgag agttttcgcc ccgaagaacg ttttccaatg atgagcactt ttaaagttct | 600 |
| gctatgtggc gcggtattat cccgtattga cgccgggcaa gagcaactcg gtcgccgcat | 660 |
| acactattct cagaatgact tggttgagta ctcaccagtc acagaaaagc atcttacgga | 720 |
| tggcatgaca gtaagagaat tatgcagtgc tgccataacc atgagtgata acactgcggc | 780 |
| caacttactt ctgacaacga tcggaggacc gaaggagcta accgcttttt tgcacaacat | 840 |
| gggggatcat gtaactcgcc ttgatcgttg ggaaccggag ctgaatgaag ccataccaaa | 900 |
| cgacgagcgt gacaccacga tgcctgtagc aatggcaaca cgttgcgca aactattaac | 960 |
| tggcgaacta cttactctag cttcccggca caattaata gactggatgg aggcggataa | 1020 |
| agttgcagga ccacttctgc gctcggccct tccggctggc tggtttattg ctgataaatc | 1080 |
| tggagccggt gagcgtgggt ctcgcggtat cattgcagca ctggggccag atggtaagcc | 1140 |
| ctcccgtatc gtagttatct acacgacggg gagtcaggca actatggatg aacgaaatag | 1200 |
| acagatcgct gagataggtg cctcactgat taagcattgg taactgtcag accaagttta | 1260 |
| ctcatatata ctttagattg atttaaaact tcatttttaa tttaaaagga tctaggtgaa | 1320 |
| gatccttttt gataatctca tgaccaaaat cccttaacgt gagttttcgt tccactgagc | 1380 |
| gtcagacccc gtagaaaaga tcaaaggatc ttcttgagat ccttttttc tgcgcgtaat | 1440 |
| ctgctgcttg caaacaaaaa aaccaccgct accagcggtg gtttgtttgc cggatcaaga | 1500 |
| gctaccaact ctttttccga aggtaactgg cttcagcaga gcgcagatac caaatactgt | 1560 |
| tcttctagtg tagccgtagt taggccacca cttcaagaac tctgtagcac cgcctacata | 1620 |
| cctcgctctg ctaatcctgt taccagtggc tgctgccagt ggcgataagt cgtgtcttac | 1680 |
| cgggttggac tcaagacgat agttaccgga taaggcgcag cggtcgggct gaacggggggg | 1740 |
| ttcgtgcaca cagcccagct tggagcgaac gacctacacc gaactgagat acctacagcg | 1800 |
| tgagctatga gaaagcgcca cgcttcccga agggagaaag gcggacaggt atccggtaag | 1860 |
| cggcagggtc ggaacaggag agcgcacgag ggagcttcca gggggaaacg cctggtatct | 1920 |
| ttatagtcct gtcgggtttc gccacctctg acttgagcgt cgatttttgt gatgctcgtc | 1980 |
| aggggggcgg agcctatgga aaaacgccag caacgcggcc ttttacggt tcctggcctt | 2040 |
| ttgctggcct tttgctcaca tgttctttcc tgcgttatcc cctgattctg tggataaccg | 2100 |
| tattaccgcc tttgagtgag ctgataccgc tcgccgcagc cgaacgaccg agcgcagcga | 2160 |
| gtcagtgagc gaggaagcgg aagagcgccc aatacgcaaa ccgcctctcc ccgcgcgttg | 2220 |

```
gccgattcat taatgcagct ggcacgacag gtttcccgac tggaaagcgg gcagtgagcg    2280
caacgcaatt aatgtgagtt agctcactca ttaggcaccc caggctttac actttatgct    2340
tccggctcgt atgttgtgtg gaattgtgag cggataacaa tttcacacag gaaacagcta    2400
tgaccatgat tacgccaagc tcgcggccgc agtactctgc agattttatg caaaattaaa    2460
gtcttgtgac aacagctttc tccttaagtg caaatatcgc ccattctttc ctcttttcgt    2520
atataaatgc tgtaatagta ggatgtcgta cccgtaaagg tacgacattg aatattaata    2580
tactcctaag tttactttcc caatatttat attaggacgt ccccttcggg taaataaatt    2640
ttagtggcag tggtaccgcc actccctatt ttaatactgc gaaggaggca gttggcaggc    2700
aactcgtcgt tcgcagtata taaatatcca ctaatattta tattcccgta aggggacgtc    2760
ccgaagggga aggggaaaga agcagtcgcc tccttgcgaa aaggtttact tgcccgacca    2820
gtgaaaagca tgctgtaaga tataaatcta ccctgaaagg gatgcatttc accataatac    2880
tatacaaatg gtgttaccct tgaggatca taacggtgct actggaatat atggtctctt    2940
catggataga cgatagccat ttatttaccc attaggggga cattagtggc ctgtcactgc    3000
tccttacgag acgccagtgg acgttcgtcc tagaaaattt atgcgctgcc tagaagcccc    3060
aaaagggaag tttactgact cgttagagcg tgcgctaaca ggtttaaata cttcaatatg    3120
tatattagga cgccggtggc agtggtaccg ccactgccac cgtcggagga cgtcccttac    3180
ggtatattat atactaggat tttaatactc cgaaggaggc agtggcggta ccactgccac    3240
taatatttat attcccgtaa gggacgtcct ccttcggagt atgtaaacat tctaagttta    3300
cttgcccaat atttatatta ggcagttggc aggcaactgc tagctctcct ccttcggagt    3360
atgtaaacat cgcagtatat aaatatccac taatatttat attcccgtaa ggggacgtcc    3420
cgaaggggaa ggggaaggac gtcagtggca gttgcctgcc aactgcctag gcaagtaaac    3480
ttaggagtat ataaatatag gcagtcgcgg taccactgcc actgacgtcc tgccaactgc    3540
ctaggcaagt aaacttaagt ggcactaaaa tgcatttgcc cgaaggggaa ggaggacgcc    3600
agtggcagtg gtaccgccac tgcctccttc ggagtattaa aatcctagta tgtaaatctg    3660
ctagcgcagg aaataaattt tattctattt atatactccg ttaggaggta agtaaacccc    3720
ttccccttcg ggacgtcagt gcagttgcct gccaactgcc taatataaat attagaccac    3780
taaagtttgg caactgccaa ctgttgtcct tcggaggaaa aaaaatggtt aactcgcaag    3840
cagttaacat aactaaagtt tgttacttta ccgaagacgt ttaccctttc tcggttaagg    3900
agacggagac agttgcactg tgactgccta gtatagcaat tttgttttg tttatatgct    3960 cgacaaaatg actttcataa aaatataaag tagttagcta gttatttat atcactataa    4020 ctagggttct cagaggcacc gaagtcactt gtaaaaatag tactttttaa cttgtttaat    4080
cttcgtgttc ttcaaaagga tcacgtaatt tttttgaagg tggaccaaaa ctaacataaa    4140
ctgaatagcc agttacactt aacagaagaa accataaaaa aaaggtaaag aaaaaagctg    4200
gactttccat agctcattta ataataaaat tattctcttt tcaacatatc tcttagatag    4260
ttcaaaagac ttgacgactg tgtcccacat ttttaaacaa aattaatcta ctcaaaattt    4320
tgccctgaga aagaataact tacttcgttt ttgcagtagc cattcatgtc actttgaaac    4380
tgtccttaca aagttaaaca ttaattaaaa attatttaat ttttatataa caatattat    4440 attaaataaa aaatgaacaa agaacttcta agatcgtctt tagtgagtaa ttaaagagtt    4500
ttacttacca gacaaggcag ttttttcatt cttttaaagc aggcagttct gaaggggaaa    4560
agggactgcc tactgcggtc ctaggtaaat acatttttat gcaatttatt tcttgtgcta    4620
```

```
gtaggtttct atactcacaa gaagcaaccc cttgacgaga gaacgttatc ctcagagtat    4680
ttataatcct gagagggaat gcactgaaga atattttcct tattttttac agaaagtaaa    4740
taaaatagcg ctaataacgc ttaattcatt taatcaatta tggcaacagg aacttctaaa    4800
gctaaaccat caaaagtaaa ttcagacttc caagaacctg gtttagttac accattaggt    4860
actttattac gtccacttaa ctcagaagca ggtaaagtat taccaggctg gggtacaact    4920
gttttaatgg ctgtatttat cctttttattt gcagcattct tattaatcat tttagaaatt    4980
tacaacagtt cttttaatttt agatgacgtt tctatgagtt gggaaacttt agctaaagtt    5040
tcttaatttt atttaacaca aacataaaat ataaaactgt ttgttaaggc tagctgctaa    5100
gtcttctttt cgctaaggta aactaagcaa ctcaaccata tttatattcg gcagtggcac    5160
cgccaactgc cactggcctt ccgttaagat aaacgcgtgg atctcacgtg actagtgtcg    5220
agtggtaccg ccactgccta gtatataaat atcggcagtt ggcaggatat ttatatactc    5280
cgaaggaact tgttagccga taggcgaggc aactgccact aaaatttatt tgcctcctaa    5340
cggagcatta aaatccctaa gtttacttgc ccgtaagggg aagggacgt ccactaatat    5400 ttatattagg cagttggcag gcaacaataa atacatttgt cccgtaaggg gacgtcctgc    5460
caactgccta tggtagctat taagtatata tatatgaaaa gtgtgtataa actaaactaa    5520
aataaaccag gtatggttaa ccagatttat tttagtttaa aaaaaaatta gttgtttgag    5580
ctagagttag ttgaagctaa gtctagatta accggttcct ttatcatcat catctttgta    5640
atcacttcca ccgccacctg agccttgaaa gtataagttt tcaccggtac ccttgcgagc    5700
taaacaacta cttactaatg aagtgtctgt ccatgagttt ccagaagaag tagggggtttc    5760 ggttaataca taagttgaat caaaagaacc agcacccccaa cctacataac ctaagtacac    5820
gtcagagttt tgatttaagt actgaatttg ttgacacatg tcttggatac aactctgcac    5880
gtttccacca cctgtttcag ttaaaatggc ttggcgatta ttttgacgta accaagttgc    5940
taaaggacta aaagcaccat caatattatt tgtggtacat tcggcgtgtg ttccgctatt    6000
atcagaatca agatatttat gtacatcgaa tattaagtta gtggtactac cgtctgggtt    6060
agtcacttga ctaagagcag ctgcgctacc gtcagaaata aaagcgccgg cagattgcca    6120
atcgttgcct ggtaaactaa tgaattgtga tgttgcacca gcattacgaa tagcagttac    6180
tacttcttgc acagttgcag cccaagtatt tatgttcaca tcgtgaggtt cattcataat    6240
accgaaccaa acacgtgatt gactagcata ttttgaagct aattggctcc ataatgatgt    6300
aaattgagca ttagttggac caccttgacc aataatacca ccgttccaac gggcataatt    6360
atgaatatca acaatacaat aggcacctaa agataagcaa ccttgtacta attgatcata    6420
tttactaatt gatgtactat ctaagttacc acctaaattg ttgttaacta agtattgcca    6480
gcccactggt aaacggaaaa tagtcatacc atcttcattt acaaagtgtt gcatttgacc    6540
aatgccatct ggataattgt ttgagccagt aaaatttttt aaaggggggat aaactttact    6600 ggtaacacat gtaccatcgg tagtacaacc aaaatcgaaa cctgcaatat taacaccagc    6660
gaaacgtact ccagaagatg taggaggtgt gctgctagaa gtgctagtag cacgagttgt    6720
tgtagttgga cctgaaggag ggcgagttga tgttgttata gttgttgcac ctggaataca    6780
ttgagcatag taaggattta aggtactaca tgctgagcca ggagcacaat tggtaggacc    6840
agaccaacca ataccaccac actgaccccca aacagtctgt tgagcaacag caccaccata    6900
taagatagat gcagcaagta ataatggtgc tacgcttttg tttggtacca tatgcgtgta    6960
tctccaaaat aaaaaaacaa ctcatcgtta cgttaaattt attattattt aatttaatc    7020
```

```
attgtgtatt taatattata acttatataa aataaaatta aaaataagca ttttttacac    7080
acatattttt aaataaatct ttaaacgggt tatatatagt tatatatatg ggactagaac    7140
tgctttgtgc atagtcatca caattattat attataaacc atgaataaag gttttattat    7200
tatgatataa aaatgcataa aatttttata aattttgcaa gtaaaatata taattaggaa    7260
aaaatttaaa atttaaaatg ttagtcaagt ttacaactaa tacttttaat tttgtatttt    7320
aagtattgga cattttgtg  gaattaaatg taccaaatat ccatttaatt tcatactagt    7380
gatatctacg taatcgatga attcgatccc atttttataa ctggatctca aaatacctat    7440
aaacccattg ttcttctctt ttagctctaa gaacaatcaa tttataaata tatttattat    7500
tatgctataa tataaatact atataaatac atttaccttt ttataaatac atttaccttt    7560
tttttaattt gcatgatttt aatgcttatg ctatcttttt tatttagtcc ataaaaccttt    7620 taaaggacct tttcttatgg gatatttata ttttcctaac aaagcaatcg gcgtcataaa    7680
ctttagttgc ttacgacgcc tgtggacgtc ccccccttcc ccttacgggc aagtaaactt    7740
agggatttta atgcaataaa taaatttgtc ctcttcgggc aaatgaattt tagtatttaa    7800
atatgacaag ggtgaaccat tacttttgtt aacaagtgat cttaccactc actattttg    7860 ttgaatttta aacttattta aaattctcga gaaagatttt aaaaataaac ttttttaatc    7920
ttttatttat tttttctttt ttcgtatgga attgcccaat attattcaac aatttatcgg    7980
aaacagcgtt ttagagccaa ataaaattgg tcagtcgcca tcggatgttt attcttttaa    8040
tcgaaataat gaaactttt  ttcttaagcg atctagcact ttatatacag agaccacata    8100
cagtgtctct cgtgaagcga aaatgttgag ttggctctct gagaaattaa aggtgcctga    8160
actcatcatg acttttcagg atgagcagtt tgaatttatg atcactaaag cgatcaatgc    8220
aaaaccaatt tcagcgcttt ttttaacaga ccaagaattg cttgctatct ataaggaggc    8280
actcaatctg ttaaattcaa ttgctattat tgattgtcca tttatttcaa acattgatca    8340
tcggttaaaa gagtcaaaat ttttattga  taaccaactc cttgacgata tagatcaaga    8400
tgattttgac actgaattat ggggagacca taaaacttac ctaagtctat ggaatgagtt    8460
aaccgagact cgtgttgaag aaagattggt tttttctcat ggcgatatca cggatagtaa    8520
tatttttata gataaattca atgaaatta  ttttttagac cttggtcgtg ctgggttagc    8580
agatgaattt gtagatatat cctttgttga acgttgccta agagaggatg catcggagga    8640
aactgcgaaa atattttaa  agcatttaaa aaatgataga cctgacaaaa ggaattattt    8700
tttaaaactt gatgaattga attgattcca agcattatct aaaatactct gcaggcacgc    8760
tagcttgtac tcaagctcgt aacgaaggtc gtgaccttgc tcgtgaaggt ggcgacgtaa    8820
ttcgttcagc ttgtaaatgg tctccagaac ttgctgctgc atgtgaagtt tggaaagaaa    8880
ttaaattcga atttgatact attgacaaac tttaattttt attttcatg  atgtttatgt    8940 gaatagcata aacatcgttt ttattttat  ggtgtttagg ttaaatacct aaacatcatt    9000
ttacattttt aaaattaagt tctaaagtta tcttttgttt aaatttgcct gtctttataa    9060
attacgatgt gccagaaaaa taaatcttta gctttttatt atagaattta tctttatgta    9120
ttatatttta taagttataa taaaagaaat agtaacatac taaagcggat gtagcgcgtt    9180
tatcttaacg gaaggaattc ggcgcctacg tacccgggtc gcgaggatcc acgcgttaat    9240
agctcacttt tctttaaatt taattttta  tttaaaggtg taagcaaatt gcctgacgag    9300
agatccactt aaaggatgac agtggcgggc tactgcctac ttccctccgg gataaaattt    9360
atttgaaaaa cgttagttac ttcctaacgg agcattgaca tccccatatt tatattagga    9420
```

| | | | |
|---|---|---|---|
| cgtccccttc | gggtaaataa | attttagtgg | acgtcccctt cgggcaaata aatttagtg | 9480 |
| gacaataaat | aaatttgttg | cctgccaact | gcctaggcaa gtaaacttgg gagtattaaa | 9540 |
| ataggacgtc | agtggcagtt | gcctgccaac | tgcctatatt tatatactgc gaagcaggca | 9600 |
| gtggcggtac | cactgccact | ggcgtcctaa | tataaatatt gggcaactaa agtttatagc | 9660 |
| agtattaaca | tcctatattt | atatactccg | aaggaacttg ttagccgata ggcgaggcaa | 9720 |
| caaatttatt | tattgtcccg | taaaaggatg | cctccagcat cgaaggggaa ggggacgtcc | 9780 |
| taggccataa | aactaagggg | aaatccatag | taactgatgt tataaattta tagactccaa | 9840 |
| aaaacagctg | cgttataaat | aacttctgtt | aaatatggcc aaggggacag gggcactttc | 9900 |
| aactaagtgt | acattaaaaa | ttgacaattc | aattttttt aattataata tatatttagt | 9960 |
| aaaatataac | aaaaagcccc | catcgtctag | gtagaattcc agctggcggc cgccctatg | 10019 |

<210> SEQ ID NO 31
<211> LENGTH: 9431
<212> TYPE: DNA
<213> ORGANISM: Artificial Sequence
<220> FEATURE:
<223> OTHER INFORMATION: Description of Artificial Sequence: Synthetic
 construct

<400> SEQUENCE: 31

| | | | |
|---|---|---|---|
| gtgcactctc | agtacaatct | gctctgatgc | cgcatagtta agccagcccc gacacccgcc | 60 |
| aacacccgct | gacgcgccct | gacgggcttg | tctgctcccg gcatccgctt acagacaagc | 120 |
| tgtgaccgtc | tccgggagct | gcatgtgtca | gaggttttca ccgtcatcac cgaaacgcgc | 180 |
| gagacgaaag | ggcctcgtga | tacgcctatt | tttataggtt aatgtcatga taataatggt | 240 |
| ttcttagacg | tcaggtggca | cttttcgggg | aaatgtgcgc ggaaccccta tttgtttatt | 300 |
| tttctaaata | cattcaaata | tgtatccgct | catgagacaa taaccctgat aaatgcttca | 360 |
| ataatattga | aaaaggaaga | gtatgagtat | tcaacatttc cgtgtcgccc ttattccctt | 420 |
| ttttgcggca | ttttgccttc | ctgtttttgc | tcacccagaa acgctggtga agtaaaaga | 480 |
| tgctgaagat | cagttgggtg | cacgagtggg | ttacatcgaa ctggatctca acagcggtaa | 540 |
| gatccttgag | agttttcgcc | ccgaagaacg | ttttccaatg atgagcactt ttaaagttct | 600 |
| gctatgtggc | gcggtattat | cccgtattga | cgccgggcaa gagcaactcg gtcgccgcat | 660 |
| acactattct | cagaatgact | tggttgagta | ctcaccagtc acagaaaagc atcttacgga | 720 |
| tggcatgaca | gtaagagaat | tatgcagtgc | tgccataacc atgagtgata acactgcggc | 780 |
| caacttactt | ctgacaacga | tcggaggacc | gaaggagcta accgcttttt tgcacaacat | 840 |
| gggggatcat | gtaactcgcc | ttgatcgttg | ggaaccggag ctgaatgaag ccataccaaa | 900 |
| cgacgagcgt | gacaccacga | tgcctgtagc | aatggcaaca acgttgcgca aactattaac | 960 |
| tggcgaacta | cttactctag | cttcccggca | acaattaata gactggatgg aggcggataa | 1020 |
| agttgcagga | ccacttctgc | gctcggccct | tccggctggc tggtttattg ctgataaatc | 1080 |
| tggagccggt | gagcgtgggt | ctcgcggtat | cattgcagca ctggggccag atggtaagcc | 1140 |
| ctcccgtatc | gtagttatct | acacgacggg | gagtcaggca actatggatg aacgaaatag | 1200 |
| acagatcgct | gagataggtg | cctcactgat | taagcattgg taactgtcag accaagttta | 1260 |
| ctcatatata | ctttagattg | atttaaaact | tcatttttaa tttaaaagga tctaggtgaa | 1320 |
| gatcctttt | gataatctca | tgaccaaaat | cccttaacgt gagttttcgt tccactgagc | 1380 |
| gtcagacccc | gtagaaaaga | tcaaaggatc | ttcttgagat cctttttttc tgcgcgtaat | 1440 |

```
ctgctgcttg caaacaaaaa aaccaccgct accagcggtg gtttgtttgc cggatcaaga   1500
gctaccaact cttttttccga aggtaactgg cttcagcaga gcgcagatac caaatactgt   1560
tcttctagtg tagccgtagt taggccacca cttcaagaac tctgtagcac cgcctacata   1620
cctcgctctg ctaatcctgt taccagtggc tgctgccagt ggcgataagt cgtgtcttac   1680
cgggttggac tcaagacgat agttaccgga taaggcgcag cggtcgggct gaacgggggg   1740
ttcgtgcaca cagcccagct tggagcgaac gacctacacc gaactgagat acctacagcg   1800
tgagctatga gaaagcgcca cgcttcccga agggagaaag gcggacaggt atccggtaag   1860
cggcagggtc ggaacaggag agcgcacgag ggagcttcca gggggaaacg cctggtatct   1920
ttatagtcct gtcgggtttc gccacctctg acttgagcgt cgattttttgt gatgctcgtc   1980 agggggggcgg agcctatgga aaaacgccag caacgcggcc ttttttacggt tcctggcctt   2040 ttgctggcct tttgctcaca tgttctttcc tgcgttatcc cctgattctg tggataaccg   2100
tattaccgcc tttgagtgag ctgataccgc tcgccgcagc cgaacgaccg agcgcagcga   2160
gtcagtgagc gaggaagcgg aagagcgccc aatacgcaaa ccgcctctcc ccgcgcgttg   2220
gccgattcat taatgcagct ggcacgacag gtttcccgac tggaaagcgg gcagtgagcg   2280
caacgcaatt aatgtgagtt agctcactca ttaggcaccc caggctttac actttatgct   2340
tccggctcgt atgttgtgtg gaattgtgag cggataacaa tttcacacag gaaacagcta   2400
tgaccatgat tacgccaagc tcgcggccgc agtactctgc agattttatg caaaattaaa   2460
gtcttgtgac aacagctttc tccttaagtg caaatatcgc ccattctttc ctcttttcgt   2520
atataaatgc tgtaatagta ggatgtcgta cccgtaaagg tacgacattg aatattaata   2580
tactcctaag tttactttcc caatatttat attaggacgt ccccttcggg taaataaatt   2640
ttagtggcag tggtaccgcc actccctatt ttaatactgc gaaggaggca gttggcaggc   2700
aactcgtcgt tcgcagtata taaatatcca ctaatattta tattcccgta aggggacgtc   2760
ccgaagggga aggggaaaga agcagtcgcc tccttgcgaa aaggtttact tgcccgacca   2820
gtgaaaagca tgctgtaaga tataaatcta ccctgaaagg gatgcatttc accataatac   2880
tatacaaatg gtgttaccct ttgaggatca taacggtgct actggaatat atggtctctt   2940
catggataga cgatagccat ttatttaccc attaagggga cattagtggc ctgtcactgc   3000
tccttacgag acgccagtgg acgttcgtcc tagaaaattt atgcgctgcc tagaagcccc   3060
aaaagggaag tttactgact cgttagagcg tgcgctaaca ggtttaaata cttcaatatg   3120
tatattagga cgccggtggc agtggtaccg ccactgccac cgtcggagga cgtcccttac   3180
ggtatattat atactaggat tttaatactc cgaaggaggc agtggcggta ccactgccac   3240
taatatttat attcccgtaa gggacgtcct ccttcggagt atgtaaacat tctaagttta   3300
cttgcccaat atttatatta ggcagttggc aggcaactgc tagctctcct ccttcggagt   3360
atgtaaacat cgcagtatat aaatatccac taatatttat attcccgtaa ggggacgtcc   3420
cgaaggggaa ggggaaggac gtcagtggca gttgcctgcc aactgcctag gcaagtaaac   3480
ttaggagtat ataaatatag gcagtcgcgg taccactgcc actgacgtcc tgccaactgc   3540
ctaggcaagt aaacttaagt ggcactaaaa tgcatttgcc cgaaggggaa ggaggacgcc   3600
agtggcagtg gtaccgccac tgcctccttc ggagtattaa aatccagta tgtaaatctg   3660 ctagcgcagg aaataaattt tattctattt atatactccg ttaggaggta agtaaacccc   3720
ttccccttcg gacgtcagt gcagttgcct gccaactgcc taatataaat attagaccac   3780
taaagtttgg caactgccaa ctgttgtcct tcggaggaaa aaaaatggtt aactcgcaag   3840
```

```
cagttaacat aactaaagtt tgttacttta ccgaagacgt ttacccttc tcggttaagg      3900 agacggagac agttgcactg tgactgccta gtatagcaat tttgttttg tttatatgct      3960 cgacaaaatg actttcataa aaatataaag tagttagcta gttatttat atcactataa      4020 ctagggttct cagaggcacc gaagtcactt gtaaaaatag tacttttaa cttgtttaat      4080 cttcgtgttc ttcaaaagga tcacgtaatt ttttgaagg tggaccaaaa ctaacataaa      4140
ctgaatagcc agttacactt aacagaagaa accataaaaa aaggtaaag aaaaaagctg      4200 gactttccat agctcattta ataataaat tattctcttt tcaacatatc tcttagatag      4260
ttcaaaagac ttgacgactg tgtcccacat ttttaaacaa aattaatcta ctcaaaattt      4320
tgccctgaga aagaataact tacttcgttt ttgcagtagc cattcatgtc actttgaaac      4380
tgtccttaca aagttaaaca ttaattaaaa attatttaat ttttatataa caaatattat      4440
attaaataaa aaatgaacaa agaacttcta agatcgtctt tagtgagtaa ttaaagagtt      4500
ttacttacca gacaaggcag ttttttcatt cttttaaagc aggcagttct gaaggggaaa      4560
agggactgcc tactgcggtc ctaggtaaat acatttttat gcaatttatt tcttgtgcta      4620
gtaggtttct atactcacaa gaagcaaccc cttgacgaga gaacgttatc ctcagagtat      4680
ttataatcct gagagggaat gcactgaaga atattttcct tatttttac agaaagtaaa      4740 taaaatagcg ctaataacgc ttaattcatt taatcaatta tggcaacagg aacttctaaa      4800
gctaaaccat caaaagtaaa ttcagacttc caagaacctg gtttagttac accattaggt      4860
actttattac gtccacttaa ctcagaagca ggtaaagtat taccaggctg gggtacaact      4920
gttttaatgg ctgtatttat ccttttattt gcagcattct tattaatcat tttagaaatt      4980
tacaacagtt cttaattttt agatgacgtt tctatgagtt gggaaacttt agctaaagtt      5040
tcttaatttt atttaacaca aacataaaat ataaactgt ttgttaaggc tagctgctaa      5100 gtcttcttt cgctaaggta aactaagcaa ctcaaccata tttatattcg gcagtggcac      5160
cgccaactgc cactggcctt ccgttaagat aaacgcgtgg atctcacgtg actagtgtcg      5220
agtggtaccg ccactgccta gtatataaat atcggcagtt ggcaggatat ttatatactc      5280
cgaaggaact tgttagccga taggcgaggc aactgccact aaaatttatt tgcctcctaa      5340
cggagcatta aaatccctaa gtttacttgc ccgtaagggg aagggacgt ccactaatat      5400 ttatattagg cagttggcag gcaacaataa atacatttgt cccgtaaggg gacgtcctgc      5460
caactgccta tggtagctat taagtatata tatatgaaaa gtgtgtataa actaaactaa      5520
aataaaccag gtatggttaa ccagatttat tttagtttaa aaaaaaatta gttgtttgag      5580
ctagagttag ttgaagctaa gtctagatta accggttcct ttatcatcat catctttgta      5640
atcacttcca ccgccacctg agccttgaaa gtataagttt tcaccggtac cgctaacagt      5700
gatagaagca ctacctgatg aaaaataacc ttcaacagct acaatttgat agtccattgt      5760
acctaatgtt aaaccttgtt gagcccatgc attaaagtgg tttgctgtat taacactacc      5820
acttgaacga tgattacgtc ttacactcca gtattggtag aaagtggcag ttccaattat      5880
agatggttga tttacgcgtt gagtacgata aatatcataa actgatccat ctgaagtaac      5940
ttcacctaat ttagtagcac ctgttgaagg gttgtatgta ccaaagttct ctacaatata      6000
atattcaatt aatgggttac ggctccaacc gtatacactt aaataagaat taccattagg      6060
gttgtaacta ccagagaaat tgattacctt attctttgta ccaggttgcc aacctttcc      6120 tccaacaaaa ttgcctgagt tactccaatt tacactaaat tgaccaccag gtccattagt      6180
atatgtaaca ccaccgtgtc catcattcca gtaagaataa agtaaccgt tattgtaacc      6240
```

```
tgtacctggt tgaattgttt gacgtttttc tactgcaact gattccactt cagcagctgg    6300
acggcaactt gcacgtgaag gtggagatgc tgctaaaaga cttgtgaaag atactggtac    6360
catatgcgtg tatctccaaa ataaaaaaac aactcatcgt tacgttaaat ttattattat    6420
ttaattttaa tcattgtgta tttaatatta taacttatat aaaataaaat taaaaataag    6480 catttttttac acacatattt ttaaataaat ctttaaacgg gttatatata gttatatata    6540
tgggactaga actgctttgt gcatagtcat cacaattatt atattataaa ccatgaataa    6600
aggttttatt attatgatat aaaaatgcat aaaattttta taaattttgc aagtaaaata    6660
tataattagg aaaaaattta aaatttaaaa tgttagtcaa gttacaact aatacttta     6720 attttgtatt ttaagtattg gacatttttg tggaattaaa tgtaccaaat atccatttaa    6780
tttcatacta gtgatatcta cgtaatcgat gaattcgatc ccatttttat aactggatct    6840
caaaatacct ataaacccat tgttcttctc ttttagctct aagaacaatc aatttataaa    6900
tatatttatt attatgctat aatataaata ctatataaat acatttacct ttttatataat   6960 acatttacct tttttttaat ttgcatgatt ttaatgctta tgctatcttt tttatttagt    7020
ccataaaacc tttaaaggac cttttcttat gggatattta tattttccta acaaagcaat    7080
cggcgtcata aactttagtt gcttacgacg cctgtggacg tccccccctt ccccttacgg    7140
gcaagtaaac ttagggattt taatgcaata aataaatttg tcctcttcgg gcaaatgaat    7200
tttagtattt aaatatgaca agggtgaacc attacttttg ttaacaagtg atcttaccac    7260
tcactatttt tgttgaattt taaacttatt taaaattctc gagaaagatt ttaaaaataa    7320
acttttttaa tcttttattt atttttttctt ttttcgtatg gaattgccca atattattca    7380
acaatttatc ggaaacagcg ttttagagcc aaataaaatt ggtcagtcgc catcggatgt    7440
ttattctttt aatcgaaata atgaaacttt ttttcttaag cgatctagca ctttatatac    7500
agagaccaca tacagtgtct ctcgtgaagc gaaaatgttg agttggctct ctgagaaatt    7560
aaaggtgcct gaactcatca tgactttca ggatgagcag tttgaattta tgatcactaa     7620
agcgatcaat gcaaaaccaa tttcagcgct tttttaaca gaccaagaat tgcttgctat    7680
ctataaggag gcactcaatc tgttaaattc aattgctatt attgattgtc catttatttc    7740
aaacattgat catcggttaa aagagtcaaa atttttatt gataaccaac tccttgacga     7800
tatagatcaa gatgattttg acactgaatt atggggagac cataaaactt acctaagtct    7860 atgaatgag ttaaccgaga ctcgtgttga agaaagattg gttttttctc atggcgatat     7920 cacgatagt aatatttta tagataaatt caatgaaatt tatttttag accttggtcg       7980 tgctgggtta gcagatgaat tgtagatat atcccttgtt gaacgttgcc taagagagga    8040
tgcatcggag gaaactgcga aaatatttt aaagcattta aaaaatgata gacctgacaa     8100
aaggaattat tttttaaaac ttgatgaatt gaattgattc caagcattat ctaaatact     8160 ctgcaggcac gctagcttgt actcaagctc gtaacgaagg tcgtgacctt gctcgtgaag    8220
gtggcgacgt aattcgttca gcttgtaaat ggtctccaga acttgctgct gcatgtgaag    8280 tttgaaaga aattaaattc gaatttgata ctattgacaa actttaattt ttattttca      8340 tgatgtttat gtgaatagca taaacatcgt ttttattttt atggtgttta ggttaaatac    8400
ctaaacatca ttttacatt ttaaaattaa gttctaaagt tatctttgt ttaaatttgc      8460 ctgtctttat aaattacgat gtgccagaaa ataaaatct tagcttttta ttatagaatt     8520
tatctttatg tattatattt tataagttat aataaaagaa atagtaacat actaaagcgg    8580
atgtagcgcg tttatcttaa cggaaggaat tcggcgccta cgtacccggg tcgcgaggat    8640
```

-continued

```
ccacgcgtta atagctcact tttctttaaa tttaattttt aatttaaagg tgtaagcaaa    8700
ttgcctgacg agagatccac ttaaaggatg acagtggcgg gctactgcct acttccctcc    8760
gggataaaat ttatttgaaa aacgttagtt acttcctaac ggagcattga catccccata    8820
tttatattag gacgtcccct tcgggtaaat aaattttagt ggacgtcccc ttcgggcaaa    8880
taaattttag tggacaataa ataaatttgt tgcctgccaa ctgcctaggc aagtaaactt    8940
gggagtatta aaataggacg tcagtggcag ttgcctgcca actgcctata tttatatact    9000
gcgaagcagg cagtggcggt accactgcca ctggcgtcct aatataaata ttgggcaact    9060
aaagtttata gcagtattaa catcctatat ttatatactc cgaaggaact tgttagccga    9120
taggcgaggc aacaaattta tttattgtcc cgtaaaagga tgcctccagc atcgaagggg    9180
aagggacgt cctaggccat aaaactaaag ggaaatccat agtaactgat gttataaatt     9240
tatagactcc aaaaaacagc tgcgttataa ataacttctg ttaaatatgg ccaaggggac    9300
aggggcactt tcaactaagt gtacattaaa aattgacaat tcaatttttt ttaattataa    9360
tatatattta gtaaaatata acaaaaagcc cccatcgtct aggtagaatt ccagctggcg    9420
gccgccctat g                                                        9431
```

US 8,669,059 B2

HIGH THROUGHPUT SCREENING OF GENETICALLY MODIFIED PHOTOSYNTHETIC ORGANISMS

CROSS REFERENCE TO RELATED CASES

This application is a continuation of U.S. patent application Ser. No. 12/156,432, filed May 30, 2008 (pending), which claims the benefit of U.S. Provisional Application No. 60/941,452, filed Jun. 1, 2007, U.S. Provisional Application No. 61/070,384, filed Mar. 20, 2008, and also U.S. Provisional Application No. 61/070,437, filed Mar. 20, 2008, each of which are herein incorporated by reference in their entireties.

INCORPORATION OF SEQUENCE LISTING

The file named "P33775US02SeqList.txt," which is 164,845 bytes in size (measured in Windows XP) and which was created on Aug. 6, 2012, is herein expressly incorporated by reference.

BACKGROUND OF THE INVENTION

Fuel is becoming increasingly more expensive. Also, fuel refinery is associated with the generation of pollutants and global warming. There is an increasing need in the industry to find cheaper, safer, and more environmentally unharmful ways to generate fuels. The development of means to produce fuel from biological material is an essential component of the future energy landscape. One of the most important elements in the production of fuel from biologic materials is the ability to digest or reduce certain molecular structures, such as cellulose, to molecular species recognizable as substrate for fuel generating processes, such as fermentation.

Molecular biology and genetic engineering hold promise for the production of large quantities of biologically active molecules that can be used to produce such fuels. For example, production of enzymes capable of breaking down organic materials into fuels hold promise to address the increasing needs for alternative fuels. A primary advantage of using genetic engineering techniques for producing such enzymes is that the methods allow for the generation of large amounts of a desired protein. In many cases, the only other way to obtain sufficient quantities of biological materials from non-engineered secretion sources is by purifying the naturally occurring biological material from cells of an organism that produce the agent. Thus, prior to the advent of genetic engineering, enzymes capable of degrading organic materials could only be isolated by growing the organism, typically a bacterial or fungal species, in large quantities and extracting the protein. Such procedures are often complex and economically prohibitive for use in fuel production.

Although genetic engineering provides a means to produce large amounts of a biological material, particularly proteins and nucleic acids, there are limitations to currently available methods. Bacteria provide an environment suitable to the production of such enzymes; however, byproducts produced by some bacteria would contaminate fuel sources. Thus, even where bacteria can be used to produce the biological material, additional steps such as purification or refining may be required to obtain biologically active material and/or biofuel. Furthermore, the use of non-photosynthetic systems requires the addition of costly sugar or other organic carbon sources to feed the recombinant organism. Additionally, there is typically a large capital investment associated with building fermenters.

Recombinant proteins also can be produced in eukaryotic cells, including, for example, fungi, insect cells and mammalian cells, which may provide the necessary environment to process an expressed protein into a biologically active agent. However, these systems typically suffer from the same cost prohibitions (sugar/organic carbon sources and fermenters). Thus, a need exists for methods to conveniently produce enzymes that are biologically active, can produce large quantities of enzymes and/or provide a host organism which is compatible with production of degradative enzymes.

SUMMARY OF THE INVENTION

Presented herein are compositions and methods for the production of biomass degrading enzymes and biofuels. The inventions disclosed herein provide novel methods for the production of biomass degrading enzymes, typically in genetically modified photosynthetic organisms such as algae and cyanobacteria. Also presented herein are compositions and methods for transforming photosynthetic organisms and methods of screening transformants.

Accordingly, one aspect of the present invention provides a vector comprising a nucleic acid encoding a biomass degrading enzyme and a promoter configured for expression of the nucleic acids in a non-vascular photosynthetic organism. Vectors of the present invention may contain nucleic acids encoding more than one biomass degrading enzyme and, in other instances, may contain nucleic acids encoding polypeptides which covalently link biomass degrading enzymes. Biomass degrading enzymes may include cellulolytic enzymes, hemicellulolytic enzymes and ligninolytic enzymes. More specifically, the biomass degrading enzymes may be exo-β-glucanase, endo-β-glucanase, β-glucosidase, endoxylanase, or lignase. Nucleic acids encoding the biomass degrading enzymes may be derived from fungal or bacterial sources, for example, those encoding exo-β-glucanase in *Trichoderma viride*, exo-β-glucanase in *Trichoderma reesei*, exo-β-glucanase in *Aspergillus aculeatus*, endo-β-glucanase in *Trichoderma reesei*, endo-β-glucanase in *Aspergillus niger*, β-glucosidase in *Trichoderma reesei*, β-glucosidase in *Aspergillus niger* endoxylanase in *Trichoderma reesei*, and endoxylanase in *Aspergillus niger*. Other nucleic acids encoding biomass degrading enzymes may be homologous to the genes from these organisms A vector of the present invention may also contain a selectable marker, allowing for direct screening of transformed organisms. The vectors of the present invention may be capable of stable transformation of multiple photosynthetic organisms, including, but not limited to, photosynthetic bacteria (including cyanobacteria), cyanophyta, prochlorophyta, rhodophyta, chlorophyta, heterokontophyta, tribophyta, glaucophyta, chlorarachniophytes, euglenophyta, euglenoids, haptophyta, chrysophyta, cryptophyta, cryptomonads, dinophyta, dinoflagellata, pyrmnesiophyta, bacillariophyta, xanthophyta, eustigmatophyta, raphidophyta, phaeophyta, and phytoplankton. Other vectors of the present invention are capable of stable transformation of *C. reinhardtii*, *D. salina* or *H. pluvalis*. Still other vectors contain nucleic acids which are biased to an organism's (e.g., *C. reinhardtii*) codon preference. Specific vectors of the present invention contain sequences provided herein (SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, or SEQ ID NO. 27).

Host cells comprising the vectors of the present invention are also provided. In some instances, the host cell is a non-vascular photosynthetic organism, for example, an organism classified as photosynthetic bacteria (including cyanobacteria), cyanophyta, prochlorophyta, rhodophyta, chlorophyta, heterokontophyta, tribophyta, glaucophyta, chlorarachniophytes, euglenophyta, euglenoids, haptophyta, chrysophyta, cryptophyta, cryptomonads, dinophyta, dinoflagellata, pyrmnesiophyta, bacillariophyta, xanthophyta, eustigmatophyta, raphidophyta, phaeophyta, and phytoplankton. A host cell of the present invention may also be a microalga species including, but not limited to, *C. reinhardtii, D. salina* or *H. pluvalis*. In other instances, the host cell may be one or more cells of a multicellular photosynthetic organism. For some embodiments, the host cell may be grown in the absence of light and/or in the presence of an organic carbon source.

The present invention also provides compositions containing one or more exogenous biomass degrading enzymes derived from one or more non-vascular photosynthetic organisms. In some instances, these compositions may also contain elements of the non-vascular photosynthetic organisms. The ratio (w/w) of enzymes to elements of the organisms may be at least 1:10, or the elements may be found only in trace amounts. Some of the compositions comprise at least one of the following enzymes: exo-β-glucanase, endo-β-glucanase, β-glucosidase, endoxylanase, and/or lignase; where the enzyme(s) is isolated from one or more of the following organisms: *C. reinhardtii, D. salina, H. pluvalis*, photosynthetic bacteria (including cyanobacteria), cyanophyta, prochlorophyta, rhodophyta, chlorophyta, heterokontophyta, tribophyta, glaucophyta, chlorarachniophytes, euglenophyta, euglenoids, haptophyta, chrysophyta, cryptophyta, cryptomonads, dinophyta, dinoflagellata, pyrmnesiophyta, bacillariophyta, xanthophyta, eustigmatophyta, raphidophyta, phaeophyta, and phytoplankton. For some embodiments, the organism may be grown in the absence of light and/or in the presence of an organic carbon source.

The present invention also provides a composition containing a plurality of vectors each of which encodes a different biomass degrading enzyme and a promoter for expression of said biomass degrading enzymes in a chloroplast. Such compositions may contain multiple copies of a particular vector encoding a particular enzyme. In some instances, the vectors will contain nucleic acids encoding cellulolytic, hemicellulolytic and/or ligninolytic enzymes. More specifically, the plurality of vectors may contain vectors capable of expressing exo-β-glucanase, endo-β-glucanase, β-glucosidase, endoxylanase and/or lignase. Some of the vectors of this embodiment are capable of insertion into a chloroplast genome and such insertion can lead to disruption of the photosynthetic capability of the transformed chloroplast. Insertion of other vectors into a chloroplast genome does not disrupt photosynthetic capability of the transformed chloroplast. Some vectors provide for expression of biomass degrading enzymes which are sequestered in a transformed chloroplast. Still other vectors may contain specific sequences provided herein (SEQ ID NO. 19, SEQ ID NO. 20, SEQ ID NO. 21, SEQ ID NO. 22, or SEQ ID NO. 23, SEQ ID NO. 24, SEQ ID NO. 25, SEQ ID NO. 26, or SEQ ID NO. 27). The present invention also provides an algal cell containing the vector compositions described above and specifically provides *C. reinhardtii, D. salina* or *H. pluvalis* cells containing the vector compositions. For some embodiments, the cell may be grown in the absence of light and/or in the presence of an organic carbon source.

Another vector of the present invention encodes a plurality of distinct biomass degrading enzymes and a promoter for expression of the biomass degrading enzymes in a non-vascular photosynthetic organism. The biomass degrading enzymes may be one or more of cellulollytic, hemicellulolytic or ligninolytic enzymes. In some vectors, the plurality of distinct biomass degrading enzymes is two or more of exo-β-glucanase, endo-β-glucanase, β-glucosidase, lignase and endoxylanase. In some embodiments, the plurality of enzymes is operatively linked. In other embodiments, the plurality of enzymes is expressed as a functional protein complex. Insertion of some vectors into a host cell genome does not disrupt photosynthetic capability of the organism. Vectors encoding a plurality of distinct enzymes, may lead to production of enzymes which are sequestered in a chloroplast of a transformed organism. The present invention also provides an algal cell or cyanobacterial cell transformed with a vector encoding a plurality of distinct enzymes. In some instances, the algal cell is *C. reinhardtii, D. salina* or *H. pluvalis*. In other instances, the cyanobacterial cell is a species of the genus *Synechocystis* or the genus *Synechococcus* or the genus *Athrospira*. For some embodiments, the organism may be grown in the absence of light and/or in the presence of an organic carbon source.

Yet another aspect of the present invention provides a genetically modified chloroplast producing one or more biomass degrading enzymes. Such enzymes may be cellulolytic, hemicellulolytic or ligninolytic enzymes, and more specifically, may be an exo-β-glucanase, an endo-β-glucanase, a β-glucosidase, an endoxylanase, a lignase and/or combinations thereof. The one or more enzymes are be sequestered in the chloroplast in some embodiments. The present invention also provides photosynthetic organisms containing the genetically modified chloroplasts of the present invention.

Yet another aspect provides a method for preparing a biomass-degrading enzyme. This method comprises the steps of (1) transforming a photosynthetic, non-vascular organism to produce or increase production of said biomass-degrading enzyme and (2) collecting the biomass-degrading enzyme from said transformed organism. Transformation may be conducted with a composition containing a plurality of different vectors encoding different biomass degrading enzymes. Transformation may also be conducted with a vector encoding a plurality of distinct biomass degrading enzymes. Any or all of the enzymes may be operatively linked to each other. In some instances, a chloroplast is transformed. This method of the invention may have one or more additional steps, including: (a) harvesting transformed organisms; (b) drying transformed organisms; (c) harvesting enzymes from a cell medium; (d) mechanically disrupting transformed organisms; or (e) chemically disrupting transformed organisms. The method may also comprise further purification of an enzyme through performance liquid chromatography. In some instances the transformed organism is an alga or a photosynthetic bacteria, e.g., cyanobacteria. For some embodiments, the organism may be grown in the absence of light and/or in the presence of an organic carbon source.

Still another method of the present invention allows for preparing a biofuel. One step of this method includes treating a biomass with one or more biomass degrading enzymes derived from a photosynthetic, non-vascular organism for a sufficient amount of time to degrade at least a portion of said biomass. The biofuel produced may be ethanol. The enzymes of this method may contain at least traces of said photosynthetic non-vascular organism from which they are derived. Additionally, the enzymes useful for some embodiments of this method include cellulolytic, hemicellulolytic and ligninolytic enzymes. Specific enzymes useful for some aspects of this method include exo-β-glucanase, endo-β-glucanase, β-glucosidase, endoxylanase, and/or lignase. The organisms of this method may include photosynthetic bacteria (including cyanobacteria), cyanophyta, prochlorophyta, rhodophyta, chlorophyta, heterokontophyta, tribophyta, glaucophyta, chlorarachniophytes, euglenophyta, euglenoids, haptophyta, chrysophyta, cryptophyta, cryptomonads, dinophyta, dinoflagellata, pyrmnesiophyta, bacillariophyta, xanthophyta, eustigmatophyta, raphidophyta, phaeophyta, and phytoplankton. Other organisms used for this method are microalgae including, but not limited to *C. reinhardtii, D. salina* and *H. pluvalis*. For some embodiments, the organism may be grown in the absence of light and/or in the presence of an organic carbon source. Multiple types of biomass including agricultural waste, paper mill waste, corn stover, wheat stover, soy stover, switchgrass, duckweed, poplar trees, woodchips, sawdust, wet distiller grain, dray distiller grain, human waste, newspaper, recycled paper products, or human garbage may be treated with this method of the invention. Biomass may also be derived from a high-cellulose content organism, such as switchgrass or duckweed. The enzyme(s) used in this method may be liberated from the organism and this liberation may involve chemical or mechanical disruption of the cells of the organism. In an alternate embodiment, the enzyme(s) are secreted from the organism and then collected from a culture medium. The treatment of the biomass may involve a fermentation process, which may utilize a microorganism other than the organism which produced the enzyme(s). In some instances the non-vascular photosynthetic organism may be added to a saccharification tank. This method of the invention may also comprise the step of collecting the biofuel. Collection may be performed by distillation. In some instances, the biofuel is mixed with another fuel.

An additional method of the present invention provides for making at least one biomass degrading enzyme by transforming a chloroplast to make a biomass degrading enzyme. The biomass degrading enzyme may be a cellulolytic enzyme, a hemicellulolytic enzyme, or a ligninolytic enzyme, and specifically may be exo-β-glucanase, endo-β-glucanase, β-glucosidase, endoxylanase, or lignase. In some instances, the biomass degrading enzyme is sequestered in the transformed chloroplast. The method may further involve disrupting, via chemical or mechanical means, the transformed chloroplast to release the biomass degrading enzyme(s). In some instances, multiple enzymes will be produced by a transformed chloroplast. The biomass degrading enzymes may be of fungal or bacterial origin, for example, exo-β-glucanase, endo-β-glucanase, β-glucosidase, endoxylanase, lignase, or a combination thereof.

Yet another method of the present invention provides for screening a transformed non-vascular photosynthetic organism, by amplifying a first nucleic acid sequence from a chloroplast of said organism and amplifying a second nucleic acid sequence from said chloroplast of said organism and determining the plasmic state of said organism based on results from amplification of said first sequence and second sequence. In some instances the first and second amplifying step is performed simultaneously. The first nucleic acid sequence may be an endogenous chloroplast genome sequence and the second nucleic acid sequence may be at least partially from an exogenous nucleic acid. In some instances, a third nucleic acid sequence from the chloroplast may be amplified as a control. This third nucleic acid sequence may be a wild-type sequence that remains intact after integration of exogenous nucleic acid(s). Where this third nucleic acid is amplified, such amplification may be performed concurrently with the first or second amplifying step, or all three amplifications may be performed concurrently. For amplifications of this method, the specific primers provided herein—SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, or SEQ ID NO. 15—may be utilized. Amplification of the first and/or second nucleic acid may utilize more than thirty cycles of PCR. In some instances, determining the plasmic state is performed by visual analysis of products from the amplifying steps. One or more amplifications may be performed using real-time or quantitative PCR.

The plasmic state determined by this method may be homoplasmy and the organism tested may be a microalga, specifically, one of the microalga species *C. reinhardtii, D. salina* or *H. pluvalis*. In this method, the organism may contain an exogenous nucleic acid which contains a gene of interest and a selectable marker. The gene of interest may encode a biomass degrading enzyme, for example a cellulolytic, hemicellulolytic or lignolytic enzyme. Specifically, the biomass degrading enzyme may be exo-β-glucanase, endo-β-glucanase, β-glucosidase, endoxylanase or lignase. Additionally, the exogenous nucleic acid may be one of the nucleic acids specifically provided herein—SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, or SEQ ID NO. 31.

The present invention also provides a non-vascular photosynthetic organism containing a homoplasmic chloroplast population, where the chloroplast population comprises an exogenous nucleic acid and where the homoplasmic state of the chloroplast population is determined by at least two different PCR reactions. In some instances, the chloroplast population is more than one chloroplast. The non-vascular photosynthetic organism may be a microalga, specifically one of the species *C. reinhardtii, D. salina* or *H. pluvalis*. The organism may be screened using at least two different PCR reactions performed simultaneously. These PCR reactions may utilize one of the specific primers disclosed herein—SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, or SEQ ID NO. 15. The PCR reactions may utilize more than thirty cycles.

The organism may contain an exogenous nucleic acid comprising at least one gene of interest and a selectable marker. This gene may encode a biomass degrading enzyme, specifically a cellulolytic, hemicellulolytic or ligninolytic enzyme. Even more specifically, the biomass degrading enzyme may be exo-β-glucanase, endo-β-glucanase, β-glucosidase, endoxylanase or lignase. The exogenous nucleic acid present in this organism of the present invention may be on of the nucleic acids specifically described herein—SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, or SEQ ID NO. 31.

Another method is provided herein for producing a genetically-modified homoplasmic non-vascular photosynthetic organism. This method involves transforming at least one chloroplast of the organism with an exogenous nucleic acid, amplifying a first nucleic acid sequence and a second nucleic acid sequence, and determining the plasmic state of the organism based on results from the amplifying step. The first and second nucleic acid sequences may be within the chloroplast genome. Additionally, the first nucleic acid sequence may be an endogenous chloroplast sequence. The second nucleic acid sequence may be at least partially from the exogenous nucleic acid. This method may also involve amplifying a third nucleic acid sequence from the chloroplast as a control. In some instances the third nucleic acid is a wild-type sequence that remains intact after integration of an exogenous nucleic acid. This method may involve PCR using one of the specifically disclosed primers herein—SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, or SEQ ID NO. 15. Amplification of the first and second nucleic acid sequences may utilize more than thirty cycles of PCR. The determination of plasmic state using this method may involve visual analysis of the products of the amplifying step(s).

The plasmic state determined by this method may be homoplasmy and the organism may be a microalga, specifically one of the species C. reinhardtii, D. salina or H. pluvalis. The exogenous nucleic acid may contain at least one gene of interest and a selectable marker. In some instances, the gene of interest encodes a biomass degrading enzyme, specifically a cellulolytic, hemicellulolytic or ligninolytic enzyme. Even more specifically the biomass degrading enzyme may be exo-β-glucanase, endo-β-glucanase, β-glucosidase, endoxylanase or lignase. Moreover, the exogenous nucleic acid may be one specifically described herein—SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, or SEQ ID NO. 31.

Another embodiment of the present invention is a kit for determining plasmic state of a genetically-modified non-vascular photosynthetic organism. Such a kit may contain amplification primer(s) for amplifying a first nucleic acid sequence of a chloroplast genome corresponding to an endogenous sequence and amplification primer(s) for amplifying a second nucleic acid sequence of a chloroplast genome that is an introduced or non-naturally occurring sequence. A kit may also contain a PCR buffer and/or amplification primer(s) for amplifying a control nucleic acid sequence. A kit may contain one or more of the PCR primers specifically disclosed herein—SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, or SEQ ID NO. 15. The primer(s) for amplifying a first nucleic acid sequence in a kit of the present invention, may bind to at least a portion of a psbA 5'UTR, a psbA coding sequence, an psbC 5' UTR, a psbD 5' UTR, an atpA 5' UTR, or a 3HB locus. In some instances, at least one of the primer(s) for amplifying a second nucleic acid sequence will bind to at least a portion of a sequence encoding a biomass degrading enzyme, such as a cellulolytic, hemicellulolytic or ligninolytic enzyme. Specific biomass degrading enzymes encoded by the second nucleic acid may be exo-β-glucanase, endo-β-glucanase, β-glucosidase, endoxylanase or lignase. The primers may amplify at least a portion of one or more of the sequences specifically disclosed herein—SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, or SEQ ID NO. 31. Additionally, the kit may contain instructions for use.

SUMMARY OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 illustrates primer pairs for PCR screening of transformants and expected band profiles for wild-type, heteroplasmic and homoplasmic strains.

FIG. 4 illustrates results from PCR screening and Western blot analysis of endo-β-glucanase transformed C. reinhardtii clones.

FIG. 7 illustrates results from PCR screening and Western blot analysis of endoxylanase transformed C. reinhardtii clones.

FIG. 8 illustrates determination of the level of endo-β-glucanase protein produced by transformed C. reinhardtii clones.

FIG. 14 illustrates results from PCR screening and Western blot analysis of endo-β-glucanase transformed C. reinhardtii clones.

FIG. 16 illustrates results from PCR screening and Western blot analysis of exo-β-glucanase transformed C. reinhardtii clones.

FIG. 17 illustrates activity of bacterially-produced biomass degrading enzymes.

DETAILED DESCRIPTION OF THE INVENTION

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991. Standard reference literature teaching general methodologies and principles of yeast genetics useful for selected aspects of the invention include: Sherman et al. "Laboratory Course Manual Methods in Yeast Genetics", Cold Spring Harbor Laboratory, Cold Spring Harbor, N.Y., 1986 and Guthrie et al., "Guide to Yeast Genetics and Molecular Biology", Academic, New York, 1991.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges can independently be included or excluded in the range, and each range where either, neither or both limits are included in the smaller ranges is also encompassed, subject to any specifically excluded limit in the stated range. Where the stated range includes one or both of the limits, ranges excluding either or both of those included limits are also included.

The present invention relates to the production of enzymes, e.g., biomass degrading enzymes, by genetically modified organisms. Another aspect of the present invention relates to compositions and methods for using biologic material to create products, such as ethanol, using biomass degrading enzymes produced by photosynthetic microorganisms, such as, but not limited to, algae. Typically, photosynthetic organisms do not possess all of the necessary enzymes to degrade biomass. The present invention takes advantage of the ability to introduce exogenous nucleic acids into algal cells, and particularly into the chloroplasts of those cells. One advantage of using molecular biology and genetic engineering to create enzyme-expressing and/or enzymatic pathway-expressing algal strains is the potential for the production of large quantities of active enzymes.

Figure 1:
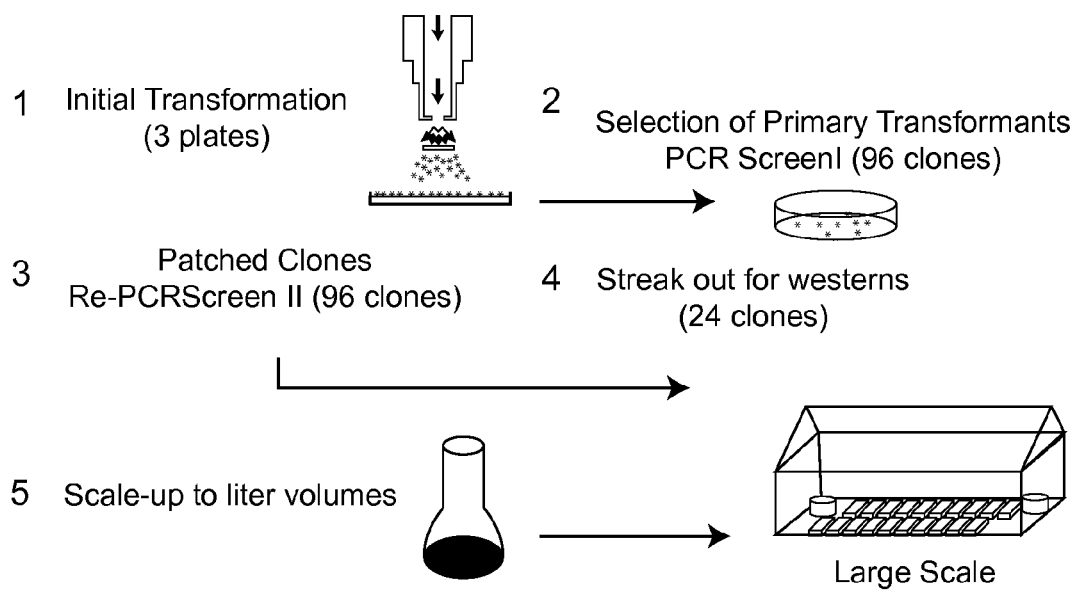
FIG. 1 illustrates transformation of alga cells, selection, confirmation, and scaling of production of enzymes.

One approach to construction of a genetically manipulated strain of alga is diagramed as a flow chart in FIG. 1. As can be seen, alga cells (e.g., *Chlamydomonas reinhardti, Dunaliella salina, Hematococcus pluvalis*) are transformed with a nucleic acid which encodes a gene of interest, typically a biomass degrading enzyme. In some embodiments, a transformation may introduce nucleic acids into any plastid of the host alga cell (e.g., chloroplast). Transformed cells are typically plated on selective media following introduction of exogenous nucleic acids. This method may also comprise several steps for screening. Initially, a screen of primary transformants is typically conducted to determine which clones have proper insertion of the exogenous nucleic acids. Clones which show the proper integration may be patched and re-screened to ensure genetic stability. Such methodology ensures that the transformants contain the genes of interest. In many instances, such screening is performed by polymerase chain reaction (PCR); however, any other appropriate technique known in the art may be utilized. Many different methods of PCR are known in the art (e.g., nested PCR, real time PCR). For any given screen, one of skill in the art will recognize that PCR components may be varied to achieve optimal screening results. For example, magnesium concentration may need to be adjusted upwards when PCR is performed on disrupted alga cells as many such organisms have magnesium chelators. In such instances, magnesium concentration may need to be adjusted upward, or downward (compared to the standard concentration in commercially available PCR kits) by 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 mM. Thus, after adjusting, final magnesium concentration in a PCR reaction may be, for example 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5 mM or higher. Particular examples are utilized in the examples described herein; however, one of skill in the art will recognize that other PCR techniques may be substituted for the particular protocols described. Following screening for clones with proper integration of exogenous nucleic acids, typically clones are screened for the presence of the encoded protein. Protein expression screening typically is performed by Western blot analysis and/or enzyme activity assays.

Following confirmation of nucleic acid integration and/or protein expression, selected clones may be scaled up for production of biofuels through biomass degradation, first in smaller volumes of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more liters. Following initial scaling up, larger scale degradation of biomass may be performed in larger quantities. One example of a partially closed bioreactor system is shown in FIG. 1, step 6. However, growth of the transformed strains for biomass degradation and/or biofuel production can also be accomplished in man-made structures such as ponds, aqueducts, reservoirs and/or landfills. Alternately, the strains can also be grown directly in naturally occurring bodies of water, e.g., in ocean, sea, lakes, or rivers. In some cases, transformed strains are grown near ethanol production plants or other facilities. Alternately, the biomass degrading cells may be grown near regions (e.g., electrical generating plants, concrete plants, oil refineries, other industrial facilities, cities, highways, etc.) generating $CO_2$. As such, the methods disclosed herein further contemplate business methods for selling carbon credits to ethanol plants or other facilities or regions generating $CO_2$ while making or catalyzing the production of fuels by growing one or more of the modified organisms described herein near the ethanol production plant.

The present invention contemplates making biomass degrading enzymes by transforming host cells (e.g., alga cells such as *C. reinhardtii, D. salina, H. pluvalis* and cyanobacterial cells) and/or organisms comprising host cells with nucleic acids encoding one or more different biomass degrading enzymes (e.g., cellulolytic enzymes, hemicellulolytic enzymes, xylanases, lignases and cellulases). In some embodiments, a single enzyme may be produced. For example, a cellulase which breaks down pretreated cellulose fragments into double glucose molecules (cellobiose) or a cellulase which splits cellobiose into glucose, may be produced.

Some host cells may be transformed with multiple genes encoding one or more enzymes. For example, a single transformed cell may contain exogenous nucleic acids encoding an entire biodegradation pathway. One example of a pathway might include genes encoding an exo-β-glucanase (acts on the cellulose end chain), an endo-β-glucanase (acts on the interior portion of a cellulose chain), β-glucosidase (avoids reaction inhibitors by/degrades cellobiose), and endoxylanase (acts on hemicellulose cross linking). Such cells transformed with entire pathways and/or enzymes extracted from them, can degrade certain components of biomass. Constructs may contain multiple copies of the same gene, and/or multiple genes encoding the same enzyme from different organisms, and/or multiple genes with mutations in one or more parts of the coding sequences.

Alternately, biomass degradation pathways can be created by transforming host cells with the individual enzymes of the pathway and then combining the cells producing the individual enzymes. This approach allows for the combination of enzymes to more particularly match the biomass of interest by altering the relative ratios of the multiple transformed strains. For example, two times as many cells expressing the first enzyme of a pathway may be added to a mix where the first step of the reaction pathway is the limiting step.

Following transformation with enzyme-encoding constructs, the host cells and/or organisms are grown. The biomass degrading enzymes may be collected from the organisms/cells. Collection may be by any means known in the art, including, but not limited to concentrating cells, mechanical or chemical disruption of cells, and purification of enzymes from cell cultures and/or cell lysates. Cells and/or organisms can be grown and then the enzyme(s) collected by any means. One method of extracting the enzyme is by harvesting the host cell or a group of host cells and then drying the host cell(s). The enzyme(s) from the dried host cell(s) are then harvested by crushing the cells to expose the enzyme. The whole product of crushed cells is then used to degrade biomass. Many methods of extracting proteins from intact cells are well known in the art, and are also contemplated herein (e.g., introducing an exogenous nucleic acid construct in which an enzyme-encoding sequence is operably linked to a sequence encoding a secretion signal—excreted enzyme is isolated from the growth medium). Following extraction of the protein from the cells/organisms and/or the surrounding medium, the protein may be purified from the crude extract such that the enzyme may comprise 1, 2, 3, 4, 5, 6, 7, 8, 9, 10, 11, 12, 13, 14, 15, 16, 17, 18, 19, 20, 30, 40, 50, 60, 70, 80, 90, 95, 99 percent or higher of the total protein. Purification steps include, but are not limited to, using HPLC, affinity columns, and antibody-based purification methods.

Extracting and utilizing the biomass-degrading enzyme can also be accomplished by expressing a vector containing nucleic acids that encode a biomass production-modulation molecule in the host cell. In this embodiment, the host cell produces the biomass, and also produces a biomass-degrading enzyme. The biomass-degrading enzyme can then degrade the biomass produced by the host cell. In some instances, vector used for the production of a biomass-degrading enzyme may not be continuously active. Such vectors can comprise one or more activatable promoters and one or more biomass-degrading enzymes. Such promoters activate the production of biomass-degrading enzymes, for example, after the biomass has grown to sufficient density or reached certain maturity.

A method of the invention can be performed by introducing a recombinant nucleic acid molecule into a chloroplast, wherein the recombinant nucleic acid molecule includes a first polynucleotide, which encodes at least one polypeptide (i.e., 1, 2, 3, 4, or more). In some embodiments, a polypeptide is operatively linked to a second, third, fourth, fifth, sixth, seventh, eighth, ninth, tenth and/or subsequent polypeptide. For example, several enzymes in a biodegradation pathway may be linked, either directly or indirectly, such that products produced by one enzyme in the pathway, once produced, are in close proximity to the next enzyme in the pathway.

For transformation of chloroplasts, one major benefit of the present invention is the utilization of a recombinant nucleic acid construct which contains both a selectable marker and one or more genes of interest. Typically, transformation of chloroplasts is performed by co-transformation of chloroplasts with two constructs: one containing a selectable marker and a second containing the gene(s) of interest. Screening of such transformants is laborious and time consuming for multiple reasons. First, the time required to grow some transformed organisms is lengthy. Second, transformants must be screened both for presence of the selectable marker and for the presence of the gene(s) of interest. Typically, secondary screening for the gene(s) of interest is performed by Southern blot (see, e.g. PCT/US2007/072465).

Figure 2:
FIG. 2 illustrates two constructs for insertion of a gene into a chloroplast genome.
Figure 2:
Figure 12A:
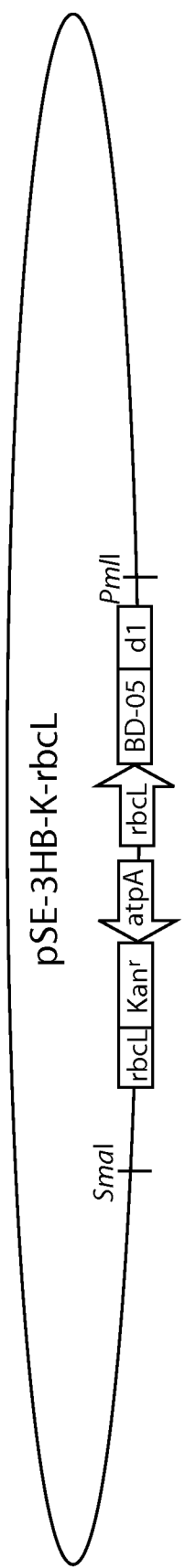
FIG. 12 is a graphic representation of two exogenous DNA constructs for insertion into a chloroplast genome.
Figure 12B:
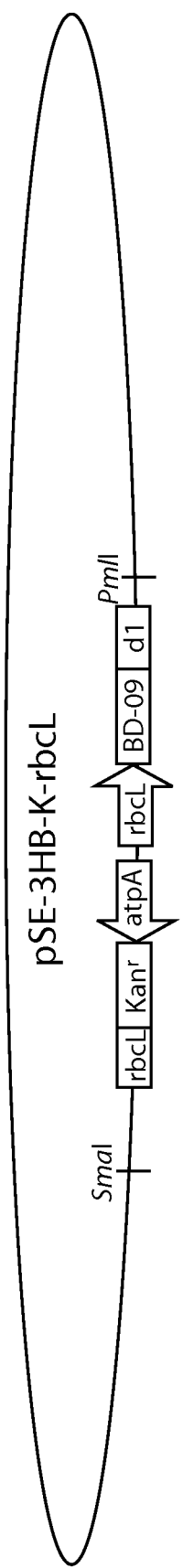

Constructs of the current invention (FIG. 2, FIG. 9 and FIG. 12), allow for a PCR-based screening method in which transformants can be screened using a combination of primers specific for the insert and wild-type sequences (FIG. 3, lanes: G—gene specific reaction; C—control reaction; WT—wild type reaction; M—multiplex). This methodology provides a rapid screening process and advances over older techniques. For example, selection of transformants receiving unlinked markers inherently yields a lower percentage of clones with the transgenes. Because of this, the likelihood of obtaining homoplasmic lines from a primary transformation is low. By linking the marker and the gene(s) of interest, the likelihood of obtaining transgenic clones with the transgene, especially homoplasmic clones, is improved on the first pass. Specific PCR protocols for screening transformants are detailed in the Examples below, but one of skill in the art will recognize that these protocols may be altered to provide quantitative analysis of transformants. For example, different ratios of primers for a particular reaction may be utilized to compare insert copy number to a control reaction. Such variation may be performed where the multiplex reactions (FIG. 3, row M) are run concurrently or separately.

Determination of insert copy number may be important in some embodiments where an optimal level of expression of the exogenous gene(s) of interest is, in part, determined by gene copy number. For example, transformation of an alga host cell (e.g., *C. reinhardtii, D. salina, H. pluvalis*) which results in incorporation of the exogenous nucleic acid in less than half of the copies of the chloroplast genomes in a cell may yield little or no detectable expression of the gene(s) of interest. Alternately, incorporation of exogenous nucleic acid in all the copies of the chloroplast genomes in a cell may yield little or no detectable expression of the gene(s) of interest where there are few initial copies of the genome (e.g., quantitative PCR analysis will allow for exclusion of homoplasmic clones which have low insert copy number, and thus may not have sufficiently high production of the gene and/or polypeptide of interest). In other embodiments, there may be an optimum level of incorporation of exogenous nucleic acid. In some instances, exogenous DNA may encode a protein which, whether through transcriptional, translational, or other control mechanisms, is optimally produced when it is present in a particular range of copy number. Thus, determining the copy number of such exogenous DNA, for example by quantitative PCR, may allow selection and/or production of transformed organisms which produce protein(s) of interest at an efficient level.

Additionally, recombinant nucleic acid molecules of the present invention may be operatively linked to a second and/or subsequent nucleotide sequence. For example, the nucleotide sequences encoding enzymes of a biodegradation pathway may be operatively linked such that expression of these sequences may be controlled with a single inducing stimulus or controlled by a single transcriptional activator. Such systems are similar to bacterial operons (e.g., the *Escherischia coli* Lac operon). However, these groupings of operatively linked nucleotide sequences in the present invention are synthetic and designed to function in plant plastids, preferably are incorporated into the chloroplast genome.

As used herein, the term "operatively linked" means that two or more molecules are positioned with respect to each other such that they act as a single unit and affect a function attributable to one or both molecules or a combination thereof. For example, a polynucleotide encoding a polypeptide can be operatively linked to a transcriptional or translational regulatory element, in which case the element confers its regulatory effect on the polynucleotide similarly to the way in which the regulatory element would affect a polynucleotide sequence with which it normally is associated with in a cell. A first polynucleotide coding sequence also can be operatively linked to a second (or more) coding sequence such that a chimeric polypeptide can be expressed from the operatively linked coding sequences. The chimeric polypeptide produced from such a construct can be a fusion protein, in which the two (or more) encoded peptides are translated into a single polypeptide, i.e., are covalently bound through a peptide bond, either directly or with a short spacer region.

In chloroplasts, regulation of gene expression generally occurs after transcription, and often during translation initiation. This regulation is dependent upon the chloroplast translational apparatus, as well as nuclear-encoded regulatory factors (see Barkan and Goldschmidt-Clermont, *Biochemie* 82:559-572, 2000; Zerges, *Biochemie* 82:583-601, 2000). The chloroplast translational apparatus generally resembles that in bacteria; chloroplasts contain 70S ribosomes; have mRNAs that lack 5' caps and generally do not contain 3' poly-adenylated tails (Harris et al., *Microbiol. Rev.* 58:700-754, 1994); and translation is inhibited in chloroplasts and in bacteria by selective agents such as chloramphenicol.

Some methods of the present invention take advantage of proper positioning of a ribosome binding sequence (RBS) with respect to a coding sequence. It has previously been noted that such placement of an RBS results in robust translation in plant chloroplasts (see U.S. Application 2004/0014174, incorporated herein by reference), and that polypeptides that an advantage of expressing polypeptides in chloroplasts is that the polypeptides do not proceed through cellular compartments typically traversed by polypeptides expressed from a nuclear gene and, therefore, are not subject to certain post-translational modifications such as glycosylation. As such, the polypeptides and protein complexes produced by some methods of the invention can be expected to be produced without such post-translational modification.

The following discussion is provided by way of background only and applicant does not intend the disclosed invention to be limited, either in scope, or by theory, to the disclosure of mechanisms of chloroplast gene regulation. In chloroplasts, ribosome binding and proper translation start site selection are thought to be mediated, at least in part, by cis-acting RNA elements. One example of a potential regulator has been identified within the 5'UTR's of chloroplast mRNAs (Alexander et al., *Nucl. Acids Res.* 26:2265-2272, 1998; Hirose and Sugiura, *EMBO J.* 15:1687-1695, 1996; Mayfield et al., *J. Cell Biol.* 127:1537-1545, 1994; Sakamoto et al., *Plant J.* 6:503-512, 1994, each of which is incorporated herein by reference). These elements may interact with nuclear-encoded factors.

Many chloroplast mRNAs contain elements resembling prokaryotic RBS elements (Bonham-Smith and Bourque, *Nucl. Acids Res.* 17:2057-2080, 1989; Ruf and Kossel, *FEBS Lett.* 240:41-44, 1988, each of which is incorporated herein by reference). However, the functional utility of these RBS sequences in chloroplast translation has been unclear as several studies have shown differing effects of these elements on translation (Betts and Spremulli, *J. Biol. Chem.* 269:26456-26465, 1994; Hirose et al., *FEBS Lett.* 430:257-260, 1998; Fargo et al., *Mol. Gen. Genet.* 257:271-282, 1998; Koo and Spremulli, *J. Biol. Chem.* 269:7494-7500, 1994; Rochaix, *Plant Mol. Biol.* 32:327-341, 1996). Interpretation of these results has been complicated by the lack of a consensus for chloroplast RBS elements, and because the mutations generated to study these putative RBS sequences may have altered the context of other important sequences within the 5'UTR.

Some aspects (e.g., vectors) of the present invention may include an RBS. Such RBSs can be chemically synthesized, or can be isolated from a naturally occurring nucleic acid molecule (e.g., isolation from a chloroplast gene). In addition, to an RBS, embodiments with a 5'UTR can include transcriptional regulatory elements such as a promoter. As with RBSs utilized for the present invention, a 5'UTR may be chemically synthesized, or can be isolated from a naturally occurring nucleic acid molecule. Non-limiting examples of 5'UTRs which may be used for the present invention include, but art not limited to, an atpA 5'UTR; a psbC 5'UTR, a psbD 5'UTR, a psbA 5'UTR, a rbcL 5'UTR and/or a 16S rRNA 5'UTR. A ribonucleotide sequence may further include an initiation codon, (e.g., an AUG codon), operatively linked to an RBS. Initiation codons may be endogenous (e.g., naturally occurring in a cloned gene) or can be synthetic (e.g., inserted in a linker polypeptide or PCR primer).

An isolated ribonucleotide sequence may be obtained by any method known in the art, including, but not limited to being chemically synthesized, generated using an enzymatic method, (e.g., generated from a DNA or RNA template using a DNA dependent RNA polymerase or an RNA dependent RNA polymerase). A DNA template encoding the ribonucleotide of the invention can be chemically synthesized, can be isolated from a naturally occurring DNA molecule, or can be derived from a naturally occurring DNA sequence that is modified to have the required characteristics.

The term "polynucleotide" or "nucleotide sequence" or "nucleic acid molecule" is used broadly herein to mean a sequence of two or more deoxyribonucleotides or ribonucleotides that are linked together by a phosphodiester bond. As such, the terms include RNA and DNA, which can be a gene or a portion thereof, a cDNA, a synthetic polydeoxyribonucleic acid sequence, or the like, and can be single stranded or double stranded, as well as a DNA/RNA hybrid. Furthermore, the terms as used herein include naturally occurring nucleic acid molecules, which can be isolated from a cell, as well as synthetic polynucleotides, which can be prepared, for example, by methods of chemical synthesis or by enzymatic methods such as by the polymerase chain reaction (PCR). It should be recognized that the different terms are used only for convenience of discussion so as to distinguish, for example, different components of a composition, except that the term "synthetic polynucleotide" as used herein refers to a polynucleotide that has been modified to reflect chloroplast codon usage.

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. Depending on the use, however, a polynucleotide also can contain nucleotide analogs, including non-naturally occurring synthetic nucleotides or modified naturally occurring nucleotides. Nucleotide analogs are well known in the art and commercially available, as are polynucleotides containing such nucleotide analogs (Lin et al., *Nucl. Acids Res.* 22:5220-5234, 1994; Jellinek et al., *Biochemistry* 34:11363-11372, 1995; Pagratis et al., *Nature Biotechnol.* 15:68-73, 1997). Generally, a phosphodiester bond links the nucleotides of a polynucleotide of the present invention, however other bonds, including a thiodiester bond, a phosphorothioate bond, a peptide-like bond and any other bond known in the art may be utilized to produce synthetic polynucleotides (Tam et al., *Nucl. Acids Res.* 22:977-986, 1994; Ecker and Crooke, *BioTechnology* 13:351360, 1995).

A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally are chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995). Polynucleotides useful for practicing a method of the present invention may be isolated from any organism. Typically, the biodegradative enzymes utilized in practicing the present invention are encoded by nucleotide sequences from bacteria or fungi. Non-limiting examples of such enzymes and their sources are shown in Table I. Such polynucleotides may be isolated and/or synthesized by any means known in the art, including, but not limited to cloning, sub-cloning, and PCR.

One or more codons of an encoding polynucleotide can be biased to reflect chloroplast codon usage. Most amino acids are encoded by two or more different (degenerate) codons, and it is well recognized that various organisms utilize certain codons in preference to others. Such preferential codon usage, which also is utilized in chloroplasts, is referred to herein as "chloroplast codon usage". The codon bias of *Chlamydomonas reinhardtii* has been reported. See U.S. Application 2004/0014174.

The term "biased," when used in reference to a codon, means that the sequence of a codon in a polynucleotide has been changed such that the codon is one that is used preferentially in the target which the bias is for, e.g., alga cells, chloroplasts, or the like. A polynucleotide that is biased for chloroplast codon usage can be synthesized de novo, or can be genetically modified using routine recombinant DNA techniques, for example, by a site directed mutagenesis method, to change one or more codons such that they are biased for chloroplast codon usage. Chloroplast codon bias can be variously skewed in different plants, including, for example, in alga chloroplasts as compared to tobacco. Generally, the chloroplast codon bias selected reflects chloroplast codon usage of the plant which is being transformed with the nucleic acids of the present invention. For example, where *C. reinhardtii* is the host, the chloroplast codon usage is biased to reflect alga chloroplast codon usage (about 74.6% AT bias in the third codon position).

One method of the invention can be performed using a polynucleotide that encodes a first polypeptide and at least a second polypeptide. As such, the polynucleotide can encode, for example, a first polypeptide and a second polypeptide; a first polypeptide, a second polypeptide, and a third polypeptide; etc. Furthermore, any or all of the encoded polypeptides can be the same or different. The polypeptides expressed in chloroplasts of the microalga *C. reinhardtii* may be assembled to form functional polypeptides and protein complexes. As such, a method of the invention provides a means to produce functional protein complexes, including, for example, dimers, trimers, and tetramers, wherein the subunits of the complexes can be the same or different (e.g., homodimers or heterodimers, respectively).

The term "recombinant nucleic acid molecule" is used herein to refer to a polynucleotide that is manipulated by human intervention. A recombinant nucleic acid molecule can contain two or more nucleotide sequences that are linked in a manner such that the product is not found in a cell in nature. In particular, the two or more nucleotide sequences can be operatively linked and, for example, can encode a fusion polypeptide, or can comprise an encoding nucleotide sequence and a regulatory element. A recombinant nucleic acid molecule also can be based on, but manipulated so as to be different, from a naturally occurring polynucleotide, (e.g. biased for chloroplast codon usage, insertion of a restriction enzyme site, insertion of a promoter, insertion of an origin of replication). A recombinant nucleic acid molecule may further contain a peptide tag (e.g., His-6 tag), which can facilitate identification of expression of the polypeptide in a cell. Additional tags include, for example: a FLAG epitope, a c-myc epitope; biotin; and glutathione S-transferase. Such tags can be detected by any method known in the art (e.g., anti-tag antibodies, streptavidin). Such tags may also be used to isolate the operatively linked polypeptide(s), for example by affinity chromatography.

Composition:

Nucleic Acids

The compositions herein comprise nucleic acids which encode one or more different biomass degrading enzymes and/or one or more different biomass-production modulating agent and vectors of such nucleic acids. The nucleic acids can be heterologous to a photosynthetic host cell to which they are inserted. The vector can include one or a plurality of copies of the nucleic acids which encode the biomass degrading enzymes and/or one or a plurality of copies of the nucleic acids which encode the biomass-production modulating agents. When using a plurality of copies, at least 2, 3, 4, 5, 6 7, 8, 9, or 10 copies of the nucleic acids (e.g., encoding a single biomass degrading enzyme) can be inserted into a single vector. This allows for an increased level of their production in the host cell.

A recombinant nucleic acid molecule useful in a method of the invention can be contained in a vector. Furthermore, where the method is performed using a second (or more) recombinant nucleic acid molecules, the second recombinant nucleic acid molecule also can be contained in a vector, which can, but need not, be the same vector as that containing the first recombinant nucleic acid molecule. The vector can be any vector useful for introducing a polynucleotide into a chloroplast and, preferably, includes a nucleotide sequence of chloroplast genomic DNA that is sufficient to undergo homologous recombination with chloroplast genomic DNA, for example, a nucleotide sequence comprising about 400 to 1500 or more substantially contiguous nucleotides of chloroplast genomic DNA. Chloroplast vectors and methods for selecting regions of a chloroplast genome for use as a vector are well known (see, for example, Bock, J. Mol. Biol. 312: 425-438, 2001; see, also, Staub and Maliga, *Plant Cell* 4:39-45, 1992; Kavanagh et al., *Genetics* 152:1111-1122, 1999, each of which is incorporated herein by reference).

In some instances, such vectors include promoters. Promoters useful for the present invention may come from any source (e.g., viral, bacterial, fungal, protist, animal). The promoters contemplated herein can be specific to photosynthetic organisms, non-vascular photosynthetic organisms, and vascular photosynthetic organisms (e.g., algae, flowering plants). As used herein, the term "non-vascular photosynthetic organism," refers to any macroscopic or microscopic organism, including, but not limited to, algae, cyanobacteria and photosynthetic bacteria, which does not have a vascular system such as that found in higher plants. In some instances, the nucleic acids above are inserted into a vector that comprises a promoter of a photosynthetic organism, e.g., algae. The promoter can be a promoter for expression in a chloroplast and/or other plastid. In some instances, the nucleic acids are chloroplast based. Examples of promoters contemplated for insertion of any of the nucleic acids herein into the chloroplast include those disclosed in US Application No. 2004/0014174. The promoter can be a constitutive promoter or an inducible promoter. A promoter typically includes necessary nucleic acid sequences near the start site of transcription, (e.g., a TATA element).

A "constitutive" promoter is a promoter that is active under most environmental and developmental conditions. An "inducible" promoter is a promoter that is active under environmental or developmental regulation. Examples of inducible promoters/regulatory elements include, for example, a nitrate-inducible promoter (Back et al, *Plant Mol. Biol.* 17:9 (1991)), or a light-inducible promoter, (Feinbaum et al, Mol Gen. Genet. 226:449 (1991); Lam and Chua, Science 248:471 (1990)), or a heat responsive promoter (Muller et al., Gene 111: 165-73 (1992)).

The entire chloroplast genome of *C. reinhardtii* is available to the public on the world wide web, at the URL "biology.duke.edu/chlamy_genome/-chloro.html" (see "view complete genome as text file" link and "maps of the chloroplast genome" link), each of which is incorporated herein by reference (J. Maul, J. W. Lilly, and D. B. Stern, unpublished results; revised Jan. 28, 2002; to be published as GenBank Acc. No. AF396929). Generally, the nucleotide sequence of the chloroplast genomic DNA is selected such that it is not a portion of a gene, including a regulatory sequence or coding sequence, particularly a gene that, if disrupted due to the homologous recombination event, would produce a deleterious effect with respect to the chloroplast, for example, for replication of the chloroplast genome, or to a plant cell containing the chloroplast. In this respect, the website containing the *C. reinhardtii* chloroplast genome sequence also provides maps showing coding and non-coding regions of the chloroplast genome, thus facilitating selection of a sequence useful for constructing a vector of the invention. For example, the chloroplast vector, p322, which was used in experiments disclosed herein, is a clone extending from the Eco (Eco RI) site at about position 143.1 kb to the Xho (Xho I) site at about position 148.5 kb (see, world wide web, at the URL "biology.duke.edu/chlamy_genome/chloro.html", and clicking on "maps of the chloroplast genome" link, and "140-150 kb" link; also accessible directly on world wide web at URL "biology.duke.edu/chlamy/chloro/chloro140.html"; see, also, Example 1).

A vector utilized in the practice of the invention also can contain one or more additional nucleotide sequences that confer desirable characteristics on the vector, including, for example, sequences such as cloning sites that facilitate manipulation of the vector, regulatory elements that direct replication of the vector or transcription of nucleotide sequences contain therein, sequences that encode a selectable marker, and the like. As such, the vector can contain, for example, one or more cloning sites such as a multiple cloning site, which can, but need not, be positioned such that a heterologous polynucleotide can be inserted into the vector and operatively linked to a desired element. The vector also can contain a prokaryote origin of replication (ori), for example, an *E. coli* ori or a cosmid ori, thus allowing passage of the vector in a prokaryote host cell, as well as in a plant chloroplast, as desired.

A regulatory element, as the term is used herein, broadly refers to a nucleotide sequence that regulates the transcription or translation of a polynucleotide or the localization of a polypeptide to which it is operatively linked. Examples include, but are not limited to, an RBS, a promoter, enhancer, transcription terminator, an initiation (start) codon, a splicing signal for intron excision and maintenance of a correct reading frame, a STOP codon, an amber or ochre codon, an IRES. Additionally, a cell compartmentalization signal (i.e., a sequence that targets a polypeptide to the cytosol, nucleus, chloroplast membrane or cell membrane). Such signals are well known in the art and have been widely reported (see, e.g., U.S. Pat. No. 5,776,689).

A vector or other recombinant nucleic acid molecule may include a nucleotide sequence encoding a reporter polypeptide or other selectable marker. The term "reporter" or "selectable marker" refers to a polynucleotide (or encoded polypeptide) that confers a detectable phenotype. A reporter generally encodes a detectable polypeptide, for example, a green fluorescent protein or an enzyme such as luciferase, which, when contacted with an appropriate agent (a particular wavelength of light or luciferin, respectively) generates a signal that can be detected by eye or using appropriate instrumentation (Giacomin, *Plant Sci.* 116:59-72, 1996; Scikantha, *J. Bacteriol.* 178:121, 1996; Gerdes, *FEBS Lett.* 389:44-47, 1996; see, also, Jefferson, *EMBO J.* 6:3901-3907, 1997, fl-glucuronidase). A selectable marker generally is a molecule that, when present or expressed in a cell, provides a selective advantage (or disadvantage) to the cell containing the marker, for example, the ability to grow in the presence of an agent that otherwise would kill the cell.

A selectable marker can provide a means to obtain prokaryotic cells or plant cells or both that express the marker and, therefore, can be useful as a component of a vector of the invention (see, for example, Bock, supra, 2001). Examples of selectable markers include, but are not limited to, those that confer antimetabolite resistance, for example, dihydrofolate reductase, which confers resistance to methotrexate (Reiss, *Plant Physiol.* (*Life Sci. Adv.*) 13:143-149, 1994); neomycin phosphotransferase, which confers resistance to the aminoglycosides neomycin, kanamycin and paromycin (Herrera-Estrella, *EMBO J.* 2:987-995, 1983), hygro, which confers resistance to hygromycin (Marsh, *Gene* 32:481-485, 1984), trpB, which allows cells to utilize indole in place of tryptophan; hisD, which allows cells to utilize histinol in place of histidine (Hartman, *Proc. Natl. Acad. Sci., USA* 85:8047, 1988); mannose-6-phosphate isomerase which allows cells to utilize mannose (WO 94/20627); ornithine decarboxylase, which confers resistance to the ornithine decarboxylase inhibitor, 2-(difluoromethyl)-DL-ornithine (DFMO; McConlogue, 1987, In: Current Communications in Molecular Biology, Cold Spring Harbor Laboratory ed.); and deaminase from *Aspergillus terreus*, which confers resistance to Blasticidin S (Tamura, *Biosci. Biotechnol. Biochem.* 59:2336-2338, 1995). Additional selectable markers include those that confer herbicide resistance, for example, phosphinothricin acetyltransferase gene, which confers resistance to phosphinothricin (White et al., *Nucl. Acids Res.* 18:1062, 1990; Spencer et al., *Theor. Appl. Genet.* 79:625-631, 1990), a mutant EPSPV-synthase, which confers glyphosate resistance (Hinchee et al., *BioTechnology* 91:915-922, 1998), a mutant acetolactate synthase, which confers imidazolione or sulfonylurea resistance (Lee et al., *EMBO J.* 7:1241-1248, 1988), a mutant psbA, which confers resistance to atrazine (Smeda et al., *Plant Physiol.* 103:911-917, 1993), or a mutant protoporphyrinogen oxidase (see U.S. Pat. No. 5,767,373), or other markers conferring resistance to an herbicide such as glufosinate. Selectable markers include polynucleotides that confer dihydrofolate reductase (DHFR) or neomycin resistance for eukaryotic cells and tetracycline; ampicillin resistance for prokaryotes such as *E. coli*; and bleomycin, gentamycin, glyphosate, hygromycin, kanamycin, methotrexate, phleomycin, phosphinotricin, spectinomycin, streptomycin, sulfonamide and sulfonylurea resistance in plants (see, for example, Maliga et al., Methods in Plant Molecular Biology, Cold Spring Harbor Laboratory Press, 1995, page 39).

Reporter genes have been successfully used in chloroplasts of higher plants, and high levels of recombinant protein expression have been reported. In addition, reporter genes have been used in the chloroplast of *C. reinhardtii*, but, in most cases very low amounts of protein were produced. Reporter genes greatly enhance the ability to monitor gene expression in a number of biological organisms. In chloroplasts of higher plants, β-glucuronidase (uidA, Staub and Maliga, *EMBO J.* 12:601-606, 1993), neomycin phosphotransferase (nptII, Carrer et al., *Mol. Gen. Genet.* 241:49-56, 1993), adenosyl-3-adenyltransferase (aadA, Svab and Maliga, *Proc. Natl. Acad. Sci., USA* 90:913-917, 1993), and the *Aequorea victoria* GFP (Sidorov et al., *Plant J.* 19:209-216, 1999) have been used as reporter genes (Heifetz, *Biochemie* 82:655-666, 2000). Each of these genes has attributes that make them useful reporters of chloroplast gene expression, such as ease of analysis, sensitivity, or the ability to examine expression in situ. Based upon these studies, other heterologous proteins have been expressed in the chloroplasts of higher plants such as *Bacillus thuringiensis* Cry toxins, conferring resistance to insect herbivores (Kota et al., *Proc. Natl. Acad. Sci., USA* 96:1840-1845, 1999), or human somatotropin (Staub et al., *Nat. Biotechnol.* 18:333-338, 2000), a potential biopharmaceutical. Several reporter genes have been expressed in the chloroplast of the eukaryotic green alga, *C. reinhardtii*, including aadA (Goldschmidt-Clermont, *Nucl. Acids Res.* 19:4083-4089 1991; Zerges and Rochaix, *Mol. Cell. Biol.* 14:5268-5277, 1994), uidA (Sakamoto et al., *Proc. Natl. Acad. Sci., USA* 90:477-501, 19933, Ishikura et al., *J. Biosci. Bioeng.* 87:307-314 1999), *Renilla luciferase* (Minko et al., *Mol. Gen. Genet.* 262:421-425, 1999) and the amino glycoside phosphotransferase from *Acinetobacter baumanii*, aphA6 (Bateman and Purton, *Mol. Gen. Genet.* 263:404-410, 2000).

In some instances, the vectors of the present invention will contain elements such as an *E. coli* or *S. cerevisiae* origin of replication. Such features, combined with appropriate selectable markers, allows for the vector to be "shuttled" between the target host cell and the bacterial and/or yeast cell. The ability to passage a shuttle vector of the invention in a secondary host may allow for more convenient manipulation of the features of the vector. For example, a reaction mixture containing the vector and putative inserted polynucleotides of interest can be transformed into prokaryote host cells such as *E. coli*, amplified and collected using routine methods, and examined to identify vectors containing an insert or construct of interest. If desired, the vector can be further manipulated, for example, by performing site directed mutagenesis of the inserted polynucleotide, then again amplifying and selecting vectors having a mutated polynucleotide of interest. A shuttle vector then can be introduced into plant cell chloroplasts, wherein a polypeptide of interest can be expressed and, if desired, isolated according to a method of the invention.

A polynucleotide or recombinant nucleic acid molecule of the invention, can be introduced into plant chloroplasts using any method known in the art. A polynucleotide can be introduced into a cell by a variety of methods, which are well known in the art and selected, in part, based on the particular host cell. For example, the polynucleotide can be introduced into a plant cell using a direct gene transfer method such as electroporation or microprojectile mediated (biolistic) transformation using a particle gun, or the "glass bead method," or by pollen-mediated transformation, liposome-mediated transformation, transformation using wounded or enzyme-degraded immature embryos, or wounded or enzyme-degraded embryogenic callus (Potrykus, *Ann. Rev. Plant. Physiol. Plant Mol. Biol.* 42:205-225, 1991).

The term "exogenous" is used herein in a comparative sense to indicate that a nucleotide sequence (or polypeptide) being referred to is from a source other than a reference source, or is linked to a second nucleotide sequence (or polypeptide) with which it is not normally associated, or is modified such that it is in a form that is not normally associated with a reference material. For example, a polynucleotide encoding an biomass degrading enzyme is heterologous with respect to a nucleotide sequence of a plant chloroplast, as are the components of a recombinant nucleic acid molecule comprising, for example, a first nucleotide sequence operatively linked to a second nucleotide sequence, as is a mutated polynucleotide introduced into a chloroplast where the mutant polynucleotide is not normally found in the chloroplast.

Plastid transformation is a routine and well known method for introducing a polynucleotide into a plant cell chloroplast (see U.S. Pat. Nos. 5,451,513, 5,545,817, and 5,545,818; WO 95/16783; McBride et al., *Proc. Natl. Acad. Sci., USA* 91:7301-7305, 1994). In some embodiments, chloroplast transformation involves introducing regions of chloroplast DNA flanking a desired nucleotide sequence, allowing for homologous recombination of the exogenous DNA into the target chloroplast genome. In some instances one to 1.5 kb flanking nucleotide sequences of chloroplast genomic DNA may be used. Using this method, point mutations in the chloroplast 16S rRNA and rps12 genes, which confer resistance to spectinomycin and streptomycin, can be utilized as selectable markers for transformation (Svab et al., *Proc. Natl. Acad. Sci., USA* 87:8526-8530, 1990), and can result in stable homoplasmic transformants, at a frequency of approximately one per 100 bombardments of target leaves.

Microprojectile mediated transformation also can be used to introduce a polynucleotide into a plant cell chloroplast (Klein et al., *Nature* 327:70-73, 1987). This method utilizes microprojectiles such as gold or tungsten, which are coated with the desired polynucleotide by precipitation with calcium chloride, spermidine or polyethylene glycol. The microprojectile particles are accelerated at high speed into a plant tissue using a device such as the BIOLISTIC PD-1000 particle gun (BioRad; Hercules Calif.). Methods for the transformation using biolistic methods are well known in the art (see, e.g.; Christou, *Trends in Plant Science* 1:423-431, 1996). Microprojectile mediated transformation has been used, for example, to generate a variety of transgenic plant species, including cotton, tobacco, corn, hybrid poplar and papaya. Important cereal crops such as wheat, oat, barley, sorghum and rice also have been transformed using microprojectile mediated delivery (Duan et al., *Nature Biotech.* 14:494-498, 1996; Shimamoto, *Curr. Opin. Biotech.* 5:158-162, 1994). The transformation of most dicotyledonous plants is possible with the methods described above. Transformation of monocotyledonous plants also can be transformed using, for example, biolistic methods as described above, protoplast transformation, electroporation of partially permeabilized cells, introduction of DNA using glass fibers, the glass bead agitation method, and the like.

Transformation frequency may be increased by replacement of recessive rRNA or r-protein antibiotic resistance genes with a dominant selectable marker, including, but not limited to the bacterial aadA gene (Svab and Maliga, *Proc. Natl. Acad. Sci., USA* 90:913-917, 1993). Approximately 15 to 20 cell division cycles following transformation are generally required to reach a homoplastidic state. It is apparent to one of skill in the art that a chloroplast may contain multiple copies of its genome, and therefore, the term "homoplasmic"

or "homoplasmy" refers to the state where all copies of a particular locus of interest are substantially identical. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein.

The methods of the present invention are exemplified using the microalga, *C. reinhardtii*. The use of microalgae to express a polypeptide or protein complex according to a method of the invention provides the advantage that large populations of the microalgae can be grown, including commercially (Cyanotech Corp.; Kailua-Kona Hi.), thus allowing for production and, if desired, isolation of large amounts of a desired product. However, the ability to express, for example, functional mammalian polypeptides, including protein complexes, in the chloroplasts of any plant allows for production of crops of such plants and, therefore, the ability to conveniently produce large amounts of the polypeptides. Accordingly, the methods of the invention can be practiced using any plant having chloroplasts, including, for example, macroalgae, for example, marine algae and seaweeds, as well as plants that grow in soil, for example, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea ultilane*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugar cane (*Saccharum* spp.), oats, duckweed (Lemna), barley, tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals such as azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum are also included. Additional ornamentals useful for practicing a method of the invention include impatiens, Begonia, Pelargonium, Viola, Cyclamen, Verbena, Vinca, Tagetes, Primula, Saint Paulia, Agertum, Amaranthus, Antihirrhinum, Aquilegia, Cineraria, Clover, Cosmo, Cowpea, Dahlia, Datura, Delphinium, Gerbera, Gladiolus, Gloxinia, Hippeastrum, Mesembryanthemum, Salpiglossos, and Zinnia. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (*Tsuga ultilane*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Leguminous plants useful for practicing a method of the invention include beans and peas. Beans include guar, locust bean, fenugreek, soybean, garden beans, cowpea, mung bean, lima bean, fava bean, lentils, chickpea, etc. Legumes include, but are not limited to, *Arachis*, e.g., peanuts, *Vicia*, e.g., crown vetch, hairy vetch, adzuki bean, mung bean, and chickpea, *Lupinus*, e.g., lupine, *trifolium, Phaseolus*, e.g., common bean and lima bean, *Pisum*, e.g., field bean, *Melilotus*, e.g., clover, *Medicago*, e.g., alfalfa, *Lotus*, e.g., trefoil, lens, e.g., lentil, and false indigo. Preferred forage and turf grass for use in the methods of the invention include alfalfa, orchard grass, tall fescue, perennial ryegrass, creeping bent grass, and redtop. Other plants useful in the invention include *Acacia*, aneth, artichoke, arugula, blackberry, canola, cilantro, clementines, escarole, eucalyptus, fennel, grapefruit, honey dew, jicama, kiwifruit, lemon, lime, mushroom, nut, okra, orange, parsley, persimmon, plantain, pomegranate, poplar, radiata pine, radicchio, Southern pine, sweetgum, tangerine, triticale, vine, yams, apple, pear, quince, cherry, apricot, melon, hemp, buckwheat, grape, raspberry, *chenopodium*, blueberry, nectarine, peach, plum, strawberry, watermelon, eggplant, pepper, cauliflower, *Brassica*, e.g., broccoli, cabbage, ultilan sprouts, onion, carrot, leek, beet, broad bean, celery, radish, pumpkin, endive, gourd, garlic, snapbean, spinach, squash, turnip, ultilane, chicory, groundnut and zucchini. Thus, the compositions contemplated herein include host organisms comprising any of the above nucleic acids. The host organism can be any chloroplast-containing organism.

The term "plant" is used broadly herein to refer to a eukaryotic organism containing plastids, particularly chloroplasts, and includes any such organism at any stage of development, or to part of a plant, including a plant cutting, a plant cell, a plant cell culture, a plant organ, a plant seed, and a plantlet. A plant cell is the structural and physiological unit of the plant, comprising a protoplast and a cell wall. A plant cell can be in the form of an isolated single cell or a cultured cell, or can be part of higher organized unit, for example, a plant tissue, plant organ, or plant. Thus, a plant cell can be a protoplast, a gamete producing cell, or a cell or collection of cells that can regenerate into a whole plant. As such, a seed, which comprises multiple plant cells and is capable of regenerating into a whole plant, is considered plant cell for purposes of this disclosure. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, roots, and the like. A part of a plant useful for propagation includes, for example, seeds, fruits, cuttings, seedlings, tubers, rootstocks, and the like.

A method of the invention can generate a plant containing chloroplasts that are genetically modified to contain a stably integrated polynucleotide (Hager and Bock, *Appl. Microbiol. Biotechnol.* 54:302-310, 2000). Accordingly, the present invention further provides a transgenic (transplastomic) plant, e.g. *C. reinhardtii*, which comprises one or more chloroplasts containing a polynucleotide encoding one or more heterologous polypeptides, including polypeptides that can specifically associate to form a functional protein complex.

In some instances, transformants and/or transplastomic plants comprising a recombinant polynucleotide encoding a single enzyme of a particular biodegradative pathway (e.g., the cellulosic pathway), may be combined with transformants comprising recombinant polynucleotides encoding the other enzymes of the biodegradative pathway. For example, where a biochemical pathway utilizes four enzymes to produce a product from a substrate, four transformant lines may be combined to provide the enzymes of that pathway. Such combinations may contain as many transformant lines as is necessary to comprise a mixture of cells producing the entire enzyme pathway, or a portion thereof. Additionally, such combinations may comprise different ratios of cells of the different transformants. For example, where one enzyme of a degradative pathway is the rate limiting step in the pathway, a combination of cells may contain 2, 3, 4, 5, 6, 7, 8, 9, 10 times or higher numbers of cells producing the rate limiting enzyme. One of skill in the art will recognize that multiple combinations of ratios of transformants may be achieved through simple methods (e.g., weighing dried tranformants and combining). Alternately, individual enzymes may be isolated from the transformants (e.g., "cracking" algal transformants to isolate sequestered enzymes) and then combined following isolation. Such approaches may allow for tailoring of enzyme concentrations to different biomass or other substrate materials which may contain different relative ratios of substrates or other components.

In some instances, a protein produced by a transgenic organism of the present invention is isolated after it is produced. Therefore, the present invention also contemplates a method of producing a heterologous polypeptide or protein complex in a chloroplast or in a transgenic plant which may include a step of isolating an expressed polypeptide or protein complex from the plant cell chloroplasts. As used herein, the term "isolated" or "substantially purified" means that a polypeptide or polynucleotide being referred to is in a form that is relatively free of proteins, nucleic acids, lipids, carbohydrates or other materials with which it is naturally associated. An isolated polypeptide (or polynucleotide) may constitute at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent of a sample.

A polypeptide or protein complex can be isolated from chloroplasts using any method suitable for the particular polypeptide or protein complex, including, for example, salt fractionation methods and chromatography methods such as an affinity chromatography method using a ligand or receptor that specifically binds the polypeptide or protein complex. A determination that a polypeptide or protein complex produced according to a method of the invention is in an isolated form can be made using well known methods, for example, by performing electrophoresis and identifying the particular molecule as a relatively discrete band or the particular complex as one of a series of bands. Accordingly, the present invention also provides an isolated polypeptide or protein complex produced by a method of the invention. In some instances, an enzyme of the present invention may be produced but sequestered in the chloroplast. In such embodiments, access to the active enzyme may be had upon "cracking" the cells containing the enzyme (e.g., using mechanical, chemical, and/or biological means to disrupt the cell wall). The timing of such cracking may be planned to occur at the time the enzyme(s) produced by the cells are to be utilized to perform their enzymatic capabilities. In other instances, the enzyme may be secreted by the host cell. In such instances, the enzyme may be collected directly from the culture medium of the organism. Enzymes present in such media may be used directly, without purification, may be dried (e.g., air dried, lyophilized), and/or may be subjected to purification by any means known in the art (e.g., affinity chromatography, high performance liquid chromatography).

Examples of biomass-degrading enzymes and the nucleic acids that encode those enzymes are shown in Table I. Non-limiting examples of biomass-degrading enzymes include: cellulolytic enzymes, hemicellulolytic enzymes, pectinolytic enzymes, xylanases, ligninolytic enzymes, cellulases, cellobiases, softening enzymes (e.g., endopolygalacturonase), amylases, lipases, proteases, RNAses, DNAses, inulinase, lysing enzymes, phospholipases, pectinase, pullulanase, glucose isomerase, endoxylanase, beta-xylosidase, alpha-L-arabinofuranosidase, alpha-glucoronidase, alpha-galactosidase, acetylxylan esterase, and feruloyl esterase. Examples of genes that encode such enzymes include, but are not limited to, amylases, cellulases, hemicellulases, (e.g., β-glucosidase, endocellulase, exocellulase), exo-β-glucanase, endo-β-glucanase and xylanse (endoxylanase and exoxylanse). Examples of ligninolytic enzymes include, but are not limited to, lignin peroxidase and manganese peroxidase from *Phanerochaete chryososporium*. One of skill in the art will recognize that these enzymes are only a partial list of enzymes which could be used in the present invention.

TABLE 1

Examples of Biomass-degrading enzymes

| # | Target (family) | Source | AA | NCBI prot. ID |
|---|---|---|---|---|
| | Exo-β-glucanase | | | |
| 1. | CBH I (7) | *Trichoderma viride* | 514 | AAQ76092 |
| 2. | CBH II (6) | *T. reesei* | 471 | AAA72922 |
| 3. | CBH I (7) | *Aspergillus aculeatus* | 540 | BAA25183 |
| | Endo-β-glucanase | | | |
| 4. | EG I (7) | *T. reesei* | 459 | AAA34212 |
| 5. | EG III (5) | *T. reesei* | 218 | AAA34213 |
| 6. | EG V (45) | *T. reesei* | 242 | CAA83846 |
| 7. | EGL A (12) | *A. niger* | 239 | CAA11964 |
| | β-glucosidase | | | |
| 8. | BGL I (3) | *T. reesei* | 744 | AAA18473 |
| 9. | BGL II (1) | *T. reesei* | 466 | BAA74959 |
| 10. | BGL I (3) | *A. niger* | 860 | ABG46337 |
| | Endoxylanase | | | |
| 11. | XYN I (11) | *T. reesei* | 222 | CAA49293 |
| 12. | XYN II (11) | *T. reesei* | 229 | CAA49294 |

Biomass-production modulating agents include agents that increase biomass production in an organism, e.g., photosynthetic organism.

Host Cells/Organism

The present invention also contemplates a host cell transformed with one or more of the nucleic acids herein. In preferred embodiments, the host cell is photosynthetic. In some cases, the host cell is photosynthetic and non-vascular. In other cases, the host cell is photosynthetic and vascular. The host cell can be eukaryotic or prokaryotic.

The host cell is transfected with a vector described herein (e.g., a vector comprising one or more biomass degrading enzymes and/or one or more biomass-production modulating agents). The vector may contain a plastid promoter or a nucleic promoter for transfecting a chloroplast or other plastid of the host cell. The vector may also encode a fusion protein or agent that selectively targets the vector product to the chloroplast or other plastid. Transfection of a host cell can occur using any method known in the art.

A host organism is an organism comprising a host cell. In preferred embodiments, the host organism is photosynthetic. A photosynthetic organism is one that naturally photosynthesizes (has a plastid) or that is genetically engineered or otherwise modified to be photosynthetic. In some instances, a photosynthetic organism may be transformed with a construct of the invention which renders all or part of the photosynthetic apparatus inoperable. In some instances it is non-vascular and photosynthetic. The host cell can be prokaryotic. Examples of some prokaryotic organisms of the present invention include, but are not limited to cyanobacteria (e.g., *Synechococcus, Synechocystis, Athrospira*). The host organism can be unicellular or multicellular. In most embodiments, the host organism is eukaryotic (e.g. green algae). Examples of organisms contemplated herein include, but are not limited to, rhodophyta, chlorophyta, heterokontophyta, tribophyta, glaucophyta, chlorarachniophytes, euglenoids, haptophyta, cryptomonads, dinoflagellata, and phytoplankton.

A host organism may be grown under conditions which permit photosynthesis, however, this is not a requirement (e.g., a host organism may be grown in the absence of light). In some instances, the host organism may be genetically modified in such a way that photosynthetic capability is diminished and/or destroyed (see examples below). In growth conditions where a host organism is not capable of photosynthesis (e.g., because of the absence of light and/or genetic modification), typically, the organism will be provided with the necessary nutrients to support growth in the absence of photosynthesis. For example, a culture medium in (or on) which an organism is grown, may be supplemented with any required nutrient, including an organic carbon source, nitrogen source, phosphorous source, vitamins, metals, lipids, nucleic acids, micronutrients, or an organism-specific requirement. Organic carbon sources includ any source of carbon which the host organism is able to metabolize including, but not limited to, acetate, simple carbohydrates (e.g., glucose, sucrose, lactose), complex carbohydrates (e.g., starch, glycogen), proteins, and lipids. One of skill in the art will recognize that not all organisms will be able to sufficiently metabolize a particular nutrient and that nutrient mixtures may need to be modified from one organism to another in order to provide the appropriate nutrient mix.

A host organism can be grown on land, e.g., ponds, aqueducts, landfills, or in closed or partially closed bioreactor systems. The host organisms herein can also be grown directly in water, e.g., in ocean, sea, on lakes, rivers, reservoirs, etc. In embodiments where algae are mass-cultured, the algae can be grown in high density photobioreactors Methods of mass-culturing algae are known. For example, algae can be grown in high density photobioreactors (see, e.g., Lee et al, *Biotech. Bioengineering* 44:1161-1167, 1994) and other bioreactors (such as those for sewage and waste water treatments) (e.g., Sawayama et al, *Appl. Micro. Biotech.*, 41:729-731, 1994). Additionally, algae may be mass-cultured to remove heavy metals (e.g., Wilkinson, *Biotech. Letters*, 11:861-864, 1989), hydrogen (e.g., U.S. Patent Application Publication No. 20030162273), and pharmaceutical compounds In some cases, host organism(s) are grown near ethanol production plants or other facilities or regions (e.g., electrical generating plants, concrete plants, oil refineries, other industrial facilities, cities, highways, etc.) generating $CO_2$. As such, the methods herein contemplate business methods for selling carbon credits to ethanol plants or other facilities or regions generating $CO_2$ while making or catalyzing the production of fuels by growing one or more of the modified organisms described herein near the ethanol production plant.

Biomass

As used herein, "biomass" is any organic material. In some instances, biomass is substantially free or free of starch and simple sugars. Biomass can be broken down into starch or simple sugars that can be subsequently utilized for the production of fuel. Any cellulosic or lignocellulosic material and materials comprising cellulose, hemicellulose, lignin, starch, oligosaccharides and/or monosaccharides are also considered to be biomass. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, paper, shrubs and bushes, vegetables, fruits, flowers and animal manure.

Agricultural waste is one form of biomass used for the production of fuel. Non-limiting examples of agricultural waste include corn stover, wheat stover, and soy stover. Another source of biomass in this invention is a high cellulose content organism. A high cellulose content organism is an organism whose weight is at least 30% or more attributable to biomass that is substantially free of starch or simple sugars. High cellulose content organism(s) can be selectively grown in large quantities to produce biomass, which can be degraded with biomass-degrading enzyme(s) of this invention to create starch and simple sugars. Examples of high cellulose content organisms include, but are not limited to: willow, duckweed, sugarbeets, and switchgrass.

A third example of biomass comprises organisms that are genetically modified to have an increased cellulose or biomass. Such organisms are optionally photosynthetic and may comprise a host cell incorporating a vector that encodes a biomass production-modulating agent. In some instances, the same vector can encode both a biomass production-modulating agent and a biomass-degrading enzyme. In some instances, the vector encoding the biomass production-modulating agent and the vector encoding the biomass degrading enzyme are separate.

Fuel Production

The present invention relates to methods of producing a biofuel. Such methods comprise expressing a gene encoding a biomass-degrading enzyme in a photosynthetic organism (e.g., non-vascular). The method further comprises utilizing the biomass-degrading enzyme and breaking down biomass with the enzyme. To produce a biofuel, the method may further involve refining the degraded biomass. The final product (e.g., ethanol) may then be mixed with one or more other biofuels.

The invention relates to a method of producing a biofuel comprising expressing a vector or vectors encoding a biomass-degrading enzyme, a biomass-degrading enzymatic pathway, and/or a biomass production-modulating agent in photosynthetic organism (e.g., non-vascular). In this embodiment, the host cell comprising the vector could then both make and degrade its own biomass. The method can comprise extracting only the product of the biomass degradation. In this manner, the enzyme would not have to be extracted to use for the creation of a biofuel. The production of the biofuel may further involve refining the product of the breaking down of the biomass. The production of biofuel may also involve the utilization of saccharification tanks. Such devices are well known in the art, see, for example U.S. Pat. Nos. 5,114,491; 5,534,075; and 5,559,031 (each of which is herein incorporated by reference).

In some embodiments, the biofuel is ethanol or other biologically produced alcohols. The refining may include a fermentation step to produce ethanol from products of biomass degradation including starch and simple sugars. Thus, refining may include using microorganisms which are capable of fermenting starch, simple sugars, and/or biomass materials, including, but not limited to *Saccharomyces cerevisiae* and *Zymomonas mobilis*.

The following examples merely illustrate the invention disclosed herein, but do not limit it.

EXAMPLES

Example 1

Production of Endo-β-glucanase in *C. reinhardtii*

In this example a nucleic acid encoding endo-β-glucanase from *T. reesei* was introduced into *C. reinhardtii*. Transforming DNA (SEQ ID NO. 20, Table 4) is shown graphically in FIG. 2A. In this instance the segment labeled "Transgene" is the endo-β-glucanase encoding gene (SEQ ID NO. 16, Table 3), the segment labeled "psbA 5' UTR" is the 5' UTR and promoter sequence for the psbA gene from *C. reinhardtii*, the segment labeled "psbA 3' UTR" contains the 3' UTR for the psbA gene from *C. reinhardtii*, and the segment labeled "Selection Marker" is the kanamycin resistance encoding gene from bacteria, which is regulated by the 5' UTR and promoter sequence for the atpA gene from *C. reinhardtii* and the 3' UTR sequence for the rbcL gene from *C. reinhardtii*. The transgene cassette is targeted to the psbA loci of *C. reinhardtii* via the segments labeled "5' Homology" and "3' Homology," which are identical to sequences of DNA flanking the psbA locus on the 5' and 3' sides, respectively. All DNA manipulations carried out in the construction of this transforming DNA were essentially as described by Sambrook et al., Molecular Cloning: A Laboratory Manual (Cold Spring Harbor Laboratory Press 1989) and Cohen et al., *Meth. Enzymol.* 297, 192-208, 1998.

For these experiments, all transformations were carried out on *C. reinhardtii* strain 137c (mt+). Cells were grown to late log phase (approximately 7 days) in the presence of 0.5 mM 5-fluorodeoxyuridine in TAP medium (Gorman and Levine, *Proc. Natl. Acad. Sci., USA* 54:1665-1669, 1965, which is incorporated herein by reference) at 23° C. under constant illumination of 450 Lux on a rotary shaker set at 100 rpm. Fifty ml of cells were harvested by centrifugation at 4,000×g at 23° C. for 5 min. The supernatant was decanted and cells resuspended in 4 ml TAP medium for subsequent chloroplast transformation by particle bombardment (Cohen et al., supra, 1998). All transformations were carried out under kanamycin selection (150 µg/ml) in which resistance was conferred by the gene encoded by the segment in FIG. 2 labeled "Selection Marker." (Chlamydomonas Stock Center, Duke University).

PCR was used to identify transformed strains. For PCR analysis, $10^6$ algae cells (from agar plate or liquid culture) were suspended in 10 mM EDTA and heated to 95° C. for 10 minutes, then cooled to near 23° C. A PCR cocktail consisting of reaction buffer, MgCl2, dNTPs, PCR primer pair(s) (Table 2 and shown graphically in FIG. 3A), DNA polymerase, and water was prepared. Algae lysate in EDTA was added to provide template for reaction. Magnesium concentration is varied to compensate for amount and concentration of algae lysate in EDTA added. Annealing temperature gradients were employed to determine optimal annealing temperature for specific primer pairs.

To identify strains that contain the endo-β-glucanase gene, a primer pair was used in which one primer anneals to a site within the psbA 5'UTR (SEQ ID NO. 1) and the other primer anneals within the endo-3-glucanase coding segment (SEQ ID NO. 3). Desired clones are those that yield a PCR product of expected size. To determine the degree to which the endogenous gene locus is displaced (heteroplasmic vs. homoplasmic), a PCR reaction consisting of two sets of primer pairs were employed (in the same reaction). The first pair of primers amplifies the endogenous locus targeted by the expression vector and consists of a primer that anneals within the psbA 5'UTR (SEQ ID NO. 8) and one that anneals within the psbA coding region (SEQ ID NO. 9). The second pair of primers (SEQ ID NOs. 6 and 7) amplifies a constant, or control region that is not targeted by the expression vector, so should produce a product of expected size in all cases. This reaction confirms that the absence of a PCR product from the endogenous locus did not result from cellular and/or other contaminants that inhibited the PCR reaction. Concentrations of the primer pairs are varied so that both reactions work in the same tube; however, the pair for the endogenous locus is 5× the concentration of the constant pair. The number of cycles used was >30 to increase sensitivity. The most desired clones are those that yield a product for the constant region but not for the endogenous gene locus. Desired clones are also those that give weak-intensity endogenous locus products relative to the control reaction.

Results from this PCR on 96 clones were determined and the results are shown in FIG. 4. FIG. 4A shows PCR results using the transgene-specific primer pair. As can be seen, multiple transformed clones are positive for insertion of the exo-β-glucanase gene (e.g. numbers 1-14). FIG. 4B shows the PCR results using the primer pairs to differentiate homoplasmic from heteroplasmic clones. As can be seen, multiple transformed clones are either homoplasmic or heteroplasmic to a degree in favor of incorporation of the transgene (e.g. numbers 1-14). Unnumbered clones demonstrate the presence of wild-type psbA and, thus, were not selected for further analysis.

TABLE 2

PCR primers.

| SEQ ID NO. | Use | Sequence |
|---|---|---|
| 1. | psbA 5' UTR forward primer | GTGCTAGGTAACTAACGTTTGATTTTT |
| 2. | Exo-β-glucanase reverse primer | AACCTTCCACGTTAGCTTGA |
| 3. | Endo-β-glucanase reverse primer | GCATTAGTTGGACCACCTTG |
| 4. | β-glucosidase reverse primer | ATCACCTGAAGCAGGTTTGA |
| 5. | Endoxylanase reverse primer | GCACTACCTGATGAAAAATAACC |
| 6. | Control forward primer | CCGAACTGAGGTTGGGTTTA |
| 7. | Control reverse primer | GGGGGAGCGAATAGGATTAG |
| 8. | psbA 5' UTR forward primer (wild-type) | GGAAGGGGACGTAGGTACATAAA |
| 9. | psbA 3' reverse primer (wild-type) | TTAGAACGTGTTTTGTTCCCAAT |
| 10. | psbC 5' UTR forward primer | TGGTACAAGAGGATTTTTGTTGTT |
| 11. | psbD 5' UTR forward primer | AAATTTAACGTAACGATGAGTTG |
| 12. | atpA 5' UTR forward primer | CCCCTTACGGGCAAGTAAAC |
| 13. | 3HB forward primer (wild-type) | CTCGCCTATCGGCTAACAAG |
| 14. | 3HB forward primer (wild-type) | CACAAGAAGCAACCCCTTGA |

To ensure that the presence of the endo-β-glucanase-encoding gene led to expression of the endo-β-glucanase protein, a Western blot was performed. Approximately $1\times10^8$ algae cells were collected from TAP agar medium and suspended in 0.5 ml of lysis buffer (750 mM Tris, pH=8.0, 15% sucrose, 100 mM beta-mercaptoethanol). Cells were lysed by sonication (5×30 sec at 15% power). Lysate was mixed 1:1 with loading buffer (5% SDS, 5% beta-mercaptoethanol, 30% sucrose, bromophenol blue) and proteins were separated by SDS-PAGE, followed by transfer to PVDF membrane. The membrane was blocked with TBST+5% dried, nonfat milk at 23° C. for 30 min, incubated with anti-FLAG antibody (diluted 1:1,000 in TBST+5% dried, nonfat milk) at 4° C. for 10 hours, washed three times with TBST, incubated with horseradish-linked anti-mouse antibody (diluted 1:10,000 in TBST+5% dried, nonfat milk) at 23° C. for 1 hour, and washed three times with TBST. Proteins were visualized with chemiluminescent detection. Results from multiple clones (FIG. 4C) show that expression of the endo-β-glucanase gene in C. reinhardtii cells resulted in production of the protein.

Cultivation of C. reinhardtii transformants for expression of endo-β-glucanase was carried out in liquid TAP medium at 23° C. under constant illumination of 5,000 Lux on a rotary shaker set at 100 rpm, unless stated otherwise. Cultures were maintained at a density of $1\times10^7$ cells per ml for at least 48 hr prior to harvest.

To determine if the endo-β-glucanase produced by transformed alga cells was functional, endo-β-glucanase activity was tested using a filter paper assay (Xiao et al., Biotech. Bioengineer. 88, 832-37, 2004). Briefly, 500 ml of algae cell culture was harvested by centrifugation at 4000×g at 4° C. for 15 min. The supernatant was decanted and the cells resuspended in 10 ml of lysis buffer (100 mM Tris-HCl, pH=8.0, 300 mM NaCl, 2% Tween-20). Cells were lysed by sonication (10×30 sec at 35% power). Lysate was clarified by centrifugation at 14,000×g at 4° C. for 1 hour. The supernatant was removed and incubated with anti-FLAG antibody-conjugated agarose resin at 4° C. for 10 hours. Resin was separated from the lysate by gravity filtration and washed 3× with wash buffer ((100 mM Tris-HCl, pH=8.0, 300 mM NaCl, 2% Tween-20). Endo-β-glucanase was eluted by incubation of the resin with elution buffer (TBS, 250 ug/ml FLAG peptide). Results from Western blot analysis of samples collect after each step (FIG. 4D) show that the endo-β-glucanase protein was isolated. A 20 µl aliquot of diluted enzyme was added into wells containing 40 µl of 50 mM NaAc buffer and a filter paper disk. After 60 minutes incubation at 50° C., 120 µl of DNS was added to each reaction and incubated at 95° C. for 5 minutes. Finally, a 36 µl aliquot of each sample was transferred to the wells of a flat-bottom plate containing 160 µl water. The absorbance at 540 nm was measured. The results for two transformed strains indicated that the isolated enzyme was functional (absorbance of 0.33 and 0.28).

Example 2

Production of Exo-β-Glucanase in C. reinhardtii

In this example a nucleic acid encoding exo-β-glucanase from T. viride was introduced into C. reinhardtii. Transforming DNA (SEQ ID NO. 19, Table 4) is shown graphically in FIG. 2A. In this instance the segment labeled "Transgene" is the exo-β-glucanase encoding gene (SEQ ID NO. 15, Table 3), the segment labeled "psbA 5' UTR" is the 5' UTR and promoter sequence for the psbA gene from C. reinhardtii, the segment labeled "psbA 3' UTR" contains the 3' UTR for the psbA gene from C. reinhardtii, and the segment labeled "Selection Marker" is the kanamycin resistance encoding gene from bacteria, which is regulated by the 5' UTR and promoter sequence for the atpA gene from C. reinhardtii and the 3' UTR sequence for the rbcL gene from C. reinhardtii. The transgene cassette is targeted to the psbA loci of C.

reinhardtii via the segments labeled "5' Homology" and "3' Homology," which are identical to sequences of DNA flanking the psbA locus on the 5' and 3' sides, respectively. All DNA manipulations carried out in the construction of this transforming DNA were essentially as described by Sambrook et al., Molecular Cloning: A Laboratory Manual (Cold Spring Harbor Laboratory Press 1989) and Cohen et al., *Meth. Enzymol.* 297, 192-208, 1998.

For these experiments, all transformations were carried out on *C. reinhardtii* strain 137c (mt+). Cells were grown to late log phase (approximately 7 days) in the presence of 0.5 mM 5-fluorodeoxyuridine in TAP medium (Gorman and Levine, *Proc. Natl. Acad. Sci., USA* 54:1665-1669, 1965, which is incorporated herein by reference) at 23° C. under constant illumination of 450 Lux on a rotary shaker set at 100 rpm. Fifty ml of cells were harvested by centrifugation at 4,000×g at 23° C. for 5 min. The supernatant was decanted and cells resuspended in 4 ml TAP medium for subsequent chloroplast transformation by particle bombardment (Cohen et al., supra, 1998). All transformations were carried out under kanamycin selection (150 µg/ml), in which resistance was conferred by the gene encoded by the segment in FIG. 2 labeled "Selection Marker." (Chlamydomonas Stock Center, Duke University).

PCR was used to identify transformed strains. For PCR analysis, $10^6$ algae cells (from agar plate or liquid culture) were suspended in 10 mM EDTA and heated to 95° C. for 10 minutes, then cooled to near 23° C. A PCR cocktail consisting of reaction buffer, MgCl2, dNTPs, PCR primer pair(s) (Table 2 and shown graphically in FIG. 3A), DNA polymerase, and water was prepared. Algae lysate in EDTA was added to provide template for reaction. Magnesium concentration is varied to compensate for amount and concentration of algae lysate in EDTA added. Annealing temperature gradients were employed to determine optimal annealing temperature for specific primer pairs.

To identify strains that contain the exo-β-glucanase gene, a primer pair was used in which one primer anneals to a site within the psbA 5'UTR (SEQ ID NO. 1) and the other primer anneals within the exo-β-glucanase coding segment (SEQ ID NO. 2). Desired clones are those that yield a PCR product of expected size. To determine the degree to which the endogenous gene locus is displaced (heteroplasmic vs. homoplasmic), a PCR reaction consisting of two sets of primer pairs were employed (in the same reaction). The first pair of primers amplifies the endogenous locus targeted by the expression vector and consists of a primer that anneals within the psbA 5'UTR (SEQ ID NO. 8) and one that anneals within the psbA coding region (SEQ ID NO. 9). The second pair of primers (SEQ ID NOs. 6 and 7) amplifies a constant, or control region that is not targeted by the expression vector, so should produce a product of expected size in all cases. This reaction confirms that the absence of a PCR product from the endogenous locus did not result from cellular and/or other contaminants that inhibited the PCR reaction. Concentrations of the primer pairs are varied so that both reactions work in the same tube; however, the pair for the endogenous locus is 5× the concentration of the constant pair. The number of cycles used was >30 to increase sensitivity. The most desired clones are those that yield a product for the constant region but not for the endogenous gene locus. Desired clones are also those that give weak-intensity endogenous locus products relative to the control reaction.

Figures 5A, 5B:
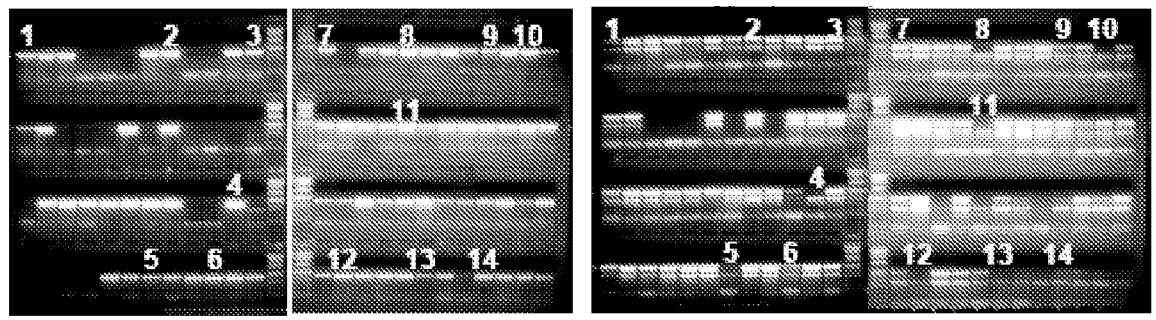
FIG. 5 illustrates results from PCR screening and Western blot analysis of exo-β-glucanase transformed C. reinhardtii clones.
Figure 5C:
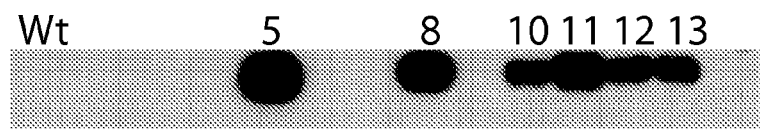
Figure 5D:
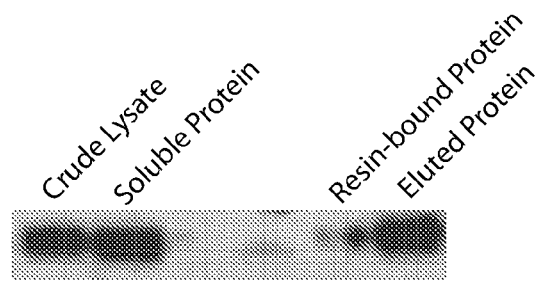
Figure 6A:
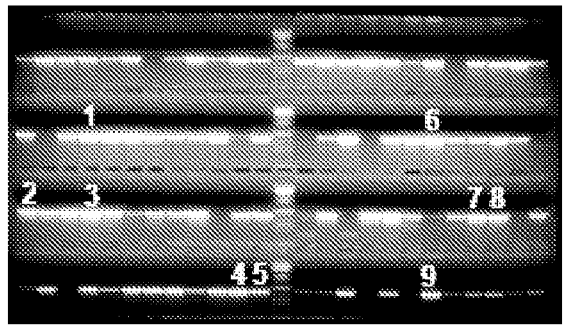
FIG. 6 illustrates results from PCR screening and Western blot analysis of β-glucosidase transformed C. reinhardtii clones.
Figure 6B:
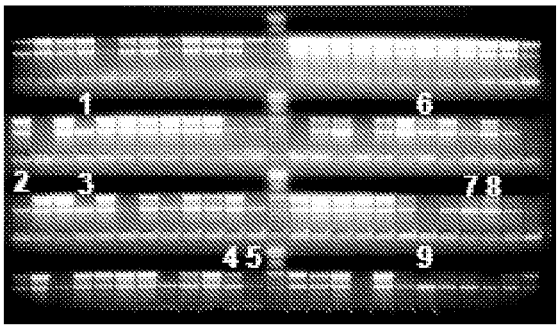
Figure 6C:
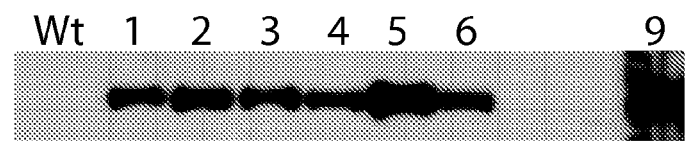
Figure 6D:
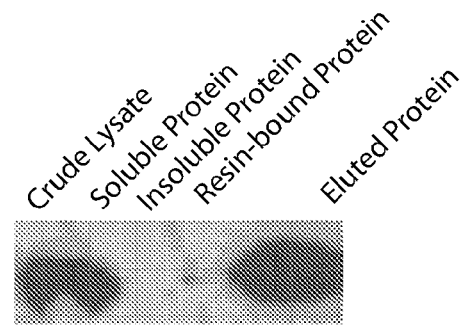

Results from this PCR on 96 clones were determined and the results are shown in FIG. 5. FIG. 5A shows PCR results using the transgene-specific primer pair. As can be seen, multiple transformed clones are positive for insertion of the endo-β-glucanase gene (e.g. numbers 1-14). FIG. 4B shows the PCR results using the primer pairs to differentiate homoplasmic from heteroplasmic clones. As can be seen, multiple transformed clones are either homoplasmic or heteroplasmic to a degree in favor of incorporation of the transgene (e.g. numbers 1-14). Unnumbered clones demonstrate the presence of wild-type psbA and, thus, were not selected for further analysis.

To ensure that the presence of the exo-β-glucanase-encoding gene led to expression of the exo-β-glucanase protein, a Western blot was performed. Approximately $1 \times 10^8$ algae cells were collected from TAP agar medium and suspended in 0.5 ml of lysis buffer (750 mM Tris, pH=8.0, 15% sucrose, 100 mM beta-mercaptoethanol). Cells were lysed by sonication (5×30 sec at 15% power). Lysate was mixed 1:1 with loading buffer (5% SDS, 5% beta-mercaptoethanol, 30% sucrose, bromophenol blue) and proteins were separated by SDS-PAGE, followed by transfer to PVDF membrane. The membrane was blocked with TBST+5% dried, nonfat milk at 23° C. for 30 min, incubated with anti-FLAG antibody (diluted 1:1,000 in TBST+5% dried, nonfat milk) at 4° C. for 10 hours, washed three times with TBST, incubated with horseradish-linked anti-mouse antibody (diluted 1:10,000 in TBST+5% dried, nonfat milk) at 23° C. for 1 hour, and washed three times with TBST. Proteins were visualized with chemiluminescent detection. Results from multiple clones (FIG. 5C) show that expression of the exo-β-glucanase gene in *C. reinhardtii* cells resulted in production of the protein.

Cultivation of *C. reinhardtii* transformants for expression of endo-β-glucanase was carried out in liquid TAP medium at 23° C. under constant illumination of 5,000 Lux on a rotary shaker set at 100 rpm, unless stated otherwise. Cultures were maintained at a density of $1 \times 10^7$ cells per ml for at least 48 hr prior to harvest.

To determine if the exo-β-glucanase produced by transformed alga cells was functional, exo-β-glucanase activity was tested using a filter paper assay (Xiao et al., *Biotech. Bioengineer.* 88, 832-37, 2004). Briefly, 500 ml of algae cell culture was harvested by centrifugation at 4000×g at 4° C. for 15 min. The supernatant was decanted and the cells resuspended in 10 ml of lysis buffer (100 mM Tris-HCl, pH=8.0, 300 mM NaCl, 2% Tween-20). Cells were lysed by sonication (10×30 sec at 35% power). Lysate was clarified by centrifugation at 14,000×g at 4° C. for 1 hour. The supernatant was removed and incubated with anti-FLAG antibody-conjugated agarose resin at 4° C. for 10 hours. Resin was separated from the lysate by gravity filtration and washed 3× with wash buffer (100 mM Tris-HCl, pH=8.0, 300 mM NaCl, 2% Tween-20). Exo-β-glucanase was eluted by incubation of the resin with elution buffer (TBS, 250 ug/ml FLAG peptide). Results from Western blot analysis of samples collect after each step (FIG. 5D) show that the exo-β-glucanase protein was isolated. A 20 µl aliquot of diluted enzyme was added into wells containing 40 µl of 50 mM NaAc buffer and a filter paper disk. After 60 minutes incubation at 50° C., 120 µl of DNS was added to each reaction and incubated at 95° C. for 5 minutes. Finally, a 36 µl aliquot of each sample was transferred to the wells of a flat-bottom plate containing 160 µl water. The absorbance at 540 nm was measured. The results for two transformed strains indicated that the isolated enzyme was functional (absorbance of 0.20 and 0.45).

Example 3

Production of β-glucosidase in *C. reinhardtii*

In this example a nucleic acid encoding β-glucosidase from *T. reesei* was introduced into *C. reinhardtii*. Transforming DNA (SEQ ID NO. 21, Table 4) is shown graphically in FIG. 2A. The amino acid sequence encoded by this gene is shown in Table 3. In this instance the segment labeled "Transgene" is the β-glucosidase encoding gene (SEQ ID NO. 17, Table 3), the segment labeled "psbA 5' UTR" is the 5' UTR and promoter sequence for the psbA gene from *C. reinhardtii*, the segment labeled "psbA 3' UTR" contains the 3' UTR for the psbA gene from *C. reinhardtii*, and the segment labeled "Selection Marker" is the kanamycin resistance encoding gene from bacteria, which is regulated by the 5' UTR and promoter sequence for the atpA gene from *C. reinhardtii* and the 3' UTR sequence for the rbcL gene from *C. reinhardtii*. The transgene cassette is targeted to the psbA loci of *C. reinhardtii* via the segments labeled "5' Homology" and "3' Homology," which are identical to sequences of DNA flanking the psbA locus on the 5' and 3' sides, respectively. All DNA manipulations carried out in the construction of this transforming DNA were essentially as described by Sambrook et al., Molecular Cloning: A Laboratory Manual (Cold Spring Harbor Laboratory Press 1989) and Cohen et al., *Meth. Enzymol.* 297, 192-208, 1998.

For these experiments, all transformations were carried out on *C. reinhardtii* strain 137c (mt+). Cells were grown to late log phase (approximately 7 days) in the presence of 0.5 mM 5-fluorodeoxyuridine in TAP medium (Gorman and Levine, *Proc. Natl. Acad. Sci., USA* 54:1665-1669, 1965, which is incorporated herein by reference) at 23° C. under constant illumination of 450 Lux on a rotary shaker set at 100 rpm. Fifty ml of cells were harvested by centrifugation at 4,000×g at 23° C. for 5 min. The supernatant was decanted and cells resuspended in 4 ml TAP medium for subsequent chloroplast transformation by particle bombardment (Cohen et al., supra, 1998). All transformations were carried out under kanamycin selection (150 μg/ml), in which resistance was conferred by the gene encoded by the segment in FIG. 2 labeled "Selection Marker." (Chlamydomonas Stock Center, Duke University).

PCR was used to identify transformed strains. For PCR analysis, $10^6$ algae cells (from agar plate or liquid culture) were suspended in 10 mM EDTA and heated to 95° C. for 10 minutes, then cooled to near 23° C. A PCR cocktail consisting of reaction buffer, MgCl2, dNTPs, PCR primer pair(s) (Table 2 and shown graphically in FIG. 3A), DNA polymerase, and water was prepared. Algae lysate in EDTA was added to provide template for reaction. Magnesium concentration was varied to compensate for amount and concentration of algae lysate in EDTA added. Annealing temperature gradients were employed to determine optimal annealing temperature for specific primer pairs.

To identify strains that contain the β-glucosidase gene, a primer pair was used in which one primer anneals to a site within the psbA 5'UTR (SEQ ID NO. 1) and the other primer anneals within the β-glucosidase coding segment (SEQ ID NO. 4). Desired clones are those that yield a PCR product of expected size. To determine the degree to which the endogenous gene locus is displaced (heteroplasmic vs. homoplasmic), a PCR reaction consisting of two sets of primer pairs were employed (in the same reaction). The first pair of primers amplifies the endogenous locus targeted by the expression vector and consists of a primer that anneals within the psbA 5'UTR (SEQ ID NO. 8) and one that anneals within the psbA coding region (SEQ ID NO. 9). The second pair of primers (SEQ ID NOs. 6 and 7) amplifies a constant, or control region that is not targeted by the expression vector, so should produce a product of expected size in all cases. This reaction confirms that the absence of a PCR product from the endogenous locus did not result from cellular and/or other contaminants that inhibited the PCR reaction. Concentrations of the primer pairs are varied so that both reactions work in the same tube; however, the pair for the endogenous locus is 5× the concentration of the constant pair. The number of cycles used was >30 to increase sensitivity. The most desired clones are those that yield a product for the constant region but not for the endogenous gene locus. Desired clones are also those that give weak-intensity endogenous locus products relative to the control reaction.

Results from this PCR on 96 clones were determined and the results are shown in FIG. 6. FIG. 6A shows PCR results using the transgene-specific primer pair. As can be seen, multiple transformed clones are positive for insertion of the endo-β-glucanase gene (e.g. numbers 1-9). FIG. 6B shows the PCR results using the primer pairs to differentiate homoplasmic from heteroplasmic clones. As can be seen, multiple transformed clones are either homoplasmic or heteroplasmic to a degree in favor of incorporation of the transgene (e.g. numbers 1-9). Unnumbered clones demonstrate the presence of wild-type psbA and, thus, were not selected for further analysis.

To ensure that the presence of the β-glucosidase-encoding gene led to expression of the β-glucosidase protein, a Western blot was performed. Approximately $1\times10^8$ algae cells were collected from TAP agar medium and suspended in 0.5 ml of lysis buffer (750 mM Tris, pH=8.0, 15% sucrose, 100 mM beta-mercaptoethanol). Cells were lysed by sonication (5×30 sec at 15% power). Lysate was mixed 1:1 with loading buffer (5% SDS, 5% beta-mercaptoethanol, 30% sucrose, bromophenol blue) and proteins were separated by SDS-PAGE, followed by transfer to PVDF membrane. The membrane was blocked with TBST+5% dried, nonfat milk at 23° C. for 30 min, incubated with anti-FLAG antibody (diluted 1:1,000 in TBST+5% dried, nonfat milk) at 4° C. for 10 hours, washed three times with TBST, incubated with horseradish-linked anti-mouse antibody (diluted 1:10,000 in TBST+5% dried, nonfat milk) at 23° C. for 1 hour, and washed three times with TBST. Proteins were visualized with chemiluminescent detection. Results from multiple clones (FIG. 6C) show that expression of the β-glucosidase gene in *C. reinhardtii* cells resulted in production of the protein.

To determine if the β-glucosidase produced by transformed alga cells was functional, β-glucosidase activity was tested using an enzyme function assay. Briefly, 500 ml of algae cell culture was harvested by centrifugation at 4000×g at 4° C. for 15 min. The supernatant was decanted and the cells resuspended in 10 ml of lysis buffer (100 mM Tris-HCl, pH=8.0, 300 mM NaCl, 2% Tween-20). Cells were lysed by sonication (10×30 sec at 35% power). Lysate was clarified by centrifugation at 14,000×g at 4° C. for 1 hour. The supernatant was removed and incubated with anti-FLAG antibody-conjugated agarose resin at 4° C. for 10 hours. Resin was separated from the lysate by gravity filtration and washed 3× with wash buffer ((100 mM Tris-HCl, pH=8.0, 300 mM NaCl, 2% Tween-20). β-glucosidase was eluted by incubation of the resin with elution buffer (TBS, 250 ug/ml FLAG peptide). Western blot analysis of samples collect after each step (FIG. 6D) show that the β-glucosidase protein was isolated. For each sample tested, 50 μl of p-Nitrophenyl-/3-D-glucoside (substrate), 90 μl of 0.1 M sodium acetate buffer (pH 4.8), and 10 μl enzyme was added to a microplate well. The reaction was incubated at 50° C. for one hour and then the reaction was stopped with a glycine buffer. The absorbance of the liberated p-nitrophenol was measured at 430 nm. The results for two transformed strains indicated that the isolated enzyme was functional (absorbance of 0.157 and 0.284).

Example 4

Production of Endoxylanase in *C. reinhardtii*

In this example a nucleic acid encoding endoxylanase from *T. reesei* was introduced into *C. reinhardtii*. Transforming DNA (SEQ ID NO. 22, Table 4) is shown graphically in FIG. 2A. The amino acid sequence encoded by this gene is shown in Table 3. In this instance the segment labeled "Transgene" is the endoxylanase encoding gene (SEQ ID NO. 18, Table 3), the segment labeled "psbA 5' UTR" is the 5' UTR and promoter sequence for the psbA gene from *C. reinhardtii*, the segment labeled "psbA 3' UTR" contains the 3' UTR for the psbA gene from *C. reinhardtii*, and the segment labeled "Selection Marker" is the kanamycin resistance encoding gene from bacteria, which is regulated by the 5' UTR and promoter sequence for the atpA gene from *C. reinhardtii* and the 3' UTR sequence for the rbcL gene from *C. reinhardtii*. The transgene cassette is targeted to the psbA loci of *C. reinhardtii* via the segments labeled "5' Homology" and "3' Homology," which are identical to sequences of DNA flanking the psbA locus on the 5' and 3' sides, respectively. All DNA manipulations carried out in the construction of this transforming DNA were essentially as described by Sambrook et al., Molecular Cloning: A Laboratory Manual (Cold Spring Harbor Laboratory Press 1989) and Cohen et al., *Meth. Enzymol.* 297, 192-208, 1998.

For these experiments, all transformations were carried out on *C. reinhardtii* strain 137c (mt+). Cells were grown to late log phase (approximately 7 days) in the presence of 0.5 mM 5-fluorodeoxyuridine in TAP medium (Gorman and Levine, *Proc. Natl. Acad. Sci., USA* 54:1665-1669, 1965, which is incorporated herein by reference) at 23° C. under constant illumination of 450 Lux on a rotary shaker set at 100 rpm. Fifty ml of cells were harvested by centrifugation at 4,000×g at 23° C. for 5 min. The supernatant was decanted and cells resuspended in 4 ml TAP medium for subsequent chloroplast transformation by particle bombardment (Cohen et al., supra, 1998). All transformations were carried out under kanamycin selection (150 µg/ml), in which resistance was conferred by the gene encoded by the segment in FIG. 2 labeled "Selection Marker." (Chlamydomonas Stock Center, Duke University).

PCR was used to identify transformed strains. For PCR analysis, $10^6$ algae cells (from agar plate or liquid culture) were suspended in 10 mM EDTA and heated to 95° C. for 10 minutes, then cooled to near 23° C. A PCR cocktail consisting of reaction buffer, MgCl2, dNTPs, PCR primer pair(s) (Table 2 and shown graphically in FIG. 3A), DNA polymerase, and water was prepared. Algae lysate in EDTA was added to provide template for reaction. Magnesium concentration is varied to compensate for amount and concentration of algae lysate in EDTA added. Annealing temperature gradients were employed to determine optimal annealing temperature for specific primer pairs.

To identify strains that contain the endoxylanase gene, a primer pair was used in which one primer anneals to a site within the psbA 5'UTR (SEQ ID NO. 1) and the other primer anneals within the endoxylanase coding segment (SEQ ID NO. 5). Desired clones are those that yield a PCR product of expected size. To determine the degree to which the endogenous gene locus is displaced (heteroplasmic vs. homoplasmic), a PCR reaction consisting of two sets of primer pairs were employed (in the same reaction). The first pair of primers amplifies the endogenous locus targeted by the expression vector and consists of a primer that anneals within the psbA 5'UTR (SEQ ID NO. 8) and one that anneals within the psbA coding region (SEQ ID NO. 9). The second pair of primers (SEQ ID NOs. 6 and 7) amplifies a constant, or control region that is not targeted by the expression vector, so should produce a product of expected size in all cases. This reaction confirms that the absence of a PCR product from the endogenous locus did not result from cellular and/or other contaminants that inhibited the PCR reaction. Concentrations of the primer pairs are varied so that both reactions work in the same tube; however, the pair for the endogenous locus is 5× the concentration of the constant pair. The number of cycles used was >30 to increase sensitivity. The most desired clones are those that yield a product for the constant region but not for the endogenous gene locus. Desired clones are also those that give weak-intensity endogenous locus products relative to the control reaction.

Results from this PCR on 96 clones were determined and the results are shown in FIG. 7. FIG. 7A shows PCR results using the transgene-specific primer pair. As can be seen, multiple transformed clones are positive for insertion of the endo-β-glucanase gene (e.g. numbers 1-9). FIG. 7B shows the PCR results using the primer pairs to differentiate homoplasmic from heteroplasmic clones. As can be seen, multiple transformed clones are either homoplasmic or heteroplasmic to a degree in favor of incorporation of the transgene (e.g. numbers 1-9). Unnumbered clones demonstrate the presence of wild-type psbA and, thus, were not selected for further analysis.

To ensure that the presence of the endoxylanase-encoding gene led to expression of the endoxylanase protein, a Western blot was performed. Approximately $1 \times 10^8$ algae cells were collected from TAP agar medium and suspended in 0.5 ml of lysis buffer (750 mM Tris, pH=8.0, 15% sucrose, 100 mM beta-mercaptoethanol). Cells were lysed by sonication (5×30 sec at 15% power). Lysate was mixed 1:1 with loading buffer (5% SDS, 5% beta-mercaptoethanol, 30% sucrose, bromophenol blue) and proteins were separated by SDS-PAGE, followed by transfer to PVDF membrane. The membrane was blocked with TBST+5% dried, nonfat milk at 23° C. for 30 min, incubated with anti-FLAG antibody (diluted 1:1,000 in TBST+5% dried, nonfat milk) at 4° C. for 10 hours, washed three times with TBST, incubated with horseradish-linked anti-mouse antibody (diluted 1:10,000 in TBST+5% dried, nonfat milk) at 23° C. for 1 hour, and washed three times with TBST. Proteins were visualized with chemiluminescent detection. Results from multiple clones (FIG. 7C) show that expression of the endoxylanase gene in *C. reinhardtii* cells resulted in production of the protein.

To determine if the endoxylanase produced by transformed alga cells was functional, endoxylanase activity was tested using an enzyme function assay. Briefly, 500 ml of algae cell culture was harvested by centrifugation at 4000×g at 4° C. for 15 min. The supernatant was decanted and the cells resuspended in 10 ml of lysis buffer (100 mM Tris-HCl, pH=8.0, 300 mM NaCl, 2% Tween-20). Cells were lysed by sonication (10×30 sec at 35% power). Lysate was clarified by centrifugation at 14,000×g at 4° C. for 1 hour. The supernatant was removed and incubated with anti-FLAG antibody-conjugated agarose resin at 4° C. for 10 hours. Resin was separated from the lysate by gravity filtration and washed 3× with wash buffer ((100 mM Tris-HCl, pH=8.0, 300 mM NaCl, 2% Tween-20). Endoxylanase was eluted by incubation of the resin with elution buffer (TBS, 250 ug/ml FLAG peptide). Results from Western blot analysis of samples collect after each step (FIG. 7D) show that the Endoxylanase protein was isolated. To test for enzyme function, 0.5 ml aliquots of diluted enzyme preparation were added to glass test tubes and equilibrated at 40° C. for 5 minutes. A Xylazyme AX test tablet (Megazyme) was added to initiate the reaction. After 30 minutes, the reaction was terminated by adding 10 ml Trizma base solution with vigorous stirring. The tubes were incubated at room temperature for 5 minutes and the reaction was stirred again. The reaction was then filtered through a Whatman No. 1 (9 cm) filter circle. The filtrate was then clarified by microcentrifugation. The absorbance of the filtrate was measured at 590 nm. The results indicate that, for crude enzyme extracts from two different clones, endoxylanase activity was present (absorbance of 0.974 and 0.488).

Example 5

Determination of Level of Protein Expression in a *C. reinhardtii* Strain Producing Exogenous Endo-β-Glucanase Western blot analysis of proteins was done as follows. Approximately $1 \times 10^8$ algae cells were collected from liquid cultures growing in TAP medium at 23° C. under constant illumination of 5,000 Lux on a rotary shaker set at 100 rpm. Cells were suspended in 0.5 ml of lysis buffer (750 mM Tris, pH=8.0, 15% sucrose, 100 mM beta-mercaptoethanol) and lysed by sonication (5×30 sec at 15% power). Lysates were centrifuged at 14,000 RPM for 15 minutes at 4° C. and the supernatant was collected. Total soluble protein concentrations were determined using BioRad's protein assay reagent. The sample concentrations were then normalized to one another. The FLAG control protein was a FLAG tagged bacterial alkaline phosphatase protein standard (Sigma-Aldrich, St. Louis, Mo.). Lysate was mixed 1:1 with loading buffer (5% SDS, 5% beta-mercaptoethanol, 30% sucrose, bromophenol blue) and proteins were separated by SDS-PAGE, followed by transfer to PVDF membrane. The membrane was blocked with TBST+5% dried, nonfat milk at 23° C. for 30 min, incubated with anti-FLAG antibody (diluted 1:1,000 in TBST+5% dried, nonfat milk) at 4° C. for 10 hours, washed three times with TBST, incubated with horseradish-linked anti-mouse antibody (diluted 1:10,000 in TBST+5% dried, nonfat milk) at 23° C. for 1 hour, and washed three times with TBST. Proteins were visualized with chemiluminescent detection.

To ascertain the level of cellulase accumulating in the transformants under different growth conditions, we carried out the titration shown in FIG. 8. Five, ten and twenty μg of total protein from a transformant expressing endo-β-glucanase (BD5-26) were separated along with 10, 50, 100 and 200 ug of a control protein. Both proteins contain the FLAG epitope tag on their carboxy terminus, thus a direct comparison can be made between the two proteins to determine expression levels. A comparison of the signal intensity between the 5 ug samples form either 24 or 48 hours growth, show a signal greater than the 50 ng control peptide and close in intensity to the 100 ng sample. A 1% total protein expression level would equal 1/100 or 50 ng of a 5 ug sample. The intensity here shows a signal equal to a level of twice that, or 100 ng in the 5 ug sample which is equal to 2% of total protein.

TABLE 3

Amino Acid Sequences of Cellulolytic Enzymes.

| SEQ ID NO. | Sequence | Source |
|---|---|---|
| 15 | MVPYRKLAVISAFLATARAQSACTLQSETHPPLTWQKCSSGGTCTQQTGSVVIDANWRWTHATNSSTNCYEDGNTWSSTLCPDNETCAKNCCLDGAAYASTYGVTTSGNSLSIGFVTQSAQKNVGARLYLMASDTTYQEFTLLGNEFSFDVDVSQLPCGLNGALYFVSMDADGGVSKYPTNTAGAKYGTGYCDSQCPRDLKFINGQANVEGWEPSSNNANTGIGGHGSCCSEMDIWEANSISEALTPHPCTTVGQEICEGDGCGGTYSDNRYGGTCDPDGDWDPYRLGNTSFYGPGSSFTLDTTKKLTVVTQFETSGAINRYYVQNGVTFQQPNAELGSYSGNGLNDDYCTAEEAEFGGSSFSDKGGLTQFKKATSGGMVLVMSLWDDYYANMLWLDSTYPTNETSSTPGAVRGSCSTSSGVPAQVESQSPNAKVTFSNIKFGPIGSTGDPSGGNPPGGNPPGTTTTRRPATTTGSSPGPTQSHYGQCGGIGYSGPTVCASGTTCQVLNPYYSQCLGTGENLYFQGSGGGGSDYKDDDDKGTG | Exo-β-glucanase from *T. viride* |
| 16 | MVPNKSVAPLLLAASILYGGAVAQQTVWGQCGGIGWSGPTNCAPGSACSTLNPYYAQCIPGATTITTSTREPPSGPTTTTRATSTSSSTPPTSSGVRFAGVNIAGFDFGCTTDGTCVTSKVYPPLKNFTGSNNYPDGIGQMQHFVNEDGMTIFRLPVGWQYLVNNNLGGNLDSTSISKYDQLVQGCLSLGAYCIVDIHNYARWNGGIIGQGFGPTNAQFTSLWSQLASKYASQSRVWFGIMNEPHDVNINTWAATVQEVVTAIRNAGATSQFISLPGNDWQAGAFISDGSAAALSQVTNPDGSTTNLIFDVHKYLDSDNSGTHAECTTNNIDGAFSPLATWLRQNNRQAILTETGGGNVQSCIQDMCQQIQYLNQNSDVYLGYVGWGAGSFDSTYVLTETPTSSGNSWTDTSLVSSCLARKGTGENLYFQGSGGGGSDYKDDDDKGTG | Endo-β-glucanase from *T. reesei* |
| 17 | MVPLPKDFQWGFATAAYQIEGAVDQDGRGPSIWDTFCAQPGKIADGSSGVTACDSYNRTAEDIALLKSLGAKSYRFSISWSRIIPEGGRGDAVNQAGIDHYVKFVDDLLDAGITPFITLFHWDLPEGLHQRYGGLLNRTEFPLDFENYARVMFRALPKVRNWITFNEPLCSAIPGYGSGTFAPGRQSTSEPWTVGHNILVAHGRAVKAYRDDFKPASGDGQIGIVLNGDFTYPWADAADPADKEAERRLEFFTAWFADPIYLGDYPASMRKQLGDRLPTFTPEEERALVHGSNDFYGMNHYTSNY1RHRSSPASADDTVGNVDVLFTNKQGNCIGPETQSPWLRPCAAGFRDFLVWISKRYGYPPIYVTENGTSIKGESDLPKEKILEDDFRVKYYNEYIRAMVTAVELDGVNVKGYFAWSLMDNFEWADGYVTRFGVTYVDYENGQKRFPKKSAKSLKPLFDELIAAAGTGENLYFQGSGGGGSDYKDDDDKGTG | β-glucosidase from *T. reesei* |
| 18 | MVPVSFTSLLAASPPSRASCRPAAEVESVAVEKRQTIQPGTGYNNGYFYSYWNDGHGGVTYTNGPGGQFSVNWSNSGNFVGGKGWQPGTKNKVINFSGSYNPNGNSYLSVYGWSRNPLIEYYIVENFGTYNPSTGATKLGEVTSDGSVYDIYRTQRVNQPSIIGTATFYQYWSVRRNHRSSGSVNTANHFNAWAQQGLTLGTMDYQIVAVfromEGYFSSGSASITVSGTGENLYFQGSGGGGSDYKDDDDKGTG | Endo-xylanase from *T. reesei* |

Example 6

Figure 9A:
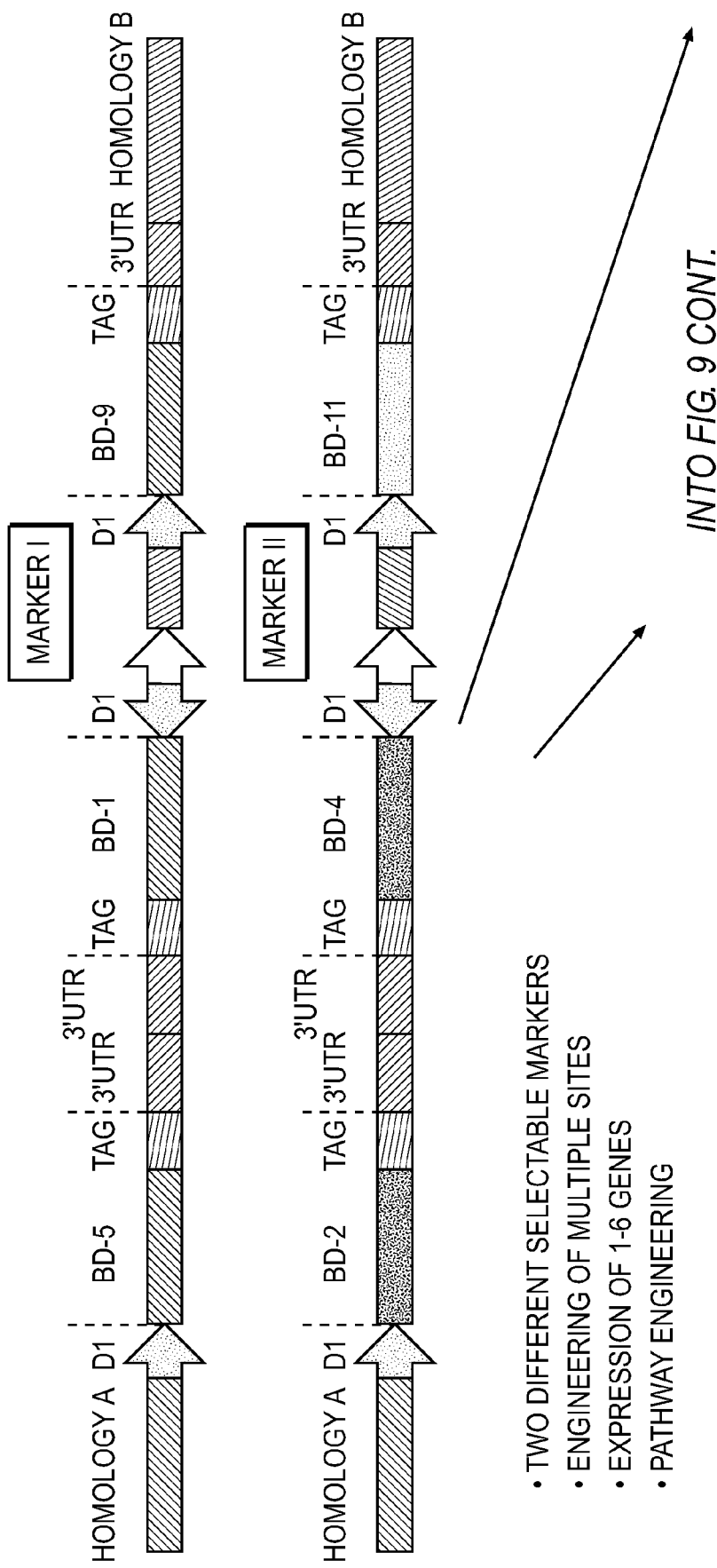
FIG. 9 is a graphic representation of an embodiment of the present invention, showing generalized constructs for insertion of multiple genes into a chloroplast genome.
Figure 9:
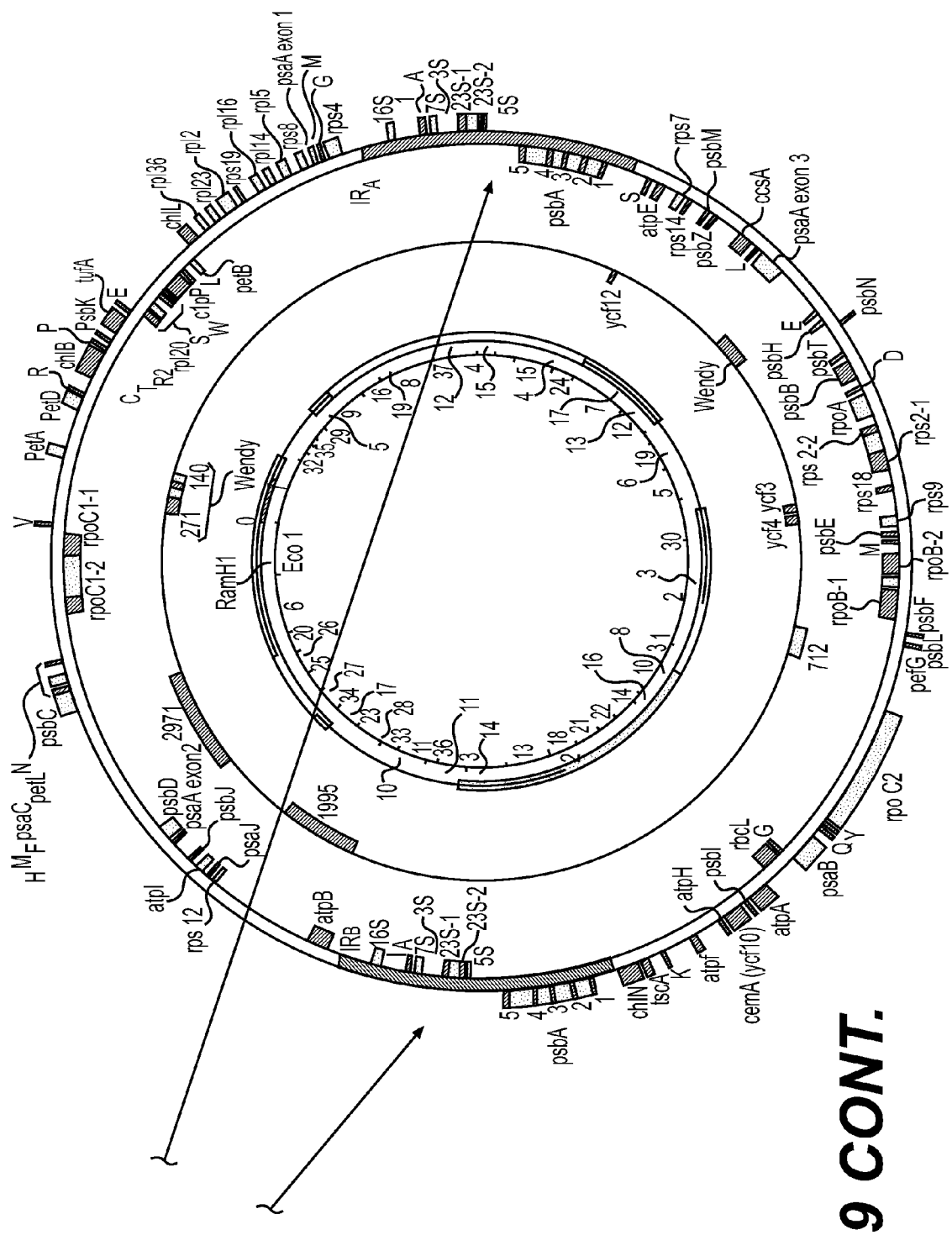

Construction of a C. reinhardtii Strain Transformed with Multiple Biodegradative Enzyme-Encoding Genes In this example a strain containing multiple biomass degrading (BD) enzyme-encoding genes using two separate constructs is described. One of skill in the art will realize that such an approach is provided merely by way of example. Transformation of a strain with a single construct containing all the genes of interest is performed generally as described in prior examples. An example of constructs which could be used to transform such a strain is shown in FIG. 9. As can be seen in the figure, two polynucleotides are constructed for the delivery of multiple genes into a host alga cell. The upper construct contains three enzyme-coding sequences (FIG. 9 BD-5, BD-1, and BD-9). The lower construct contains three enzyme-coding sequences (FIG. 9 BD-2, BD-4, and BD-11). The numbers used in this figure are meant only to indicate that different enzymes are encoded by each gene. In some instances, the genes encode different enzymes in one or more biomass degrading pathways. In other instances, one or more of the genes encode the same enzyme, but one may be a mutated form or some may be from multiple organisms. Both constructs contain terminal regions which have homology to the C. reinhardtii genome to facilitate integration into the chloroplast genome. Proper transformation, integration, protein production and protein function is analyzed as described above.

Each construct contains a selectable marker (FIG. 9 Marker I and Marker II). The C. reinhardtii cells are transformed as described above. Introduction of the two constructs can be by co-transformation with both constructs. In such instances, potential transformants are selected by growth on TAP medium supplemented with substances which will select for the presence of both markers (e.g., streptomycin and kanamycin resistance).

The genes of both constructs may be placed under control of a single transcriptional control, in essence introducing a synthetic operon ("chloroperon") into the chloroplasts of the alga cells. Such an approach allows for an entire pathway to be engineered into a chloroplast. Alternately, the separate constructs may be placed under control of different transcriptional regulators. Additionally, each gene so introduced may be placed under control of different transcriptional regulators.

Example 7

Construction of a C. reinhardtii Strain Transformed with a Construct that Does Not Disrupt Photosynthetic Capability In this example a nucleic acid encoding endo-β-glucanase from *T. reesei* was introduced into *C. reinhardtii*. Transforming DNA (SEQ ID NO. 30, Table 4) is shown graphically in FIG. 2B. In this instance the segment labeled "Transgene" is the endo-β-glucanase encoding gene (SEQ ID NO. 16, Table 3), the segment labeled 5' UTR is the 5' UTR and promoter sequence for the psbD gene from *C. reinhardtii*, the segment labeled 3' UTR contains the 3' UTR for the psbA gene from *C. reinhardtii*, and the segment labeled "Selection Marker" is the kanamycin resistance encoding gene from bacteria, which is regulated by the 5' UTR and promoter sequence for the atpA gene from *C. reinhardtii* and the 3' UTR sequence for the rbcL gene from *C. reinhardtii*. The transgene cassette is targeted to the 3HB locus of *C. reinhardtii* via the segments labeled "5' Homology" and "3' Homology," which are identical to sequences of DNA flanking the 3HB locus on the 5' and 3' sides, respectively. All DNA manipulations carried out in the construction of this transforming DNA were essentially as described by Sambrook et al., Molecular Cloning: A Laboratory Manual (Cold Spring Harbor Laboratory Press 1989) and Cohen et al., *Meth. Enzymol.* 297, 192-208, 1998.

For these experiments, all transformations were carried out on *C. reinhardtii* strain 137c (mt+). Cells were grown to late log phase (approximately 7 days) in the presence of 0.5 mM 5-fluorodeoxyuridine in TAP medium (Gorman and Levine, *Proc. Natl. Acad. Sci., USA* 54:1665-1669, 1965, which is incorporated herein by reference) at 23° C. under constant illumination of 450 Lux on a rotary shaker set at 100 rpm. Fifty ml of cells were harvested by centrifugation at 4,000×g at 23° C. for 5 min. The supernatant was decanted and cells resuspended in 4 ml TAP medium for subsequent chloroplast transformation by particle bombardment (Cohen et al., supra, 1998). All transformations were carried out under kanamycin selection (100 μg/ml), in which resistance was conferred by the gene encoded by the segment in FIG. 2B labeled "Selection Marker." (Chlamydomonas Stock Center, Duke University).

PCR was used to identify transformed strains. For PCR analysis, $10^6$ algae cells (from agar plate or liquid culture) were suspended in 10 mM EDTA and heated to 95° C. for 10 minutes, then cooled to near 23° C. A PCR cocktail consisting of reaction buffer, MgCl2, dNTPs, PCR primer pair(s) (Table 2 and shown graphically in FIG. 3B), DNA polymerase, and water was prepared. Algae lysate in EDTA was added to provide template for reaction. Magnesium concentration is varied to compensate for amount and concentration of algae lysate in EDTA added. Annealing temperature gradients were employed to determine optimal annealing temperature for specific primer pairs.

To identify strains that contain the endo-β-glucanase gene, a primer pair was used in which one primer anneals to a site within the psbD 5'UTR (SEQ ID NO. 11) and the other primer anneals within the endo-β-glucanase coding segment (SEQ ID NO. 3). Desired clones are those that yield a PCR product of expected size. To determine the degree to which the endogenous gene locus is displaced (heteroplasmic vs. homoplasmic), a PCR reaction consisting of two sets of primer pairs were employed (in the same reaction). The first pair of primers amplifies the endogenous locus targeted by the expression vector (SEQ ID NOs. 13 and 14). The second pair of primers (SEQ ID NOs. 6 and 7) amplifies a constant, or control region that is not targeted by the expression vector, so should produce a product of expected size in all cases. This reaction confirms that the absence of a PCR product from the endogenous locus did not result from cellular and/or other contaminants that inhibited the PCR reaction. Concentrations of the primer pairs are varied so that both reactions work in the same tube; however, the pair for the endogenous locus is 5× the concentration of the constant pair. The number of cycles used was >30 to increase sensitivity. The most desired clones are those that yield a product for the constant region but not for the endogenous gene locus. Desired clones are also those that give weak-intensity endogenous locus products relative to the control reaction.

Results from this PCR on 96 clones were determined and the results are shown in FIG. 14. FIG. 14A shows PCR results using the transgene-specific primer pair. As can be seen, multiple transformed clones are positive for insertion of the endo-β-glucanase gene (e.g. numbers 1, 4, and 14). FIG. 14B shows the PCR results using the primer pairs to differentiate homoplasmic from heteroplasmic clones. As can be seen, multiple transformed clones are either homoplasmic or heteroplasmic to a degree in favor of incorporation of the transgene (e.g. numbers 1, 4, and 14). Unnumbered clones demonstrate the presence of wild-type psbA and, thus, were not selected for further analysis.

To ensure that the presence of the endo-β-glucanase-encoding gene led to expression of the endo-β-glucanase protein, a Western blot was performed. Approximately 1×10$^8$ algae cells were collected from TAP agar medium and suspended in 0.5 ml of lysis buffer (750 mM Tris, pH=8.0, 15% sucrose, 100 mM beta-mercaptoethanol). Cells were lysed by sonication (5×30 sec at 15% power). Lysate was mixed 1:1 with loading buffer (5% SDS, 5% beta-mercaptoethanol, 30% sucrose, bromophenol blue) and proteins were separated by SDS-PAGE, followed by transfer to PVDF membrane. The membrane was blocked with TBST+5% dried, nonfat milk at 23° C. for 30 min, incubated with anti-FLAG antibody (diluted 1:1,000 in TBST+5% dried, nonfat milk) at 4° C. for 10 hours, washed three times with TBST, incubated with horseradish-linked anti-mouse antibody (diluted 1:10,000 in TBST+5% dried, nonfat milk) at 23° C. for 1 hour, and washed three times with TBST. Proteins were visualized with chemiluminescent detection. Results from multiple clones (FIG. 14C) show that expression of the endo-β-glucanase gene in C. reinhardtii cells resulted in production of the protein.

Similar results were seen (FIG. 15) with a similar construct containing the endoxylanase gene from T. reesei (SEQ ID NO. 31, Table 4). The construct containing the endoxylanase gene is depicted in FIG. 2B. In this instance the segment labeled "Transgene" is the endoxylanase encoding gene (SEQ ID NO. 18, Table 3), the segment labeled 5' UTR is the 5' UTR and promoter sequence for the psbD gene from C. reinhardtii, the segment labeled 3' UTR contains the 3' UTR for the psbA gene from C. reinhardtii, and the segment labeled "Selection Marker" is the kanamycin resistance encoding gene from bacteria, which is regulated by the 5' UTR and promoter sequence for the atpA gene from C. reinhardtii and the 3' UTR sequence for the rbcL gene from C. reinhardtii. The transgene cassette is targeted to the 3HB locus of C. reinhardtii via the segments labeled "5' Homology" and "3' Homology," which are identical to sequences of DNA flanking the 3HB locus on the 5' and 3' sides, respectively. All DNA manipulations carried out in the construction of this transforming DNA were essentially as described by Sambrook et al., Molecular Cloning: A Laboratory Manual (Cold Spring Harbor Laboratory Press 1989) and Cohen et al., Meth. Enzymol. 297, 192-208, 1998.

Figure 15A:
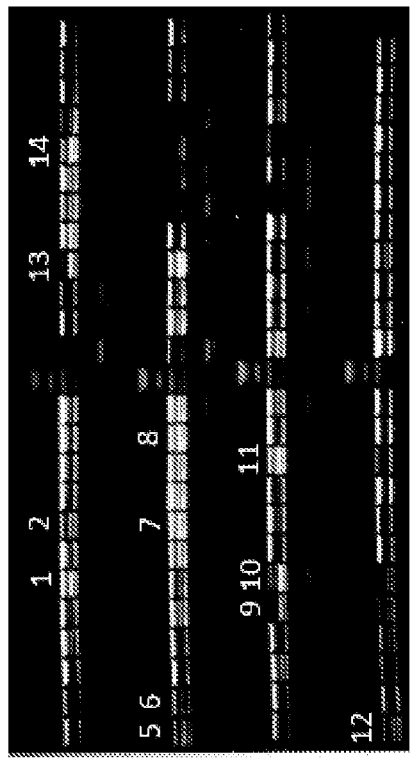
FIG. 15 illustrates results from PCR screening and Western blot analysis of endoxylanase transformed C. reinhardtii clones.
Figure 15B:
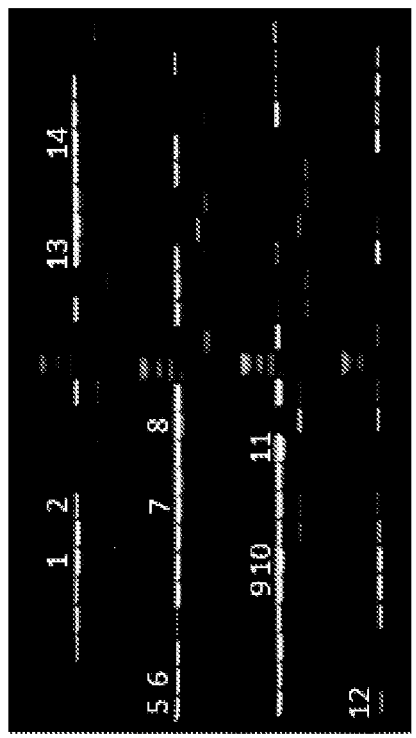
Figure 15C:
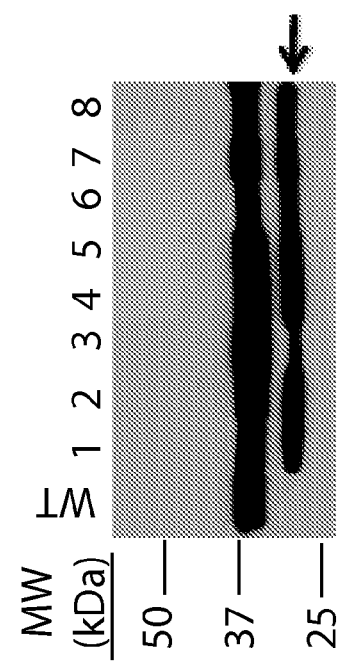

FIG. 15A shows PCR using the gene-specific primer pair. As can be seen, multiple transformed clones are positive for insertion of the endoxylanase gene. FIG. 15B shows the PCR results using the primer pairs to differentiate homoplasmic from heteroplasmic clones. As can be seen, multiple transformed clones are either homoplasmic or heteroplasmic to a degree in favor of incorporation of the transgene. Unnumbered clones demonstrate the presence of wild-type psbA and, thus, were not selected for further analysis. Western blot analysis demonstrating protein expression is demonstrated in FIG. 15C.

Similar results were seen (FIG. 16) with a similar construct containing the exo-β-glucanase gene from T. viride (SEQ ID NO. 29, Table 4). The construct containing the exo-β-glucanase gene is depicted in FIG. 2B. In this instance the segment labeled "Transgene" is the exo-β-glucanase encoding gene (SEQ ID NO. 15, Table 3), the segment labeled 5' UTR is the 5' UTR and promoter sequence for the psbD gene from C. reinhardtii, the segment labeled 3' UTR contains the 3' UTR for the psbA gene from C. reinhardtii, and the segment labeled "Selection Marker" is the kanamycin resistance encoding gene from bacteria, which is regulated by the 5' UTR and promoter sequence for the atpA gene from C. reinhardtii and the 3' UTR sequence for the rbcL gene from C. reinhardtii. The transgene cassette is targeted to the 3HB locus of C. reinhardtii via the segments labeled "5' Homology" and "3' Homology," which are identical to sequences of DNA flanking the 3HB locus on the 5' and 3' sides, respectively. All DNA manipulations carried out in the construction of this transforming DNA were essentially as described by Sambrook et al., Molecular Cloning: A Laboratory Manual (Cold Spring Harbor Laboratory Press 1989) and Cohen et al., Meth. Enzymol. 297, 192-208, 1998.

FIG. 16A shows PCR using the gene-specific primer pair. As can be seen, multiple transformed clones are positive for insertion of the endoxylanase gene. FIG. 16B shows the PCR results using the primer pairs to differentiate homoplasmic from heteroplasmic clones. As can be seen, multiple transformed clones are either homoplasmic or heteroplasmic to a degree in favor of incorporation of the transgene. Unnumbered clones demonstrate the presence of wild-type psbA and, thus, were not selected for further analysis. Western blot analysis demonstrating protein expression is demonstrated in FIG. 16C.

TABLE 4

Vector Sequences

| SEQ ID NO. | Sequence | Use |
|---|---|---|
| 19 | GCACTTTTCGGGGAAATGTGCGCGGAACCCCTATTTGTTTATTTTTCTAAATACATTCAAATATGTATC CGCTCATGAGACAATAACCCTGATAAATGCTTCAATAATATTGAAAAAGGAAGAGTATGAGTATTCAAC ATTTCCGTGTCGCCCTTATTCCCTTTTTTGCGGCATTTTGCCTTCCTGTTTTTGCTCACCCAGAAACGC TGGTGAAAGTAAAAGATGCTGAAGATCAGTTGGGTGCACGAGTGGGTTACATCGAACTGGATCTCAACA GCGGTAAGATCCTTGAGAGTTTTCGCCCCGAAGAACGTTTTCCAATGATGAGCACTTTTAAAGTTCTGC TATGTGGCGCGGTATTATCCCGTATTGACGCCGGGCAAGAGCAACTCGGTCGCCGCATACACTATTCTC AGAATGACTTGGTTGAGTACTCACCAGTCACAGAAAAGCATCTTACGGATGGCATGACAGTAAGAGAAT TATGCAGTGCTGCCATAACCATGAGTGATAACACTGCGGCCAACTTACTTCTGACAACGATCGGAGGAC CGAAGGAGCTAACCGCTTTTTTGCACAACATGGGGGATCATGTAACTCGCCTTGATCGTTGGGAACCGG AGCTGAATGAAGCCATACCAAACGACGAGCGTGACACCACGATGCCTGTAGCAATGGCAACAACGTTGC GCAAACTATTAACTGGCGAACTACTTACTCTAGCTTCCCGGCAACAATTAATAGACTGGATGGAGGCGG ATAAAGTTGCAGGACCACTTCTGCGCTCGGCCCTTCCGGCTGGCTGGTTTATTGCTGATAAATCTGGAG CCGGTGAGCGTGGGTCTCGCGGTATCATTGCAGCACTGGGGCCAGATGGTAAGCCCTCCCGTATCGTAG TTATCTACACGACGGGGAGTCAGGCAACTATGGATGAACGAAATAGACAGATCGCTGAGATAGGTGCCT CACTGATTAAGCATTGGTAACTGTCAGACCAAGTTTACTCATATATACTTTAGATTGATTTAAAACTTC ATTTTTAATTTAAAAGGATCTAGGTGAAGATCCTTTTTGATAATCTCATGACCAAAATCCCTTAACGTG | Exo-β-glucanase insertion cassette (D1 KAN-BD01) |

TABLE 4-continued

Vector Sequences

| SEQ ID NO. | Sequence | Use |
|---|---|---|
| | AGTTTTCGTTCCACTGAGCGTCAGACCCCGTAGAAAAGATCAAAGGATCTTCTTGAGATCCTTTTTTTC<br>TGCGCGTAATCTGCTGCTTGCAAACAAAAAAACCACCGCTACCAGCGGTGGTTTGTTTGCCGGATCAAG<br>AGCTACCAACTCTTTTTCCGAAGGTAACTGGCTTCAGCAGAGCGCAGATACCAAATACTGTCCTTCTAG<br>TGTAGCCGTAGTTAGGCCACCACTTCAAGAACTCTGTAGCACCGCCTACATACCTCGCTCTGCTAATCC<br>TGTTACCAGTGGCTGCTGCCAGTGGCGATAAGTCGTGTCTTACCGGGTTGGACTCAAGACGATAGTTAC<br>CGGATAAGGCGCAGCGGTCGGGCTGAACGGGGGGTTCGTGCACACAGCCCAGCTTGGAGCGAACGACCT<br>ACACCGAACTGAGATACCTACAGCGTGAGCTATGAGAAAGCGCCACGCTTCCCGAAGGGAGAAAGGCGG<br>ACAGGTATCCGGTAAGCGGCAGGGTCGGAACAGGAGAGCGCACGAGGGAGCTTCCAGGGGGAAACGCCT<br>GGTATCTTTATAGTCCTGTCGGGTTTCGCCACCTCTGACTTGAGCGTCGATTTTTGTGATGCTCGTCAG<br>GGGGGCGGAGCCTATGGAAAAACGCCAGCAACGCGGCCTTTTTACGGTTCCTGGCCTTTTGCTGGCCTT<br>TTGCTCACATGTTCTTTCCTGCGTTATCCCCTGATTCTGTGGATAACCGTATTACCGCTTTGAGTGAG<br>CTGATACCGCTCGCCGCAGCCGAACGACCGAGCGCAGCGAGTCAGTGAGCGAGGAAGCGGAAGAGCGCC<br>CAATACGCAAACCGCCTCTCCCCGCGCGTTGGCCGATTCATTAATGCAGCTGGCACGACAGGTTTCCCG<br>ACTGGAAAGCGGGCAGTGAGCGCAACGCAATTAATGTGAGTTAGCTCACTCATTAGGCACCCCAGGCTT<br>TACACTTTATGCTTCCGGCTCGTATGTTGTGTGGAATTGTGAGCGGATAACAATTTCACACAGGAAACA<br>GCTATGACCATGATTACGCCAAGCTCGAAATTAACCCTCACTAAAGGGAACAAAAGCTGGAGCTCCACC<br>GCGGTGGCGGCCGCTCTAGCACTAGTGGATCGCCCGGGCTGCAGGAATTCcatatttagataaacgatt<br>tcaagcagcagaattagctttattagaacaaacttgtaaagaaatgaatgtaccaatgccgcgcattgt<br>agaaaaaccagataattattatcaaattcgacgtatacgtgaattaaaacctgatttaacgattactgg<br>aatggcacatgcaaatccattagaagctcgaggtattacaacaaaatggtcagttgaatttacttttgc<br>tcaaattcatggatttactaatacacgtgaaattttagaattagtaacacagcctcttagacgcaatct<br>aatgtcaaatcaatctgtaaatgctatttcttaatataaatcccaaaagatttttttttataatactgag<br>acttcaacacttacttgtttttatttttttgtagttacaattcactcacgtttaaagacattggaaaatga<br>ggcaggacgttagtcgatatttatacactcttaagtttacttgcccaatatttatattaggacgtcccc<br>ttcgggtaaataaattttagtggcagtggtaccaccactgcctattttaatactccgaagcatataaat<br>atacttcggagtatataaatatccactaatatttatattaggcagttggcaggcaacaataaataaatt<br>tgtcccgtaagggacgtcccgaaggggaaggggaagaaggcagttgcctcgcctatcggctaacaagt<br>tccttggagtatataaccgcctacaggtaactaaagaacattttgttacccgtagggggtttatacttc<br>taattgcttcttctgaacaataaaatggtttgtgtggtctgggctaggaaacttgtaacaatgtgtagt<br>gtcgcttccgcttcccttcgggacgtccccttcgggtaagtaaacttaggagtattaaatcgggacgtc<br>cccttcgggtaaataaatttcagtggacgtcccccttacgggacgccagtagacgtcagtggcagttgcc<br>tcgcctatcggctaacaagttccttcggagtatataaatatagaatgtttacatactcctaagtttact<br>tgcctccttcggagtatataaatatcccgaaggggaaggaggacgccagtggcagtggtaccgccactg<br>cctgcttcctccttcggagtatgtaaacccttcgggcaactaaagtttatcgcagtatataaatatag<br>gcagttggcaggcaactgccactgacgtcctattttaatactccgaaggaggcagttggcaggcaactg<br>ccactgacgtcccgtaagggtaaggggacgtccactggcgtcccgtaagggaaggggacgtaggtaca<br>taaatgtgctaggtaactaacgtttgattttttgtggtataatatatgtaccatgcttttaatagaagc<br>ttgaatttataaattaaaatattttacaatattttacggagaaattaaaactttaaaaaaattaacat<br>ATGGTACCATATCGTAAACTTGCTGTTATTAGTGCTTTCTTAGCTACTGCTCGTGCACAGTCAGCATGT<br>ACCTTACAATCTGAAACTCATCCTCCATTAACATGGCAAAAATGTTCTTCAGGAGGTACTTGTACACAA<br>CAAACTGGCTCTGTAGTAATTGATGCTAACTGGCGTTGGACACATGCCACTAATAGTTCAACTAATTGT<br>TATGACGGTAATACTTGGTCATCAACACTTTGTCCCGATAACGAAACTTGTGCTAAAAATTGTTGTTTA<br>GATGGTGCAGCTTACGCTTCAACTTACGGCGTTACTACATCAGGTAACTCATTATCAATTGGTTTCGTG<br>ACTCAATCAGCACAAAAAAATGTAGGCGCACGTTTATACTTAATGGCAAGTGACACAACCTATCAAGAA<br>TTTACATTATTAGGTAATGAGTTCAGTTTCGACGTAGATGTGAGTCAATTACCATGTGGTTTAAATGGT<br>GCTCTTTATTTCGTTTCAATGGACGCTGATGGCGGTGTAAGCAAATATCCTACTAATACAGCAGGTGCT<br>AAATACGGAACAGGCTATTGTGATTCTCAGTGTCCTCGTGATTTAAAGTTTATTAACGGTCAAGCTAAC<br>GTGGAAGGTTGGGAACCAAGTAGTAATAATGCAAATACTGGATTGGTGGTCACGGATCTTGTTGTTCT<br>GAAATGGATATTTGGGAAGCTAATTCAATTAGTGAAGCATTAACTCCACATCCTTGTACTACCGTTGGC<br>CAAGAAATTTGTGAAGGCGACGGTTGCGGTGGAACATACAGTGATAACCGTTATGGTGGTACATGTGAT<br>CCTGATGGCTGCGATTGGGACCCATATCGTTTAGGAAATACATCTTTTTATGGACCAGGAAGTTCATTC<br>ACATTAGATACAACTAAAAAGTTAACAGTTGTTACACAGTTCGAAACTAGCGGTGCTATTAATCGTTAT<br>TACGTGCAAAATGGTGTAACTTTTCAACAACCAAATGCAGAATTAGGTTCTTATTCTGGTAACGGCCTT<br>AATGACGATTATTGTACAGCAGAAGAAGCAGAATTTGGTGGTAGCAGCTTCTCAGATAAAGGTGGTTTA<br>ACTCAATTCAAGAAAGCAACATCAGGTGGTATGGTTTTAGTTATGTCATTATGGGATGACTATTATGCT<br>AATATGTTATGGTTAGATAGTACATATCCTACAGACGAAACTTCAAGCACTCCTGGTGCTGTTCGTGGT<br>TCATGTTCAACTTCAAGTGGTGTACCTGTCAAGTTGAAAGCCAAAGTCCTAATGCAAAAGTAACTTTT<br>AGTAATATCAAATTTGGTCCAATTGGCTCTACAGGCGATCCTTCAGGTGGTAATCCACCAGGTGGAAAT<br>CCACCTGGCACCACTACAACACGTCGTCCTGCTACTACCACAGGTTCTTCTCCTGGACCAACACAATCT<br>CATTACGGTCAATGTGGTGGTATTGGTTATTCAGGTCCAACTGTGTGTGCATCAGGAACTACATGTCAA<br>GTTTTAAATCCATATTATAGCCAATGTTTAGGTACCGGTGAAAACTTATACTTTCAAGGCTCAGGTGGC<br>GGTGGAAGTGATTACAAAGATGATGATGATAAAGGAACCGGTTAATCTAGActtagcttcaactaactc<br>tagctcaaacaactaattttttttaaactaaaataaatctggttaaccatacctggtttatttagtt<br>tagtttatacacacttttcatatatatatacttaatagctaccataggcagttggcaggacgtcccctt<br>acgggacaaatgtatttattgttgcctgccaactgcctaatataacaatcattagtggacgtccccttccc<br>ttacgggcaagtaaacttagggattttaatgctccgttaggaggcaaataaattttagtggcagttgcc<br>tcgcctatcggctaacaagttccttcggagtatataaatatcctgccaactgccgatatttatatacta<br>ggcagtggcggtaccactcgacGGATCCTACGTAATCGATGAATTCGATCCCATTTTTATAACTGGTCT<br>CAAAATACCTATAAACCCATTGTTCTTCTCTTTTAGCTCTAAGAACAATCAATTTATAAATATATTTAT<br>TATTATGCTATAATATAAATACTATATAAATACATTTACCTTTTTATAAATACATTTACCTTTTTTTA<br>ATTTGCATGATTTTAATGCTTATGCTATCTTTTTTATTTAGTCCATAAAACCTTTAAAGGACCTTTTCT<br>TATGGGATATTTATATTTTCCTAACAAAGCAATCGGCGTCATAAACTTTAGTTGCTTACGACGCCTGTG<br>GACGTCCCCCCCTTCCCCTTACGGGCAAGTAAACTTAGGGATTTTAATGCAATAAATAAATTTGTCCTC<br>TTCGGGCAAATGAATTTTAGTATTTAAATATGACAAGGGTGAACCATTACTTTTGTTAACAAGTGATCT | |

TABLE 4-continued

Vector Sequences

| SEQ ID NO. | Sequence | Use |
|---|---|---|
| | TACCACTCACTATTTTTGTTGAATTTTAAACTTATTTAAAATTCTCGAGAAAGATTTTAAAAATAAACT<br>TTTTTAATCTTTTATTTATTTTTTCTTTTTTcgtatggaattgcccaatattattcaacaatttatcgg<br>aaacagcgttttagagccaaataaaattggtcagtcgccatcggatgtttattcttttaatcgaaataa<br>tgaaacttttttttcttaagcgatctagcacttttatatacagagaccacatacagtgtctctcgtgaagc<br>gaaaatgttgagttggctctctgagaaattaaaggtgcctgaactcatcatgacttttcaggatgagca<br>gtttgaatttatgatcactaaagcgatcaatgcaaaaccaatttcagcgcttttttttaacagaccaaga<br>attgcttgctatctataaggaggcactcaatctgttaaattcaattgctattattgattgtccatttat<br>ttcaaacattgatcatcggttaaaagagtcaaaatttttttattgataaccaactccttgacgatataga<br>tcaagatgattttgacactgaattatggggagaccataaaacttacctaagtctatggaatgagttaac<br>cgagactcgtgttgaagaaagattggttttttctcatggcgatatcacggatagtaatattttttataga<br>taaattcaatgaaatttatttttttagaccttggtcgtgctgggttagcagatgaatttgtagatatatc<br>ctttgttgaacgttgcctaagagaggatgcatcggaggaaactgcgaaaatattttttaaagcatttaaa<br>aaatgatagacctgacaaaaggaattattttttaaaacttgatgaattgaattgaTTCCAAGCATTATC<br>TAAAATACTCTGCAGGCACGCTAGCTTGTACTCAAGCTCGTAACGAAGGTCGTGACCTTGCTCGTGAAG<br>GTGGCGACGTAATTCGTTCAGCTTGTAAATGGTCTCCAGAACTTGCTGCTGCATGTGAAGTTTGGAAAG<br>AAATTAAATTCGAATTTGATACTATTGACAAACTTTAATTTTTATTTTTCATGATGTTTATGTGAATAG<br>CATAAACATCGTTTTTATTTTTTATGGTGTTTAGGTTAAATACCTAAACATCATTTTACATTTTTAAAA<br>TTAAGTTCTAAAGTTATCTTTTGTTTAAATTTGCCTGTGCTTTATAAATTACGATGTGCCAGAAAAATA<br>AAATCTTAGCTTTTTATTATAGAATTTATCTTTATGTATTATATTTTATAAGTTATAATAAAAGAAATA<br>GTAACATACTAAAGCGGATGTAGCGCGTTTATCTTAACGGAAGGAATTCGGCGCCTACGTAGGATCCgt<br>atccatgctagcaatatctgatggtacttgcatttcataagtttggcctggaataaccaccgtttcgga<br>agtacctgtcgctttaagttttatagctaaatctaaagtttcttttaagtcttttagctgtattaaatac<br>tccacgactttcccttacgggacaataaataaattgtcccctttccccttacgtgacgtcagtggcagt<br>tgcctgccaactgcctccttcggagtattaaaatcctatatttatatactcctaagtttacttgcccaa<br>tatttatattaggcagttggcaggcaactgccactgacgtcccgaaggggaaggggaaggacgtcccct<br>tcgggtaaataaatttagtggcagtggtaccaccactgcctgcttcctccttcccttcgggcaagta<br>aacttagaataaaatttatttgctgcgctagcaggtttacatactcctaagtttacttgcccgaagggg<br>aaggaggacgtcccccttacgggaatataaatattagtggcagtggtacaataaataaattgtatgtaaa<br>cccccttcgggcaactaaagtttatcgcagtatataaatatagaatgtttacatactccgaaggaggacg<br>ccagtggcagtggtaccgccactgcctgtccgcagtattaacatcctatttttaatactccgaaggaggc<br>agttggcaggcaactgccactaatatttatattcccgtaaggggacgtcctaatttaatactccgaagg<br>aggcagttggcaggcaactgccactaaaatttatttgcctcctaacggagcattaaaatcccgaaggggg<br>acgtcccgaaggggaaggggaaggaggcaactgcctgcttcctccttcccctcgggcaagtaaactta<br>gaataaaatttatttgctgcgctcgcaggtttacatactcctaagtttacttgcccgaaggggaaggag<br>gacgtcccccttacgggaatataaatattagtggcagtggtacaataaataaattgtatgtaaacccctt<br>cgggcaactaaagtttatcgcagtatataaatatcggcagttggcaggcaactgccactaaaattcatt<br>tgcccgaaggggacgtccactaatatttatattcccgtaaggggacgtcccgaaggggaaggggacgtc<br>ctaaacggagcattaaaatccctaagtttacttgcctaggcagttggcaggatatttatatacgatatt<br>aatacttttgctactggcacactaaaatttatttgcccgtaaggggacgtccttcggtggttatataaa<br>taatcccgtaggggagggggatgtcccgtaggggagggggagtggagctccaacggaggttggagct<br>tctttggtttcctaggcattatttaaatattttttaaccctagcactagaactgagattccagacggcg<br>acccgtaaagttcttcagtcccctcagcttttttcacaaccaagttcgggatggattggtgtgggtccaa<br>ctgagcaaagagcaccaaggttaactgcatctctgtgagatgctagttaaactaagcttagcttagctc<br>ataaacgatagttacccgcaagggtttatgtaattatattataaggtcaaatcaaacggcctttagta<br>tatctcggctaaagccattgctgactgtacacctgataccctatataacggcttgtctagccgcggcctt<br>agagagcactcatcttgagtttagcttcctacttagatgctttcagcagttatctatccatgcgtagct<br>acccagcgtttcccattggaatgagaactggtacacaattggcatgtccttttcaggtcctctcgtacta<br>tgaaaggctactctcaatgctcaacgcctacaccggatatggaccaaactgctcacgcatgaaattt<br>taaagccgaataaaacttgcggtctttaaaactaaccccttttactttcgtaaaggcatggactatgtct<br>tcatcctgctactgttaatggcaggagtcggcgtattatactttcccactCTCGAGGGGGGGCCCGGTA<br>CCCAATTCGCCCTATAGTGAGTCGTATTACAATTCACTGGCCGTCGTTTTACAACGTCGTGACTGGGAA<br>AACCCTGGCGTTACCCAACTTAATCGCCTTGCAGCACATCCCCCTTTCGCCAGCTGGCGTAATAGCGAA<br>GAGGCCCGCACCGATCGCCCTTCCCAACAGTTGCGCAGCCTGAATGGCGAATGGGACGCGCCCTGTAGC<br>GGCGCATTAAGCGCGGCGGGTGTGGTGGTTACGCGCAGCGTGACCGCTACACTTGCCAGCGCCCTAGCG<br>CCCGCTCCTTTCGCTTTCTTCCCTTCCTTTCTCGCCACGTTCGCCGGCTTTCCCCGTCAAGCTCTAAAT<br>CGGGGGCTCCCTTTAGGGTTCCGATTTAGTGCTTTACGGCACCTCGACCCCAAAAAACTTGATTAGGGT<br>GATGGTTCACGTAGTGGGCCATCGCCCTGATAGACGGTTTTTCGCCCTTTGACGTTGGAGTCCACGTTC<br>TTTAATAGTGGACTCTTGTTCCAAACTGGAACAACACTCAACCCTATCTCGGTCTATTCTTTTGATTTA<br>TAAGGGATTTTGCCGATTTCGGCCTATTGGTTAAAAAATGAGCTGATTTAACAAAAATTTAACGCGAAT<br>TTTAACAAAATATTAACGCTTACAATTTAGGTG | |
| 20 | GCACTTTTCGGGGAAATGTGCGCGGAACCCCTATTTGTTTATTTTTCTAAATACATTCAAATATGTATC<br>CGCTCATGAGACAATAACCCTGATAAATGCTTCAATAATATTGAAAAGGAAGAGTATGAGTATTCAAC<br>ATTTCCGTGTCGCCCTTATTCCCTTTTTTGCGGCATTTTGCCTTCCTGTTTTTGCTCACCCAGAAACGC<br>TGGTGAAAGTAAAAGATGCTGAAGATCAGTTGGGTGCACGAGTGGGTTACATCGAACTGGATCTCAACA<br>GCGGTAAGATCCTTGAGAGTTTTCGCCCCGAAGAACGTTTTCCAATGATGAGCACTTTTAAAGTTCTGC<br>TATGTGGCGCGGTATTATCCCGTATTGACGCCGGGCAAGAGCAACTCGGTCGCCGCATACACTATTCTC<br>AGAATGACTTGGTTGAGTACTCACCAGTCACAGAAAAGCATCTTACGGATGGCATGACAGTAAGAGAAT<br>TATGCAGTGCTGCCATAACCATGAGTGATAACACTGCGGCCAACTTACTTCTGACAACGATCGGAGGAC<br>CGAAGGAGCTAACCGCTTTTTTGCACAACATGGGGGATCATGTAACTCGCCTTGATCGTTGGGAACCGG<br>AGCTGAATGAAGCCATACCAAACGACGAGCGTGACACCACGATGCCTGTAGCAATGGCAACAACGTTGC<br>GCAAACTATTAACTGGCGAACTACTTACTCTAGCTTCCCGGCAACAATTAATAGACTGGATGGAGGCGG<br>ATAAAGTTGCAGGACCACTTCTGCGCTCGGCCCTTCCGGCTGGCTGGTTTATTGCTGATAAATCTGGAG<br>CCGGTGAGCGTGGGTCTCGCGGTATCATTGCAGCACTGGGGCCAGATGGTAAGCCCTCCCGTATCGTAG | Endo-β-glucanase insertion cassette (D1 KAN-BD05) |

TABLE 4-continued

Vector Sequences

| SEQ ID NO. | Sequence | Use |
|---|---|---|
| | TTATCTACACGACGGGGAGTCAGGCAACTATGGATGAACGAAATAGACAGATCGCTGAGATAGGTGCCT CACTGATTAAGCATTGGTAACTGTCAGACCAAGTTTACTCATATATACTTTAGATTGATTTAAAACTTC ATTTTTAATTTAAAAGGATCTAGGTGAAGATCCTTTTTGATAATCTCATGACCAAAATCCCTTAACGTG AGTTTTCGTTCCACTGAGCGTCAGACCCCGTAGAAAAGATCAAAGGATCTTCTTGAGATCCTTTTTTTC TGCGCGTAATCTGCTGCTTGCAAACAAAAAAACCACCGCTACCAGCGGTGGTTTGTTTGCCGGATCAAG AGCTACCAACTCTTTTTCCGAAGGTAACTGGCTTCAGCAGAGCGCAGATACCAAATACTGTCCTTCTAG TGTAGCCGTAGTTAGGCCACCACTTCAAGAACTCTGTAGCACCGCCTACATACCTCGCTCTGCTAATCC TGTTACCAGTGGCTGCTGCCAGTGGCGATAAGTCGTGTCTTACCGGGTTGGACTCAAGACGATAGTTAC CGGATAAGGCGCAGCGGTCGGGCTGAACGGGGGGTTCGTGCACACAGCCCAGCTTGGAGCGAACGACCT ACACCGAACTGAGATACCTACAGCGTGAGCTATGAGAAAGCGCCACGCTTCCCGAAGGGAGAAAGGCGG ACAGGTATCCGGTAAGCGGCAGGGTCGGAACAGGAGAGCGCACGAGGGAGCTTCCAGGGGGAAACGCCT GGTATCTTTATAGTCCTGTCGGGTTTCGCCACCTCTGACTTGAGCGTCGATTTTTGTGATGCTCGTCAG GGGGGCGGAGCCTATGGAAAAACGCCAGCAACGCGGCCTTTTTACGGTTCCTGGCCTTTTGCTGGCCTT TTGCTCACATGTTCTTTCCTGCGTTATCCCTGATTCTGTGGATAACCGTATTACCGCCTTTGAGTGAG CTGATACCGCTCGCCGCAGCCGAACGACCGAGCGCAGCGAGTCAGTGAGCGAGGAAGCGGAAGAGCGCC CAATACGCAAACCGCCTCTCCCCGCGCGTTGGCCGATTCATTAATGCAGCTGGCACGACAGGTTTCCCG ACTGGAAAGCGGGCAGTGAGCGCAACGCAATTAATGTGAGTTAGCTCACTCATTAGGCACCCCAGGCTT TACACTTTATGCTTCCGGCTCGTATGTTGTGTGGAATTGTGAGCGGATAACAATTTCACACAGGAAACA GCTATGACCATGATTACGCCAAGCTCGAAATTAACCCTCACTAAAGGGAACAAAAGCTGGAGCTCCACC GCGGTGGCGGCCGCTCTAGCACTAGTGGATCGCCCGGGCTGCAGGAATTCcatatttagataaacgatt tcaagcagcagaattagctttattagaacaaacttgtaaagaaagaatgtaccaatgccgcgcattgta gaaaaaccagataattattatcaaattcgacgtatacgtgaattaaaacctgatttaacgattactgga atggcacatgcaaatccattagaagctcgaggtattacaacaaaatggtcagttgaatttacttttgct caaattcatggatttactaatacacgtgaaattttagaattagtaacagcctcttagacgcaatcta atgtcaaatcaatctgtaaatgctatttcttaatataaatcccaaaagattttttttataatactgaga cttcaacacttacttgtttttattttttgtagttacaattcactcacgttaaagacattggaaaatgag gcaggacgttagtcgatatttatacactcttaagtttacttgcccaatatttatattaggacgtcccct tcgggtaaataaattttagtggcagtggtaccaccactgcctattttaatactccgaagcatataaata tacttcggagtatataaatatccactaatatttatattaggcagttggcaggcaacaataaataaattt gtcccgtaaggggacgtcccgaaggggaaggggaagaaggcagttgcctcgcctatcggctaacaagtt cctttggagtatataaccgcctacaggtaacttaaagaacatttgttacccgtaggggtttatacttct aattgcttcttctgaacaataaaatggtttgtgtggtctgggctaggaaacttgtaacaatgtgtagtg tcgcttccgcttcccttcgggacgtccccttcgggtaagtaaacttaggagtattaaatcgggacgtcc ccttcgggtaaataaatttcagtggacgtcccccttacgggacgccagtagacgtcagtggcagttgcct cgcctatcggctaacaagttccttcggagtatataaatatagaatgtttacatactcctaagtttactt gcctccttcggagtatataaatatcccgaaggggaaggaggacgccagtgcagtggtaccgccactgc ctgcttcctccttcggagtatgtaaacccttcgggcaactaaagtttatcgcagtatataaatatagg cagttggcaggcaactgccactgacgtcctatttttaatactccgaaggaggcagttggcaggcaactgc cactgacgtcccgtaaggggtaagggacgtccactggcgtcccgtaagggaaggggacgtaggtacat aaatgtgctaggtaactaacgtttgatttttgtggtataatatgtgaccatgcttttaatagaagct tgaattatataaattaaaatattttttacaatatttttacggagaaatttaaaactttaaaaaaattaacatA TGGTACCAAACAAAAGCGTAGCACCATTATTACTTGCTGCATCTATCTTATATGGTGGTGCTGTTGCTC AACAGACTGTTTGGGGTCAGTGTGGTGGTATTGGTTGGTCTGGTCCTACCAATTGTGCTCCTGGCTCAG CATGTAGTACCTTAAATCCTTACTATGCTCAATGTATTCCAGGTGCAACAACTATAACAACATCAACTC GCCCTCCTTCAGGTCCAACTACAACAACTCGTGCTACTAGCACTTCTAGCAGCACACCTCCTACATCTT CTGGAGTACGTTTCGCTGGTGTTAATATTGCAGGTTTCGATTTTGGTTGTACTACCGATGGTACATGTG TTACCAGTAAAGTTTATCCCCCTTTAAAAAATTTTACTGGCTCAAACAATTATCCAGATGGCATTGGTC AAATGCAACACTTTGTAAATGAAGATGGTATGACTATTTTCCGTTTACCAGTGGGCTGGCAATACTTAG TTAACAACAATTTAGGTGGTAACTTAGATAGTACATCAATTAGTAAATATGATCAATTAGTACAAGGTT GCTTATCTTTAGGTGCCTATTGTATTGTTGATATTCATAATTATGCCCGTTGGAACGGTGGTATTATTG GTCAAGGTGGTCCAACTAATGCTCAATTTACATCATTATGGAGCCAATTAGCTTCAAAATATGCTAGTC AATCACGTGTTTGGTTCGGTATTATGAATGAACCTCACGATGTGAACATAAATACTTGGGCTGCAACTG TGCAAGAAGTAGTAACTGCTATTCGTAATGCTGGTGCAACATCACAATTCATTAGTTTACCAGGCAACG ATTGGCAATCTGCCGGCGCTTTTATTTCTGACGGTAGCGCAGCTGCTCTTAGTCAAGTGACTAACCCAG ACGGTAGTACCACTAACTTAATATTCGATGTACATAAATATCTTGATTCTGATAATAGCGGAACACACG CCGAATGTACCACAAATAATATTGATGGTGCTTTTAGTCCTTTAGCAACTTGGTTACGTCAAAATAATC GCCAAGCCATTTTAACTGAAACAGGTGGTGGAAACGTGCAGAGTTGTATCCAAGACATGTGTCAACAA TTCAGTACTTAAATCAAAACTCTGACGTGTACTTAGGTTATGTAGGTTGGGGTGCTGGTTCTTTTGATT CAACTTATGTATTAACCGAAACCCCTACTTCTTCTGGAAACTCATGGACAGACACTTCATTAGTAAGTA GTTGTTTAGCTCGCAAGGGTACCGGTGAAAACTTATACTTTCAAGGCTCAGGTGGCGGTGGAAGTGATT ACAAAGATGATGATAAAGGAACCGGTTAATCTAGActtagcttcaactaactctagctcaaacaac taatttttttttaaactaaaataaatctggttaaccatacctggtttatttagtttagtttatacaca ctttttcatatatatatacttaatagctaccataggcagttggcaggacgtcccctttacgggacaaatgt atttattgttgcctgccaactgcctaatataaatattagtggacgtcccccttcccttacgggcaagta aacttagggatttaatgctccgttaggaggcaaataaatttagtggcagttgcctcgcctatcggct aacaagttccttcggagtatataaatatcctgccaactgccgatatttatatactaggcagtggcggta ccactcgacGGATCCTACGTAATCGATGAATTCGATCCCATTTTTATAACTGGTCTCAAAATACCTATA AACCCATTGTTCTTCTCTTTTAGCTCTAAGAACAATCAATTTATAAATATATTTATTATTATGCTATAA TATAAATCTATATAAATACATTTACCTTTTATAAATACATTTACCCTTTTTAATTTGCATGATTT TAATGCTTATGCTATCTTTTTTATTTAGTCCATAAAACCCTTTAAAGGACCTTTTCTTATGGGATATTTA TATTTTCCTAACAAAGCAATCGGCGTCATAAACTTTAGTTGCTTACGACGCCTGTGACGTCCCCCCCT TCCCCTTACGGGCAAGTAAACTTAGGGATTTTAATGCAATAAATAAATTTGTCCTCTTCGGGCAAATGA ATTTTAGTATTTAAATATGACAAGGGTGAACCATTACTTTTGTTAACAAGTGATCTTACCACTCACTAT TTTTGTTGAATTTTAAACTTATTTAAAATTCTCGAGAAAGATTTAAAAATAAACTTTTTTAATCTTTT | |

TABLE 4-continued

Vector Sequences

| SEQ ID NO. | Sequence | Use |
|---|---|---|
| | ATTTATTTTTTCTTTTTTcgtatggaattgcccaatattattcaacaatttatcggaaacagcgttttagagccaaataaaattggtcagtcgccatcggatgtttattcttttaatcgaaataatgaaacttttttt cttaagcgatctagcactttatatacagagaccacatacagtgtctctcgtgaagcgaaaatgttgagt tggctctctgagaaattaaaggtgcctgaactcatcatgacttttcaggatgagcagtttgaatttatg atcactaaagcgatcaatgcaaaaccaatttcagcgcttttttaacagaccaagaattgcttgctatc tataaggaggcactcaatctgttaaattcaattgctattattgattgtccatttatttcaaacattgat catcggttaaaagagtcaaaatttttttattgataaccaactccttgacgatatagatcaagatgatttt gacactgaattatggggagaccataaaacttacctaagtctatggaatgagttaaccgagactcgtgtt gaagaaagattggttttttctcatggcgatatcacggatagtaatatttttatagataaattcaatgaa atttatttttagaccttggtcgtgctgggttagcagatgaatttgtagatatatcctttgttgaacgt tgcctaagagaggatgcatcggaggaaactgcgaaaatattttttaaagcatttaaaaaatgatagacct gacaaaaggaattatttttttaaaacttgatgaattgaattgaTTCCAAGCATTATCTAAATACTCTGC AGGCACGCTAGCTTGTACTCAAGCTCGTAACGAAGGTCGTGACCTTGCTCGTGAAGGTGGCGACGTAAT TCGTTCAGCTTGTAAATGGTCTCCAGAACTTGCTGCTGCATGTGAAGTTTGGAAAGAAATTAAATTCGA ATTTGATACTATTGACAAACTTTAATTTTTATTTTTCATGATGTTTATGTGAATAGCATAAACATCGTT TTTATTTTTATGGTGTTTAGGTTAAATACCTAAACATCATTTTACATTTTTAAAATTAAGTTCTAAAG TTATCTTTTGTTTAAATTTGCCTGTGCTTTATAAATTACGATGTGCCAGAAAAATAAAATCTTAGCTTT TTATTATAGAATTTATCTTTATGTATTATATTTTATAAGTTATAATAAAAGAAATAGTAACATACTAAA GCGGATGTAGCGCGTTTATCTTAACGGAAGGAATTCGGCGCCTACGTAGGATCCgtatccatgctagca atatctgatggtacttgcatttcataagtttggcctggaataaccaccgtttcggaagtacctgtcgct ttaagttttatagctaaatctaaagtttctttaagtcttttagctgtattaaatactccacgacttttcc cttacgggacaataaataaatttgtccccttcccttacgtgacgtcagtggcagttgcctgccaactg cctccttcggagtattaaaatcctatatttatatactcctaagtttacttgcccaatatttatattagg cagttggcaggcaactgccactgacgtcccgaagggaagggaaggaacgtcccttcgggtaaataaa ttttagtggcagtggtaccaccactgcctgcttcctccttcccttcgggcaagtaaacttagaataaa atttatttgctgcgctagcaggtttacatactcctaagtttacttgcccgaaggggaaggaggacgtcc ccttacgggaatataaatattagtggcagtggtacaataaataaattgtatgtaaacccttcgggcaa ctaaagtttatcgcagtatataaatatagaatgtttacatactccgaaggaggacgccgtggcagtgg taccgccactgcctgtccgcagtattaacatcctatttaatactccgaaggaggcagttggcaggcaa ctgccactaatatttatattcccgtaaggggacgtcctaatttaatactccgaaggaggcagttggcag gcaactgccactaaaatttatttgcctcctaacggagcattaaaatcccgaagggacgtcccgaaggg gaaggggaaggaggcaactgcctgcttcctccttcccttcgggcaagtaaacttagaataaaatttat ttgctgcgctagcaggtttacatactcctaagtttacttgcccgaaggggaaggaggacgtccccttac gggaatataaatattagtggcagtggtacaataaataaattgtatgtaaaccccttcgggcaactaaag tttatcgcagtatataaatatcggcagttggcaggcaactgccactaaaattcatttgcccgaaggga cgtccactaatatttatattcccgtaaggggacgtccgaaggaggacgtcctaaacggagcat taaaatccctaagtttacttgcctaggcagttggcaggatatttatatacgatattaatactttttgcta ctggcacactaaaatttatttgccgtaaggggacgtccttcggtggttatataaataatcccgtaggg ggaggggatgtcccgtaggggagggagtggaggctccaacggaggttggagcttctttggtttcct aggcattatttaaatattttttaaccctagcactagaactgagatccagacggcgaccgtaaagttc ttcagtcccctcagcttttttcacaaccaagttcgggatggattggtgtgggtccaactgagcaaagagc accaaggttaactgcatctctgtgagatgctagttaaactaagcttagcttagctcataaacgatagtt acccgcaaggggttatgtaattatattataaggtcaaaatcaaacggcctttagtatatctcggctaaa gccattgctgactgtacacctgatacctatatataagcgcttgtctagccgcggcctttagagagcactcat cttgagtttagcttcctacttagatgcttcagcagttatctatccatgcgtagctacccagcgtttcc cattggaatgagaactggtacacaattggcatgtcctttcaggtcctctcgtactatgaaaggctactc tcaatgctctaacgcctacaccggatatgggaccaaactgtctcacgcatgaaattttaaagccgaataa aacttgcggtctttaaaactaaccccttttactttcgtaaaggcatggactatgtcttcatcctgctact gttaatggcaggagtcggcgtattatacttttcccactCTCGAGGGGGGGCCCGGTACCCAATTCGCCCT ATAGTGAGTCGTATTACAATTCACTGGCCGTCGTTTTACAACGTCGTGACTGGGAAAACCCTGGCGTTA CCCAACTTAATCGCCTTGCAGCACATCCCCCTTTCGCCAGCTGGCGTAATAGCGAAGAGGCCCGCACCG ATCGCCCTTCCCAACAGTTGCGCAGCCTGAATGGCGAATGGGACGCGCCCTGTAGCGGCGCATTAAGCG CGGCGGGTGTGGTGGTTACGCGCAGCGTGACCGCTACACTTGCCAGCGCCCTAGCGCCCGCTCCTTTCG CTTTCTTCCCTTCCTTTCTCGCCACGTTCGCCGGCTTTCCCCGTCAAGCTCTAAATCGGGGGCTCCCTT TAGGGTTCCGATTTAGTGCTTTACGGCACCTCGACCCCAAAAAACTTGATTAGGGTGATGGTTCACGTA GTGGGCCATCGCCCTGATAGACGGTTTTTCGCCCTTTGACGTTGGAGTCCACGTTCTTTAATAGTGGAC TCTTGTTCCAAACTGGAACAACACTCAACCCTATCTCGGTCTATTCTTTTGATTTATAAGGGATTTTGC CGATTTCGGCCTATTGGTTAAAAAATGAGCTGATTTAACAAAAATTTAACGCGAATTTTAACAAAATAT TAACGCTTACAATTTAGGTG | |
| 21 | GCACTTTTCGGGGAAATGTGCGCGGAACCCCTATTTGTTTATTTTTCTAAATACATTCAAATATGTATC CGCTCATGAGACAATAACCCTGATAAATGCTTCAATAATATTGAAAAAGGAAGAGTATGAGTATTCAAC ATTTCCGTGTCGCCCTTATTCCCTTTTTTGCGGCATTTTGCCTTCCTGTTTTTGCTCACCCAGAAACGC TGGTGAAAGTAAAAGATGCTGAAGATCAGTTGGGTGCACGAGTGGGTTACATCGAACTGGATCTCAACA GCGGTAAGATCCTTGAGAGTTTTCGCCCCGAAGAACGTTTTCCAATGATGAGCACTTTTAAAGTTCTGC TATGTGGCGCGGTATTATCCCGTATTGACGCCGGGCAAGAGCAACTCGGTCGCCGCATACACTATTCTC AGAATGACTTGGTTGAGTACTCACCAGTCACAGAAAAGCATCTTACGGATGGCATGACAGTAAGAGAAT TATGCAGTGCTGCCATAACCATGAGTGATAACACTGCGGCCAACTTACTTCTGACAACGATCGGAGGAC CGAAGGAGCTAACCGCTTTTTTGCACAACATGGGGGATCATGTAACTCGCCTTGATCGTTGGGAACCGG AGCTGAATGAAGCCATACCAAACGACGAGCGTGACACCACGATGCCTGTAGCAATGGCAACAACGTTGC GCAAACTATTAACTGGCGAACTACTTACTCTAGCTTCCCGGCAACAATTAATAGACTGGATGGAGGCGG ATAAAGTTGCAGGACCACTTCTGCGCTCGGCCCTTCCGGCTGGCTGGTTTATTGCTGATAAATCTGGAG CCGGTGAGCGTGGGTCTCGCGGTATCATTGCAGCACTGGGGCCAGATGGTAAGCCCTCCCGTATCGTAG TTATCTACACGACGGGGAGTCAGGCAACTATGGATGAACGAAATAGACAGATCGCTGAGATAGGTGCCT | β-glucosidase insertion cassette (D1 KAN-BD09) |

TABLE 4-continued

Vector Sequences

| SEQ ID NO. | Sequence | Use |
|---|---|---|
| | CACTGATTAAGCATTGGTAACTGTCAGACCAAGTTTACTCATATATACTTTAGATTGATTTAAAACTTC<br>ATTTTTAATTTAAAAGGATCTAGGTGAAGATCCTTTTTGATAATCTCATGACCAAAATCCCTTAACGTG<br>AGTTTTCGTTCCACTGAGCGTCAGACCCCGTAGAAAAGATCAAAGGATCTTCTTGAGATCCTTTTTTTC<br>TGCGCGTAATCTGCTGCTTGCAAACAAAAAAACCACCGCTACCAGCGGTGGTTTGTTTGCCGGATCAAG<br>AGCTACCAACTCTTTTTCCGAAGGTAACTGGCTTCAGCAGAGCGCAGATACCAAATACTGTCCTTCTAG<br>TGTAGCCGTAGTTAGGCCACCACTTCAAGAACTCTGTAGCACCGCCTACATACCTCGCTCTGCTAATCC<br>TGTTACCAGTGGCTGCTGCCAGTGGCGATAAGTCGTGTCTTACCGGGTTGGACTCAAGACGATAGTTAC<br>CGGATAAGGCGCAGCGGTCGGGCTGAACGGGGGGTTCGTGCACACAGCCCAGCTTGGAGCGAACGACCT<br>ACACCGAACTGAGATACCTACAGCGTGAGCTATGAGAAAGCGCCACGCTTCCCGAAGGGAGAAAGGCGG<br>ACAGGTATCCGGTAAGCGGCAGGGTCGGAACAGGAGAGCGCACGAGGGAGCTTCCAGGGGGAAACGCCT<br>GGTATCTTTATAGTCCTGTCGGGTTTCGCCACCTCTGACTTGAGCGTCGATTTTTGTGATGCTCGTCAG<br>GGGGGCGGAGCCTATGGAAAAACGCCAGCAACGCGGCCTTTTTACGGTTCCTGGCCTTTTGCTGGCCTT<br>TTGCTCACATGTTCTTTCCTGCGTTATCCCCTGATTCTGTGGATAACCGTATTACCGCCTTTGAGTGAG<br>CTGATACCGCTCGCCGCAGCCGAACGACCGAGCGCAGCGAGTCAGTGAGCGAGGAAGCGGAAGAGCGCC<br>CAATACGCAAACCGCCTCTCCCCGCGCGTTGGCCGATTCATTAATGCAGCTGGCACGACAGGTTTCCCG<br>ACTGGAAAGCGGGCAGTGAGCGCAACGCAATTAATGTGAGTTAGCTCACTCATTAGGCACCCCAGGCTT<br>TACACTTTATGCTTCCGGCTCGTATGTTGTGTGGAATTGTGAGCGGATAACAATTTCACACAGGAAACA<br>GCTATGACCATGATTACGCCAAGCTCGAAATTAACCCTCACTAAAGGGAACAAAAGCTGGAGCTCCACC<br>GCGGTGGCGGCCGCTCTAGCACTAGTGGATCGCCCGGGCTGCAGGAATTCcatatttagataaacgatt<br>tcaagcagcagaattagctttattagaacaaacttgtaaagaaatgaatgtaccaatgccgcgcattgt<br>agaaaaaccagataattattatcaaattcgacgtatacgtgaattaaaacctgatttaacgattactgg<br>aatggcacatgcaaatccattagaagctcgaggtattacaacaaaatggtcagttgaatttacttttgc<br>tcaaattcatggatttactaataacacgtgaaattttagaattagtaacacagcctcttagacgcaatct<br>aatgtcaaatcaatctgtaaatgctatttcttaatataaatccaaaagatttttttttataatactgag<br>acttcaacacttacttgtttttatttttttgtagttacaattcactcacgtttaaagacattggaaaatga<br>ggcaggacgttagtcgatatttatacactcttaagtttacttgcccaatatttatattaggacgtcccc<br>ttcgggtaaataaattttagtggcagtggtaccaccactgcctattttaatactccgaagcatataaat<br>atacttcggagtatataaatatccactaatatttatattaggcagttggcaggcaacaataaataaatt<br>tgtcccgtaaggggacgtcccgaaggggaaggggaagaaggcagttgcctcgcctatcggctaacaagt<br>tccttttggagtatataaccgcctacaggtaacttaaagaacatttgttacccgtaggggtttatacttc<br>taattgcttcttctgaacaataaaatggtttgtgtggtctggctaggaaacttgtaacaatgtgtagt<br>gtcgcttccgcttccttcgggacgtcccttcgggtaagtaaacttaggagtattaaatcgggacgtc<br>cccttcgggtaaataaattttcagtggacgtcccctttacgggacgccagtagacgtcagtggcagttgcc<br>tcgcctatcggctaacaagttccttcggagtatataaatatagaatgtttacatactcctaagtttact<br>tgcctccttcggagtatataaatatcccgaaggggaaggaggacgccagtggcagtggtaccgccactg<br>cctgcttcctccttcggagtatgtaaaccccttcgggcaactaaagtttatcgcagtatataaatatag<br>gcagttggcaggcaactgccactgacgtcctcatttttaatactccgaaggaggcagttggcaggcaactg<br>ccactgacgtcccgtaaggtaaggggacgtccactggcgtcccgtaaggggaagggacgtaggtaca<br>taaatgtgctaggtaactaacgtttgattttttgtggtataatatatgtaccatgcttttaatagaagc<br>ttgaatttataaattaaaattattttttacaatattttacggagaaattaaacttaaaaaaattaacat<br>ATGGTACCATTACCAAAGGATTTCCAATGGGGTTTCGCTACCGCAGCTTATCAAATTGAAGGTGCAGTT<br>GATCAAGATGGACGTGGACCTTCTATTTGGGACACATTCTGTGCACAACCAGGTAAAATTGCTGATGGT<br>TCATCAGGTGTAACAGCATGTGACTCATATAATCGTACAGCTGAAGACATTGCACTTTTAAAATCTTTA<br>GGTGCTAAATCATATCGTTTCTCTATCTCATGGTCAAGAATTATTCCTGAAGGTGGCCGTGGTGACGCA<br>GTAAATCAAGCTGGTATTGATCACTATGTTAAATTTGTAGATGACTTATTAGACGCAGGTATTACACCT<br>TTTATCACTTTATTTCACTGGGATTTACCTGAAGGTTTACACCAACGTTATGGTGGTCTTTTAAACCGT<br>ACAGAATTTCCTTTAGATTTCGAAAACTATGCAAGAGTTATGTTTCGTGCACTTCCCAAAGTAAGAAAC<br>TGGATTACTTTTAATGAACCTTTATGTTCTGCTATTCCTGGTTATGGTTCAGGCACCTTTGCCCCAGGC<br>AGACAAAGTACAAGTGAGCCCTGGACAGTGGGCCATAACATTTTAGTAGCTCACGGTAGAGCTGTAAAA<br>GCATATAGAGATGATTTCAAACCTGCTTCAGGTGATGGTCAAATAGGTATTGTTAAATGGTGACTTC<br>ACATATCCCTGGGATGCCGCTGATCCTGCAGATAAAGAAGCCGCTGAACGTCGCTTAGAATTTTTCACT<br>GCTTGGTTTGCTGACCCCATCTATCTTGGTGATTATCCTGCTTCAATGCGTAAACAATTAGGTGATCGT<br>TTACCTACTTTTTACACCAGAAGAACGTGCTTTAGTTCATGGTAGTAATGACTTTTATGGTATGAACCAC<br>TATACTTCAAACTATATTCGTCACCGTAGCTCACCCGCAAGTGCTGATGACACAGTAGGTAATGTAGAT<br>GTTTTATTTACTAATAAACAAGGTAATTGTATCGGTCCTGAAACACAGAGCCCCTGGCTTCGTCCTTGT<br>GCAGCTGGTTTCCGTGACTTCCTTGTATGGATAAGCAAACGTTATGGTTATCCACCAATTTATGTTACA<br>GAAAACGGAACATCAATAAAAAGGTGAAAGTGACTTACCAAAGGAAAAGATTCTTGAAGATGATTTTCGT<br>GTTAAGTATTATAACGAATACATTAGAGCTATGGTTACAGCCGTTGAATTAGATGGTGTAAATGTAAAA<br>GGTTATTTCGCATGGTCTTTAATGGATAACTTTGAATGGGCTGATGGTTACGTTACACGTTTTGGTGTA<br>ACCTACGTTGATTACGAAAACGGCCAAAACGTTTCCCTAAAAAGAGTGCTAAAAGTTTAAAACCTTTA<br>TTTGATGAATTAATAGCTGCTGCAGGTACCGGTGAAAACTTATACTTTCAAGGTCAGGTGGCGGTGGA<br>AGTGATTACAAAGATGATGATGATAAAGGAACCGGTTAATCTAGActtagcttcaactaactctagctc<br>aaacaactaattttttttttaaactaaaataaatctggttaaccatacctggtttatttagtttagttt<br>atacacacttttcatatatatatacttaatagctaccataggcagttggcaggacgtccccttacggga<br>caaatgtatttattgttgcctgccaactgcctaatataaatattagtggacgtcccccttccccttacgg<br>gcaagtaaacttagggattttaatgctccgttaggaggcaaataaattttagtggcagttgcctcgcct<br>atcggctaacaagttccttcggagtatataaatatcctgccaactgccgatatttatatactaggcagt<br>ggcggtaccactcgacGGATCCTACGTAATCGATGAATTCGATCCCATTTTTATAACTGGTCTCAAAAT<br>ACCTATAAACCCATTGTTCTTCTCTTTTAGCTCTAAGAACAATCAATTTATAAATATATTTATTAT<br>GCTATAATATAAATACTATATAAATACATTTACCTTTTTATAAATACATTTACCTTTTTTTAATTTGC<br>ATGATTTTAATGCTTATGCTATCTTTTTTATTTAGTCCATAAAACCTTTAAAGGACCTTTTCTTATGGG<br>ATATTTATATTTTCCTAACAAAGCAATCGGCGTCATAAACTTAGTTGCTTACGACGCCTGTGGACGTC<br>CCCCCCTTCCCCTTACGGGCAAGTAAACTTAGGGATTTTAATGCAATAAATAAATTTGTCCTCTTCGGG<br>CAAATGAATTTTAGTATTTAAATATGACAAGGGTGAACCATTACTTTTGTTAACAAGTGATCTTACCAC | |

TABLE 4-continued

Vector Sequences

| SEQ ID NO. | Sequence | Use |
|---|---|---|
| | TCACTATTTTTGTTGAATTTTAAACTTATTTAAAATTCTCGAGAAAGATTTTAAAAATAAACTTTTTA<br>ATCTTTTATTTATTTTTCTTTTTTcgtatggaattgcccaatattattcaacaatttatcggaaacag<br>cgttttagagccaaataaaattggtcagtcgccatcggatgtttattcttttaatcgaaataatgaaac<br>ttttttttcttaagcgatctagcactttatatacagagaccacatacagtgtctctcgtgaagcgaaaat<br>gttgagttggctctctgagaaattaaaggtgcctgaactcatcatgacttttcaggatgagcagtttga<br>atttatgatcactaaagcgatcaatgcaaaaccaatttcagcgatttttaacagaccaagaattgctt<br>gctatctataaggaggcactcaatctgttaaattcaattgctattattgattgtccatttatttcaaac<br>attgatcatcggttaaaagagtcaaaatttttattgataaccaactccttgacgatatagatcaagat<br>gattttgacactgaattatggggagaccataaaacttacctaagtctatggaatgagttaaccgagact<br>cgtgttgaagaaagattggtttttttctcatggcgatatcacggatagtaatattttatagataaattc<br>aatgaaatttattttttagacctggtcgtgctgggttagcagatgaatttgtagatatatcctttgtt<br>gaacgttgcctaagagaggatgcatcggaggaaactgcgaaaatattttttaaagcatttaaaaaatgat<br>agacctgacaaaaggaattatttttaaaacttgatgaattgaattgaTTCCAAGCATTATCTAAAATA<br>CTCTGCAGGCACGCTAGCTTGTACTCAAGCTCGTAACGAAGGTCGTGACCTTGCTCGTGAAGGTGGCGA<br>CGTAATTCGTTCAGCTTGTAAATGGTCTCCAGAACTTGCTGCTGCATGTGAAGTTTGGAAAGAAATTAA<br>ATTCGAATTTGATACTATTGACAAACTTTAATTTTATTTTCATGATGTTATGTGAATAGCATAAAC<br>ATCGTTTTATTTTTATGGTGTTTAGGTTAAATACCTAAACATCATTTTACATTTTTAAAATTAAGTT<br>CTAAAGTTATCTTTTGTTTAAATTTGCCTGTGCTTTATAAATTACGATGTGCCAGAAAAATAAAATCTT<br>AGCTTTTTATTATAGAATTTATCTTTATGTATTATATTTTAAGTTATAATAAAAGAAATAGTAACAT<br>ACTAAAGCGGATGTAGCGCGTTTATCTTAACGGAAGGAATTCGGCGCCTACGTAGGATCCgtatccatg<br>ctagcaatatctgatggtacttgcatttcataagtttggcctggaataaccaccgttcggaagtacct<br>gtcgctttaagtttatagctaaatctaaagtttcttaagtcttttagctgtattaaatactccacga<br>ctttcccttacgggacaataaataaatttgtcccctttccccttacgtgacgtcagtggcagttgcctgc<br>caactgcctccttcggagtattaaaatcctatatttatatactcctaagtttacttgcccaatatttat<br>attaggcagttggcaggcaactgccactgacgtcccgaaggggaaggggaaggacgtcccccttcgggta<br>aataaaatttagtggcagtggtaccaccactgcctgcttcctccttcccctttcgggcaagtaaacttag<br>aataaaatttatttgctgcgctagcaggtttacatactcctaagtttacttgcccgaaggggaaggagg<br>acgtcccctttacgggaatataaatattagtggcagtggtacaataaatttgtatgtaaaccccttc<br>gggcaactaaagtttatcgcagtatataaatatagaatgtttacatactccgaaggaggacgccagtgg<br>cagtggtaccgccactgcctgtccgcagtattaacatcctattttaatactccgaaggaggcagttggc<br>aggcaactgccactaatatttatattcccgtaaggggacgtcctaatttaatactccgaaggaggcagt<br>tggcaggcaactgccactaaaatttatttgcctcctaacgagcattaaaatcccgaaggggacgtccc<br>gaaggggaaggggaaggaggcaactgcctgcttcctccttcccctttcgggcaagtaaacttagaataaa<br>atttatttgctgcgctagcaggtttacatactcctaagtttacttgcccgaaggggaaggaggacgtcc<br>ccttacgggaatataaatattagtggcagtggtacaataaataaattgtatgtaaaccccttcgggcaa<br>ctaaagtttatcgcagtatataaatatcggcagttggcaggcaactgccactaaaattcatttgcccga<br>aggggacgtccactaatatttatattcccgtaaggggacgtcccgaaggggaaggggacgtcctaaacg<br>gagcattaaaatccctaagtttacttgcctaggcagttggcaggatatttatatacgatattaatactt<br>ttgctactggcacactaaaatttatttgcccgtaaggggacgtccttcggtggttatataaataatccc<br>gtaggggaggggatgtcccgtaggggaggggagtggaggctccaacggaggttggagcttcttttgg<br>tttcctaggcattatttaaatatttttttaacccctagcactagaactgagattccagacggcgacccgta<br>aagttcttcagtcccctcagcttttcacaaccaagtccgggatggattggtgtgggtccaactgagca<br>aagagcaccaaggttaactgcatctctgtgagatgctagttaaactaagcttagcttagctcataaacg<br>atagttacccgcaagggggttatgtaattatatttataaggtcaaaatcaaacggccttttagtatatctcg<br>gctaaagccattgctgactgtacacctgatacctatataacggcttgtctagccgcggccttagagagc<br>actcatcttgagtttagcttcctacttagatgctttcagcagttatctatccatgcgtagctacccagc<br>gtttcccattggaatgagaactggtacacaattggcatgtccttcaggtcctctcgtactatgaaagg<br>ctactctcaatgctctaacgcctacaccggatatggaccaaactgtctcacgcatgaaattttaaagcc<br>gaataaaacttgcggtctttaaaactaaccccctttactttcgtaaaggcatggactatgtcttcatcct<br>gctactgttaatggcaggagtcggcgtattatactttcccactCTCGAGGGGGGGCCCGGTACCCAATT<br>CGCCCTATAGTGAGTCGTATTACAATTCACTGGCCGTCGTTTTACAACGTCGTGACTGGGAAAACCCTG<br>GCGTTACCCAACTTAATCGCCTTGCAGCACATCCCCCTTTCGCCAGCTGGCGTAATAGCGAAGAGGCCC<br>GCACCGATCGCCCTTCCCAACAGTTGCGCAGCCTGAATGGCGAATGGGACGCGCCCTGTAGCGGCGCAT<br>TAAGCGCGGCGGGTGTGGTGGTTACGCGCAGCGTGACCGCTACACTTGCCAGCGCCCTAGCGCCCGCTC<br>CTTTCGCTTTCTTCCCTTCCTTTCTCGCCACGTTCGCCGGCTTTCCCCGTCAAGCTCTAAATCGGGGGC<br>TCCCTTTAGGGTTCCGATTTAGTGCTTTACGGCACCTCGACCCCAAAAAACTTGATTAGGGTGATGGTT<br>CACGTAGTGGGCCATCGCCCTGATAGACGGTTTTTCGCCCTTTGACGTTGGAGTCCACGTTCTTTAATA<br>GTGGACTCTTGTTCCAAACTGGAACAACACTCAACCCTATCTCGGTCTATTCTTTTGATTTATAAGGGA<br>TTTTGCCGATTTCGGCCTATTGGTTAAAAAATGAGCTGATTTAACAAAAATTTAACGCGAATTTTAACA<br>AAATATTAACGCTTACAATTTAGGTG | |
| 22 | GCACTTTTCGGGGAAATGTGCGCGGAACCCCTATTTGTTTATTTTTCTAAATACATTCAAATATGTATC<br>CGCTCATGAGACAATAACCCTGATAAATGCTTCAATAATATTGAAAAAGGAAGAGTATGAGTATTCAAC<br>ATTTCCGTGTCGCCCTTATTCCCTTTTTTGCGGCATTTTGCCTTCCTGTTTTTGCTCACCCAGAAACGC<br>TGGTGAAAGTAAAAGATGCTGAAGATCAGTTGGGTGCACGAGTGGGTTACATCGAACTGGATCTCAACA<br>GCGGTAAGATCCTTGAGAGTTTTCGCCCCGAAGAACGTTTTCCAATGATGAGCACTTTTAAAGTTCTGC<br>TATGTGGCGCGGTATTATCCCGTATTGACGCCGGGCAAGAGCAACTCGGTCGCCGCATACACTATTCTC<br>AGAATGACTTGGTTGAGTACTCACCAGTCACAGAAAAGCATCTTACGGATGGCATGACAGTAAGAGAAT<br>TATGCAGTGCTGCCATAACCATGAGTGATAACACTGCGGCCAACTTACTTCTGACAACGATCGGAGGAC<br>CGAAGGAGCTAACCGCTTTTTTGCACAACATGGGGGATCATGTAACTCGCCTTGATCGTTGGGAACCGG<br>AGCTGAATGAAGCCATACCAAACGACGAGCGTGACACCACGATGCCTGTAGCAATGGCAACAACGTTGC<br>GCAAACTATTAACTGGCGAACTACTTACTCTAGCTTCCCGGCAACAATTAATAGACTGGATGGAGGCGG<br>ATAAAGTTGCAGGACCACTTCTGCGCTCGGCCCTTCCGGCTGGCTGGTTTATTGCTGATAAATCTGGAG<br>CCGGTGAGCGTGGGTCTCGCGGTATCATTGCAGCACTGGGGCCAGATGGTAAGCCCTCCCGTATCGTAG | Endo-<br>xylanase<br>insertion<br>cassette<br>(D1 KAN-<br>BD11) |

TABLE 4-continued

Vector Sequences

| SEQ ID NO. | Sequence | Use |
|---|---|---|
| | TTATCTACACGACGGGGAGTCAGGCAACTATGGATGAACGAAATAGACAGATCGCTGAGATAGGTGCCT<br>CACTGATTAAGCATTGGTAACTGTCAGACCAAGTTTACTCATATATACTTTAGATTGATTTAAAACTTC<br>ATTTTTAATTTAAAAGGATCTAGGTGAAGATCCTTTTTGATAATCTCATGACCAAAATCCCTTAACGTG<br>AGTTTTCGTTCCACTGAGCGTCAGACCCCGTAGAAAAGATCAAAGGATCTTCTTGAGATCCTTTTTTTC<br>TGCGCGTAATCTGCTGCTTGCAAACAAAAAAACCACCGCTACCAGCGGTGGTTTGTTTGCCGGATCAAG<br>AGCTACCAACTCTTTTTCCGAAGGTAACTGGCTTCAGCAGAGCGCAGATACCAAATACTGTCCTTCTAG<br>TGTAGCCGTAGTTAGGCCACCACTTCAAGAACTCTGTAGCACCGCCTACATACCTCGCTCTGCTAATCC<br>TGTTACCAGTGGCTGCTGCCAGTGGCGATAAGTCGTGTCTTACCGGGTTGGACTCAAGACGATAGTTAC<br>CGGATAAGGCGCAGCGGTCGGGCTGAACGGGGGGTTCGTGCACACAGCCCAGCTTGGAGCGAACGACCT<br>ACACCGAACTGAGATACCTACAGCGTGAGCTATGAGAAAGCGCCACGCTTCCCGAAGGGAGAAAGGCGG<br>ACAGGTATCCGGTAAGCGGCAGGGTCGGAACAGGAGAGCGCACGAGGGAGCTTCCAGGGGGAAACGCCT<br>GGTATCTTTATAGTCCTGTCGGGTTTCGCCACCTCTGACTTGAGCGTCGATTTTTGTGATGCTCGTCAG<br>GGGGGCGGAGCCTATGGAAAAACGCCAGCAACGCGGCCTTTTTACGGTTCCTGGCCTTTTGCTGGCCTT<br>TTGCTCACATGTTCTTTCCTGCGTTATCCCTGATTCTGTGGATAACCGTATTACCGCCTTTGAGTGAG<br>CTGATACCGCTCGCCGCAGCCGAACGACCGAGCGCAGCGAGTCAGTGAGCGAGGAAGCGGAAGAGCGCC<br>CAATACGCAAACCGCCTCTCCCCGCGCGTTGGCCGATTCATTAATGCAGCTGGCACGACAGGTTTCCCG<br>ACTGGAAAGCGGGCAGTGAGCGCAACGCAATTAATGTGAGTTAGCTCACTCATTAGGCACCCCAGGCTT<br>TACACTTTATGCTTCCGGCTCGTATGTTGTGTGGAATTGTGAGCGGATAACAATTTCACACAGGAAACA<br>GCTATGACCATGATTACGCCAAGCTCGAAATTAACCCTCACTAAAGGGAACAAAAGCTGGAGCTCCACC<br>GCGGTGGCGGCCGCTCTAGCACTAGTGGATCGCCCGGGCTGCAGGAATTCcatatttagataaacgatt<br>tcaagcagcagaattagctttattagaacaaacttgtaaagaaatgaatgtaccaatgccgcgcattgt<br>agaaaaaccagataattattatcaaattcgacgtatacgtgaattaaaacctgatttaacgattactgg<br>aatggcacatgcaaatccattagaagctcgaggtattacaacaaaatggtcagttgaatttacttttgc<br>tcaaattcatggatttactaatacacgtgaaattttagaattagtaacacagcctcttagacgcaatct<br>aatgtcaaatcaatctgtaaatgctatttcttaatataaatcccaaaagatttttttttataatactgag<br>acttcaacacttacttgttttttattttttgtagttacaattcactcacgttaaagacattggaaaatga<br>ggcaggacgttagtcgatatttatacactcttaagtttacttgcccaatatttatattaggacgtcccc<br>ttcgggtaaataaatttttagtggcagtggtaccaccactgccatttttaatactccgaagcatataaat<br>atacttcggagtatataaatatccactaatatttatattaggcagttggcaggcaacaataaataaatt<br>tgtcccgtaaggggacgtcccgaaggggaaggggaagaaggcagttgcctcgcctatcggctaacaagt<br>tcctttggagtatataaccgcctacaggtaacttaaagaacatttgtttacccgtaggggtttatacttc<br>taattgcttcttctgaacaataaaatggtttgtgtggctgggctaggaaacttgtaacaatgtgtagt<br>gtcgcttccgcttcccttcgggacgtccccttcgggtaagtaaacttaggagtattaaatcgggacgtc<br>cccttcgggtaaataaatttcagtggacgtcccccttacgggacgccagtagacgtcagtggcagttgcc<br>tcgcctatcggctaacaagttccttcggagtatataaatatagaatgtttacatactcctaagtttact<br>tgcctcctccggagtatataaatatcccgaaggggaaggaggacgccagtggcagtggtaccgccactg<br>cctgcttcctccttcggagtatgtaaaccccttcgggcaactaaagtttatcgcagtatataaatatag<br>gcagttggcaggcaactgccactgacgtcctatttttaatactccgaaggaggcagttggcaggcaactg<br>ccactgacgtcccgtaagggtaaggggacgtccactggcgtcccgtaaggggaaggggacgtaggtaca<br>taaatgctaggtaactaacgtttgatttttttgtggtaaatatatgtaccatgctttaatagaagc<br>ttgaatttataaattaaaatattttttacaatattttacggagaaattaaaactttaaaaaaattaacat<br>ATGGTACCAGTATCTTTCACAAGTCTTTTAGCAGCATCTCCACCTTCACGTGCAAGTTGCCGTCCAGCT<br>GCTGAAGTGGAATCAGTTGCAGTAGAAAAACGTCAAACAATTCAACCAGGTACAGGTTACAATAACGGT<br>TACTTTTTATTCTTACTGGAATGATGGACACGGTGGTGTTACATATACTAATGGACCTGGTGGTCAATTT<br>AGTGTAAATTGGAGTAACTCAGGCAATTTTGTTGGAGGAAAAGGTTGGCAACCTGGTACAAAGAATAAG<br>GTAATCAATTTCTCTGGTAGTTACAACCCTAATGGTAATTCTTATTTAAGTGTATACGGTTGGAGCCGT<br>AACCCATTAATTGAATATTATATTGTAGAGAACTTTGGTACATACAACCCTTCAACAGGTGCTACTAAA<br>TTAGGTGAAGTTACTTCAGATGGATCAGTTTATGATATTTATCGTACTCAACGCGTAAATCAACCATCT<br>ATAATTGGAACTGCCACTTTCTACCAATACTGGAGTGTAAGACGTAATCATCGTTCAAGTGGTAGTGTT<br>AATACAGCAAACCACTTTAATGCATGGGCTCAACAAGGTTTAACATTAGGTACAATGGACTATCAAATT<br>GTAGCTGTTGAAGGTTATTTTTCATCAGGTAGTGCTTCTATCACTGTTAGCGGTACCGGTGAAAACTTA<br>TACTTTCAAGGCTCAGGTGGCGGTGGAAGTGATTACAAAGATGATGATGATAAAGGAACCGGTTAATCT<br>AGAActtagcttcaactaactctagctcaaacaactaatttttttttaaactaaaataaatctggttaac<br>catacctggtttattttagtttagtttatacacactttttcatatatatatacttaatagctaccatagg<br>cagttggcaggacgtcccccttacgggacaaatgtatttattgttgcctgccaactgctaatataaata<br>ttagtggacgtcccccttcccttacgggcaagtaaacttagggatttaatgctccgttaggaggcaaa<br>taaattttagtggcagttgcctcgcctatcggctaacaagttccttcggagtatataaatatcctgca<br>actgccgatatttatatactaggcagtggcggtaccactcgacGGATCCTACGTAATCGATGAATTCGA<br>TCCCATTTTTATAACTGGTCTCAAAATACCTATAAACCCATTGTTCTTCTCTTTTAGCTCTAAGAACAA<br>TCAATTTATAAATATATTTATTATTATGCTATAATATAAATACTATATAAATACATTTACCTTTTTATA<br>AATACATTTACCTTTTTTTAATTTGCATGATTTTAATGCTTATGCTATCTTTTTTATTTAGTCCATAA<br>AACCTTTAAAGGACCTTTTCTTATGGGATATTTATATTTCCTAACAAAGCAATCGGCGTCATAAACTTT<br>TAGTTGCTTACGACGCCTGTGGACGTCCCCCCCTTCCCTTACGGGCAAGTAAACTTAGGGATTTTAAT<br>GCAATAAATAAATTTGTCCTCTTCGGGCAAATGAATTTTAGTATTTAAATATGACAAGGGTGAACCATT<br>ACTTTTGTTAACAAGTGATCTTACCACTCACTATTTTTGTTGAATTTTAAACTTATTTAAAATTCTCGA<br>GAAAGATTTTAAAAATAAACTTTTTTAATCTTTTATTTATTTTTTCTTTTTTcgtatggaattgcccaa<br>tattattcaacaatttatcggaaacagcgttttagagccaaataaaattggtcagtcgccatcggatgt<br>ttattcttttaatcgaaataatgaaacttttttttcttaagcgatctagcactttatatacagagaccac<br>atacagtgtctctcgtgaagcgaaaatgttgagttggctctctgagaaattaaaggtgcctgaactcat<br>catgacttttcaggatgagcagtttgaatttatgatcactaaagcgatcaatgcaaaaccaatttcagc<br>gcttttttttaacagaccaagaattgcttgctatctataaggaggcactcaatctgttaaattcaattgc<br>tattattgattgtccatttatttcaaacattgatcatcggttaaaagagtcaaaattttttattgataa<br>ccaactccttgacgatagatcaagatgattttgacactgaattatggggagaccataaaacttacct<br>aagtctatggaatgagttaaccgagactcgtgttgaagaaagattggtttttttctcatggcgatatcac | |

TABLE 4-continued

Vector Sequences

| SEQ ID NO. | Sequence | Use |
|---|---|---|
| | ggatagtaatattttatagataaattcaatgaaatttattttttagaccttggtcgtgctgggttagc<br>agatgaatttgtagatatatcctttgttgaacgttgcctaagagaggatgcatcggaggaaactgcgaa<br>aatattttaaagcatttaaaaaatgatagacctgacaaaaggaattattttttaaaacttgatgaatt<br>gaattgaTTCCAAGCATTATCTAAATACTCTGCAGGCACGCTAGCTTGTACTCAAGCTCGTAACGAAG<br>GTCGTGACCTTGCTCGTGAAGGTGGCGACGTAATTCGTTCAGCTTGTAAATGGTCTCCAGAACTTGCTG<br>CTGCATGTGAAGTTTGGAAAGAAATTAAATTCGAATTTGATACTATTGACAAACTTTAATTTTTATTTT<br>TCATGATGTTTATGTGAATAGCATAAACATCGTTTTTATTTTTTATGGTGTTTAGGTTAAATACCTAAA<br>TCATCATTTTACATTTTTAAAATTAAGTCTAAAGTTATCTTTTGTTTAAATTTGCCTGTGCTTTATAAA<br>TTACGATGTGCCAGAAAAATAAAATCTTAGCTTTTTATTATAGAATTTATCTTTATGTATTATATTTTA<br>TAAGTTATAATAAAAGAAATAGTAACATACTAAAGCGGATGTAGCGCGTTTATCTTAACGGAAGGAATT<br>CGGCGCCTACGTAGGATCCgtatccatgctagcaatatctgatggtacttgcattttcataagtttggcc<br>tggaataaccaccgtttcggaagtacctgtcgctttaagttttatagctaaatctaaagtttctttaag<br>tcttttagctgtattaaatactccacgactttcccttacgggacaataaataaatttgtccccttcccc<br>ttacgtgacgtcagtggcagttgcctgccaactgctccttcggagtattaaaatcctatatttatata<br>ctcctaagtttacttgcccaatatttatattaggcagttggcaggcaactgccactgacgtcccgaagg<br>ggaaggggaaggacgtcccccttcgggtaaataaattttagtggcagtggtaccaccactgcctgcttcc<br>tccttccccttcgggcaagtaaacttagaataaaattttattgctgcgctagcaggtttacatactcct<br>aagtttacttgcccgaaggggaaggaggacgtcccccttacgggaatataaatattagtggcagtggtac<br>aataaataaattgtatgtaaaccccttcgggcaactaaagtttatcgcagtatataaatatagaatgtt<br>tacatactccgaaggaggacgccagtggcagtggtaccgccactgctgtccgcagtattaacatccta<br>ttttaatactccgaaggaggcagttggcaggcaactgccactaatatttatattcccgtaaggggacgt<br>cctaatttaatactccgaaggaggcagttggcaggcaactgccactaaaatttatttgcctcctaacgg<br>agcattaaaatcccgaaggggacgtcccgaaggggaaggggaaggaggcaactgcctgcttcctccttc<br>cccttcgggcaagtaaacttagaataaaatttatttgctgcgctagcaggtttacatactcctaagttt<br>acttgcccgaaggggaaggaggacgtcccccttacgggaatataaatattagtggcagtggtacaataaa<br>taaattgtatgtaaaccccttcgggcaactaaagtttatcgcagtatataaatatcggcagttggcagg<br>caactgccactaaaattcatttgcccgaaggggacgtccactaatatttatattcccgtaaggggacgt<br>cccgaaggggaaggggacgtcctaaacggagcattaaaatccctaagtttacttgcctaggcagttggc<br>aggatatttatatacgatattaatactttttgctactggcacactaaaatttatttgcccgtaagggac<br>gtccttcggtggttatataaataatcccgtagggggaggggatgtcccgtagggggaggggagtggag<br>gctccaacggaggttggagcttctttggtttcctaggcattatttaaatattttttaaccctagcacta<br>gaactgagattccagacggcgaccccgtaaagttcttcagtccctcagctttttcacaaccaagttcgg<br>gatggattggtgtgggtccaactgagcaaagagcaccaaggttaactgcatctagtgagatgctagtta<br>aactaagcttagcttagctcataaacgatagttacccgcaaggggttatgtaattatattataaggtca<br>aaatcaaacggcctttagtatatctcggctaaagccattgctgactgtacacctgatacctatataacg<br>gcttgtctagccgcggccttagagagcactcatcttgagtttagcttcctacttagatgctttcagcag<br>ttatctatccatgcgtagctacccagcgtttcccattggaatgagaactggtacacaattggcatgtcc<br>tttcaggtcctctcgtactatgaaaggctactctcaatgctctaacgcctacaccggatatggaccaaa<br>tctgtctcacgcatgaaatttaaagccgaataaaacttgcggtctttaaaactaaccccttttactttcg<br>taaaggcatggactatgtatcatcctgctactgttaatggcaggagtcggcgtattatactttcccact<br>CTCGAGGGGGGGCCCGGTACCCAATTCGCCCTATAGTGAGTCGTATTACAATTCACTGGCCGTCGTTTT<br>GACAACGTCGTGACTGGGAAAACCCTGGCTTACCCAACTTAATCGCCTTGCAGCACATCCCCCTTTCGC<br>CAGCTGGCGTAATAGCGAAGAGGCCCGCACCGATCGCCCTTCCCAACAGTTGCGCAGCCTGAATGGCGA<br>ATGGGACGCGCCCTGTAGCGGCGCATTAAGCGCGGCGGGTGTGGTGGTTACGCGCAGCGTGACCGCTAC<br>ACTTGCCAGCGCCCTAGCGCCCGCTCCTTTCGCTTTCTTCCCTTCCTTTCTCGCCACGTTCGCCGGCTT<br>TCCCCGTCAAGCTCTAAATCGGGGGCTCCCTTTAGGGTTCCGATTTAGTGCTTTACGGCACCTCGACCC<br>CAAAAAACTTGATTAGGGTGATGGTTCACGTAGTGGGCCATCGCCCTGATAGACGGTTTTTCGCCCTTT<br>GACGTTGGAGTCCACGTTCTTTAATAGTGGACTCTTGTTCCAAACTGGAACAACACTCAACCCTATCTC<br>GGTCTATTCTTTTGATTTATAAGGGATTTTGCCGATTTCGGCCTATTGGTTAAAAAATGAGCTGATTTA<br>ACAAAAATTTAACGCGAATTTTAACAAAATATTAACGCTTACAATTTAGGTG | |
| 23 | GTGCACTCTCAGTACAATCTGCTCTGATGCCGCATAGTTAAGCCAGCCCCGACACCCGCCAACACCCGC<br>TGACGCGCCCTGACGGGCTTGTCTGCTCCCGGCATCCGCTTACAGACAAGCTGTGACCGTCTCCGGGAG<br>CTGCATGTGTCAGAGGTTTTCACCGTCATCACCGAAACGCGCGAGACGAAAGGGCCTCGTGATACGCCT<br>ATTTTTATAGGTTAATGTCATGATAATAATGGTTTCTTAGACGTCAGGTGGCACTTTTCGGGGAAATGT<br>GCGCGGAACCCCTATTTGTTTATTTTTCTAAATACATTCAAATATGTATCCGCTCATGAGACAATAACC<br>CTGATAAATGCTTCAATAATATTGAAAAAGGAAGAGTATGAGTATTCAACATTTCCGTGTCGCCCTTAT<br>TCCCTTTTTTGCGGCATTTTGCCTTCCTGTTTTTGCTCACCCAGAAACGCTGGTGAAAGTAAAAGATGC<br>TGAAGATCAGTTGGGTGCACGAGTGGGTTACATCGAACTGGATCTCAACAGCGGTAAGATCTTGAGAG<br>TTTTCGCCCCGAAGAACGTTTTCCAATGATGAGCACTTTTAAAGTTCTGCTATGTGGCGCGGTATTATC<br>CCGTATTGACGCCGGGCAAGAGCAACTCGGTCGCCGCATACACTATTCTCAGAATGACTTGGTTGAGTA<br>CTCACCAGTCACAGAAAAGCATCTTACGGATGGCATGACAGTAAGAGAATTATGCAGTGCTGCCATAAC<br>CATGAGTGATAACACTGCGGCCAACTTACTTCTGACAACGATCGGAGGACCGAAGGAGCTAACCGCTTT<br>TTTGCACAACATGGGGGATCATGTAACTCGCCTTGATCGTTGGGAACCGGAGCTGAATGAAGCCATACC<br>AAACGACGAGCGTGACACCACGATGCCTGTAGCAATGGCAACAACGTTGCGCAAACTATTAACTGGCGA<br>ACTACTTACTCTAGCTTCCCGGCAACAATTAATAGACTGGATGGAGGCGGATAAAGTTGCAGGACCACT<br>TCTGCGCTCGGCCCTTCCGGCTGGCTGGTTTATTGCTGATAAATCTGGAGCCGGTGAGCGTGGGTCTCG<br>CGGTATCATTGCAGCACTGGGGCCAGATGGTAAGCCCTCCCGTATCGTAGTTATCTACACGACGGGGAG<br>TCAGGCAACTATGGATGAACGAAATAGACAGATCGCTGAGATAGGTGCCTCACTGATTAAGCATTGGTA<br>ACTGTCAGACCAAGTTTACTCATATATACTTTAGATTGATTTAAAACTTCATTTTTAATTTAAAAGGAT<br>CTAGGTGAAGATCCTTTTTGATAATCTCATGACCAAAATCCCTTAACGTGAGTTTTCGTTCCACTGAGC<br>GTCAGACCCCGTAGAAAAGATCAAAGGATCTTCTTGAGATCCTTTTTTTCTGCGCGTAATCTGCTGCTT<br>GCAAACAAAAAAACCACCGCTACCAGCGGTGGTTTGTTTGCCGGATCAAGAGCTACCAACTCTTTTTCC<br>GAAGGTAACTGGCTTCAGCAGAGCGCAGATACCAAATACTGTTCTTCTAGTGTAGCCGTAGTTAGGCCA | β-gluco-<br>sidase<br>insertion<br>(3HB KAN-<br>rbcL-BD09) |

TABLE 4-continued

Vector Sequences

| SEQ ID NO. | Sequence | Use |
|---|---|---|
| | CCACTTCAAGAACTCTGTAGCACCGCCTACATACCTCGCTCTGCTAATCCTGTTACCAGTGGCTGCTGC | |
| | CAGTGGCGATAAGTCGTGTCTTACCGGGTTGGACTCAAGACGATAGTTACCGGATAAGGCGCAGCGGTC | |
| | GGGCTGAACGGGGGGTTCGTGCACACAGCCCAGCTTGGAGCGAACGACCTACACCGAACTGAGATACCT | |
| | ACAGCGTGAGCTATGAGAAAGCGCCACGCTTCCCGAAGGGAGAAAGGCGGACAGGTATCCGGTAAGCGG | |
| | CAGGGTCGGAACAGGAGAGCGCACGAGGGAGCTTCCAGGGGGAAACGCCTGGTATCTTTATAGTCCTGT | |
| | CGGGTTTCGCCACCTCTGACTTGAGCGTCGATTTTTGTGATGCTCGTCAGGGGGGCGGAGCCTATGGAA | |
| | AAACGCCAGCAACGCGGCCTTTTTACGGTTCCTGGCTTTTGCTGGCCTTTTGCTCACATGTTCTTTCC | |
| | TGCGTTATCCCCTGATTCTGTGGATAACCGTATTACCGCCTTTGAGTGAGCTGATACCGCTCGCCGCAG | |
| | CCGAACGACCGAGCGCAGCGAGTCAGTGAGCGAGGAAGCGGAAGAGCGCCCAATACGCAAACCGCCTCT | |
| | CCCCGCGCGTTGGCCGATTCATTAATGCAGCTGGCACGACAGGTTTCCCGACTGGAAAGCGGGCAGTGA | |
| | GCGCAACGCAATTAATGTGAGTTAGCTCACTCATTAGGCACCCCAGGCTTTACACTTTATGCTTCCGGC | |
| | TCGTATGTTGTGTGGAATTGTGAGCGGATAACAATTTCACACAGGAAACAGCTATGACCATGATTACGC | |
| | CaagctcgcggccgcagtactCTGCAGATTTTATGCAAAATTAAAGTCTTGTGCAACAGCTTTCTCCT | |
| | TAAGTGCAAATATCGCCCATTCTTTCCTCTTTTCGTATATAAATGCTGTAATAGTAGGATGTCGTACCC | |
| | GTAAAGGTACGACATTGAATATTAATATACTCCTAAGTTTTCCCAATATTTATATTAGGACGTCC | |
| | CCTTCGGGTAAATAAATTTTAGTGGCAGTGGTACCGCCACTCCCTATTTTAATACTGCGAAGGAGGCAG | |
| | TTGGCAGGCAACTCGTCGTTCGCAGTATATAAATATCCACTAATATTTATATTCCCGTAAGGGGACGTC | |
| | CCGAAGGGGAAGGGGAAAGAAGCAGTCGCCTCCTTGCGAAAGGTTTACTTGCCCGACCAGTGAAAAGC | |
| | ATGCTGTAAGATATAAATCTACCCTGAAAGGGATGCATTTCACCATAATACTATACAAATGGTGTTACC | |
| | CTTTGAGGATCATAACGGTGCTACTGGAATATATGGTCTCTTCATGGATAGACGATAGCCATTTATTTA | |
| | CCCATTAAGGGGACATTAGTGGCCTGTCACTGCTCCTTACGAGACGCCAGTGGACGTTCGTCCTAGAAA | |
| | ATTTATGCGCTGCCTAGAAGCCCCAAAAGGGAAGTTTACTGACTCGTTAGAGCGTGCGCTAACAGGTTT | |
| | AAATACTTCAATATGTATATTAGGACGCCGGTGGCAGTGGTACCGCCACTGCCACCGTCGGAGGACGTC | |
| | CCTTACGGTATATTATATACTAGGATTTTAATACTCCGAAGGAGGCAGTGGCGGTACCACTGCCACTAA | |
| | TATTTATATTCCCGTAAGGGACGTCCTCCTTCGGAGTATGTAAACATTCTAAGTTTACTTGCCCAATAT | |
| | TTATATTAGGCAGTTGGCAGGCAACTGCTAGCTCTCCTCCTTCGGAGTATGTAAACATCGCAGTATATA | |
| | AATATCCACTAATATTTATATTCCCGTAAGGGGACGTCCCGAAGGGGAAGGGGAAGGACCTCAGTGGCA | |
| | GTTGCCTGCCAACTGCCTAGGCAAGTAAACTTAGGAGTATAAATATAGGCAGTCGCGGTACCACTGC | |
| | CACTGACGTCCTGCCAACTGCCTAGGCAAGTAAACTTAAGTGGCACTAAAATGCATTTGCCCGAAGGGG | |
| | AAGGAGGACGCCAGTGGCAGTGGTACCGCCACTGCCTCCTTCGGAGTATTAAAATCCTAGTATGTAAAT | |
| | CTGCTAGCGCAGGAAATAAATTTTATTCTATTTATATACTCCGTTAGGAGGTAAGTAAACCCCTTCCCC | |
| | TTCGGGACGTCAGTGCAGTTGCCTGCCAACTGCCTAATATAAATATTAGCACCACTAAAGTTTGGCAACT | |
| | GCCAACTGTTGTCCTTCGGAGGAAAAAAAATGGTTAACTCGCAAGCAGTTAACATAACTAAAGTTTGTT | |
| | ACTTTACCGAAGACGTTTACCCTTTCTCGGTTAAGGAGACGGAGACAGTTGCACTGTGACTGCCTAGTA | |
| | TAGCAATTTTGTTTTTGTTTATATGCTCGACAAAATGACTTTCATAAAAATATAAAGTAGTTAGCTAGT | |
| | TATTTTATATCACTATAACTAGGGTTCTCAGAGGCACCGAAGTCACTTGTAAAAATAGTACTTTTTAAC | |
| | TTGTTTAATCTTCGTGTTCTTCAAAAGGATCACGTAATTTTTTTGAAGGTGGACCAAAACTAACATAAA | |
| | CTGAATAGCCAGTTACACTTAACAGAAGAAACCATAAAAAAAAGGTAAAGAAAAAAGCTGGACTTTCCA | |
| | TAGCTCATTTAATAATAAAATTATTCTCTTTTCAACATATCTCTTAGATAGTTCAAAAGACTTGACGAC | |
| | TGTGTCCCACATTTTTAAACAAAATTAATCTACTCAAAATTTTTACTGAGAAAGAATAACTTACTTCG | |
| | TTTTTGCAGTAGCCATTCATGTCACTTTGAAACTGTCCTTACAAAGTTAAACATTAATTAAAAATTATT | |
| | TAATTTTTATATAACAAATATTATATTAAATAAAAAATGAACAAAGAACTTCTAAGATCGTCTTTAGTG | |
| | AGTAATTAAAGAGTTTTACTTACCAGACAAGGCAGTTTTTTCATTCTTTTAAAGCAGGCAGTTCTGAAG | |
| | GGGAAAAGGGACTGCCTACTGCGGTCCTAGGTAAATACATTTTTATGCAATTTATTTCTTGTGCTAGTA | |
| | GGTTTCTATACTCACAAGAAGCAACCCCTTGACGAGAGAACGTTATCCTCAGAGTATTTATAATCCTGA | |
| | GAGGGAATGCACTGAAGAATATTTTCCTTATTTTTTACAGAAAGTAAATAAAATAGCGCTAATAACGCT | |
| | TAATTCATTTAATCAATTATGGCAACAGGAACTTCTAAAGCTAAACCATCAAAAGTAAATTCAGACTTC | |
| | CAAGAACCTGGTTTAGTTACACCATTAGGTACTTTATTACGTCCACTTAACTCAGAGCAGGTAAAGTA | |
| | TTACCAGGCTGGGGTACAACTGTTTTAATGGCTGTATTTATCCTTTTATTTGCAGCATTCTTATTAATC | |
| | ATTTTAGAAATTTACAACAGTTCTTTAATTTTAGATGACGTTTCTATGAGTTGGGAAACTTTAGCTAAA | |
| | GTTTCTTAATTTTATTTAACACAAACATAAAATATAAAACTGTTTGTTAAGGCTAGCTGCTAAGTCTTC | |
| | TTTTCGCTAAGGTAAACTAAGCAACTCAACCATATTTATATTCGGCAGTGGCACCGCCAACTGCCACTG | |
| | GCCTTCCGTTAAGATAAACGCGTggatctcacgtgactagtcacctagtgtcgagtggtaccgccactg | |
| | cctagtatataaatatcggcagttggcaggatatttatatactccgaaggaacttgttagccgataggc | |
| | gaggcaactgccactaaaatttatttgcctcctaacggagcattaaaatccctaagtttacttgcccgt | |
| | aaggggaaggggacgtccactaatatttatattaggcagttggcaggcaacaataaatacatttgtccc | |
| | gtaagggacgtcctgccaactgcctatggtagctattaagtatatatatatgaaaagtgtgtataaac | |
| | taaactaaaataaaccaggtatggttaaccagatttattttagtttaaaaaaaaaattagttgtttgagc | |
| | tagagttagttgaagctaagtctagaTTAACCGGTTCCTTTATCATCATCATCTTTGTAATCACTTCCA | |
| | CCGCCACCTGAGCCTTGAAAGTATAAGTTTTCACCGGTACCTGCAGCAGCTATTAATTCATCAAATAAA | |
| | GGTTTTAAACTTTTAGCACTCTTTTAGGGAAACGTTTTTCGTAATCAACGATAGGTTACA | |
| | CCAAAACGTGTAACGTAACCATCAGCCCATTCAAAGTTATCCATTAAAGACCATGCGAAATAACCTTTT | |
| | ACATTTACACCATCTAATTCAACGGCTGTAACCATAGCTCCTAATGTATTCGTTATAATACTTAACACGA | |
| | AAATCATCTTCAAGAATCTTTTCCTTTGGTAAGTCACTTTCACCTTTTATTGATGTTCCGTTTTCTGTA | |
| | ACATAAATTGGTGGATAACCATAACGTTTGCTTATCCATACAAGAAGTTCACGGAAACAGCTGCACAA | |
| | GGACGAAGCCAGGGCTCTGTGTTTCAGGACCGATACAATTACCTTGTTATTAGTAAATAAAACATCT | |
| | ACATTACCTACTGTGTCATCAGCACTTGCGGGTGAGCTACGGTGACAATATAGTTTGAAGTATAGTGG | |
| | TTCATACCATAAAAGTCATTACTACCATGAACTAAAGCACGTTCTTCTGGTGTAAAAGTAGGTAAACGA | |
| | TCACCTAATTGTTTACCATTGAAGCAGGATAATCAACAAGATGATGGGCGTCAGCAAACCAGCTGCACAA | |
| | AAAAATTCTAAGCGACGTTCAGCGGCTTCTTTATCTGCAGGATCAGCGGCATCCCAGGGATATGTGAAG | |
| | TCACCATTTAACACAATACCTATTTGACCATCACCTGAAGCAGGTTTGAAATCATCTCTATATGCTTTT | |
| | ACAGCTCTACCGTGAGCTACTAAAATGTTATGGCCCACTGTCCAGGGCTCACTTGTACTTTGTCTGCCT | |
| | GGGGCAAAGGTGCCTGAACCATAACCAGGAATAGCAGAACATAAAGGTTCATTAAAAGTAATCCAGTTT | |
| | CTTACTTTGGGAAGTGCACGAAACATAACTCTTGCATAGTTTTCGAAATCTAAAGGAAATTCTGTACGG | |

TABLE 4-continued

Vector Sequences

| SEQ ID NO. | Sequence | Use |
|---|---|---|
| | TTTAAAAGACCACCATAACGTTGGTGTAAACCTTCAGGTAAATCCCAGTGAAATAAAGTGATAAAAGGT<br>GTAATACCTGCGTCTAATAAGTCATCTACAAATTTAACATGTGATCAATACCAGCTTGATTTACTGCG<br>TCACCACGGCCACCTTCAGGAATAATTCTTGACCATGAGATAGAGAAACGATATGATTTAGCACCTAAA<br>GATTTTAAAAGTGCAATGTCTTCAGCTGTACGATTATATGAGTCACATGCTGTTACACCTGATGAACCA<br>TCAGCAATTTTACCTGGTTGTGCACAGAATGTGTCCCAAATAGAAGGTCCACGTCCATCTTGATCAACT<br>GCACCTTCAATTTGATAAGCTGCGGTAGCGAAACCCCATTGGAAATCCTTTGGTAATGGTACCATatgc<br>actttgcattacctccgtacaaattattttgatttctataaagttttgcttaaataaaaatttttaatt<br>tttaacgtccacccatataaataaatatggtgaaaccttttaacaacaaaaatcctcttgtaccata<br>ttaatccaaaagaattaaggacaaaagcttatctccaacatttttaaaacacagagtaaaaataatgtt<br>gttttttaagaatagaattttataacttgtattttaaatatgatctaatttatttgtgctaaaaattgca<br>gttggaaagtaattttaaaaataatttagatcatatttattaaataaagttgatttaaaacaacttaat<br>cgttttaattgttaattaaaaacataattttaaatcttttttatattaaattaccttatatactacta<br>gtgatatctacgtaatcgatgaattcgatcccatttttataactggatctcaaaatacctataaaccca<br>ttgttcttctctttagctctaagaacaatcaatttataaatatatttattattatgctataatataaa<br>tactatataaatacattacctttttataaatacatttaccttttttttaatttgcatgattttaatgc<br>ttatgctatcttttttatttagtccataaaacctttaaaggaccttttcttatgggatatttatatttt<br>cctaacaaagcaatcggcgtcataaacttagttgcttacgacgcctgtggacgtcccccccttccct<br>tacgggcaagtaaacttagggattttaatgcaataaataaatttgtcctcttcgggcaaatgaatttta<br>gtatttaaatatgacaagggtgaaccattacttttgttaacaagtgatcttaccactcactatttttgt<br>tgaattttaaacttatttaaaattctcgagaaagattttaaaaataaacttttttaatctttttatttat<br>tttttctttttttCGTATGGAATTGCCCAATATTATTCAACAATTTATCGGAAACAGCGTTTTAGAGCCA<br>AATAAAATTGGTCAGTCGCCATCGGATGTTTATTCTTTTAATCGAAATAATGAAACTTTTTTCTTAAG<br>CGATCTAGCACTTTATATACAGAGACCACATACAGTGTCTCTCGTGAGCGAAAATGTTGAGTTGGCTC<br>TCTGAGAAATTAAAGGTGCCTGAACTCATCATGACTTTTCAGGATGAGCAGTTTGAATTTATGATCACT<br>AAAGCGATCAATGCAAAACCAATTTCAGCGCTTTTTTTAACAGACCAAGAATTGCTTGCTATCTATAAG<br>GAGGCACTCAATCTGTTAAATTCAATTGCTATTATTGATTGTCCATTTATTTCAAACATTGATCATCGG<br>TTAAAAGAGTCAAAATTTTTATTGATAACCAACTCCTTGACGATATAGATCAAGATGATTTTGACACT<br>GAATTATGGGGAGACCATAAAACTTACCTAAGTCTATGGAATGAGTTAACCGAGACTCGTGTTGAAGAA<br>AGATTGGTTTTTTCTCATGGCGATATCACGGATAGTAATATTTTTATAGATAAATTCAATGAAATTTAT<br>TTTTTAGACCTTGGTCGTGCTGGGTTAGCAGATGAATTTGTAGATATATCCTTTGTTGAACGTTGCCTA<br>AGAGAGGATGCATCGGAGGAAACTGCGAAAATATTTTTAAAGCATTTAAAAAATGATAGACCTGACAAA<br>AGGAATTATTTTTAAAACTTGATGAATTGAATTGAttccaagcattatctaaaatactctgcaggcac<br>gctagcttgtactcaagctcgtaacgaaggtcgtgaccttgctcgtgaaggtggcgacgtaattcgttc<br>agcttgtaaatggtctccagaacttgctgctgcatgtgaagtttggaaagaaattaaattcgaatttga<br>tactattgacaaactttaattttattttttcatgatgtttatgtgaatagcataaacatcgttttatt<br>tttatggtgtttaaggttaaatacctaaacatcattttacattttaaaattaagttctaaagttatctt<br>ttgtttaaatttgcctgtctttataaattacgatgtgccagaaaaataaaatcttagctttttattata<br>gaatttatctttatgtattatattttataagttataataaaagaaatagtaacatactaaagcggatgt<br>agcgcgtttatcttaacggaaggaattcggcgcctacgtacccgggtcgcgaggatccACGCGTTAATA<br>GCTCACTTTTCTTTAAATTTAATTTTTAATTTAAAGGTGTAAGCAAATTGCCTGACGAGAGATCCACTT<br>AAAGGATGACAGTGGCGGGCTACTGCCTACTTCCCTCCGGGATAAAATTTATTTGAAAAACGTTAGTTA<br>CTTCCTAACGGAGCATTGACATCCCCATATTTATATTAGGACGTCCCCTTCGGGTAAATAAATTTTAGT<br>GGACGTCCCCTTCGGGCAAATAAATTTTAGTGGACAATAAATAAATTTGTTGCCTGCCAACTGCCTAGG<br>CAAGTAAACTTGGGAGTATTAAAATAGGACGTCAGTGGCAGTTGCCTGCCAACTGCCTATATTTATATA<br>CTGCGAAGCAGGCAGTGGCGGTACCACTGCCACTGGCGTCCTAATATAAATATTGGGCAACTAAAGTTT<br>ATAGCAGTATTAACATCCTATATTTATATACTCCGAAGGAACTTGTTAGCCGATAGGCGAGGCAACAAA<br>TTTATTTATTGTCCCGTAAAAGGATGCCTCCAGCATCGAAGGGGAAGGGGACGTCCTAGGCCATAAAAC<br>TAAAGGGAAATCCATAGTAACTGATGTTATAAATTTATAGACTCCAAAAACAGCTGCGTTATAAATAA<br>CTTCTGTTAAATATGGCCAAGGGGACAGGGGCACTTTCAACTAAGTGTACATTAAAAATTGACAATTCA<br>ATTTTTTTTAATTATAATATATATTTAGTAAAATATAACAAAAAGCCCCCATCGTCTAGgtagaattcc<br>agctggcggccgccctatg | |
| 24 | agatctcgatcccgcgaaattaatacgactcactatagggggaattgtgagcggataacaattcccctct<br>agaaataatttttgtttaactttaagaaggagatataCATATGGTACCATATCGTAAACTTGCTGTTATT<br>AGTGCTTTCTTAGCTACTGCTCGTGCACAGTCAGCATGTACCTTACAATCTGAAACTCATCCTCCATTA<br>ACATGGCAAAATGTTCTTCAGGAGGTACTTGTACACAACAAACTGGCTCTGTAGTAATTGATGCTAAC<br>TGGCGTTGGACACATGCCACTAATAGTTCAACTAATTGTTATGACGGTAATACTTGGTCATCAACACTT<br>TGTCCCGATAACGAAACTTGTGCTAAAAATTGTTGTTAGATGGTGCAGCTTACGCTTCAACTTACGGC<br>GTTACTACATCAGGTAACTCATTATCAATTGGTTTCGTGACTCAATCAGCACAAAAAAATGTAGGCGCA<br>CGTTTATACTTAATGGCAAGTGACACAACCTATCAAGAATTTACATTATTAGGTAATGAGTTCAGTTTC<br>GACGTAGATGTGAGTCAATTACCATGTGGTTTAAATGGCTGTCTTTATTTCGTTTCAATGGACGCTGAT<br>GGCGGTGTAAGCAAATATCCTACTAATACAGCAGGTGCTAAATACGGAACAGGCTATTGTGATTCTCAG<br>TGTCCTCGTGATTTAAAGTTTATTAACGGTCAAGCTAACGTGGAAGGTTGGGAACCAAGTAGTAATAAT<br>GCAAATACTGGAATTGGTGGTCACGGATCTTGTTGTTCTGAAATGGATATTTGGGAAGCTAATTCAATT<br>AGTGAAGCATTAACTCCACATCCTTGTACTACCGTTGCCAAGAAATTTGTGAAGGCGACGGTTGCGGT<br>GGAACATACAGTGATAACCGTTATGGTGGTACATGTGATCCTGATGGCTGCGATTGGGACCCATATCGT<br>TTAGGAAATACATCTTTTTATGGACCAGGAAGTTCATTCACATTAGATCAACTAAAAAGTTAACAGTT<br>GTTACACAGTTCGAAACTAGCGGTGCTATTAATCGTTATTACGTGCAAAATGGTGTAACTTTTCAACAA<br>CCAAATGCAGATTAGGTTCTTATTCTGGTAACGGCCTTAATGACGATTATTGTACAGCAGAAGCA<br>GAATTTGGTGGTAGCAGCTTCTCAGATAAAGGTGGTTTAACTCAATTCAAGAAAGCAACATCAGGTGGT<br>ATGGTTTTAGTTATGTCATTATGGGATGACTATTATGCTAATATGTTATGGTTAGATAGTACATATCCT<br>ACAAACGAAACTTCAAGCACTCCTGGTGCTGTTCGTGGTTCATGTTCAACTTCAAGTGGTGTACCTGCT<br>CAAGTTGAAAGCCAAAGTCCTAATGCAAAAGTAACTTTTAGTAATATCAAATTTGGTCCAATTGGCTCT<br>ACAGGCGATCCTTCAGGTGGTAATCCACCAGGTGGAAATCCACCTGGCACCACTACAACACGTCGTCCT | Exo-β-<br>glucanase<br>insertion<br>(pET-21a-<br>BD01) |

TABLE 4-continued

Vector Sequences

| SEQ ID NO. | Sequence | Use |
|---|---|---|

GCTACTACCACAGGTTCTTCTCCTGGACCAACACAATCTCATTACGGTCAATGTGGTGGTATTGGTTAT
TCAGGTCCAACTGTGTGTGCATCAGGAACTACATGTCAAGTTTTAAATCCATATTATAGCCAATGTTTA
GGTACCGGTGAAAACTTATACTTTCAAGGCTCAGGTGGCGGTGGAAGTGATTACAAAGATGATGATGAT
AAAGGAACCGGTTAATCTAGACTCGAGcaccaccaccaccaccactgagatccggctgctaacaaagcc
cgaaaggaagctgagttggctgctgccaccgctgagcaataactagcataacccttggggcctctaaa
cgggtcttgaggggttttttgctgaaaggaggaactatatccggattggcgaatgggacgcgccctgta
gcggcgcattaagcgcggcgggtgtggtgcttacgcgcagcgtgaccgctacacttgccagcgccctag
cgcccgctcctttcgctttcttcccttcctttctcgccacgttcgccggctttccccgtcaagctctaa
atcgggggctccctttagggttccgatttagtgctttacggcacctcgaccccaaaaaacttgattagg
gtgatggttcacgtagtgggccatcgccctgatagacggttttcgccctttgacgttggagtccacgt
tctttaatagtggactcttgttccaaactggaacaacactcaaccctatctcggtctattcttttgatt
tataagggattttgccgatttcggcctattggttaaaaaatgagctgatttaacaaaaatttaacgcga
attttaacaaaatattaacgtttacaatttcaggtggcacttttcggggaaatgtgcgcggaacccta
tttgtttatttttctaaatacattcaaatatgtatccgctcatgagacaataaccctgataaatgcttc
aataatattgaaaaaggaagagtatgagtattcaacattccgtgtcgcccttattccctttttttgcgg
catttttgccttcctgtttttgctcacccagaaacgctggtgaaagtaaaagatgctgaagatcagttgg
gtgcacgagtgggttacatcgaactggatctcaacagcggtaagatccttgagagttttcgccccgaag
aacgttttccaatgatgagcacttttaaagttctgctatgtggcgcggtattatcccgtattgacgccg
ggcaagagcaactcggtcgccgcatacactattctcagaatgacttggttgagtactcaccagtcacag
aaaagcatcttacggatggcatgacagtaagagaattatgcagtgctgccataaccatgagtgataaca
ctgcggccaacttacttctgacaacgatcggaggaccgaaggagctaaccgcttttttgcacaacatgg
gggatcatgtaactcgccttgatcgttgggaaccggagctgaatgaagccataccaaacgacgagcgtg
acaccacgatgcctgcagcaatggcaacaacgttgcgcaaactattaactggcgaactacttactctag
cttcccggcaacaattaatagactggatggaggcggataaagttgcaggaccacttctgcgctcggccc
ttccggctggctggtttattgctgataaatctggagccggtgagcgtgggtctcgcggtatcattgcag
cactggggccagatggtaagccctcccgtatcgtagttatctacacgacggggagtcaggcaactatgg
atgaacgaaatagacagatcgctgagataggtgcctcactgattaagcattggtaactgtcagaccaag
tttactcatatatactttagattgatttaaaacttcatttttaatttaaaaggatctaggtgaagatcct
ttttgataatctcatgaccaaaatcccttaacgtgagttttcgttccactgagcgtcagaccccgtaga
aaagatcaaaggatcttcttgagatcctttttttctgcgcgtaatctgctgcttgcaaacaaaaaaacc
accgctaccagcggtggtttgtttgccggatcaagagctaccaactctttttccgaaggtaactggctt
cagcagagcgcagataccaaatactgtccttctagtgtagccgtagttaggccaccacttcaagaactc
tgtagcaccgcctacatacctcgctctgctaatcctgttaccagtggctgctgccagtggcgataagtc
gtgtcttaccgggttggactcaagacgatagttaccggataaggcgcagcggtcgggctgaacggggggt
tcgtgcacacagcccagctggagcgaacgacctacaccgaactgagatacctacagcgtgagctatg
agaaagcgccacgcttcccgaagggagaaaggcggacaggtatccggtaagcggcagggtcggaacagg
agagcgcacgagggagcttccaggggaaacgcctggtatctttatagtcctgtcgggtttcgccacct
ctgacttgagcgtcgatttttgtgatgctcgtcaggggggcggagcctatggaaaaacgccagcaacgc
ggccttttacggttcctggccttttgctggccttttgctcacatgttctttcctgcgttatccctga
ttctgtggataacgtattaccgcctttgagtgagctgataccgctcgccgcagccgaacgaccgagcg
cagcgagtcagtgagcgaggaagcggaagagcgcctgatgcggtattttctccttacgcatctgtgcgg
tatttcacaccgcatatatggtgcactctcagtacaatctgctctgatgccgcatagttaagccagtat
acactccgctatcgctacgtgactgggtcatggctgcgccccgacacccgccaacacccgctgacgcgc
cctgacgggcttgtctgctcccggcatccgcttacagacaagctgtgaccgtctccgggagctgcatgt
gtcagaggttttcaccgtcatcaccgaaacgcgcgaggcagctgcggtaaagctcatcagcgtggtcgt
gaagcgattcacagatgtctgcctgttcatccgcgtccagctcgttgagtttctccagaagcgttaatg
tctggcttctgataaagcgggccatgttaagggcggttttttcctgtttggtcactgatgcctccgtgt
aagggggatttctgttcatgggggtaatgataccgatgaaacgagagaggatgctcacgatacgggtta
ctgatgatgaacatgcccggttactggaacgttgtgagggtaaacaactggcggtatggatgcggcggg
accagagaaaaatcactcagggtcaatgccagcgcttcgttaatacagatgtaggtgttccacagggta
gccagcagcatcctgcgatgcagatccggaacataatggtgcagggcgctgacttccgcgtttccagac
tttacgaaacacggaaaccgaagaccattcatgttgttgctcaggtcgcagacgttttgcagcagcagt
cgcttcacgttcgctcgcgtatcggtgattcattctgctaaccagtaaggcaaccccgccagcctagcc
gggtcctcaacgacaggagcacgatcatgcgcacccgtggggccgccatgccggcgataatggcctgct
tctcgccgaaacgtttggtggcgggaccagtgacgaaggcttgagcgagggcgtgcaagattccgaata
ccgcaagcgacaggccgatcatcgtcgcgctccagcgaaagcggtcctcgccgaaaatgacccagagcg
ctgccgcacctgtcctacgagttgcatgataaagaagacagtcataagtgcggcgacgatagtcatgc
cccgcgcccaccggaaggagctgactgggttgaaggctctcaaggcatcggtcgagatcccggtgcct
aatgagtgagctaacttacattaattgcgttgcgctcactgcccgctttccagtcgggaaacctgtcgt
gccagctgcattaatgaatcggccaacgcgcggggagaggcggtttgcgtatgggcgccagggtggtt
tttcttttcaccagtgagacgggcaacagctgattgcccttcaccgcctggccctgagagagttgcagc
aagcggtccacgctggtttgccccagcaggcgaaaatcctgtttgatggtggttaacggcgggatataa
catgagctgtcttcggtatcgtcgtatcccactaccgagatatccgcaccaacgcgcagcccggactcg
gtaatggcgcgcattgcgcccagcgccatctgatcgttggcaaccagcatcgcagtgggaacgatgccc
tcattcagcatttgcatggtttgttgaaaaccggacatggcactccagtcgccttcccgttccgctatc
ggctgaatttgattgcgagtgagatatttatgccagccagccagacgcagacgcgccgagacagaactt
aatgggcccgctaacagcgcgatttgctggtgacccaatgcgaccagatgctccacgcccagtcgcgta
ccgtcttcatgggagaaaataatactgttgatgggtgtcggtcagacatcaagaaataacgccgga
acattagtgcaggcagcttccacagcaatggcatcctggtcatccaggcagtagtaatcagccca
ctgacgcgttgcgcgagaagattgtgcaccgccgctttacaggcttcgacgccgcttcgttctaccatc
gacaccaccacgctggcaccagttgatcggcgcgagatttaatcgccgcgacaatttgcgacggcgcg
tgcagggccagactggaggtggcaacgccaatcagcaacgactgtttgcccgccagttgttgtgccacg
cggttgggaatgtaattcagctccgccatcgccgcttccactttttcccgcgttttcgcagaaacgtgg
ctggcctggttcaccacgcgggaaacggtctgataagagacaccggcatactctgcgacatcgtataac TABLE 4-continued Vector Sequences

| SEQ ID NO. | Sequence | Use |
|---|---|---|
| | gttactggtttcacattcaccaccctgaattgactctcttccgggcgctatcatgccataccgcgaaag gttttgcgccattcgatggtgtccgggatctcgacgctctccttatgcgactcctgcattaggaagca gcccagtagtaggttgaggccgttgagcaccgccgccgcaaggaatggtgcatgcaaggagatggcgcc caacagtcccccggccacgggcctgccaccatacccacgccgaaacaagcgctcatgagcccgaagtg gcgagcccgatcttccccatcggtgatgtcggcgatataggcgccagcaaccgcacctgtggcgccggt gatgccggccacgatgcgtccggcgtagaggatcg | |
| 25 | agatctcgatcccgcgaaattaatacgactcactatagggaattgtgagcggataacaattcccctct agaaataattttgtttaactttaagaaggagatataCATATGGTACCAAACAAAAGCGTAGCACCATTA TTACTTGCTGCATCTATCTTATATGGTGGTGCTGTTGCTCAACAGACTGTTTGGGGTCAGTGTGGTGGT ATTGGTTGGTCTGGTCCTACCAATTGTGCTCCTGGCTCAGCATGTAGTACCTTAAATCCTTACTATGCT CAATGTATTCCAGGTGCAACAACTATAACAACATCAACTCGCCCTCCTTCAGGTCCAACTACAACAACT CGTGCTACTAGCACTTCTAGCAGCACACCTCCTCACATCTTCTGGAGTACGTTTCGCTGGTGTTAATATT GCAGGTTTCGATTTTGGTTGTACTACCGATGGTACATGTGTTACCAGTAAAGTTTATCCCCCTTTAAAA AATTTTACTGGCTCAAACAATTATCCAGATGGCATTGGTCAAATGCAACACTTTGTAAATGAAGATGGT ATGACTATTTTCCGTTTACCAGTGGGCTGGCAATACTTAGTTAACAACAATTTAGGTGGTAACTTAGAT AGTACATCAATTAGTAAATATGATCAATTAGTACAAGGTTGCTTATCTTTAGGTGCCTATTGTATTGTT GATATTCATAATTATGCCCGTTGGAACGGTGGTATTATTGGTCAAGGTGGTCCAACTAATGCTCAATTT ACATCATTATGGAGCCAATTAGCTTCAAAATATGCTAGTCAATTGCTGTTTGGTTCGGTATTATGAAT GAACCTCACGATGTGAACATAAATACTTGGGCTGCAACTGTGCAAGAAGTAGTAACTGCTATTCGTAAT GCTGGTGCAACATCACAATTCATTAGTTTACCAGGCAACGATTGGCAATCTGCCGGCGCTTTTATTTCT GACGGTAGCGCAGCTGCTCTTAGTCAAGTGACTAACCCAGACGGTAGTACCACTAACTTAATATTCGAT GTACATAAATATCTTGATTCTGATAATAGCGGAACACACGCCGAATGTACCACAAATAATATTGATGGT GCTTTTAGTCCTTTAGCAACTTGGTTACGTCAAAATAATCGCCAAGCCATTTTAACTGAAACAGGTGGT GGAAACGTGCAGAGTTGTATCCAAGACATGTGTCAACAAATTCAGTACTTAAATCAAAACTCTGACGTG TACTTAGGTTATGTAGGTTGGGGTGCTGGTTCTTTTGATTCAACTTATGTATTAACCGAAACCCCTACT TCTTCTGGAAACTCATGGACAGACACTTCATTAGTAAGTAGTTGTTTAGCTCGCAAGGGTACCGGTGAA AACTTATACTTTCAAGGCTCAGGTGGCGGTGGAAGTGATTACAAAGATGATGATGATAAAGGAACCGGT TAATCTAGACTCGAGcaccaccaccaccaccactgagatccggctgctaacaaagcccgaaaggaagct gagttggctgctgccaccgctgagcaataactagcataaccccttggggcctctaaacgggtcttgagg ggttttttgctgaaaggaggaactatatccggattggcgaatgggacgcgccctgtagcggcgcattaa gcgcggcgggtgtggtggttacgcgcagcgtgaccgctacacttgccagcgccctagcgcccgctcctt tcgctttcttcccttcctttctcgccacgttcgccggctttccccgtcaagctctaaatcggggggctcc ctttagggttccgatttagtgctttacggcacctcgaccccaaaaaacttgattagggtgatggttcac gtagtgggccatcgccctgatagacggtttttcgccctttgacgttggagtccacgttctttaatagtg gactcttgttccaaactggaacaacactcaaccctatctcggtctattcttttgatttataaaggatttt tgccgatttcggcctattggttaaaaaatgagctgatttaacaaaaatttaacgcgaattttaacaaaa tattaacgtttacaatttcaggtggcacttttcggggaaatgtgcgcggaacccctatttgttatttt tctaaatacattcaaatatgtatccgctcatgagacaataaccctgataaatgcttcaataatattgaa aaaggaagagtatgagtattcaacatttccgtgtcgcccttattcccttttttgcggcattttgccttc ctgtttttgctcacccagaaacgctggtgaaagtaaaagatgctgaagatcagttgggtgcacgagtgg gttacatcgaactggatctcaacagcggtaagatccttgagagttttcgccccgaagaacgttttccaa tgatgagcacttttaaagttctgctatgtggcgcggtattatcccgtattgacgccgggcaagagcaac tcggtcgccgcatacactattctcagaatgacttggttgagtactcaccagtcacagaaaagcatctta cggatggcatgacagtaagagaattatgcagtgctgccataaccatgagtgataacactgcggccaact tacttctgacaacgatcggaggaccgaaggagctaaccgcttttttgcacaacatgggggatcatgtaa ctcgccttgatcgttgggaaccggagctgaatgaagccataccaaacgacgagcgtgacaccacgatgc ctgcagcaatggcaacaacgttgcgcaaactattaactggcgaactacttactctagcttcccggcaac aattaatagactggatggaggcggataaagttgcaggaccacttctgcgctcggcccttccggctggct ggtttattgctgataaatctggagccggtgagcgtgggtctcgcggtatcattgcagcactggggccag atggtaagccctcccgtatcgtagttatctacacgacggggagtcaggcaactatggatgaacgaaata gacagatcgctgagataggtgcctcactgattaagcattggtaactgtcagaccaagtttactcatata ctttagattgatttaaaacttcatttttaatttaaaaggatctaggtgaagatcctttttgataatc tcatgaccaaaatcccttaacgtgagttttcgttccactgagcgtcagaccccgtagaaaagatcaaag gatcttcttgagatcctttttttctgcgcgtaatctgctgcttgcaaacaaaaaaaccaccgctaccag cggtggtttgtttgccggatcaagagctaccaactctttttccgaaggtaactggcttcagcagagcgc agataccaaatactgtccttctagtgtagccgtagttaggccaccacttcaagaactctgtagcaccgc ctacatacctcgctctgctaatcctgttaccagtggctgctgccagtggcgataagtcgtgtcttaccg ggttggactcaagacgatagttaccggataaggcgcagcggtcgggctgaacggggggtcgtgcacac agcccagcttggagcgaacgacctacaccgaactgagatacctacagcgtgagctatgagaaagcgcca cgcttcccgaaggagaaaggcggacaggtatccggtaagcggcagggtcggaacaggagagcgcacga gggagcttccaggggaaacgcctggtatctttatagtcctgtcgggtttcgccacctctgacttgagc gtcgatttttgtgatgctcttcaggggcggagcctatggaaaaacgccagcaacgcggcctttttac ggttcctggccttttgctggccttttgctcacatgttctttcctgcgttatcccctgattctgtggata accgtattaccgcctttgagtgagctgataccgctcgccgcagccgaacgaccgagcgcagcgagtcag tgagcgaggaagcggaagagcgcctgatgcggtattttctccttacgcatctgtgcggtatttcacacc gcatatatggtgcactctcagtacaatctgctctgatgccgcatagttaagccagtatacactccgcta tcgctacgtgactgggtcatggctgcgccccgacacccgccaacacccgctgacgcgccctgacgggct tgtctgctcccggcatccgcttacagacaagctgtgaccgtctccgggagctgcatgtgtcagaggttt tcaccgtcatcaccgaaacgcgcgaggcagctgcggtaaagctcatcagcgtggtcgtgaagcgattca cagatgtctgcctgttcatccgcgtccagctcgttgagtttctccagaagcgttaatgtctggcttctg ataaagcgggccatgttaagggcggttttttcctgtttggtcactgatgcctccgtgtaaggggattt ctgttcatgggggtaatgataccgatgaaacgagagaggatgctcacgatacgggttactgatgatgaa catgcccggttactggaacgttgtgagggtaaacaactggcggtatggatgcggcgggaccagagaaaa | Endo-β-glucanase insertion cassette (pET-21a-BD05) |

TABLE 4-continued

Vector Sequences

| SEQ ID NO. | Sequence | Use |
|---|---|---|
| | atcactcagggtcaatgccagcgcttcgttaatacagatgtaggtgttccacagggtagccagcagcat<br>cctgcgatgcagatccggaacataatggtgcagggcgctgacttccgcgtttccagactttacgaaaca<br>cggaaaccgaagaccattcatgttgttgctcaggtcgcagacgttttgcagcagcagtcgcttcacgtt<br>cgctcgcgtatcggtgattcattctgctaaccagtcaaggcaaccccgccagcctagccgggtcctcaac<br>gacaggagcacgatcatgcgcacccgtggggccgccatgccggcgataatggcctgcttctcgccgaaa<br>cgtttggtggcgggaccagtgacgaaggcttgagcgagggcgtgcaagattccgaataccgcaagcgac<br>aggccgatcatcgtcgcgctccagcgaaagcggtcctcgccgaaaatgacccagagcgctgccggcacc<br>tgtcctacgagttgcatgataaagaagacagtcataagtgcggcgacgatagtcatgccccgcgcccac<br>cggaaggagctgactgggttgaaggctctcaagggcatcggtcgagatcccggtgcctaatgagtgagc<br>taacttacattaattgcgttgcgctcactgcccgctttccagtcgggaaacctgtcgtgccagctgcat<br>taatgaatcggccaacgcgcggggagaggcggtttgcgtattgggcgccagggtggtttttcttttcac<br>cagtgagacgggcaacagctgattgcccttcaccgcctggccctgagagagttgcagcaagcggtccac<br>gctggtttgccccagcaggcgaaaatcctgtttgatggtggttaacggcgggatataacatgagctgtc<br>ttcggtatcgtcgtatcccactaccgagatatccgcaccaacgcgcagcccggactcggtaatggcgcg<br>cattgcgcccagcgccatcgatcgttggcaaccagcatcgcagtgggaacgatgccctcattcagcat<br>ttgcatggtttgttgaaaaccggacatggcactccagtcgccttcccgttccgctatcggctgaatttg<br>attgcgagtgagatatttatgccagccagccagacgcagacgcgccgagacagaacttaatgggcccgc<br>taacagcgcgatttgctggtgacccaatgcgaccagatgctccacgcccagtcgcgtaccgtcttcatg<br>ggagaaataatactgttgatgggtgtctggtcagagacataagaataacgccggaacattagtgca<br>ggcagcttccacagcaatggcatcctggtcatccagcggatagttaatgatcagcccactgacgcgttg<br>cgcgagaagattgtgcaccgccgctttacaggcttcgacgccgcttcgttctaccatcgacaccaccac<br>gctggcacccagttgatcggcgcgagatttaatcgccgcgacaatttgcgacggcgcgtgcagggccag<br>actggaggtggcaacgccaatcagcaacgactgtttgcccgccagttgttgtgccacgcggttgggaat<br>gtaattcagctccgccatcgccgcttccacttttcccgcgttttcgcagaaacgtggctggcctggtt<br>caccacgcgggaaacggtctgataagagacaccggcatactctgcgacatcgtataacgttactggttt<br>cacattcaccaccctgaattgactctcttccgggcgctatcatgccataccgcgaaaggttttgcgcca<br>ttcgatggtgtccgggatctcgacgctctcccttatgcgactcctgcattaggaagcagcccagtagta<br>ggttgaggccgttgagcaccgccgccgcaaggaatggtgcatgcaaggagatggcgcccaacagtcccc<br>cggccacgggcctgccaccatacccacgccgaaacaagcgctcatgagcccgaagtggcgagcccgat<br>cttccccatcggtgatgtcggcgatataggcgccagcaaccgcacctgtggcgccggtgatgccggcca<br>cgatgcgtccggcgtagaggatcg | |
| 26 | agatctcgatcccgcgaaattaatacgactcactataggggaattgtgagcggataacaattcccctct<br>agaaataattttgtttaactttaagaaggagatataCATATGGTACCATTACCAAAGGATTTCCAATGG<br>GGTTTCGCTACCGCAGCTTATCAAATTGAAGGTGCAGTTGATCAAGATGGACGTGGACCTTCTATTTGG<br>GACACATTCTGTGCACAACCAGGTAAAATTGCTGATGGTTCATCAGGTGTAACAGCATGTGACTCATAT<br>AATCGTACAGCTGAAGACATTGCACTTTTAAAATCTTTAGGTGCTAAATCATATCGTTTCTCTATCTCA<br>TGGTCAAGAATTATTCCTGAAGGTGGCCGTGGTGACGCAGTAAATCAAGCTGGTATTGATCACTATGTT<br>AAATTTGTAGATGACTTATTAGACGCAGGTATTACACCTTTTATCACTTTATTTCACTGGGATTTACCT<br>GAAGGTTTACACCAACGTTATGGTGGTCTTTTAAACCGTACAGAATTTCCTTTAGATTTCGAAAACTAT<br>GCAAGAGTTATGTTTCGTGCACTTCCCAAAGTAAGAAACTGGATTACTTTTAATGAACCTTTATGTTCT<br>GCTATTCCTGGTTATGGTTCAGGCACCTTTGCCCCAGGCAGACAAAGTACAAGTGAGCCCTGGACAGTG<br>GGCCATAACATTTTAGTAGCTCACGGTAGAGCTGTAAAAGCATATAGAGATGATTTCAAACCTGCTTCA<br>GGTGATGGTCAAATAGGTATTGTGTTAAATGGTGACTTCACATATCCCTGGGATGCCGCTGATCCTGCA<br>GATAAAGAAGCCGCTGAACGTCGCTTAGAATTTTTCACTGCTTGGTTTGCTGACCCCATCTATCTTGGT<br>GATTATCCTGCTTCAATGCGTAAACAATTAGGTGATCGTTTACCTACTTTTACACCAGAAGAACGTGCT<br>TTAGTTCATGGTAGTAATGACTTTTATGGTATGAACCACTATACTTCAAACTATATTCGTCACCGTAGC<br>TCACCCGCAAGTGCTGATGACACAGTAGGTAATGTAGATGTTTTATTTACTAATAAACAAGGTAATTGT<br>ATCGGTCCTGAAACACAGAGCCCCTGGCTTCGTCCTTGTGCAGCTGGTTTCCGTGACTTCCTTGTATGG<br>ATAAGCAAACGTTATGTTATCCACCAATTTATGTTACAGAAAACGGAACATCAATAAAAGGTGAAAGT<br>GACTTACCAAAGGAAAAGATTCTTGAAGATGATTTTCGTGTTAAGTATTATAACGAATACATTAGAGCT<br>ATGGTTACAGCCGTTGAATTAGATGGTGTAAATGTAAAAGGTTATTTCGCATGGTCTTTAATGGATAAC<br>TTTGAATGGGCTGATGGTTACGTTACACGTTTTGGTGTAACCTACGTTGATTACGAAAACGGCCAAAAA<br>CGTTTCCCTAAAAAGAGTGCTAAAAGTTTAAAACCTTTATTTGATGAATTAATAGCTGCTGCAGGTACC<br>GGTGAAAACTTATACTTTCAAGGCTCAGGTGGCGGTGGAAGTGATTACAAAGATGATGATGATAAAGGA<br>ACCGGTTAATCTAGACTCGAGcaccaccaccaccaccactgagatccggctgctaacaaagcccgaaag<br>gaagctgagttggctgctgccaccgctgagcaataactaaccccttggggcctctaaacgggtc<br>ttgaggggttttttgctgaaaggaggaactatatccggattggcgaatgggacgcgccctgtagcggcg<br>cattaagcgcggcgggtgtggtggttacgcgcagcgtgaccgctacacttgccagcgccctagcgcccg<br>ctcctttcgctttcttcccttcctttctcgccacgttcgccggctttccccgtcaagctctaaatcggg<br>ggctccctttagggttccgatttagtgctttacggcacctcgaccccaaaaaacttgattagggtgatg<br>gttcacgtagtgggccatcgccctgatagacggtttttcgccctttgacgttggagtccacgttcttta<br>atagtggactcttgttccaaactggaacaacactcaaccctatctcggtctattcttttgatttataag<br>ggattttgccgatttcggcctattggttaaaaaatgagctgatttaacaaaaatttaacgcgaatttta<br>acaaaatattaacgtttacaatttcaggtggcacttttcggggaaatggcgcggaacccctattttgtt<br>tatttttctaaatacattcaaatatgtatccgctcatgagacaataaccctgataaatgcttcaataat<br>attgaaaaaggaagagtatgagtattcaacatttccgtgtcgcccttattccctttttttgcggcatttt<br>gccttcctgtttttgctcacccagaaacgctggtgaaagtaaaagatgctgaagatcagttgggtgcac<br>gagtgggttacatcgaactggatctcaacagcggtaagatccttgagagttttcgccccgaagaacgtt<br>ttccaatgatgagcacttttaaagttctgctatgtggcgcggtattatcccgtattgacgccgggcaag<br>agcaactcggtcgccgcatacactattctcagaatgacttggttgagtactcaccagtcacagaaaagc<br>atcttacggatggcatgacagtaagagaattatgcagtgctgccataaccatgagtgataacactgcgg<br>ccaacttacttctgacaacgatcggaggaccgaaggagctaaccgcttttttgcacaacatgggggatc<br>atgtaactcgccttgatcgttgggaaccggagctgaatgaagccataccaaacgacgagcgtgacacca | β-gluco- sidase insertion cassette (pET-21a- BD09) |

TABLE 4-continued

Vector Sequences

| SEQ ID NO. | Sequence | Use |
|---|---|---|
| | cgatgcctgcagcaatggcaacaacgttgcgcaaactattaactggcgaactacttactctagcttccc<br>ggcaacaattaatagactggatggaggcggataaagttgcaggaccacttctgcgctcggcccttccgg<br>ctggctggtttattgctgataaatctggagccggtgagcgtgggtctcgcggtatcattgcagcactgg<br>ggccagatggtaagccctcccgtatcgtagttatctacacgacggggagtcaggcaactatggatgaac<br>gaaatagacagatcgctgagataggtgcctcactgattaagcattggtaactgtcagaccaagtttact<br>catatatactttagattgatttaaaacttcatttttaatttaaaaggatctaggtgaagatcctttttg<br>ataatctcatgaccaaaatcccttaacgtgagttttcgttccactgagcgtcagaccccgtagaaaaga<br>tcaaaggatcttcttgagatcctttttttctgcgcgtaatctgctgcttgcaaacaaaaaaaccaccgc<br>taccagcggtggtttgtttgccggatcaagagctaccaactctttttccgaaggtaactggcttcagca<br>gagcgcagataccaaatactgtccttctagtgtagccgtagttaggccaccacttcaagaactctgtag<br>caccgcctacatacctcgctctgctaatcctgttaccagtggctgctgccagtggcgataagtcgtgtc<br>ttaccgggttggactcaagacgatagttaccggataaggcgcagcggtcgggctgaacggggggttcgt<br>gcacacagcccagcttggagcgaacgacctacaccgaactgagatacctacagcgtgagctatgagaaa<br>gcgccacgcttcccgaagggagaaaggcggacaggtatccggtaagcggcagggtcggaacaggagagc<br>gcacgagggagcttccagggggaaacgcctggtatctttatagtcctgtcgggtttcgccacctctgac<br>ttgagcgtcgatttttgtgatgctcgtcaggggggcggagcctatggaaaaacgccagcaacgcggcct<br>ttttacggttcctggccttttgctggccttttgctcacatgttctttcctgcgttatcccctgattctg<br>tggataaccgtattaccgcctttgagtgagctgataccgctcgccgcagccgaacgaccgagcgcagcg<br>agtcagtgagcgaggaagcggaagagcgcctgatgcggtattttctccttacgcatctgtgcggtattt<br>cacaccgcatatatggtgcactctcagtacaatctgctctgatgccgcatagttaagccagtatacact<br>ccgctatcgctacgtgactgggtcatggctgcgccccgacacccgccaacacccgctgacgcgccctga<br>cgggcttgtctgctcccggcatccgcttacagacaagctgtgaccgtctccgggagctgcatgtgtcag<br>aggttttcaccgtcatcaccgaaacgcgcgaggcagctgcggtaaagctcatcagcgtggtcgtgaagc<br>gattcacagatgtctgcctgttcatccgcgtccagctcgttgagtttctccagaagcgttaatgtctgg<br>cttctgataaagcgggccatgttaagggcggttttttcctgtttggtcactgatgcctccgtgtaaggg<br>ggatttctgttcatgggggtaatgataccgatgaaacgagagaggatgctcacgatacgggttactgat<br>gatgaacatgcccggttactggaacgttgtgagggtaaacaactggcggtatggatgcggcgggaccag<br>agaaaaatcactcagggtcaatgccagcgcttcgttaatacagatgtaggtgttccacagggtagccag<br>cagcatcctgcgatgcagatccggaacataatggtgcagggcgctgacttccgcgtttccagactttac<br>gaaacacggaaaccgaagaccattcatgttgttgctcaggtcgcagacgttttgcagcagcagtcgctt<br>cacgttcgctcgcgtatcggtgattcattctgctaaccagtaaggcaaccccgccagcctagccgggtc<br>ctcaacgacaggagcacgatcatgcgcacccgtggggccgccatcaccgcgcgataatggcctgcttctcg<br>ccgaaacgtttggtggcgggaccagtgacgaaggcttgagcgagggcgtgcaagattccgaataccgca<br>agcgacaggccgatcatcgtcgcgctccagcgaaagcggtcctcgccgaaaatgacccagagcgctgcc<br>ggcacctgtcctacgagttgcatgataaagaagacagtcataagtgcggcgacgatagtcatgccccgc<br>gcccaccggaaggagctgactgggttgaaggctctcaagggcatcggtcgagatcccggtgcctaatga<br>gtgagctaacttacattaattgcgttgcgctcactgcccgctttccagtcgggaaacctgtcgtgccag<br>ctgcattaatgaatcggccaacgcgcgggagaggcggtttgcgtattgggcgccagggtggtttttct<br>tttcaccagtgagacgggcaacagctgattgcccttcaccgcctggccctgagagagttgcagcaagcg<br>gtccacgctggtttgccccagcaggcgaaaatcctgtttgatggtggttaacggcgggatataacatga<br>gctgtcttcggtatcgtcgtatcccactaccgagatatccgcaccaacgcgcagcccggactcggtaat<br>ggcgcgcattgcgcccagcgccatctgatcgttggcaaccagcatcgcagtgggaacgatgccctcatt<br>cagcatttgcatggtttgttgaaaaccggacatggcactccagtcgccttcccgttccgctatcggctg<br>aatttgattgcgagtgagatatttatgccagccagccagacgcagacgcgccgagacagaacttaatgg<br>gcccgctaacagcgcgatttgctggtgacccaatgcgaccagatgctccacgcccagtcgcgtaccgtc<br>ttcatgggagaaaataatactgttgatgggtgtctggtcagagacatcaagaaataacgccggaacatt<br>agtgcaggcagcttccacagcaatggcatcctggtcatccagcggatagttaatgatcagcccactgac<br>gcgttgcgcgagaagattgtgcaccgccgctttacaggcttcgacgccgcttcgttctaccatcgacac<br>caccacgctggcacccagttgatcggcgcgagatttaatcgccgcgacaatttgcgacggcgcgtgcag<br>ggccagactggaggtggcaacgccaatcagcaacgactgtttgcccgccagttgttgtgccacgcggtt<br>gggaatgtaattcagctccgccatcgccgcttccactttttcccgcgttttcgcagaaacgtggctggc<br>ctggttcaccacgcgggaaacggtctgataagagacaccggcatactctgcgacatcgtataacgttac<br>tggttttcacattcaccaccctgaattgactctcttccgggcgctatcatgccataccgcgaaaggttttt<br>gcgccattcgatggtgtccgggatctcgacgctctccttatgcgactcctgcattaggaagcagccca<br>gtagtaggttgaggccgttgagcaccgccgccgcaaggaatggtgcatgcaaggagatggcgcccaaca<br>gtcccccggccacggggcctgccaccataccacgccgaaacaagcgctcatgagcccgaagtggcgag<br>cccgatcttccccatccggtgatgtcggcgatataggcgccagcaaccgcacctgtggcgccggtgatgc<br>cggccacgatgcgtccggcgtagaggatcg | |
| 27 | agatctcgatcccgcgaaattaatacgactcactataggggaattgtgagcggataacaattcccctct<br>agaaataattttgtttaactttaagaaggagatataCATATGGTACCAGTATCTTTCACAAGTCTTTTA<br>GCAGCATCTCCACCTTCACGTGCAAGTTGCCGTCCAGCTGCTGAAGTGGAATCAGTTGCAGTAGAAAAA<br>CGTCAAACAATTCAACCAGGTACAGGTTACAATAACGGTTACTTTTATTCTTACTGGAATGATGGACAC<br>GGTGGTGTTACATATACTAATGGACCTGGTGGTCAATTTAGTGTAAATTGGAGTAACTCAGGCAATTTT<br>GTTGGAGGAAAAGGTTGGCAACCTGGTACAAAGAATAAGGTAATCAATTTCTCTGGTAGTTACAACCCT<br>AATGGTAATTCTTATTTAAGTGTATACGGTTGGAGCCGTAACCCATTAATTGAATATTATATTGTAGAG<br>AACTTTGGTACATACAACCCTTCAACAGGTGCTACTAAATTAGGTGAAGTTACTTCAGATGGATCAGTT<br>TATGATATTTATCGTACTCAACGCGTAAATCAACCATCTATAATTGGAACTGCCACTTTCTACCAATAC<br>TGGAGTGTAAGACGTAATCATCGTTCAAGTGGTAGTGTTAATACAGCAAACCACTTTAATGCATGGGCT<br>CAACAAGGTTTAACATTAGGTACAATGGACTATCAAATTGTAGCTGTTGAAGGTTATTTTTCATCAGGT<br>AGTGCTTCTATCACTGTTAGCGGTACCGGTGAAACTTATACTTTCAAGGCTCAGGTGGCGGTGGAAGT<br>GATTACAAAGATGATGATGATAAAGGAACCGGTTAATCTAGACTCGAGcaccaccaccaccaccactga<br>gatccggctgctaacaaagcccgaaaggaagctgagttggctgctgccaccgctgagcaataactagca<br>taaccccttggggcctctaaacgggtcttgaggggttttttgctgaaaggaggaactatatccggattg | Endo-<br>xylanase<br>insertion<br>cassette<br>(pET-21a-<br>BD11) |

TABLE 4-continued

Vector Sequences

| SEQ ID NO. | Sequence | Use |
|---|---|---|
| | gcgaatgggacgcgccctgtagcggcgcattaagcgcggcgggtgtggtggttacgcgcagcgtgaccg | |
| | ctacacttgccagcgccctagcgcccgctcctttcgctttcttcccttcctttctcgccacgttcgccg | |
| | gctttccccgtcaagctctaaatcggggctcccttagggttccgatttagtgctttacggcacctcg | |
| | accccaaaaaacttgattagggtgatggttcacgtagtgggccatcgccctgatagacggtttttcgcc | |
| | ctttgacgttggagtccacgttctttaatagtggactcttgttccaaactggaacaacactcaacccta | |
| | tctcggtctattctttgattttataagggattttgccgatttcggcctattggttaaaaaatgagctga | |
| | tttaacaaaaatttaacgcgaattttaacaaaatattaacgtttacaatttcaggtggcacttttcggg | |
| | gaaatgtgcgcggaaccccctatttgtttatttttctaaatacattcaaatatgtatccgctcatgagac | |
| | aataaccctgataaatgcttcaataatattgaaaaaggaagagtatgagtattcaacatttccgtgtcg | |
| | cccttattccctttttttgcggcattttgccttcctgttttgctcacccagaaacgctggtgaaagtaa | |
| | aagatgctgaagatcagttgggtgcacgagtgggttacatcgaactggatctcaacagcggtaagatcc | |
| | ttgagagttttcgccccgaagaacgttttccaatgatgagcacttttaaagttctgctatgtggcgcgg | |
| | tattatcccgtattgacgccgggcaagagcaactcggtcgccgcatacactattctcagaatgacttgg | |
| | ttgagtactcaccagtcacagaaaagcatcttacggatggcatgacagtaagagaattatgcagtgctg | |
| | ccataaccatgagtgataacactgcggccaacttacttctgacaacgatcggaggaccgaaggagctaa | |
| | ccgcttttttgcacaacatgggggatcatgtaactcgccttgatcgttgggaaccggagctgaatgaag | |
| | ccataccaaacgacgagcgtgacaccacgatgcctgcagcaatggcaacaacgttgcgcaaactattaa | |
| | ctggcgaactacttactctagcttcccggcaacaattaatagactggatggaggcggataaagttgcag | |
| | gaccacttctgcgctcggcccttccggctggctggtttattgctgataaatctggagccggtgagcgtg | |
| | ggtctcgcggtatcattgcagcactggggccagatggtaagccctcccgtatcgtagttatctacacga | |
| | cggggagtcaggcaactatggatgaacgaaatagacagatcgctgagataggtgcctcactgattaagc | |
| | attggtaactgtcagaccaagtttactcatatatactttagattgatttaaaacttcattttaattta | |
| | aaaggatctaggtgaagatcctttttgataatctcatgaccaaaatcccttaacgtgagttttcgttcc | |
| | actgagcgtcagaccccgtagaaaagatcaaaggatcttcttgagatcctttttttctgcgcgtaatct | |
| | gctgcttgcaaacaaaaaaaccaccgctaccagcggtggtttgtttgccggatcaagagctaccaactc | |
| | tttttccgaaggtaactggcttcagcagagcgcagataccaaatactgtccttctagtgtagccgtagt | |
| | taggccaccacttcaagaactctgtagcaccgcctacatacctcgctctgctaatcctgttaccagtgg | |
| | ctgctgccagtggcgataagtcgtgtcttaccgggttggactcaagacgatagttaccggataaggcgc | |
| | agcggtcgggctgaacggggggttcgtgcacacagcccagcttggagcgaacgacctacaccgaactga | |
| | gatacctacagcgtgagctatgagaaagcgccacgcttcccgaagggagaaaggcggacaggtatccgg | |
| | taagcggcagggtcggaacaggagagcgcacgagggagcttccaggggaaacgcctggtatctttata | |
| | gtcctgtcgggtttcgccacctctgacttgagcgtcgatttttgtgatgctcgtcaggggggcggagcc | |
| | tatgaaaaacgccagcaacgcggcctttttacggttcctggccttttgctggccttttgctcacatgt | |
| | tctttcctgcgttatcccctgattctgtggataaccgtattaccgcctttgagtgagctgataccgctc | |
| | gccgcagccgaacgaccgagcgcagcgagtcagtgagcgaggaagcggaagagcgcctgatgcggtatt | |
| | ttctccttacgcatctgtgcggtatttcacaccgcatatatggtgcactctcagtacaatctgctctga | |
| | tgccgcatagttaagccagtatacactccgctatcgctacgtgactgggtcatggctgcgccccgacac | |
| | ccgccaacacccgctgacgcgccctgacgggcttgtctgctcccggcatccgcttacagacaagctgtg | |
| | accgtctccgggagctgcatgtgtcagaggttttcaccgtcatcaccgaaacgcgcgaggcagctgcgg | |
| | taaagctcatcagcgtggtcgtgaagcgattcacagatgtctgcctgttcatccgcgtccagctcgttg | |
| | agtttctccagaagcgttaatgtctggcttctgataaagcgggccatgttaagggcggttttttcctgt | |
| | ttggtcactgatgcctccgtgtaagggggatttctgttcatgggggtaatgataccgatgaaacgagag | |
| | aggatgctcacgatacgggttactgatgatgaacatgcccggttactggaacgttgtgagggtaaacaa | |
| | ctggcggtatggatgcggcgggaccagagaaaaatcactcagggtcaatgccagcgcttcgttaataca | |
| | gatgtaggtgttccacagggtagccagcagcatcctgcgatgcagatccggaacataatggtgcagggc | |
| | gctgacttccgcgtttccagactttacgaaacacggaaaccgaagaccattcatgttgttgctcaggtc | |
| | gcagacgttttgcagcagcagtcgcttcacgttcgctcgcgtatcggtgattcattctgctaaccagta | |
| | aggcaacccgccagcctagccgggtcctcaacgacaggagcacgatcatgcgcacccgtggggccgcc | |
| | atgccggcgataatggcctgcttctcgccgaaacgtttggtggcgggaccagtgacgaaggcttgagcg | |
| | agggcgtgcaagattccgaataccgcaagcgacaggccgatcatcgtcgcgctccagcgaaagcggtcc | |
| | tcgccgaaaatgacccagagcgctgccggcacctgtcctacgagttgcatgataaagaagacagtcata | |
| | agtgcggcgacgatagtcatgccccgcgcccaccggaaggagctgactgggttgaaggctctcaaggc | |
| | atcggtcgagatcccggtgcctaatgagtgagctaacttacattaattgcgttgcgctcactgcccgct | |
| | ttccagtcgggaaacctgtcgtgccagctgcattaatgaatcggccaacgcgcggggagaggcggtttg | |
| | cgtattgggcgccagggtggtttttcttttcaccagtgagacgggcaacagctgattgcccttcaccgc | |
| | ctggccctgagagttgcagcaagcggtccacgctggtttgccccagcaggcgaaaatcctgtttgat | |
| | ggtggttaacggcgggatataacatgagctgtcttcggtatcgtcgtatcccactaccgagatatccgc | |
| | accaacgcgcagcccggactcggtaatggcgcgcattgcgcccagcgccatctgatcgttggcaaccag | |
| | catcgcagtgggaacgatgccctcattcagcatttgcatggtttgttgaaaaccggacatggcactcca | |
| | gtcgccttcccgttccgctatcggctgaatttgattgcgagtgagatatttatgccagccagccagacg | |
| | cagacgcgccgagacagaacttaatgggcccgctaacagcgcgatttgctggtgacccaatgcgaccag | |
| | atgctccacgcccagtcgcgtaccgtcttcatgggagaaaataatactgttgatgggtgtctggtcaga | |
| | gacatcaagaaataaccgccggaacattagtgcaggcagcttccacagcaatggcatcctggtcatccag | |
| | cggatagttaatgatcagcccactgacgcgttgcgcgagaagattgtgcaccgccgctttacaggctt | |
| | cgacgccgcttcgttctaccatcgacaccacccacgctggcacccagttcggcggcgcagagtttaatcg | |
| | ccgcgacaatttgcgacggcgcgtgcagggccagactggaggtggcaacgccaatcagcaacgactgtt | |
| | tgcccgccagttgttgtgccacgcggttgggaatgtaattcagctccgccatcgccgcttccacttttt | |
| | cccgcgttttcgcagaaacgtggctggcctggttcaccacgcgggaaacggtctgataagagacaccgg | |
| | catactctgcgacatcgtataacgttactggtttcacattcaccaccctgaattgactctcttccggg | |
| | gctatcatgccataccgcgaaaggttttgcgccattcgatggtgtccgggatctcgacgctctcccctta | |
| | tgcgactcctgcattaggaagcagcccagtagtaggttgaggccgttgagcaccgccgccgcaaggaat | |
| | ggtgcatgcaaggagatggcgcccaacagtcccccggccacggggcctgccaccatacccacgccgaaa | |
| | caagcgctcatgagcccgaagtggcgagcccgatcttccccatcggtgatgtcggcgatataggcgcca | |
| | gcaaccgcacctgtggcgccggtgatgccggccacgatgcgtccggcgtagaggatcg | |

TABLE 4-continued

Vector Sequences

| SEQ ID NO. | Sequence | Use |
|---|---|---|
| 28 | GTGCACTCTCAGTACAATCTGCTCTGATGCCGCATAGTTAAGCCAGCCCCGACACCCGCCAACACCCGC<br>TGACGCGCCCTGACGGGCTTGTCTGCTCCCGGCATCCGCTTACAGACAAGCTGTGACCGTCTCCGGGAG<br>CTGCATGTGTCAGAGGTTTTCACCGTCATCACCGAAACGCGCGAGACGAAAGGGCCTCGTGATACGCCT<br>ATTTTTATAGGTTAATGTCATGATAATAATGGTTTCTTAGACGTCAGGTGGCACTTTTCGGGGAAATGT<br>GCGCGGAACCCCTATTTGTTTATTTTTCTAAATACATTCAAATATGTATCCGCTCATGAGACAATAACC<br>CTGATAAATGCTTCAATAATATTGAAAAAGGAAGAGTATGAGTATTCAACATTTCCGTGTCGCCCTTAT<br>TCCCTTTTTTGCGGCATTTTGCCTTCCTGTTTTTGCTCACCCAGAAACGCTGGTGAAAGTAAAAGATGC<br>TGAAGATCAGTTGGGTGCACGAGTGGGTTACATCGAACTGGATCTCAACAGCGGTAAGATCCTTGAGAG<br>TTTTCGCCCCGAAGAACGTTTTCCAATGATGAGCACTTTTAAAGTTCTGCTATGTGGCGCGGTATTATC<br>CCGTATTGACGCCGGGCAAGAGCAACTCGGTCGCCGCATACACTATTCTCAGAATGACTTGGTTGAGTA<br>CTCACCAGTCACAGAAAAGCATCTTACGGATGGCATGACAGTAAGAGAATTATGCAGTGCTGCCATAAC<br>CATGAGTGATAACACTGCGGCCAACTTACTTCTGACAACGATCGGAGGACCGAAGGAGCTAACCGCTTT<br>TTTGCACAACATGGGGGATCATGTAACTCGCCTTGATCGTTGGGAACCGGAGCTGAATGAAGCCATACC<br>AAACGACGAGCGTGACACCACGATGCCTGTAGCAATGGCAACAACGTTGCGCAAACTATTAACTGGCGA<br>ACTACTTACTCTAGCTTCCCGGCAACAATTAATAGACTGGATGGAGGCGGATAAAGTTGCAGGACCACT<br>TCTGCGCTCGGCCCTTCCGGCTGGCTGGTTTATTGCTGATAAATCTGGAGCCGGTGAGCGTGGGTCTCG<br>CGGTATCATTGCAGCACTGGGGCCAGATGGTAAGCCCTCCCGTATCGTAGTTATCTACACGACGGGGAG<br>TCAGGCAACTATGGATGAACGAAATAGACAGATCGCTGAGATAGGTGCCTCACTGATTAAGCATTGGTA<br>ACTGTCAGACCAAGTTTACTCATATATACTTTAGATTGATTTAAAACTTCATTTTTAATTTAAAAGGAT<br>CTAGGTGAAGATCCTTTTTGATAATCTCATGACCAAAATCCCTTAACGTGAGTTTTCGTTCCACTGAGC<br>GTCAGACCCCGTAGAAAAGATCAAAGGATCTTCTTGAGATCCTTTTTTTCTGCGCGTAATCTGCTGCTT<br>GCAAACAAAAAAACCACCGCTACCAGCGGTGGTTTGTTTGCCGGATCAAGAGCTACCAACTCTTTTTCC<br>GAAGGTAACTGGCTTCAGCAGAGCGCAGATACCAAATACTGTTCTTCTAGTGTAGCCGTAGTTAGGCCA<br>CCACTTCAAGAACTCTGTAGCACCGCCTACATACCTCGCTCTGCTAATCCTGTTACCAGTGGCTGCTGC<br>CAGTGGCGATAAGTCGTGTCTTACCGGGTTGGACTCAAGACGATAGTTACCGGATAAGGCGCAGCGGTC<br>GGGCTGAACGGGGGGTTCGTGCACACAGCCCAGCTTGGAGCGAACGACCTACACCGAACTGAGATACCT<br>ACAGCGTGAGCTATGAGAAAGCGCCACGCTTCCCGAAGGGAGAAAGGCGGACAGGTATCCGGTAAGCGG<br>CAGGGTCGGAACAGGAGAGCGCACGAGGGAGCTTCCAGGGGGAAACGCCTGGTATCTTTATAGTCCTGT<br>CGGGTTTCGCCACCTCTGACTTGAGCGTCGATTTTTGTGATGCTCGTCAGGGGGCGGAGCCTATGGAA<br>AAACGCCAGCAACGCGGCCTTTTTACGGTTCCTGGCCTTTTGCTGGCCTTTTGCTCACATGTTCTTTCC<br>TGCGTTATCCCCTGATTCTGTGGATAACCGTATTACCGCCTTTGAGTGAGCTGATACCGCTCGCCGCAG<br>CCGAACGACCGAGCGCAGCGAGTCAGTGAGCGAGGAAGCGGAAGAGCGCCCAATACGCAAACCGCCTCT<br>CCCCGCGCGTTGGCCGATTCATTAATGCAGCTGGCACGACAGGTTTCCCGACTGGAAAGCGGGCAGTGA<br>GCGCAACGCAATTAATGTGAGTTAGCTCACTCATTAGGCACCCCAGGCTTTACACTTTATGCTTCCGGC<br>TCGTATGTTGTGTGGAATTGTGAGCGGATAACAATTTCACACAGGAAACAGCTATGACCATGATTACGC<br>Caagctcgcggccgcagtact CTGCAGATTTTATGCAAAATTAAAGTCTTGTGACAACAGCTTTCTCCT<br>TAAGTGCAAATATCGCCCATTCTTTCCTCTTTTCGTATATAAATGCTGTAATAGTAGGATGTCGTACCC<br>GTAAAGGTACGACATTGAATATTAATATACTCCTAAGTTTACTTTCCCAATATTTATATTAGGACGTCC<br>CCTTCGGTAAATAAATTTTAGTGGCAGTGGTACCGCCACTCCTATTTTAATACTGCGAAGGAGGCAG<br>TTGGCAGGCAACTCGTCGTTCGCAGTATATAAATATCCACTAATATTTATATTCCCGTAAGGGGACGTC<br>CCGAAGGGGAAGGGAAAGAAGCAGTCGCCTCCTTGCGAAAAGGGTTTACTTGCCCGACCAGTGAAAAGC<br>ATGCTGTAAGATATAAATCTACCCTGAAAGGGATGCATTTCACCATAATACTATACAAATGGTGTTACC<br>CTTTGAGGATCATAACGGTGCTACTGGAATATATGGTCTCTTCATGGATAGACGATAGCCATTTATTTA<br>CCCATTAAGGGGACATTAGTGGCCTGTCACTGCTCCTTACGAGACGCCAGTGGACGTTCGTCCTAGAAA<br>ATTTTATGCGCTGCCTAGAAGCCCCAAAAGGGAAGTTTACTGACTCGTTAGAGCGTGCGCTAACAGGTTT<br>AAATACTTCAATATGTATATTAGGACGCCGGTGGCAGTGGTACCGCCACTGCCACCGTCGGAGGACGTC<br>CCTTACGGTATATTATATACTAGGATTTTAATACTCCGAAGGAGGCAGTGGCGGTACCACTGCCACTAA<br>TATTTATATTCCCGTAAGGGACGTCCTCCTTCGGAGTATGTAAACATTCTAAGTTTACTTGCCCAATAT<br>TTATATTAGGCAGTTGGCAGGCAACTGCTAGCTCTCCTCCTTCGGAGTATGTAAACATCGCAGTATATA<br>AATATCCACTAATATTTATATTCCCGTAAGGGGACGTCCCGAAGGGGAAGGGGAAGGACGTCAGTGGCA<br>GTTGCCTGCCAACTGCCTAGGCAAGTAAACTTAGGAGTATATAAATATAGGCAGTCGCGGTACCACTGC<br>CACTGACGTCCTGCCAACTGCCTAGGCAAGTAAACTTAAGTGGCACTAAAATGCATTTGCCCGAAGGGG<br>AAGGAGGACGCCAGTGGCAGTGGTACCGCCACTGCCTCCTTCGGAGTATTAAAATCCTAGTATGTAAAT<br>CTGCTAGCGCAGGAAATAAATTTTATTCTATTTATATACTCCGTTAGGAGGTAAGTAAACCCCTTCCCC<br>TTCGGGACGTCAGTGCAGTTGCCTGCCAACTGCCTAATATAAATATTAGACCACTAAAGTTTGGCAACT<br>GCCAACTGTTGTCCTTCGGAGGAAAAAAAATGGTTAACTCGCAGTAACATAACTAAAGTTTGTT<br>ACTTTACCGAAGACGTTTACCCTTTCTCGGTTAAGGAGACGGAGACAGTTGCACTGTGACTGCCTAGTA<br>TAGCAATTTGTTTTTGTTTATATGCTCGACAAAATGACTTTCATAAAAATATAAAGTAGTTAGCTAGT<br>TATTTTATATCACTATAACTAGGGTTCTCAGAGGCACCGAAGTCACTTGTAAAAATAGTACTTTTTAAC<br>TTGTTTAATCTTCGTGTTCTTCAAAAGGATCACGTAATTTTTTTGAAGGTGGACCAAAACTAACATAAA<br>CTGAATAGCCAGTTACACTTAACAGAAGAAACCATAAAAAAAGGTAAAGAAAAAGCTGGACTTTCCA<br>TAGCTCATTTAATAATAAAATTATTCTCTTTTCAACATATCTCTTAGATAGTTCAAAAGACTTGACGAC<br>TGTGTCCCACATTTTTAAACAAAATTAATCTACTCAAAATTTTGCCCTGAGAAAGAATAACTTACTTCG<br>TTTTTGCAGTAGCCATTCATGTCACTTTGAAACTGTCCTTACAAAGTTAACATTAATTAAAAATTATT<br>TAATTTTTATATAACAAATATTATATTAAATAAAAAATGAACAAAGAACTTCTAAGATCGTCTTTAGTG<br>AGTAATTAAAGAGTTTTACTTACCAGACAAGGCAGTTTTTTCATTCTTTTAAAGCAGGCAGTTCTGAAG<br>GGGAAAAGGGACTGCCTACTGCGGTCCTAGGTAAATACATTTTTATGCAATTTATTTCTTGTGCTAGTA<br>GGTTTCTATACTCACAAGAAGCAACCCCTTGACGAGAAATGCTTCCAGAGTATTTTAATGAATAATCGA<br>GAGGGAATGCACTGAAGAATATTTTCCTTATTTTTTACAGAAAGTAAATAAAATAGCGCTAATAACGCT<br>TAATTCATTTAATCAATTATGGCAACAGGAACTTCTAAAGCTAAACCATCAAAAGTAAATTCAGACTTC<br>CAAGAACCTGGTTTAGTTACACCATTAGGTACTTTATTACGTCCACTTAACTCAGAAGCAGGTAAAGTA<br>TTACCAGGCTGGGGTACAACTGTTTTAATGGCTGTATTTATCCTTTTATTTGCAGCATTCTTATTAATC<br>ATTTTAGAAATTTACAACAGTTCTTTAATTTTAGATGACGTTTCTATGAGTTGGGAAACTTTAGCTAAA | Endo-β-<br>glucanase<br>insertion<br>cassette<br>(pSE-3HB-<br>K-rbcL:<br>BD05) |

TABLE 4-continued

Vector Sequences

| SEQ ID NO. | Sequence | Use |
|---|---|---|
| | GTTTCTTAATTTTATTTAACACAAACATAAAATATAAAACTGTTTGTTAAGGCTAGCTGCTAAGTCTTC<br>TTTTCGCTAAGGTAAACTAAGCAACTCAACCATATTTATATTCGGCAGTGGCACCGCCAACTGCCACTG<br>GCCTTCCGTTAAGATAAACGCGTggatctcacgtgACTAGTcacctagtgtcgagtggtaccgccactg<br>cctagtatataaatatcggcagttggcaggatatttatatactccgaaggaacttgttagccgataggc<br>gaggcaactgccactaaaatttatttgcctcctaacggagcattaaaatccctaagtttacttgcccgt<br>aaggggaaggggacgtcctactaatatttatattaggcagttggcaggcaacaataaatacatttgtccc<br>gtaaggggacgtcctgccaactgcctatggtagctattaagtatatatatatgaaaagtgtgtataaac<br>taaactaaaataaaccaggtatggttaaccagatttattttagtttaaaaaaaaattagttgtttgagc<br>tagagttagttgaagctaagtctagaTTAACCGGTTCCTTTATCATCATCATCTTTGTAATCACTTCCA<br>CCGCCACCTGAGCCTTGAAAGTATAAGTTTTCACCGGTACCCTTGCGAGCTAAACAACTACTTACTAAT<br>GAAGTGTCTGTCCATGAGTTTCCAGAAGAAGTAGGGGTTTCGGTTAATACATAAGTTGAATCAAAAGAA<br>CCAGCACCCCAACCTACATAACCTAAGTACACGTCAGAGTTTTGATTTAAGTACTGAATTTGTTGACAC<br>ATGTCTTGGATACAACTCTGCACGTTTCCACCACCTGTTTCAGTTAAAATGGCTTGGCGATTATTTTGA<br>CGTAACCAAGTTGCTAAAGGACTAAAAGCACCATCAATATTATTTGTGGTACATTCGGCGTGTGTTCCG<br>CTATTATCAGAATCAAGATATTTATGTACATCGAATATTAAGTTAGTGGTACTACCGTCTGGGTTAGTC<br>ACTTGACTAAGAGCAGCTGCGCTACCGTCAGAAATAAAAGCGCCGGCAGATTGCCAATCGTTGCCTGGT<br>AAACTAATGAATTGTGATGTTGCACCAGCATTACGAATAGCAGTTACTACTTCTTGCACAGTTGCAGCC<br>CAAGTATTTATGTTCACATCGTGAGGTTCATTCATAATACCGAACCAAACACGTGATTGACTAGCATAT<br>TTTGAAGCTAATTGGCTCCATAATGATGTAAATTGAGCATTAGTTGGACCACCTTGACCAATAATACCA<br>CCGTTCCAACGGGCATAATTATGAATATCAACAATACAATAGGCACCTAAAGATAAGCAACCTTGTACT<br>AATTGATCATATTTACTAATTGATGTACTATCTAAGTTACCACCTAAATTGTTGTTAACTAAGTATTGC<br>CAGCCCACTGGTAAACGGAAAATAGTCATACCATCTTCATTTACAAAGTGTTGCATTTGACCAATGCCA<br>TCTGGATAATTGTTTGAGCCAGTAAAATTTTTTAAAGGGGGATAAACTTTACTGGTAACACATGTACCA<br>TCGGTAGTACAACCAAAATCGAAACCTGCAATATTAACACCAGCGAAACGTACTCCAGAAGATGTAGGA<br>GGTGTGCTGCTAGAAGTGCTAGTAGCACGAGTTGTTGTAGTTGGACCTGAAGGAGGGCGAGTTGATGTT<br>GTTATAGTTGTTGCACCTGGAATACATTGAGCATAGTAAGGATTTAAGGTACTACATGCTGAGCCAGGA<br>GCACAATTGGTAGGACCAGACCAACCAATACCACCACACTGACCCCAAACAGTCTGTTGAGCAACAGCA<br>CCACCATATAAGATAGATGCAGCAAGTAATAATGGTGCTACGCTTTTGTTTGGTACCATGAgcacttTg<br>cattacctccgtacaaattattttgatttctataaagttttgcttaaataaaaattttttaattttTaac<br>gtccacccatataaataataaatatggtgaaacctttaacaacaaaaatcctcttgtaccatattaatc<br>caaaagaattaaggacaaaagcttatctccaacattttTaaaacacagagtaaaaataatgttgtttTt<br>aagaatagaattttataacttgtattttaaatatgatctaattttatttgtgctaaaaattgcagttgga<br>aagtaattttaaaaataatttagatcatatttattaaataaagttgatttaaaacaacttaatcgtttt<br>taattgttaattaaaaacataattttaaatcttttTtatatttaaattaccttatatactactaggtgAC<br>TATGgatatctacgtaatcgatgaattcgatcccatttttataactggatctcaaaatacctataaacc<br>cattgttcttctcttttagctctaagaacaatcaatttataaatatatttattattatgctataatata<br>aatactatataaatacatttacctttttataaatacatttacctttttttaatttgcatgattttaat<br>gcttatgctatcttttttatttagtccataaaacctttaaaggacctttTcttatgggatatttatatt<br>ttcctaacaaagcaatcggcgtcataaactttagttgcttacgacgcctgtggacgtcccccccttccc<br>cttacgggcaagtaaacttagggatttTaatgcaataaataaatttTgtcctcttcgggcaaatgaattt<br>tagtatttaaatatgacaagggtgaaccattacttttgttaacaagtgatcttaccactcactatttTt<br>gttgaatttTaaacttatttaaaattctcgagaaagattttaaaaataaactttttTtaatcttttatttt<br>attttttcttttttCGTATGGAATTGCCCAATATTATTCAACAATTTATCGGAAACAGCGTTTTAGAGC<br>CAAATAAAATTGGTCAGTCGCCATCGGATGTTTATTCTTTTAATCGAAATAATGAAACTTTTTTCTTA<br>AGCGATCTAGCACTTTATATACAGAGACCACATACAGTGTCTCTCGTGAAGCGAAAATGTTGAGTTGGC<br>TCTCTGAGAAATTAAAGGTGCCTGAACTCATCATGACTTTTCAGGATGAGCAGTTTGAATTTATGATCA<br>CTAAAGCGATCAATGCAAAACCAATTTCAGCGCTTTTTTAACAGACCAAGAATTGCTTGCTATCTATA<br>AGGAGGCCACTCAATCTGTTAAATTCAATTGCTATTATTGATTGTCCATTTATTTCAAACATTGATCATC<br>GGTTAAAAGAGTCAAAATTTTTTATTGATAACCAACTCCTTGACGATATAGATCAAGATGATTTTGACA<br>CTGAATTATGGGGAGACCATAAAACTTACCTAAGTCTATGGAATGAGTTAACCGAGACTCGTGTTGAAG<br>AAAGATTGGTTTTTCTCATGGCGATATCACGGATAGTAATATTTTTATAGATAAATTCAATGAAATTT<br>ATTTTTTAGACCTTGGTCGTGCTGGGTTAGCAGATGAATTTGTAGATATATCCTTTGTTGAACGTTGCC<br>TAAGAGAGGATGCATCGGAGGAAACTGCGAAAATATTTTTAAAGCATTTAAAAAATGATAGACCTGACA<br>AAAGGAATTATTTTTTAAAACTTGATGAATTGAATTGAttccaagcattatctaaaatactctgcaggc<br>acgctagcttgtactcaagctcgtaacgaaggtcgtgaccttgctcgtgaaggtggcgacgtaattcgt<br>tcagcttgtaaatggtctccagaacttgctgctgcatgtgaagtttggaaagaaatTaaatTcgaattT<br>gatactattgacaaactttaattttTattttTcatgatgttatgtgaatagcataaacatcgttttta<br>tttttatggtgtttaggttaaatacctaaacatcattttacattttTaaaattaagttctaaagtTatc<br>ttttgtttaaatttgcctgtctttataaattacgatgtgccagaaaaaTaaaatcttagcttttTatta<br>tagaatttatctttatgtattatattttataagttataataaaagaaatagtaacatactaaagcggat<br>gtagcgcgtttatcttaacggaaggaattcggcgcctacgcgaggatccACGCGTTAA<br>TAGCTCACTTTTCTTTAAATTTAATTTTTAATTTAAAGGTGTAAGCAAATTGCCTGACGAGAGATCCAC<br>TTAAAGGATGACAGTGGCGGGCTACTGCCTACTTCCCTCCGGGATAAAATTTATTTGAAAAACGTTAGT<br>TACTTCCTAACGGAGCATTGACATCCCCATATTTATATTAGGACGTCCCCTTCGGGTAAATAAATTTTA<br>GTGGACGTCCCCTTCGGGCAAATAAATTTTAGTGGACAATAAATAAATTTGTTGCCTGCCAACTGCCTA<br>GGCAAGTAAACTTGGGAGTATTAAAATAGGACGTCAGTGGCAGTTGCCTGCCAACTGCCTATATTTATA<br>TACTGCGAAGCAGGCAGTGGCGGTACCACTGCCACTGCCGTCCTAATATAAATATTGGGCAACTAAAGT<br>TTATAGCAGTATTAACATCCTATATTTATATACTCCGAAGGAACTTGTTAGCCGATAGGCGAGGCAACA<br>AATTTATTTATTGTCCCGTAAAAGGATGCCTCCAGCATCGAAGGAGGGGGACGTCCTAGGCCATAAA<br>ACTAAAGGGAAATCCATAGTAACTGATGTTATAAATTTATAGACTCCAAAAACAGCTGCGTTATAAAT<br>AACTTCTGTTAAATATGGCCAAGGGGACAGGGGCACTTTCAACTAAGTGTACATTAAAAATTGACAATT<br>CAATTTTTTTAATTATAATATATATTTAGTAAAATATAACAAAAAGCCCCCATCGTCTAGgtagaatt<br>ccagctggcggccgccctatg | |

TABLE 4-continued

Vector Sequences

| SEQ ID NO. | Sequence | Use |
|---|---|---|
| 29 | GTGCACTCTCAGTACAATCTGCTCTGATGCCGCATAGTTAAGCCAGCCCCGACACCCGCCAACACCCGC TGACGCGCCCTGACGGGCTTGTCTGCTCCCGGCATCCGCTTACAGACAAGCTGTGACCGTCTCCGGGAG CTGCATGTGTCAGAGGTTTTCACCGTCATCACCGAAACGCGCGAGACGAAAGGGCCTCGTGATACGCCT ATTTTTATAGGTTAATGTCATGATAATAATGGTTTCTTAGACGTCAGGTGGCACTTTTCGGGGAAATGT GCGCGGAACCCCTATTTGTTTATTTTTCTAAATACATTCAAATATGTATCCGCTCATGAGACAATAACC CTGATAAATGCTTCAATAATATTGAAAAAGGAAGAGTATGAGTATTCAACATTTCCGTGTCGCCCTTAT TCCCTTTTTTGCGGCATTTTGCCTTCCTGTTTTTGCTCACCCAGAAACGCTGGTGAAAGTAAAAGATGC TGAAGATCAGTTGGGTGCACGAGTGGGTTACATCGAACTGGATCTCAACAGCGGTAAGATCCTTGAGAG TTTTCGCCCCGAAGAACGTTTTCCAATGATGAGCACTTTTAAAGTTCTGCTATGTGGCGCGGTATTATC CCGTATTGACGCCGGGCAAGAGCAACTCGGTCGCCGCATACACTATTCTCAGAATGACTTGGTTGAGTA CTCACCAGTCACAGAAAAGCATCTTACGGATGGCATGACAGTAAGAGAATTATGCAGTGCTGCCATAAC CATGAGTGATAACACTGCGGCCAACTTACTTCTGACAACGATCGGAGGACCGAAGGAGCTAACCGCTTT TTTGCACAACATGGGGGATCATGTAACTCGCCTTGATCGTTGGGAACCGGAGCTGAATGAAGCCATACC AAACGACGAGCGTGACACCACGATGCCTGTAGCAATGGCAACAACGTTGCGCAAACTATTAACTGGCGA ACTACTTACTCTAGCTTCCCGGCAACAATTAATAGACTGGATGGAGGCGGATAAAGTTGCAGGACCACT TCTGCGCTCGGCCCTTCCGGCTGGCTGGTTTATTGCTGATAAATCTGGAGCCGGTGAGCGTGGGTCTCG CGGTATCATTGCAGCACTGGGGCCAGATGGTAAGCCCTCCCGTATCGTAGTTATCTACACGACGGGGAG TCAGGCAACTATGGATGAACGAAATAGACAGATCGCTGAGATAGGTGCCTCACTGATTAAGCATTGGTA ACTGTCAGACCAAGTTTACTCATATATACTTTAGATTGATTTAAAACTTCATTTTTAATTTAAAAGGAT CTAGGTGAAGATCCTTTTTGATAATCTCATGACCAAAATCCCTTAACGTGAGTTTTCGTTCCACTGAGC GTCAGACCCCGTAGAAAAGATCAAAGGATCTTCTTGAGATCCTTTTTTTCTGCGCGTAATCTGCTGCTT GCAAACAAAAAAACCACCGCTACCAGCGGTGGTTTGTTTGCCGGATCAAGAGCTACCAACTCTTTTTCC GAAGGTAACTGGCTTCAGCAGAGCGCAGATACCAAATACTGTTCTTCTAGTGTAGCCGTAGTTAGGCCA CCACTTCAAGAACTCTGTAGCACCGCCTACATACCTCGCTCTGCTAATCCTGTTACCAGTGGCTGCTGC CAGTGGCGATAAGTCGTGTCTTACCGGGTTGGACTCAAGACGATAGTTACCGGATAAGGCGCAGCGGTC GGGCTGAACGGGGGGTTCGTGCACACAGCCCAGCTTGGAGCGAACGACCTACACCGAACTGAGATACCT ACAGCGTGAGCTATGAGAAAGCGCCACGCTTCCCGAAGGGAGAAAGGCGGACAGGTATCCGGTAAGCGG CAGGGTCGGAACAGGAGAGCGCACGAGGGAGCTTCCAGGGGGAAACGCCTGGTATCTTTATAGTCCTGT CGGGTTTCGCCACCTCTGACTTGAGCGTCGATTTTTGTGATGCTCGTCAGGGGGCGGAGCCTATGGAA AAACGCCAGCAACGCGGCCTTTTTACGGTTCCTGGCCTTTTGCTGGCCTTTTGCTCACATGTTCTTTCC TGCGTTATCCCCTGATTCTGTGGATAACCGTATTACCGCCTTTGAGTGAGCTGATACCGCTCGCCGCAG CCGAACGACCGAGCGCAGCGAGTCAGTGAGCGAGGAAGCGGAAGAGCGCCCAATACGCAAACCGCCTCT CCCCGCGCGTTGGCCGATTCATTAATGCAGCTGGCACGACAGGTTTCCCGACTGGAAAGCGGGCAGTGA GCGCAACGCAATTAATGTGAGTTAGCTCACTCATTAGGCACCCCAGGCTTTACACTTTATGCTTCCGGC TCGTATGTTGTGTGGAATTGTGAGCGGATAACAATTTCACACAGGAAACAGCTATGACCATGATTACGC CaagctcgcggccgcagtactCTGCAGATTTTATGCAAAATTAAAGTCTTGTGACAACAGCTTTCTCCT TAAGTGCAAATATCGCCCATTCTTTCCTCTTTTCGTATATAAATGCTGTAATAGTAGGATGTCGTACCC GTAAAGGTACGACATTGAATATTAATATACTCCTAAGTTTACTTTCCCAATATTTATATTAGGACGTCC CCTTCGGGTAAATAAATTTTAGTGGCAGTGGTACCGCCACTCCCTATTTTAATACTGCGAAGGAGGCAG TTGGCAGGCAATCTCGTCGTTCGCAGTATATAAATATCCACTAATATTTATATTCCCGTAAGGGGACGTC CCGAAGGGGAAGGGAAAGAAGCAGTCGCCTCCTTGCGAAAAGGTTTACTTGCCCGACCAGTGAAAAGC ATGCTGTAAGATATAAATCTACCCTGAAAGGGATGCATTTCACCATAATACTATACAAATGGTGTTACC CTTTGAGGATCATAACGGTGCTACTGGAATATATGGTCTCTTCATGGATAGACGATAGCCATTTATTTA CCCATTAAGGGGACATTAGTGGCCTGTCACTGCTCCTTACGAGACGCCAGTGGACGTTCGTCCTAGAAA ATTTATGCGCTGCCTAGAAGCCCCAAAAGGGAAGTTTACTGACTCGTTAGAGCGTGCGCTAACAGGTTT AAATACTTCAATATGTATATTAGGACGCCGGTGGCAGTGGTACCGCCACTGCCACCGTCGGAGGACGTC CCTTACGGTATATTATACTAGGATTTTAATACTCCGAAGGAGGCAGTGGCGGTACCACTGCCACTAA TATTTATATTCCCGTAAGGGACGTCCTCCTTCGGAGTATGTAAACATTTAAGTTTACTTGCCCAATAT TTATATTAGGCAGTTGGCAGGCAACTGCTAGCTCTCCTCCTTCGGAGTATGTAAACATCGCAGTATATA AATATCCACTAATATTTATATTCCCGTAAGGGGACGTCCCGAAGGGGAAGGGAAGGACGTCAGTGGCA GTTGCCTGCCAACTGCCTAGGCAAGTAAACTTAGGAGTATATAAATATAGGCAGTCGCGGTACCACTGC CACTGACGTCCTGCCAACTGCCTAGGCAAGTAAACTTAAGTGCACTAAAATGCATTTGCCCGAAGGGG AAGGAGGACGCCAGTGGCAGTGGTACCGCCACTGCCTCCTTCGGAGTATTAAAATCCTAGTATGTAAAT CTGCTAGCCAGGAAATAAATTTTATTCTATTTATATACTCCGTTAGGAGGTAAGTAAACCCCTTCCCC TTCGGGACGTCAGTGCAGTTGCCTGCCAACTGCCTAATATAAATATTAGACCACTAAAGTTTGGCAACT GCCAACTGTTCCTTCGGAGGAAAAAAATGGTTAACTCGCAAGCAGTTAACATAACTAAAGTTTGTT ACTTTACCGAAGCGTTTACCCTTCTCGGTTAAGGAGACGGAAGCAGTTGCACTGTGACTGCCTAGTA TAGCAATTTGTTTTTGTTTATATGCTCGACAAAATGACTTTCATAAAAATATAAAGTAGTTAGCTAGT TATTTTATATCACTATAACTAGGGTTCTCAGAGGCACCGAAGTCACTTGTAAAAATAGTACTTTTTAAC TTGTTTAATCTTCGTGTTCTTCAAAAGGATCACGTAATTTTTTTGAAGGTGGACCAAAACTAACATAAA CTGAATAGCCAGTTACACTTAACAGAAGAAACCATAAAAAAAGGTAAGAAAAAAGCTGGACTTTCCA TAGCTCATTTAATAATAAAATTATTCTCTTTTCAACATATCTCTTAGATAGTTCAAAAGACTTGACGAC TGTGTCCCACATTTTTAAACAAATTAATCTACTCAAAATTTTGCCCTGAGAAAGAATAACTTACTTCG TTTTTGCAGTAGCCATTCATGTCACTTTGAAACTGTCCTTACAAAGTTAAACATTAATTAAAAATTATT TAATTTTTATATAACAAATATTATATTAAATAAAAAATGAACAAAGAACTTCTAAGATCGTCTTTAGTG AGTAATTAAAGAGTTTTACTTACCAGACAAGGCAGTTTTTTCATTCTTTTAAAGCAGGCAGTTCTGAAG GGGAAAAGGGACTGCCTACTGCGGTCCTAGGTAAATACATTTTTATGCAATTTATTTCTTGTGCTAGTA GGTTTCTATACTCACAAGAAGCAACCCCTTGACGAGAGAACGTTATCCTCAGAGTATTTATAATCCTGA GAGGGAATGCTCGAAGAATATTTCCTTATTTTTACAGAAGAGTAAATAAAATAGCGCTAATAACGCT TAATTCATTTAATCAATTATGGCAACAGGAACTTCTAAAGCTAAACATCAAAAGTAAATTCAGACTTC CAAGAACCTGGTTTAGTTACACCATTAGGTACTTTATTACGTCCACTTAACTCAGAAGCAGGTAAAGTA TTACCAGGCTGGGGTACAACTGTTTTAATGGCTGTATTTATCCTTTTATTTGCAGCATTCTTATTAATC ATTTTAGAAATTTACAACAGTTCTTAATTTTAGATGACGTTTCTATGAGTTGGGAAACTTTAGCTAAA GTTTCTTAATTTTATTTAACACAAACATAAAATATAAAACTGTTTGTTAAGGCTAGCTGCTAAGTCTTC | Exo-β-glucanase insertion cassette (pSE-3HB-K-tD2: BD01) |

TABLE 4-continued

Vector Sequences

| SEQ ID NO. | Sequence | Use |
|---|---|---|

TTTTCGCTAAGGTAAACTAAGCAACTCAACCATATTTATATTCGGCAGTGGCACCGCCAACTGCCACTG
GCCTTCCGTTAAGATAAACGCGTggatctcacgtgACTAGTgtcgagtggtaccgccactgcctagtat
ataaatatcggcagttggcaggatatttatatactccgaaggaacttgttagccgataggcgaggcaac
tgccactaaaatttatttgcctcctaacggagcattaaaatccctaagtttacttgcccgtaaggggaa
ggggacgtccactaatatttatattaggcagttggcaggcaacaataaatacatttgtcccgtaagggg
acgtcctgccaactgcctatggtagctattaagtatatatatatgaaaagtgtgtataaactaaactaa
aataaaccaggtatggttaaccagatttattttagtttaaaaaaaaattagttgtttgagctagagtta
gtgaagctaagtctagaTTAACCGGTTCCTTTATCATCATCATCTTTGTAATCACTTCCACCGCCACCT
GAGCCTTGAAAGTATAAGTTTTCACCGGTACCTAAACATTGGCTATAATATGGATTTAAAACTTGACAT
GTAGTTCCTGATGCACACACAGTTGGACCTGAATAACCAATACCACCACATTGACCGTAATGAGATTGT
GTTGGTCCAGGAGAAGAACCTGTGGTAGTAGCAGGACGACGTGTTGTAGTGGTGCCAGGTGGATTTCCA
CCTGGTGGATTACCACCTGAAGGATCGCCTGTAGAGCCAATTGGACCAAATTTGATATTACTAAAAGTT
ACTTTTGCATTAGGACTTTGGCTTTCAACTTGAGCAGGTACACCACTTGAAGTTGAACATGAACCACGA
ACAGCACCAGGAGTGCTTGAAGTTTCGTTTGTAGGATATGTACTATCTAACCATAACATATTAGCATAA
TAGTCATCCCATAATGACATAACTAAAACCATACCACCTGATGTTGCTTTCTTGAATTGAGTTAAACCA
CCTTTATCTGAGAAGCTGCTACCACCAAATTCTGCTTCTTCTGCTGTACAATAATCGTCATTAAGGCCG
TTACCAGAATAAGAACCTAATTCTGCATTTGGTTGTTGAAAAGTTACACCATTTTGCACGTAATAACGA
TTAATAGCACCGCTAGTTTCGAACTGTGTAACAACTGTTAACTTTTTAGTTGTATCTAATGTGAATGAA
CTTCCTGGTCCATAAAAAGATGTATTTCCTAAACGATATGGGTCCCAATCGCAGCCATCAGGATCACAT
GTACCACCATAACGGTTATCACTGTATGTTCCACCGCAACCGTCGCCTTCACAAATTTCTTGGCCAACG
GTAGTACAAGGATGTGGAGTTAATGCTTCACTAATTGAATTAGCTTCCCAAATATCCATTTCAGAACAA
CAAGATCCGTGACCACCAATTCCAGTATTTGCATTATTACTACTTGGTTCCCAACCTTCCACGTTAGCT
TGACCGTTAATAAACTTTAAATCACGAGGACACTGAGAATCACAATAGCCTGTTCCGTATTTAGCACCT
GCTGTATTAGTAGGATATTTGCTTACACCGCCATCAGCGTCCATTGAAACGAAATAAAGAGCACCATTT
AAACCACATGGTAATTGACTCACATCTACGTCGAAACTGAACTCATTACCTAATAATGTAAATTCTTGA
TAGGTTGTGTCACTTGCCATTAAGTATAAACGTGCGCCTACATTTTTTTGTGCTGATTGAGTCACGAAA
CCAATTGATAATGAGTTACCTGATGTAGTAACGCCGTAAGTTGAAGCGTAAGCTGCACCATCTAAACAA
CAATTTTTAGCACAAGTTTCGTTATCGGGACAAAGTGTTGATGACCAAGTATTACCGTCATAACAATTA
GTTGAACTATTAGTGGCATGTGTCCAACGCCAGTTAGCATCAATTACTACAGAGCCAGTTTGTTGTGTA
CAAGTACCTCCTGAAGAACATTTTTGCCATGTTAATGGAGGATGAGTTTCAGATTGTAAGGTACATGCT
GACTGTGCACGAGCAGTAGCTAAGAAAGCACTAATAACAGCAAGTTTACGATATGGTACCATatgcgtg
tatctccaaaataaaaaaacaactcatcgttacgttaaatttattattatttaattttaatcattgtgt
atttaatattataacttatataaaataaaattaaaaataagcatttttttacacacatatttttaaataa
atctttaaacgggttatatatagttatatatatgggactagaactgctttgtgcatagtcatcacaatt
attatattataaaccatgaataaaggtttttattattatgatataaaaatgcataaaattttttataaatt
ttgcaagtaaaatatataattaggaaaaaatttaaaatttaaaatttagtcaagtttacaactaatac
ttttaattttgtattttaagtattggacatttttgtggaattaaatgtaccaaatatccatttaatttc
atACTAGTgatatctacgtaatcgatgaattcgatcccatttttataactggatctcaaaatacctata
aacccattgttcttctcttttagctctaagaacaatcaatttataaatatatttattattatgctataa
tataaatactatataaatacatttacctttttataaatacatttaacttttttttaattttgcatgattt
taatgcttatgctatcttttttatttagtccataaaaccttttaaaggaccttttcttatgggatattta
tattttcctaacaaagcaatcggcgtcataaactttagttgcttacgacgcctgtggacgtccccccct
tccccttacgggcaagtaaacttaggggattttaatgcaataaataaatttgtcctcttcgggcaaatga
attttagtatttaaatatgacaagggtgaaccattacttttgttaacaagtgatcttaccactcactat
ttttgttgaatttttaaacttatttaaaattctcgagaaagatttttaaaaataaaactttttttaatctttt
atttattttttcttttttCGTATGGAATTGCCCAATATTATTCAACAATTTATCGGAAACAGCGTTTTA
GAGCCAAATAAAATTGGTCAGTCGCCATCGGATGTTATTCTTTTAATCGAAATAATGAAACTTTTTTT
CTTAAGCGATCTAGCACTTTATATACAGAGACCACATACAGTGTCTCTCGTGAAGCGAAAATGTTGAGT
TGGCTCTCTGAGAAATTAAAGGTGCCTGAACTCATCATGACTTTTCAGGATGAGCAGTTTGAATTTATG
ATCACTAAAGCGATCAATGCAAAACCAATTTCAGCGCTTTTTTTAACAGACCAAGAGAATTGCTTGCTATC
TATAAGGAGGCACTCAATCTGTTAAATTCAATTGCTATTATTGATTGTCCATTTATTTCAAACATTGAT
CATCGGTTAAAAGAGTCAAAATTTTTTATTGATAACCAACTCCTTGACATATAGATCAAGATGATTTT
GACACTGAATTATGGGGAGACCATAAAACTTACCTAAGTCTATGGAATGAGTTAACCGAGACTCGTGTT
GAAGAAAGATTGGTTTTTTCTCATGGCGATATCACGGATAGTAATATTTTATAGATAAATTCAATGAA
ATTTATTTTTAGACCTTGGTCGTGCTGGGTTAGCAGATGAATTTGTAGATATATCCTTTGTTGAACGT
TGCCTAAGAGGATGCATCGGAGGAAACTGCGAAAATATTTTTAAAGCATTTAAAAAATGATAGACCT
GACAAAAGGAATTATTTTTTAAAACTTGATGAATTGAATTGAttccaagcattatctaaaatactctgc
aggcacgctagcttgtactcaagctcgtaacgaaggtcgtgaccttgctcgtgaaggtggcgacgtaat
tcgttcagcttgtaaatggtctccagaacttgctgctgcatgtgaagtttggaaagaaattaaattcga
atttgatactattgacaaactttaatttttattttcatgatgtttatgtgaatagcataaacatcgtt
tttattttatggtgtttaggttaaatacctaaacatcattttacattttttaaaattaagttctaaagt
tatcttttgttttaaatttgcctgtctttataaattacgatgtgccagaaaaataaaatcttagcttttt
attatagaatttatctttatgtattatattttataagttataataaaagaaatagtaacatactaaagc
ggatgtagcgcgtttatcttaacgaaggaattcggcgcctacgtacccgggtcgcgaggatccACGCG
TTAATAGCTCACTTTTCTTTAAATTTAATTTTTAATTTAAAAGGTGTAAGCAAATTGCCTGACGAGAAT
CCACTTAAAGGATGACAGTGGCGGGCTACTGCCTACTTCCCTCCGGGATAAAATTTATTTGAAAAACGT
TAGTTACTTCCTAACGGAGCATTGACATCCCCATATTTATATTAGGACGTCCCCTTCGGGTAAATAAAT
TTTAGTGGACGTCCCCTTCGGGCAAATAAATTTTAGTGGACAATAAATAAATTTGTTGCCTGCCAACTG
CCTAGGCAAGTAAACTTGGGAGTATTAAAATAGGACGTCAGTGGCATTTGCCTGCCAACTGCCTATATT
TATATACTGCGAAGCAGGCAGTGGCGGTACCACTGCCACTGGCGTCCTAATATAAATATTGGGCAACTA
AAGTTTATAGCAGTATTAACATCCTATATTTATATCTCCGAAGGAACTTGTTAGCCGATAGGCGAGGC
AACAAATTTATTTATTGTCCCGTAAAAGGATGCCTCCAGCATCGAAGGGAAGGGGACGTCCTAGGCCA
TAAAACTAAAGGGAAATCCATAGTAACTGATGTTATAAATTTATAGACTCCAAAAACAGCTGCGTTAT
AAATAACTTCTGTTAAATATGGCCAAGGGGACAGGGGCACTTTCAACTAAGTGTACATTAAAAATTGAC TABLE 4-continued Vector Sequences

| SEQ ID NO. | Sequence | Use |
|---|---|---|
| | AATTCAATTTTTTTAATTATAATATATATTTAGTAAAATATAACAAAAAGCCCCCATCGTCTAGgtag<br>aattccagctggcggccgccctatg | |
| 30 | GTGCACTCTCAGTACAATCTGCTCTGATGCCGCATAGTTAAGCCAGCCCCGACACCCGCCAACACCCGC<br>TGACGCGCCCTGACGGGCTTGTCTGCTCCCGGCATCCGCTTACAGACAAGCTGTGACCGTCTCCGGGAG<br>CTGCATGTGTCAGAGGTTTTCACCGTCATCACCGAAACGCGCGAGACGAAAGGGCCTCGTGATACGCCT<br>ATTTTTATAGGTTAATGTCATGATAATAATGGTTTCTTAGACGTCAGGTGGCACTTTTCGGGGAAATGT<br>GCGCGGAACCCCTATTTGTTTATTTTTCTAAATACATTCAAATATGTATCCGCTCATGAGACAATAACC<br>CTGATAAATGCTTCAATAATATTGAAAAAGGAAGAGTATGAGTATTCAACATTTCCGTGTCGCCCTTAT<br>TCCCTTTTTTGCGGCATTTTGCCTTCCTGTTTTTGCTCACCCAGAAACGCTGGTGAAAGTAAAAGATGC<br>TGAAGATCAGTTGGGTGCACGAGTGGGTTACATCGAACTGGATCTCAACAGCGGTAAGATCCTTGAGAG<br>TTTTCGCCCCGAAGAACGTTTTCCAATGATGAGCACTTTTAAAGTTCTGCTATGTGGCGCGGTATTATC<br>CGTATTGACGCCGGGCAAGAGCAACTCGGTCGCCGCATACACTATTCTCAGAATGACTTGGTTGAGTA<br>CTCACCAGTCACAGAAAAGCATCTTACGGATGGCATGACAGTAAGAGAATTATGCAGTGCTGCCATAAC<br>CATGAGTGATAACACTGCGGCCAACTTACTTCTGACAACGATCGGAGGACCGAAGGAGCTAACCGCTTT<br>TTTGCACAACATGGGGGATCATGTAACTCGCCTTGATCGTTGGGAACCGGAGCTGAATGAAGCCATACC<br>AAACGACGAGCGTGACACCACGATGCCTGTAGCAATGGCAACAACGTTGCGCAAACTATTAACTGGCGA<br>ACTACTTACTCTAGCTTCCCGGCAACAATTAATAGACTGGATGGAGGCGGATAAAGTTGCAGGACCACT<br>TCTGCGCTCGGCCCTTCCGGCTGGCTGGTTTATTGCTGATAAATCTGGAGCCGGTGAGCGTGGGTCTCG<br>CGGTATCATTGCAGCACTGGGGCCAGATGGTAAGCCCTCCCGTATCGTAGTTATCTACACGACGGGGAG<br>TCAGGCAACTATGGATGAACGAAATAGACAGATCGCTGAGATAGGTGCCTCACTGATTAAGCATTGGTA<br>ACTGTCAGACCAAGTTTACTCATATATACTTTAGATTGATTTAAAACTTCATTTTTAATTTAAAAGGAT<br>CTAGGTGAAGATCCTTTTTGATAATCTCATGACCAAAATCCCTTAACGTGAGTTTTCGTTCCACTGAGC<br>GTCAGACCCCGTAGAAAAGATCAAAGGATCTTCTTGAGATCCTTTTTTTCTGCGCGTAATCTGCTGCTT<br>GCAAACAAAAAAACCACCGCTACCAGCGGTGGTTTGTTTGCCGGATCAAGAGCTACCAACTCTTTTTCC<br>GAAGGTAACTGGCTTCAGCAGAGCGCAGATACCAAATACTGTTCTTCTAGTGTAGCCGTAGTTAGGCCA<br>CCACTTCAAGAACTCTGTAGCACCGCCTACATACCTCGCTCTGCTAATCCTGTTACCAGTGGCTGCTGC<br>CAGTGGCGATAAGTCGTGTCTTACCGGGTTGGACTCAAGACGATAGTTACCGGATAAGGCGCAGCGGTC<br>GGGCTGAACGGGGGGTTCGTGCACACAGCCCAGCTTGGAGCGAACGACCTACACCGAACTGAGATACCT<br>ACAGCGTGAGCTATGAGAAAGCGCCACGCTTCCCGAAGGGAGAAAGGCGGACAGGTATCCGGTAAGCGG<br>CAGGGTCGGAACAGGAGAGCGCACGAGGGAGCTTCCAGGGGGAAACGCCTGGTATCTTTATAGTCCTGT<br>CGGGTTTCGCCACCTCTGACTTGAGCGTCGATTTTTGTGATGCTCGTCAGGGGGCGGAGCCTATGGAA<br>AAACGCCAGCAACGCGGCCTTTTTACGGTTCCTGGCCTTTTGCTGGCCTTTTGCTCACATGTTCTTTCC<br>TGCGTTATCCCCTGATTCTGTGGATAACCGTATTACCGCCTTTGAGTGAGCTGATACCGCTCGCCGCAG<br>CCGAACGACCGAGCGCAGCGAGTCAGTGAGCGAGGAAGCGGAAGAGCGCCCAATACGCAAACCGCCTCT<br>CCCCGCGCGTTGGCCGATTCATTAATGCAGCTGGCACGACAGGTTTCCCGACTGGAAAGCGGGCAGTGA<br>GCGCAACGCAATTAATGTGAGTTAGCTCACTCATTAGGCACCCCAGGCTTTACACTTTATGCTTCCGGC<br>TCGTATGTTGTGTGGAATTGTGAGCGGATAACAATTTCACACAGGAAACAGCTATGACCATGATTACGC<br>Caagctcgcggccgcagtact CTGCAGATTTTATGCAAAATTAAAGTCTTGTGACAACAGCTTTCTCCT<br>TAAGTGCAAATATCGCCCATTCTTTCCTCTTTTCGTATATAAATGCTGTAATAGTAGGATGTCGTACCC<br>GTAAAGGTACGACATTGAATATTAATATACTCCTAAGTTTACTTTCCCAATATTTATATTAGGACGTCC<br>CCTTCGGGTAAATAAATTTTAGTGGCAGTGGTACCGCCACTCCCTATTTTAATACTGCGAAGGAGGCAG<br>TTGGCAGGCAACTCGTCGTTCGCAGTATATAAATATCCACTAATATTTATATTCCCGTAAGGGGACGTC<br>CCGAAGGGGAAGGGGAAAGAAGCAGTCGCCTCCTTGCGAAAAAGTTTACTTGCCCGACCAGTGAAAAGC<br>ATGCGTAAGATATAAATCTACCCTGAAAGGGATGCATTTCACCATAATACTATACAAATGGTGTTACC<br>CTTTGAGGATCATAACGGTGCTACTGGAATATATGGTCTCTTCATGGATAGACGATAGCCATTTATTTA<br>CCCATTAAGGGGACATTAGTGGCCTGTCACTGCTCCTTACGAGACGCCAGTGGACGTTCGTCCTAGAAA<br>ATTTATGCGTGCCTAGAAGCCCCAAAAGGGAAGTTTAACAGGTCGTTAGAGCGTGCGCTAACAGGTTT<br>AAATACTTCAATATGTATATTAGGACGCCGGTGGCAGTGGTACCGCCACTGCCACCGTCGGAGGACGTC<br>CCTTACGGTATATTATACTAGGATTTTAATACTCCGAAGGAGGCAGTGGCGGTACCACTGCCACTAA<br>TATTTATATTCCCGTAAGGGACGTCCTCCTTCGGAGTATGTAAACATTCTAAGTTTACTTGCCCAATAT<br>TTATATTAGGCAGTTGGCAGGCAACTGCTAGCTCTCCTCCTTGGACTGATGTAAACATCGCAGTATATA<br>AATATCCACTAATATTTATATTCCCGTAAGGGGACGTCCCGAAGGGGAAGGGGAAGGACGTCAGTGGCA<br>GTTGCCTGCCAACTGCCTAGGCAAGTAAACTTAGGAGTATATAAATATAGGCAGTCGCGGTACCACTGC<br>CACTGACGTCCTGCCAACTGCCTAGGCAAGTAAACTTAAGTGGCACTAAAATGCATTTGCCCGAAGGGG<br>AAGGAGGACGCCAGTGGCAGTGGTACCGCCACTGCCTCCTTCGGAGTATTAAAATCCTAGTATGTAAAT<br>CTGCTAGCGCAGGAAATAAATTTTATTCTATTTATATACTCCGTTAGGAGGTAAGTAAACCCCTTCCCC<br>TTCGGGACGTCAGTGCAGTTGCCTGCCAACTGCCTAATATAAATATTAGACCACTAAAGTTTGGCAACT<br>GCCAACTGTTGTCCTTCGGAGGAAAAAAATGGTTAACTCGCAAGCAGTTAACATAACTAAAGTTTGTT<br>ACTTTACCGAAGACGTTTACCCTTTCTCGGTTAAGGAGACGGAGACAGTTGCACTGTGACTGCCTAGTA<br>TAGCAATTTTGTTTTTGTTTATATGCTCGACAAAATGACTTTCATAAAAATAAAGTAGTTAGCTAGT<br>TATTTTATATCACTATAACTAGGGTTCTCAGAGGCACCGAAGTCACTTGTAAAAATAGTACTTTTTAAC<br>TTGTTAATCTTCGTGTTCTTCAAAAGGATCACGTAATTTTTTGAAGGTGGACCAAAACTAACATAAA<br>CTGAATAGCCAGTTACACTTAACAGAAGAAACCATAAAAAAAGGTAAAGAAAAAGCTGGACTTTCCA<br>TAGCTCATTTAATAATAAAATTATTCTCTTTTCAACATATCTCTTAGATAGTTCAAAAGACTTGACGAC<br>TGTGTCCCACATTTTTAAACAAAATTAATCTACTCAAAATTTTGCCCTGAGAAAGAATAACTTACTTCG<br>TTTTTGCAGTAGCCATTCATGTCACTTTGAAACTGTCCTTACAAAGTTAAACATTAATTAAAAATTATT<br>TAATTTTTATATAACAAATATTATATTAAATAAAAAATGAACAAAGAACTTCTAAGATCGTCTTTAGTG<br>AGTAAATAAAGAGTTTACTTACCAGACAAGGCAGTTTTTCGATTCATTTTAAAGCAGGACAGTTCTGAAG<br>GGGAAAAGGGACTGCCTACTGCGGTCCTAGGTAAATACATTTTTATGCAATTTATTTCTTGTCGTAGTA<br>GGTTTCTATACTCACAAGAAGCAACCCCTTGACGAGAACGTTATCCTCAGAGTATTTATAATCCTGA<br>GAGGGAATGCACTGAAGAATATTTTCCTTATTTTTACAGAAAGTAAATAAAATAGCGCTAATAACGCT<br>TAATTCATTTAATCAATTATGGCAACAGGAACTTCTAAAGCTAAACCATCAAAAGTAAATTCAGACTTC<br>CAAGAACCTGGTTTAGTTACACCATTAGGTACTTTATTACGTCCACTTAACTCAGAAGCAGGTAAAGTA | Endo-β-glucanase insertion cassette (pSE-3HB-K-tD2: BD05) |

TABLE 4-continued

Vector Sequences

| SEQ ID NO. | Sequence | Use |
|---|---|---|

TAATGGCTGTATTTATCCTTTTATTTGCAGCATTCTTATTAATCATTTTAGAAATTTATTACCAGGCTG
GGGTACAACTGTTTCAACAGTTCTTTAATTTTAGATGACGTTTCTATGAGTTGGGAAACTTTAGCTAAA
GTTTCTTAATTTTATTTAACACAAACATAAAATATAAAACTGTTTGTTAAGGCTAGCTGCTAAGTCTTC
TTTTCGCTAAGGTAAACTAAGCAACTCAACCATATTTATATTCGGCAGTGGCACCGCCAACTGCCACTG
GCCTTCCGTTAAGATAAACGCGTggatctcacgtgACTAGTgtcgagtggtaccgccactgcctagtat
ataaatatcggcagttggcaggatatttatatactccgaaggaacttgttagccgataggcgaggcaac
tgccactaaaatttatttgcctcctaacggagcattaaaatccctaagtttacttgcccgtaaggggaa
ggggacgtccactaatattatattaggcagttggcaggcaacaataaatacatttgtcccgtaaggggaa
cgtcctgccaactgcctatggtagctattaagtatatatatgaaaagtgtgtataaactaaactaaa
ataaaccaggtatggttaaccagatttattttagtttaaaaaaaaattagttgtttgagctagagttag
ttgaagctaagtctagaTTAACCGGTTCCTTTATCATCATCATCTTTGTAATCACTTCCACCGCCACCT
GAGCCTTGAAAGTATAAGTTTTCACCGGTACCCTTGCGAGCTAAACAACTACTTACTAATGAAGTGTCT
GTCCATGAGTTTCCAGAAGAAGTAGGGGTTTCGGTTAATACATAAGTTGAATCAAAAGAACCAGCACCC
CAACCTACATAACCTAAGTACACGTCAGAGTTTTGATTTAAGTACTGAATTTGTTGACACATGTCTTGG
ATACAACTCTGCACGTTTCCACCACCTGTTTCAGTTAAAATGGCTTGGCGATTATTTTGACGTAACCAA
GTTGCTAAAGGACTAAAAGCACCATCAATATTATTTGTGGTACATTCGGCGTGTGTTCCGCTATTATCA
GAATCAAGATATTTATGTACATCGAATATTAAGTTAGTGGTACTACCGTCTGGGTTAGTCACTTGACTA
AGAGCAGCTGCGCTACCGTCAGAAATAAAAGCGCCGGCAGATTGCCAATCGTTGCCTGGTAAACTAATG
AATTGTGATGTTGCACCAGCATTACGAATAGCAGTTACTACTTCTTGCACAGTTGCAGCCCAAGTATTT
ATGTTCACATCGTGAGGTTCATTCATAATACCGAACCAAACACGTGATTGACTAGCATATTTTGAAGCT
AATTGGCTCCATAATGATGTAAATTGAGCATTAGTTGGACCACCTTGACCAATAATACCACCGTTCCAA
CGGGCATAATTATGAATATCAACAATACAATAGGCACCTAAAGATAAGCAACCTTGTACTAATTGATCA
TATTTACTAATTGATGTACTATCTAAGTTACCACCTAAATTGTTGTTAACTAAGTATTGCCAGCCCACT
GGTAAACGGAAAATAGTCATACCATCTTCATTTACAAAGTGTTGCATTTGACCAATGCCATCTGGATAA
TTGTTTGAGCCAGTAAAATTTTTTAAAGGGGGATAAACTTTACTGGTAACACATGTACCATCGGTAGTA
CAACCAAAATCGAAACCTGCAATATTAACACCAGCGAAACGTACTCCAGAAGATGTAGGAGGTGTGCTG
CTAGAAGTGCTAGTAGCACGAGTTGTTGTAGTTGGACCTGAAGGAGGGCGAGTTGATGTTGTTATAGTT
GTTGCACCTGGAATACATTGAGCATAGTAAGGATTTAAGGTACTACATGCTGAGCCAGGAGCACAATTG
GTAGGACCAGACCAACCAATACCACCACACTGACCCCAAACAGTCTGTTGAGCAACAGCACCACCATAT
AAGATAGATGCAGCAAGTAATAATGGTGCTACGCTTTTGTTTGGTACCATatgcgtgtatctccaaaat
aaaaaaaacaactcatcgttacgttaaatttattattatttaattttaatcattgtgtatttaatattat
aacttatataaaataaaattaaaaataagcatttttacacacatattttaaataaatcttaaacgg
gttatatatagttatatatatgggactagaactgctttgtgcatagtcatcacaattattatattataa
accatgaataaaggttttattattatgatataaaaatgcataaaattttataaatttgcaagtaaaa
tatataattaggaaaaaatttaaaatttaaaatgttagtcaagtttacaactaatacttttaattttgt
attttaagtattggacattttttgtggaattaaatgtgcaaaatatccatttaatttcatACTAGTgata
tctacgtaatcgatgaattcgatcccattttttataactggatctcaaaatacctataaacccattgttc
ttctcttttagctctaagaacaatcaatttataaatatatttattattatgctataatataaatactat
ataaatacatttacctttttataaatacatttacctttttttaatttgcatgatttttaatgcttatgc
tatcttttttatttagtccataaaacctttaaaggacctttttcttatgggatatttatatttcctaac
aaagcaatcggcgtcataaacttagttgcttacgacgcctgtgacgtcccccccttccccttacgagg
caagtaaacttaggggattttaatgcaataaataaatttgtcctcttcgggcaaatgaatttagtattt
aaaatatgacaagggtgaaccattacttttgttaacaagtgatcttaccactcactatttttgttgaatt
ttaaacttatttaaaattctcgagaaagatttaaaaataaactttttttaatcttttatttattttttc
tttttcCGTATGGAATTGCCCAATATTATTCAACAATTTATCGGAAACAGCGTTTTAGAGCCAAATAAA
ATTGGTCAGTCGCCATCGGATGTTTATTCTTTTAATCGAAATAATGAAACTTTTTTTTCTTAAGCGATCT
AGCACTTTATATACAGAGACCACATACAGTGTCTCTCGTGAAGCGAAAATGTTGAGTTGGCTCTCTGAG
AAATTAAAGGTGCCTGAACTCATCATGACTTTTCAGGATGAGCAGTTTGAATTTATGATCACTAAAGCG
ATCAATGCAAAACCAATTTCAGCGCTTTTTTTAACAGACCAAGAATTGCTTGCTATCTATAAGGAGGCA
CTCAATCTGTTAAATTCAATTGCTATTATTGATTGTCCATTTATTTCAAACATTGATCATCGGTTAAAA
GAGTCAAAATTTTTTATTGATAACTCCTTGACGATATAGATCAAGATGATTTTGACACTGAATTA
TGGGGAGACCATAAAACTTACCTAAGTCTATGGAATGAGTTAACCGAGACTCGTGTTGAAGAAAGATTG
GTTTTTTCTCATGGCGATATCACGGATAGTAATATTTTTATAGATAAATTCAATGAAATTTATTTTTA
GACCTTGGTCGTGCTGGGTTAGCAGATGAATTTGTAGATATATCCTTTGTTGAACGTTGCCTAAGAGAG
GATGCATCGGAGGAAACTGCGAAAATATTTTAAAGCATTTAAAAAATGATAGACCTGACAAAAGGAAT
TATTTTTTAAAACTTGATGAATTGAATTGAttccaagcattatctaaaatactctgcaggcacgctagc
ttgtactcaagctcgtaacgaaggtcgtgaccttgctcgtgaaggtggcgacgtaattcgttcagcttg
taaatggtctccagaacttgctgctgcatgtgaagtttggaaagaaattaaattcgaatttgatactat
tgacaaactttaattttttattttttcatgatgtttatgtgaatagcataaacatcgttttattttatg
gtgtttaggttaaataccaaacatcatttttacattttaaaattaagttctaaagttatcttttgttt
aaatttgcctgtctttataaattacgatgtgccagaaaaataaatcttagcttttttattatagaattt
atctttatgtattatttttataagttataataaaagaaatagtaacatactaaagcggatgtagcgcg
tttatcttaacggaaggaattcggcgcctacgtacccgggtcgcgaggatccACGCGTTAATAGCTCAC
TTTTCTTTAAATTTAATTTTTAATTTAAAGGTGTAAGCAAATTGCCTGACGAGAGATCCACTTAAAGGA
TGACAGTGGCGGGCTACTGCCTACTTCCCTCCGGGATAAAATTTATTTGAAAAACGTTAGTTACTTCCT
AACGGAGCATTGACATCCCCATATTTATATTAGGACGTCCCCTTCGGGTAAATAAATTTTAGTGGACGT
CCCCTTCGGGCAAATAAATTTTAGTGGACAATAAATAAATTTGTTGCCTGCCAACTGCCTAGGCAAGTA
AACTTGGGAGTATTAAAATAGGACGTCAGTGGCAGTTGCCTGCCAACTGCCTATATTTATATACTGCGA
AGCAGGCAGTGGCGGTACCACTGCCACTGGCGTCCTAATATAAATATTGGGCAACTAAAGTTTATAGCA
GTATTAACATCCTATATTTATATACTCCGAAGGAACTTGTTAGCCGATAGGCGAGGCAACAAATTTATT
TATTGTCCCGTAAAGGATGCCTCCAGCATCGAAGGGGAAGGGGACGTCCTAGGCCATAAAACTAAAGG
GAAATCCATAGTAACTGATGTTATAAATTTATAGACTCCAAAAAACAGCTGCGTTATAAATAACTTCTG TABLE 4-continued Vector Sequences

| SEQ ID NO. | Sequence | Use |
|---|---|---|
| | TTAAATATGGCCAAGGGGACAGGGGCACTTTCAACTAAGTGTACATTAAAAATTGACAATTCAATTTTT TTTAATTATAATATATATTTAGTAAAATATAACAAAAAGCCCCCATCGTCTAGgtagaattccagctgg cggccgccctatg | |
| 31 | GTGCACTCTCAGTACAATCTGCTCTGATGCCGCATAGTTAAGCCAGCCCCGACACCCGCCAACACCCGC TGACGCGCCCTGACGGGCTTGTCTGCTCCCGGCATCCGCTTACAGACAAGCTGTGACCGTCTCCGGGAG CTGCATGTGTCAGAGGTTTTCACCGTCATCACCGAAACGCGCGAGACGAAAGGGCCTCGTGATACGCCT ATTTTTATAGGTTAATGTCATGATAATAATGGTTTCTTAGACGTCAGGTGGCACTTTTCGGGGAAATGT GCGCGGAACCCCTATTTGTTTATTTTTCTAAATACATTCAAATATGTATCCGCTCATGAGACAATAACC CTGATAAATGCTTCAATAATATTGAAAAAGGAAGAGTATGAGTATTCAACATTTCCGTGTCGCCCTTAT TCCCTTTTTTGCGGCATTTTGCCTTCCTGTTTTTGCTCACCCAGAAACGCTGGTGAAAGTAAAAGATGC TGAAGATCAGTTGGGTGCACGAGTGGGTTACATCGAACTGGATCTCAACAGCGGTAAGATCCTTGAGAG TTTTCGCCCCGAAGAACGTTTTCCAATGATGAGCACTTTTAAAGTTCTGCTATGTGGCGCGGTATTATC CCGTATTGACGCCGGGCAAGAGCAACTCGGTCGCCGCATACACTATTCTCAGAATGACTTGGTTGAGTA CTCACCAGTCACAGAAAAGCATCTTACGGATGGCATGACAGTAAGAGAATTATGCAGTGCTGCCATAAC CATGAGTGATAACACTGCGGCCAACTTACTTCTGACAACGATCGGAGGACCGAAGGAGCTAACCGCTTT TTTGCACAACATGGGGGATCATGTAACTCGCCTTGATCGTTGGGAACCGGAGCTGAATGAAGCCATACC AAACGACGAGCGTGACACCACGATGCCTGTAGCAATGGCAACAACGTTGCGCAAACTATTAACTGGCGA ACTACTTACTCTAGCTTCCCGGCAACAATTAATAGACTGGATGGAGGCGGATAAAGTTGCAGGACCACT TCTGCGCTCGGCCCTTCCGGCTGGCTGGTTTATTGCTGATAAATCTGGAGCCGGTGAGCGTGGGTCTCG CGGTATCATTGCAGCACTGGGGCCAGATGGTAAGCCCTCCCGTATCGTAGTTATCTACACGACGGGGAG TCAGGCAACTATGGATGAACGAAATAGACAGATCGCTGAGATAGGTGCCTCACTGATTAAGCATTGGTA ACTGTCAGACCAAGTTTACTCATATATACTTTAGATTGATTTAAAACTTCATTTTTAATTTAAAAGGAT CTAGGTGAAGATCCTTTTTGATAATCTCATGACCAAAATCCCTTAACGTGAGTTTTCGTTCCACTGAGC GTCAGACCCCGTAGAAAAGATCAAAGGATCTTCTTGAGATCCTTTTTTTCTGCGCGTAATCTGCTGCTT GCAAACAAAAAAACCACCGCTACCAGCGGTGGTTTGTTTGCCGGATCAAGAGCTACCAACTCTTTTTCC GAAGGTAACTGGCTTCAGCAGAGCGCAGATACCAAATACTGTTCTTCTAGTGTAGCCGTAGTTAGGCCA CCACTTCAAGAACTCTGTAGCACCGCCTACATACCTCGCTCTGCTAATCCTGTTACCAGTGGCTGCTGC CAGTGGCGATAAGTCGTGTCTTACCGGGTTGGACTCAAGACGATAGTTACCGGATAAGGCGCAGCGGTC GGGCTGAACGGGGGGTTCGTGCACACAGCCCAGCTTGGAGCGAACGACCTACACCGAACTGAGATACCT ACAGCGTGAGCTATGAGAAAGCGCCACGCTTCCCGAAGGGAGAAAGGCGGACAGGTATCCGGTAAGCGG CAGGGTCGGAACAGGAGAGCGCACGAGGGAGCTTCCAGGGGGAAACGCCTGGTATCTTTATAGTCCTGT CGGGTTTCGCCACCTCTGACTTGAGCGTCGATTTTTGTGATGCTCGTCAGGGGGCGGAGCCTATGGAA AAACGCCAGCAACGCGGCCTTTTTACGGTTCCTGGCCTTTTGCTGGCCTTTTGCTCACATGTTCTTTCC TGCGTTATCCCCTGATTCTGTGGATAACCGTATTACCGCCTTTGAGTGAGCTGATACCGCTCGCCGCAG CCGAACGACCGAGCGCAGCGAGTCAGTGAGCGAGGAAGCGGAAGAGCGCCCAATACGCAAACCGCCTCT CCCCGCGCGTTGGCCGATTCATTAATGCAGCTGGCACGACAGGTTTCCCGACTGGAAAGCGGGCAGTGA GCGCAACGCAATTAATGTGAGTTAGCTCACTCATTAGGCACCCCAGGCTTTACACTTTATGCTTCCGGC TCGTATGTTGTGTGGAATTGTGAGCGGATAACAATTTCACACAGGAAACAGCTATGACCATGATTACGC CaagctcgcggccgcagtactCTGCAGATTTTATGCAAAATTAAAGTCTTGTGACAACAGCTTTCTCCT TAAGTGCAAATATCGCCCATTCTTTCCTCTTTTCGTATATAAATGCTGTAATAGTAGGATGTCGTACCC GTAAAGGTACGACATTGAATATTAATATACTCCTAAGTTTACTTTCCCAATATTTATATTAGGACGTCC CCTTCGGGTAAATAAATTTTAGTGGCAGTGGTACCGCCACTCCCTATTTTAATACTGCGAAGGAGGCAG TTGGCAGGCAACTCGTCGTTCGCAGTATATAAATATCCACTAATATTTATATTCCCGTAAGGGGGACGTC CCGAAGGGGAAGGGGAAAGAAGCAGTCGCCTCCTTGCGAAAAGGTTTACTTGCCCGACCAGTGAAAAGC ATGCTGTAAGATATAAATCTACCCTGAAAGGGATGCATTTCACCATAATACTATACAAATGGTGTTACC CTTTGAGGATCATAACGGTGCTACTGGAATATATGGTCTCTTCATGGATAGACGATAGCCATTTATTTA CCCATTAAGGGGACATTAGTGGCCTGTCACTGCTCCTTACGAGACGCCAGTGGACGTTCGTCCTAGAAA ATTTATGCGCTGCCTAGAAGCCCCAAAAGGGAAGTTTACTGACTCGTTAGAGCGTGCGCTAACAGGTTT AAATACTTCAATATGTATATTAGGACGCCGGTGGCAGTGGTACCGCCACTGCCACCGTCGGAGGACGTC CCTTACGGTATATTATACTAGGATTTTAATACTCCGAAGGAGGCAGTGGCGGTACCACTGCCACTAA TATTTTATATTCCCGTAAGGGACGTCCTCCTCTTCGGAGTATGTAAACATTCTAAGTTTACTTGCCCAATAT TTATATTAGGCAGTTGGCAGGCAACTGCTAGCTCTCCTCCTTCGGAGTATGTAAACATCGCAGTATATA AATATCCACTAATATTTATATTCCCGTAAGGGGACGTCCCGAAGGGGAAGGGGAAGGACGTCAGTGGCA GTTGCCTGCCAACTGCCTAGGCAAGTAAACTTAGGAGTATATAAATATAGGCAGTCGCGGTACCACTGC CACTGACGTCCTGCCAACTGCCTAGGCAAGTAAACTTAAGTGGCACTAAAATGCATTTGCCCGAAGGGG AAGGAGGACGCCAGTGGCAGTGGTACCGCCACTGCCTCCTTGGAGTATTAAAATCCTAGTATGTAAAT CTGCTAGCGCAGGAAATAAATTTTATTCTATTTATATACTCCGTTAGGAGGTAAGTAAACCCCTTCCCC TTCGGGACGTCAGTGCAGTTGCCTGCCAACTGCCTAATATAAATATTAGACCACTAAAGTTTGGCAACT GCCAACTGTTGTCCTTCGGAGGAAAAAAATGGTTAACTCGCAAGCAGTTAACATAACTAAAGTTTGTT ACTTTACCGAAGACGTTTACCCTTTCTCGGTTAAGGAGACGGAGACAGTTGCACTGTGACTGCCTAGTA TAGCAATTTGTTTTGTTTATATGCTCGACAAAATGACTTTCATAAAAATATAAAGTAGTTAGCTAGT TATTTTATATCACTATAACTAGGGTTCTCAGAGGCACCGAAGTCACTTGTAAAAATAGTACTTTTTAAC TTGTTTAATCTTCGTGTTCTTCAAAAGGATCACGTAATTTTTTTGAAGGTGGACCAAAACTAACATAAA CTGAATAGCCAGTTACACTTAACAGAAAACCATAAAAAAGGTAAAGAAGAGACTTCTAAGATCGTCTTCCA TAGCTCATTTAATAATAAAATTATTCTCTTTTCAACATATCTCTTAGATAGTTCAAAAGACTTGACGAC TGTGTCCCACATTTTTAAACAAATTAATCTACTCAAAATTTGCCCTGAGAAAGAATAACTTACTTCG TTTTTGCAGTAGCCATTCATGTCACTTTGAAACTGTCCTTACAAAGTTAAACATTAATTAAAAATTATT TAATTTTTATATAACAAATATTATTAAATAAAAAATGAACAAGAAGAACTTCTAAGATCGTCTTTAGTG AGTAATTAAAGAGTTTACTTACCAGACAAGGCAGTTTTTTCATTCTTTTAAAGCAGGCAGTTCTGAAG GGGAAAAGGGACTGCCTACTGCGGTCCTAGGTAAATACATTTTTATGCAATTTATTTCTTGTGCTAGTA GGTTTCTATACTCACAAGAAGCAACCCCTTGACGAGAGAACGTTATCCTCAGAGTATTTATAATCCTGA GAGGGAATGCACTGAAGAATATTTTCCTTATTTTTTACAGAAAGTAAATAAAATAGCGCTAATAACGCT TAATTCATTTAATCAATTATGGCAACAGGAACTTCTAAAGCTAAACCATCAAAAGTAAATTCAGACTTC | Endo- xylanase insertion cassette (pSE-3HB- K-tD2: BD11) |

TABLE 4-continued

Vector Sequences

| SEQ ID NO. | Sequence | Use |
|---|---|---|

CAAGAACCTGGTTTAGTTACACCATTAGGTACTTTATTACGTCCACTTAACTCAGAAGCAGGTAAAGTA
TTACCAGGCTGGGGTACAACTGTTTTAATGGCTGTATTTATCCTTTTATTTGCAGCATTCTTATTAATC
ATTTTAGAAATTTACAACAGTTCTTTAATTTTAGATGACGTTTCTATGAGTTGGGAAACTTTAGCTAAA
GTTTCTTAATTTTATTTAACACAAACATAAAATATAAAACTGTTTGTTAAGGCTAGCTGCTAAGTCTTC
TTTTCGCTAAGGTAAACTAAGCAACTCAACCATATTTATATTCGGCAGTGGCACCGCCAACTGCCACTG
GCCTTCCGTTAAGATAAACGCGTggatctcacgtgACTAGTgtcgagtggtaccgccactgcctagtat
ataaatatcggcagttggcaggatatttatatactccgaaggaacttgttagccgataggcgaggcaac
tgccactaaaatttatttgcctcctaacggagcattaaaatccctaagtttacttgcccgtaaggggaa
ggggacgtccactaatatttatattaggcagttggcaggcaacaataaatacatttgtcccgtaagggg
acgtcctgccaactgcctatggtagctattaagtatatatatgaaaagtgtgtataaactaaactaa
aataaaccaggtatggttaaccagatttattttagtttaaaaaaaaattagttgtttgagctagagtta
gttgaagctaagtctagaTTAACCGGTTCCTTTATCATCATCATCTTTGTAATCACTTCCACCGCCACC
TGAGCCTTGAAAGTATAAGTTTTCACCGGTACCGCTAACAGTGATAGAAGCACTACCTGATGAAAAATA
ACCTTCAACAGCTACAATTTGATAGTCCATTGTACCTAATGTTAAACCTTGTTGAGCCCATGCATTAAA
GTGGTTTGCTGTATTAACACTACCACTTGAACGATGATTACGTCTTACACTCCAGTATTGGTAGAAAGT
GGCAGTTCCAATTATAGATGGTTGATTTACGCGTTGAGTACGATAAATATCATAAACTGATCCATCTGA
AGTAACTTCACCTAATTTAGTAGCACCTGTTGAAGGGTTGTATGTACCAAAGTTCTCTACAATATAATA
TTCAATTAATGGGTTACGGCTCCAACCGTATACACTTAAATAAGAATTACCATTAGGGTTGTAACTACC
AGAGAAATTGATTACCTTATTCTTTGTACCAGGTTGCCAACCTTTTCCTCCAACAAAATTGCCTGAGTT
ACTCCAATTTACACTAAATTGACCACCAGGTCCATTAGTATATGTAACACCACCGTGTCCATCATTCCA
GTAAGAATAAAAGTAACCGTTATTGTAACCTGTACCTGGTTGAATTGTTTGACGTTTTTCTACTGCAAC
TGATTCCACTTCAGCAGCTGGACGGCAACTTGCACGTGAAGGTGGAGATGCTGCTAAAAGACTTGTGAA
AGATACTGGTACCATatgcgtgtataccaaaataaaaaaacaactcatcgttacgttaaatttattatt
atttaatttaatcattgtgtatttaatattataacttatataaaataaaattaaaaataagcatttt
tacacacatattttaaataaatctttaaacgggttatatatagttatatatatgggactagaactgct
ttgtgcatagtcatcacaattattatattataaaccatgaataaaggttttattattatgatataaaaa
tgcataaaattttttataaattttgcaagtaaaatatataattaggaaaaaatttaaaatttaaatgtt
agtcaagttacaactaatacttttaattttgtattttaagtattggacatttttgtggaattaaatgt
accaaatatccatttaatttcatACTAGTgatatctacgtaatcgatgaattcgatcccatttttataa
ctggatctcaaaatacctataaacccattgttcttctcttttagctctaagaacaatcaatttataaat
atatttattattatgctataatataaatactatataaatacattttttataaatacatttacct
tttttttaatttgcatgattttaatgcttatgctatcttttttatttagtccataaaaccttttaaagga
cctttcttatgggatatttatattttcctaacaaagcaatcggcgtcataaactttagttgcttacga
cgcctgtggacgtcccccccttccccttacgggcaagtaaacttagggattttaatgcaataaatatt
ttgtcctcttcgggcaaatgaattttagtatttaaatatgacaagggtgaaccattacttttgttaaca
agtgatcttaccactactattttttgttgaatttttaaacttatttaaaattctcgagaaagattttaaa
aataaacttttttaatctttatttatttttcttttttCGTATGGAATTGCCCAATATTATTCAACAA
TTTATCGGAAACAGCGTTTTAGAGCCAAATAAAATTGGTCAGTCGCCATCGGATGTTTATTCTTTTAAT
CGAAATAATGAAACTTTTTTTCTTAAGCGATCTAGCACTTTATATACAGAGACCACATACAGTGTCTCT
CGTGAAGCGAAAATGTTGAGTTGGCTCTCTGAGAAATTAAAGGTGCCTGAACTCATCATGACTTTTCAG
GATGAGCAGTTTGAATTTATGATCACTAAAGCGATCAATGCAAAACCAATTTCAGCGCTTTTTTTAACA
GACCAAGAATTGCTTGCTATCTATAAGGAGGCACTCAATCTGTTAAATTCAATTGCTATTATTGATTGT
CCATTTATTTCAAACATTGATCATCGGTTAAAAGAGTCAAAATTTTTTATTGATAACCAACTCCTTGAC
GATATAGATCAAGATGATTTTGACACTGAATTATGGGGAGACCATAAAACTTACCTAAGTCTATGGAAT
GAGTTAACCGAGACTCGTGTTGAAGAAAGATTGGTTTTTTCTCATGGCGATATCACGGATAGTAATATT
TTTATAGATAAATTCAATGAAATTTATTTTTTAGACCTTGGTCGTGCTGGGTTAGCAGATGAATTTGTA
GATATATCCTTTGTTGAACGTTGCCTAAGAGAGGATGCATCGGAGGAAACTGCGAAAATATTTTTAAAG
CATTTAAAAAATGATAGACCTGACAAAAGGAATTATTTTTTAAAACTTGATGAATTGAATTGAttccaa
gcattatctaaaatactctgcaggcacgctagcttgtactcaagctcgtaacgaaggtcgtgaccttgc
tcgtgaaggtggcgacgtaattcgttcagcttgtaaatggtctccagaacttgctgctgcatgtgaagt
ttggaaagaaattaaattcgaatttgatactattgacaaactttaattttattttcatgatgtttat
gtgaatagcataaacatcgttttattttatggtgtttaggttaaatacctaaacatcattttacatt
tttaaaattaagttctaaagttatcttttgttaaatttgcctgtctttataaattacgatgtgccaga
aaaataaaatcttagcttttttattatagaatttatctttatgtattatattttataagttataataaaa
gaaatagtaacatactaaagcggatgtagcgcgtttatcttaacggaaggaattcggcgcctacgtacc
cgggtcgcgaggatccACGCGTTAATAGCTCACTTTTCTTTAAATTTAATTTTTAATTTAAAGGTGTAA
GCAAATTGCCTGACGAGAGATCCACTTAAAGGATGACAGTGGCGGGCTACTGCCTACTTCCCTCCGGGA
TAAAATTTATTTGAAAACGTTAGTTACTTCCTAACGGAGCATTGACATCCCCATATTTATATTAGGAC
GTCCCCTTCGGGTAAATAAATTTTAGTGGACGTCCCCTTCGGGCAAATAAATTTTAGTGGACAATAAAT
AAATTTGTTGCCTGCCAACTGCCTAGGCAAGTAAACTTGGGAGTATTAAAATAGGACGTCAGTGGCAGT
TGCCTGCCAACTGCCTATATTTATATACTGCGAAGCAGGCAGTGGCGGTACCACTGCCACTGGCGTCCT
AATATAAATATTGGGCAACTAAAGTTTATAGCAGTATTAACATCCTATATTTATATACTCCGAAGGAAC
TTGTTAGCCGATAGGCGAGGCAACAAATTTATTTATTGTCCCGTAAAAGGATGCCTCCAGCATCGAAGG
GGAAGGGGACGTCCTAGGCCATAAAACTAAAGGGAAATCCATAGTAACTGATGTTATAAATTTATAGAC
TCCAAAAACAGCTGCGTTATAAATAACTTCTGTTAAATATGGCCAAGGGGACAGGGGCACTTTCAACT
AAGTGTACATTAAAAATTGACAATTCAATTTTTTTAATTATAATATATATTTAGTAAAATATAACAAA
AAGCCCCCATCGTCTAGgtagaattccagaggcggccgccctatg

Example 8

Construction of a *C. reinhardtii* Strain Transformed with a Construct that Does Not Disrupt Photosynthetic Capability In this example a nucleic acid encoding endo-β-glucanase from *T. reesei* was introduced into *C. reinhardtii*. Transforming DNA (SEQ ID NO. 28, Table 4) is shown graphically in FIG. 2B. In this instance the segment labeled "Transgene" is the endo-β-glucanase encoding gene (SEQ ID NO. 16, Table 3), the segment which drives expression of the transgene (labeled 5' UTR) is the 5' UTR and promoter sequence for the psbC gene from *C. reinhardtii*, the segment labeled 3' UTR contains the 3' UTR for the psbA gene from *C. reinhardtii*, and the segment labeled "Selection Marker" is the kanamycin resistance encoding gene from bacteria, which is regulated by the 5' UTR and promoter sequence for the atpA gene from *C. reinhardtii* and the 3' UTR sequence for the rbcL gene from *C. reinhardtii*. The transgene cassette is targeted to the 3HB locus of *C. reinhardtii* via the segments labeled "5' Homology" and "3' Homology," which are identical to sequences of DNA flanking the 3HB locus on the 5' and 3' sides, respectively. All DNA manipulations carried out in the construction of this transforming DNA were essentially as described by Sambrook et al., Molecular Cloning: A Laboratory Manual (Cold Spring Harbor Laboratory Press 1989) and Cohen et al., *Meth. Enzymol.* 297, 192-208, 1998.

For these experiments, all transformations were carried out on *C. reinhardtii* strain 137c (mt+). Cells were grown to late log phase (approximately 7 days) in the presence of 0.5 mM 5-fluorodeoxyuridine in TAP medium (Gorman and Levine, *Proc. Natl. Acad. Sci., USA* 54:1665-1669, 1965, which is incorporated herein by reference) at 23° C. under constant illumination of 450 Lux on a rotary shaker set at 100 rpm. Fifty ml of cells were harvested by centrifugation at 4,000×g at 23° C. for 5 min. The supernatant was decanted and cells resuspended in 4 ml TAP medium for subsequent chloroplast transformation by particle bombardment (Cohen et al., supra, 1998). All transformations were carried out under kanamycin selection (100 μg/ml), in which resistance was conferred by the gene encoded by the segment in FIG. 2B labeled "Selection Marker." (Chlamydomonas Stock Center, Duke University).

PCR was used to identify transformed strains. For PCR analysis, $10^6$ algae cells (from agar plate or liquid culture) were suspended in 10 mM EDTA and heated to 95° C. for 10 minutes, then cooled to near 23° C. A PCR cocktail consisting of reaction buffer, MgCl2, dNTPs, PCR primer pair(s) (Table 2 and shown graphically in FIG. 3B), DNA polymerase, and water was prepared. Algae lysate in EDTA was added to provide template for reaction. Magnesium concentration is varied to compensate for amount and concentration of algae lysate in EDTA added. Annealing temperature gradients were employed to determine optimal annealing temperature for specific primer pairs.

To identify strains that contain the endo-β-glucanase gene, a primer pair was used in which one primer anneals to a site within the psbC 5'UTR (SEQ ID NO. 10) and the other primer anneals within the endo-β-glucanase coding segment (SEQ ID NO. 3). Desired clones are those that yield a PCR product of expected size. To determine the degree to which the endogenous gene locus is displaced (heteroplasmic vs. homoplasmic), a PCR reaction consisting of two sets of primer pairs were employed (in the same reaction). The first pair of primers amplifies the endogenous locus targeted by the expression vector (SEQ ID NOs. 13 and 14). The second pair of primers (SEQ ID NOs. 6 and 7) amplifies a constant, or control region that is not targeted by the expression vector, so should produce a product of expected size in all cases. This reaction confirms that the absence of a PCR product from the endogenous locus did not result from cellular and/or other contaminants that inhibited the PCR reaction. Concentrations of the primer pairs are varied so that both reactions work in the same tube; however, the pair for the endogenous locus is 5× the concentration of the constant pair. The number of cycles used was >30 to increase sensitivity. The most desired clones are those that yield a product for the constant region but not for the endogenous gene locus. Desired clones are also those that give weak-intensity endogenous locus products relative to the control reaction.

Figure 10A:
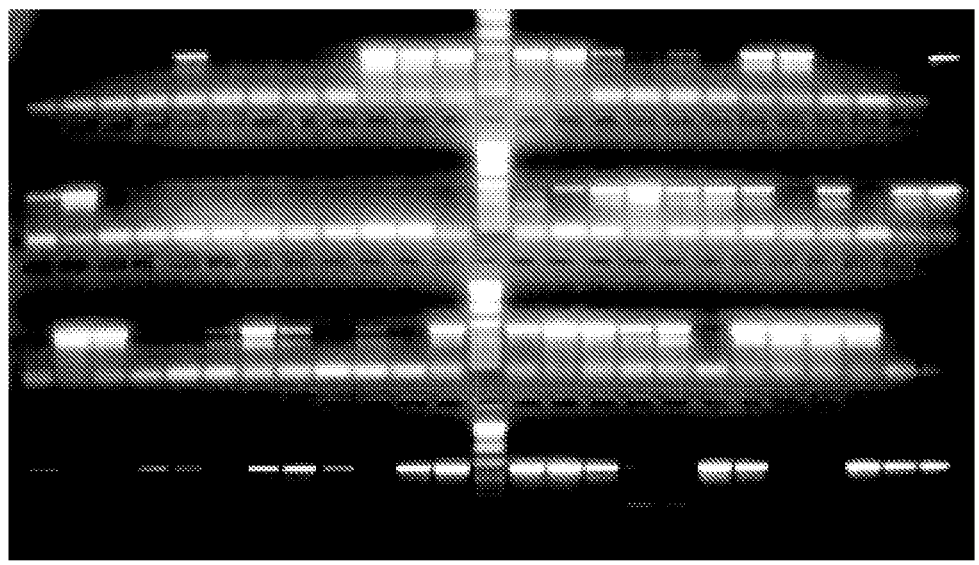
FIG. 10 illustrates results from PCR screening and Western blot analysis of endo-β-glucanase transformed C. reinhardtii clones.
Figure 10B:
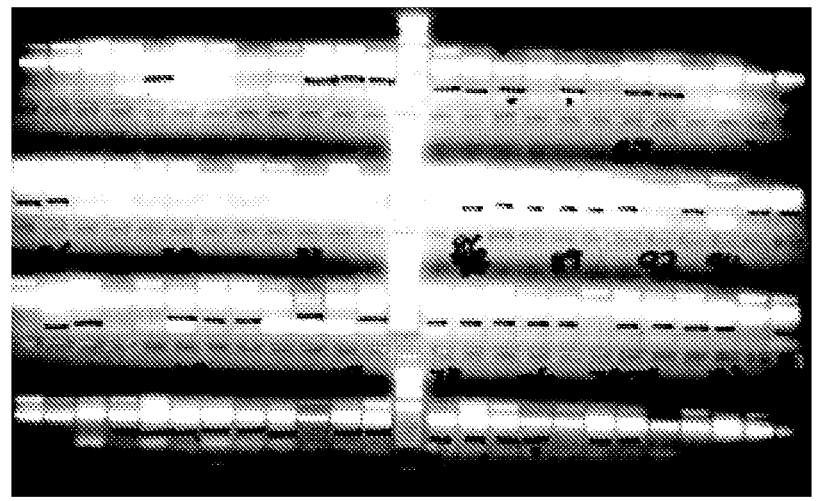
Figure 10C:
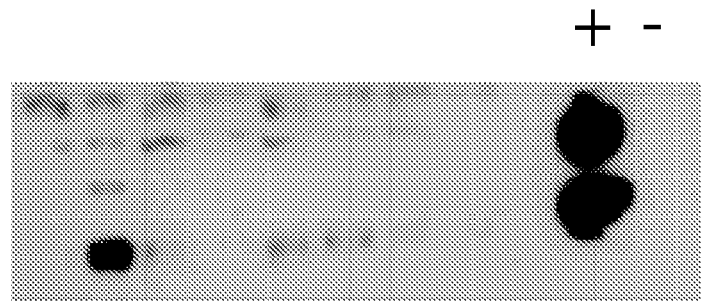

Results from this PCR on 96 clones were determined and the results are shown in FIG. 10. FIG. 10A shows PCR results using the transgene-specific primer pair. As can be seen, multiple transformed clones are positive for insertion of the endo-β-glucanase gene. FIG. 10B shows the PCR results using the primer pairs to differentiate homoplasmic from heteroplasmic clones. As can be seen, multiple transformed clones are either homoplasmic or heteroplasmic to a degree in favor of incorporation of the transgene (e.g. numbers 67, 92). Unnumbered clones demonstrate the presence of wild-type psbA and, thus, were not selected for further analysis.

To ensure that the presence of the endo-β-glucanase-encoding gene led to expression of the endo-β-glucanase protein, a Western blot was performed. Approximately $1 \times 10^8$ algae cells were collected from TAP agar medium and suspended in 0.5 ml of lysis buffer (750 mM Tris, pH=8.0, 15% sucrose, 100 mM beta-mercaptoethanol). Cells were lysed by sonication (5×30 sec at 15% power). Lysate was mixed 1:1 with loading buffer (5% SDS, 5% beta-mercaptoethanol, 30% sucrose, bromophenol blue) and proteins were separated by SDS-PAGE, followed by transfer to PVDF membrane. The membrane was blocked with TBST+5% dried, nonfat milk at 23° C. for 30 min, incubated with anti-FLAG antibody (diluted 1:1,000 in TBST+5% dried, nonfat milk) at 4° C. for 10 hours, washed three times with TBST, incubated with horseradish-linked anti-mouse antibody (diluted 1:10,000 in TBST+5% dried, nonfat milk) at 23° C. for 1 hour, and washed three times with TBST. Proteins were visualized with chemiluminescent detection. Results from multiple clones (FIG. 10C) show that expression of the endo-β-glucanase gene in *C. reinhardtii* cells resulted in production of the protein.

Similar results were seen (FIG. 11) with a similar construct containing the β-glucosidase gene from *T. reesei* (SEQ ID NO. 23, Table 4). The construct containing the endoxylanase gene is depicted in FIG. 2B. In this instance the segment labeled "Transgene" is the β-glucosidase encoding gene (SEQ ID NO. 17, Table 3), the segment which drives expression of the transgene (labeled 5' UTR) is the 5' UTR and promoter sequence for the psbC gene from *C. reinhardtii*, the segment labeled 3' UTR contains the 3' UTR for the psbA gene from *C. reinhardtii*, and the segment labeled "Selection Marker" is the kanamycin resistance encoding gene from bacteria, which is regulated by the 5' UTR and promoter sequence for the atpA gene from *C. reinhardtii* and the 3' UTR sequence for the rbcL gene from *C. reinhardtii*. The transgene cassette is targeted to the 3HB locus of *C. reinhardtii* via the segments labeled "5' Homology" and "3' Homology," which are identical to sequences of DNA flanking the 3HB locus on the 5' and 3' sides, respectively. All DNA manipulations carried out in the construction of this transforming DNA were essentially as described by Sambrook et al., Molecular Cloning: A Laboratory Manual (Cold Spring Harbor Laboratory Press 1989) and Cohen et al., *Meth. Enzymol.* 297, 192-208, 1998.

Figure 11A:
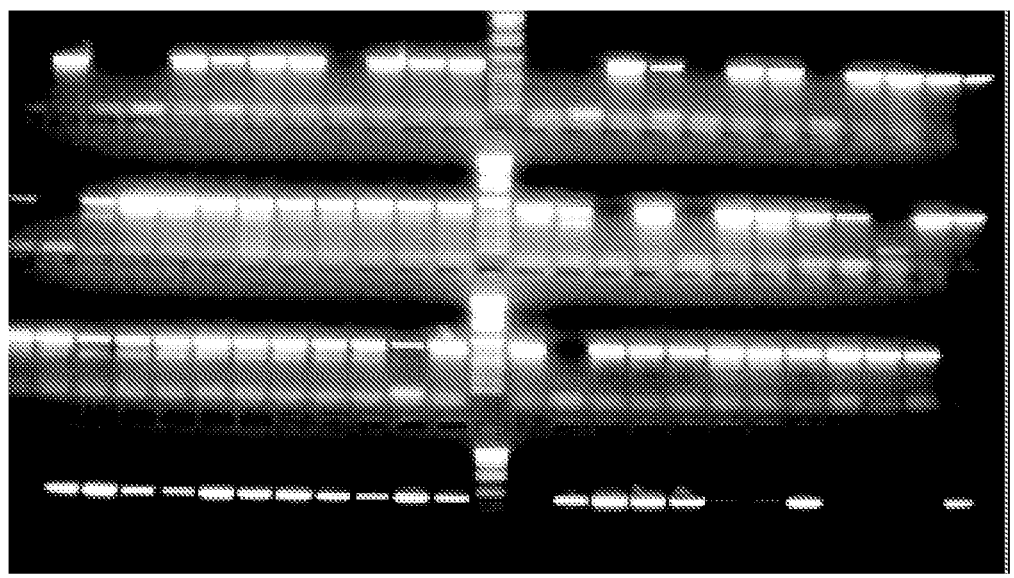
FIG. 11 illustrates results from PCR screening and Western blot analysis of β-glucosidase transformed C. reinhardtii clones.
Figure 11B:
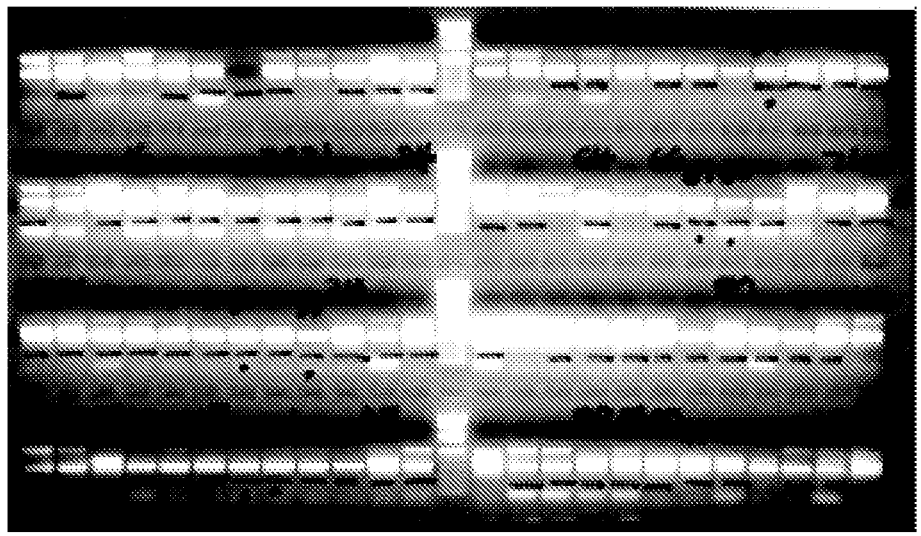
Figure 11C:
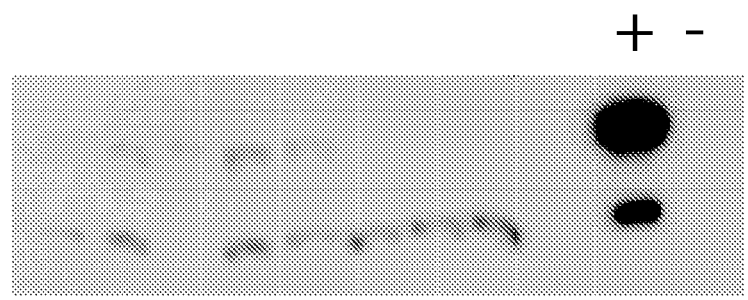

FIG. 11A shows PCR using the gene-specific primer pair. As can be seen, multiple transformed clones are positive for insertion of the β-glucosidase gene. FIG. 11B shows the PCR results using the primer pairs to differentiate homoplasmic from heteroplasmic clones. As can be seen, multiple transformed clones are either homoplasmic or heteroplasmic to a degree in favor of incorporation of the transgene (e.g. numbers 16, 64). Unnumbered clones demonstrate the presence of wild-type psbA and, thus, were not selected for further analysis. Western blot analysis demonstrating protein expression is demonstrated in FIG. 11C.

Example 9

Figure 13A:
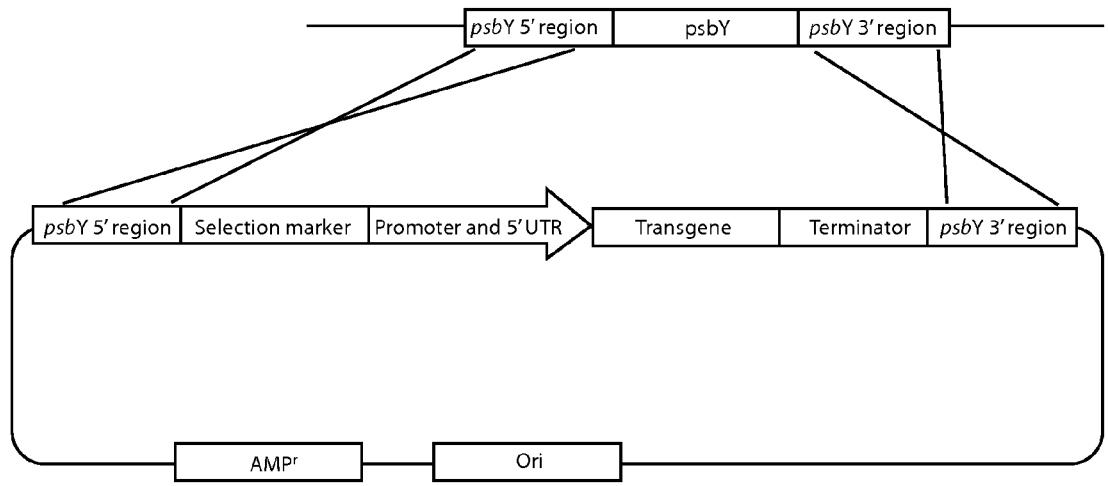
FIG. 13 is a graphic representation of two exogenous DNA constructs for insertion into a cyanobacterial genome.
Figure 13B:
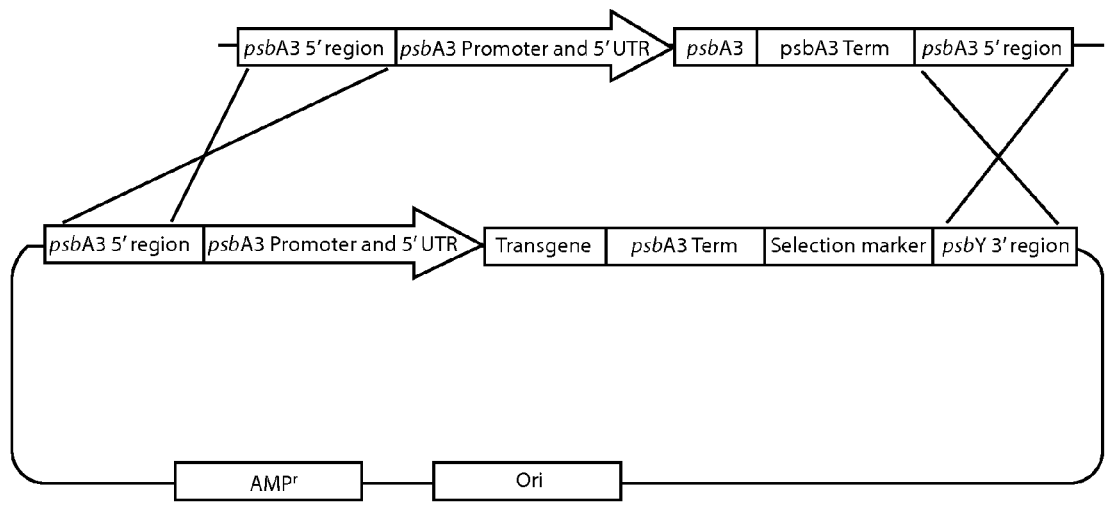

Construction of a Cyanobacteria Strain Expressing a Biomass Degrading Enzyme Construct that Does Not Disrupt Photosynthetic Capability In this example, a construct is made which is capable of insertion into a selected cyanobacteria species (e.g., *Synechocystis* sp. strain PCC6803, *Synechococcus* sp. strain PCC7942, Thermosynechococcus elongates BP-1, and Prochloroccus marina). Examples of such constructs are represented graphically in FIG. 13. In addition to the transgene and regulatory sequences (e.g., promoter and terminator), typically, such constructs will contain a suitable selectable marker (e.g., an antibiotic resistance gene). The transgene may be any gene of interest, but is preferably a biomass degrading enzyme (e.g., a cellulolytic, hemicellulolytic, ligninolytic enzyme). A cassette, or portion of the vector, may be integrated into the host cell genome via homologous recombination when the exogenous DNA to be inserted is flanked by regions which share homology to portions of the cyanobacterial genome. Alternately, the construct may be a self-replicating vector which does not integrate into the host cell genome, but stably or transiently transforms the host cell. In some instances, regulatory elements, transgenes, and/or selectable markers may need to be biased to the preferred codon usage of the host organism. All DNA manipulations are carried out essentially as described by Sambrook et al., Molecular Cloning: A Laboratory Manual (Cold Spring Harbor Laboratory Press 1989) and Cohen et al., *Meth. Enzymol.* 297, 192-208, 1998.

Transformation of *Synechocystis* with a construct of the present invention can be carried out by any method known in the art. (See, e.g., Dzelzkalns and Bogorad, *J. Bacteriol.* 165: 964-71 (1986)). For this example *Synechocystis* sp. strain 6803 is grown to a density of approximately $2 \times 10^8$ cells per ml and harvested by centrifugation. The cell pellet is resuspended in fresh BG-11 medium (ATCC Medium 616) at a density of $1 \times 10^9$ cells per ml and used immediately for transformation. One-hundred microliters of these cells are mixed with 5 ul of a mini-prep solution containing the construct and the cells are incubated with light at 30° C. for 4 hours. This mixture is then plated onto nylon filters resting on BG-11 agar supplemented with TES pH 8.0 and grown for 12-18 hours. The filters are then transferred to BG-11 agar+TES+5 ug/ml ampicillin and allowed to grow until colonies appear, typically within 7-10 days.

Colonies are then picked into BG-11 liquid media containing 5 ug/ml ampicillin and grown for 5 days. The transformed cells are incubated under low light intensity for 1-2 days and thereafter moved to normal growth conditions. These cells are then transferred to BG-11 media containing 10 ug/ml ampicilin and allowed to grow for 5 days. Cells were then harvested for PCR analysis to determine the presence of the exogenous insert. Western blots may be performed (essentially as described above) to determine expression levels of the protein(s) encoded by the inserted construct.

Example 10

Expression of Biomass Degrading Enzymes in *Escherichia coli*

In this example a nucleic acid encoding endo-β-glucanase from *T. reesei* was cloned into pET-21a using the NdeI and XhoI restriction sites present in both the gene and pET-21a. The resulting vector (SEQ ID NO. 25, Table 4) was transformed into *E. coli* BL-21 cells. Expression was induced when cell density reached OD=0.6. Cells were grown at 30° C. for 5 hours and then harvested. Purification was essentially as described previously. Activity of the enzymes expressed in bacteria was determined using assays essentially as described in previous examples. The results of these analyses are shown in FIG. 17 (Lane 2).

Nucleic acids encoding exo-β-glucanase, β-glucosidase and endoxylanase were also cloned into pET-21. The resulting vectors (SEQ ID NOs. 24, 26 and 27, respectively, Table 4) were transformed into *E. coli* BL-21 cells. Expression was induced when cell density reached OD=0.6. Cells were grown at 30° C. for 5 hours and then harvested. Purification was essentially as described previously. Activity of the enzymes expressed in bacteria was determined using assays essentially as described in previous examples. The results of these analyses are shown in FIG. 17 (Lane 1: exo-β-glucanase; Lane 3: β-glucosidase; and Lane 4: endoxylanase). Enzyme activity was also measured, essentially as previously described. Results, which are presented in background-subtracted values, are provided in Table 5.

TABLE 5

Enzyme activity of bacterially-produced biomass degrading enzymes

| Enzyme Added | Filter paper assay | β-glucosidase assay | Xylanase assay |
|---|---|---|---|
| Control (TBS) | 0.000 | 0.000 | 0.000 |
| endo-β-glucanase | 0.194 | 0.000 | 0.020 |
| β-glucosidase | 0.006 | 0.525 | 0.000 |
| endoxylanase | 0.000 | 0.011 | 3.131 |

This data, along with the data shown in previous examples, demonstrates that the enzymes encoded by the vectors described herein can be functionally expressed by both algae and bacteria, despite the codon bias built into the sequences.

Various modifications, processes, as well as numerous structures that may be applicable herein will be apparent. Various aspects, features or embodiments may have been explained or described in relation to understandings, beliefs, theories, underlying assumptions, and/or working or prophetic examples, although it will be understood that any particular understanding, belief, theory, underlying assumption, and/or working or prophetic example is not limiting. Although the various aspects and features may have been described with respect to various embodiments and specific examples herein, it will be understood that any of same is not limiting with respect to the full scope of the appended claims or other claims that may be associated with this application.

The invention claimed is:

1. A method of determining the plasmic state in a non-vascular photosynthetic organism that has been transformed with an exogenous sequence comprising:
providing in a mixture for a polymerase chain reaction (PCR)
a first primer pair, wherein a first primer of said first primer pair anneals to a selected site in the chloroplast genome of said organism, a second primer of said first primer pair anneals to a flanking region of said selected site, and said first primer pair is capable of amplifying a first endogenous chloroplast sequence,
a second primer pair wherein a first primer of said second primer pair and a second primer of said second primer pair anneal to a second endogenous chloroplast nucleic acid sequence that is not said first endogenous chloroplast sequence,
a polymerase, and
a chloroplast nucleic acid molecule from said organism;
performing a polymerase chain reaction (PCR); and
analyzing the product of said reaction,
wherein said selected site is deleted or disrupted when an exogenous nucleic acid is incorporated into said non-vascular photosynthetic organism.

2. The method of claim 1, wherein said exogenous nucleic acid sequence comprises at least one gene of interest and a selectable marker.

3. The method of claim 2, wherein said gene of interest encodes a biomass degrading enzyme.

4. The organism of claim 1, wherein said non-vascular photosynthetic organism is a microalga and said plasmic state is homoplasmy.

5. The method of claim 1, wherein said plasmic state is the degree of heteroplasmy.

6. The method of claim 1, wherein said polymerase chain reaction (PCR) comprises more than 30 cycles.

7. The method of claim 1, wherein an amplification product of said first primer pair comprises an untranslated region (UTR) and a coding region.

8. The method of claim 7, wherein said untranslated region is a 5' untranslated region.

9. The method of claim 1, further comprising:
providing a second reaction comprising:
a third primer pair wherein a first primer of said third primer pair anneals to said flanking region of said selected site and a second primer of said third primer pair anneals to a said exogenous nucleic acid sequence,
a polymerase, and
a nucleic acid molecule from said organism; and
performing a polymerase chain reaction (PCR); and
analyzing the product of said second reaction.

10. The method of claim 9, wherein an amplification product of said third primer pair comprises a portion of said flanking region of said selected site and at least a portion of said exogenous nucleic acid sequence.

11. The method of claim 9, wherein said second polymerase chain reaction (PCR) comprises more than 30 cycles.

12. The method of claim 1, wherein said reaction further comprises a third primer pair, wherein a first primer of said third primer pair anneals to said flanking region of said selected site and a second primer of said third primer pair anneals to said exogenous nucleic acid sequence.

13. The method of claim 12, wherein an amplification product of said third primer pair comprises a portion of said flanking region of said selected site and a portion of said exogenous nucleic acid sequence.

14. A method of producing a genetically-modified homoplasmic non-vascular photosynthetic organism comprising:
transforming at least one chloroplast of said non-vascular photosynthetic organism with an exogenous nucleic acid sequence;
providing in a polymerase chain reaction (PCR):
a first primer pair, wherein at least one primer of said first primer pair anneals to a selected site that is deleted or disrupted by the incorporation of said exogenous nucleic acid sequence, and said first primer pair is capable of amplifying a first endogenous chloroplast sequence,
a second primer pair, wherein a first primer of said second primer pair and a second primer of said second primer pair anneal to a second chloroplast nucleic acid sequence that is not deleted or disrupted by said incorporation of said exogenous nucleic acid sequence, a polymerase; and a chloroplast DNA from said organism; and performing a PCR reaction;

analyzing the product of said PCR reaction; and selecting a homoplasmic non-vascular photosynthetic organism based on the absence of a product from said first primer pair.

15. The method of claim 14, wherein said exogenous nucleic acid sequence comprises at least one gene of interest and a selectable marker.

16. The method of claim 15, wherein said gene of interest encodes a biomass degrading enzyme.

17. The method of claim 14, wherein said non-vascular photosynthetic organism is a microalga.

18. The method of claim 14, further providing a second reaction comprising a third primer pair wherein at least one of a first primer and a second primer of said third primer pair anneals to said exogenous nucleic acid sequence.

19. The method of claim 18, wherein an amplification product of said third primer pair comprises a portion of said exogenous nucleic acid sequence and a nucleic acid sequence flanking said exogenous nucleic acid sequence.

20. The method of claim 14, wherein an amplification product of said first endogenous chloroplast sequence comprises an untranslated region (UTR) and a coding region.

21. The method of claim 20, wherein said untranslated region is a 5' untranslated region.

22. The method of claim 14, wherein said PCR reaction further comprises a third primer pair, wherein at least one of a first primer and a second primer of said third primer pair anneals to said exogenous nucleic acid sequence.

23. The method of claim 22, wherein an amplification product of said third primer pair comprises at least a portion of said exogenous nucleic acid sequence.

24. The method of claim 14, wherein said PCR reaction comprises more than 30 cycles.

25. The method of claim 1, wherein said selected site is deleted when said exogenous nucleic acid is incorporated into said non-vascular photosynthetic organism.

26. The method of claim 14, wherein said segment of said selected site is deleted when said exogenous nucleic acid is incorporated into said non-vascular photosynthetic organism.

* * * * *

UNITED STATES PATENT AND TRADEMARK OFFICE
CERTIFICATE OF CORRECTION

PATENT NO. : 8,669,059 B2  
APPLICATION NO. : 13/585758  
DATED : March 11, 2014  
INVENTOR(S) : Stephen Mayfield et al.

It is certified that error appears in the above-identified patent and that said Letters Patent is hereby corrected as shown below:

On the title page, (60), please change "60/070,384" to --61/070,384--.

Signed and Sealed this
Twenty-second Day of July, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,669,059 B2
APPLICATION NO. : 13/585758
DATED : March 11, 2014
INVENTOR(S) : Stephen Mayfield et al.

It is certified that error appears in the above-identified patent and that said Letters Patent is hereby corrected as shown below:

In the Claims

In Claim 4 (column 207, line 56), please change "organism" to --method--.

Signed and Sealed this
Fifth Day of May, 2015

Michelle K. Lee
*Director of the United States Patent and Trademark Office*